US011923065B2

(12) United States Patent
Rosenberg et al.

(10) Patent No.: US 11,923,065 B2
(45) Date of Patent: Mar. 5, 2024

(54) SYSTEMS AND METHODS FOR USING ARTIFICIAL INTELLIGENCE AND MACHINE LEARNING TO DETECT ABNORMAL HEART RHYTHMS OF A USER PERFORMING A TREATMENT PLAN WITH AN ELECTROMECHANICAL MACHINE

(71) Applicant: ROM Technologies, Inc., Brookfield, CT (US)

(72) Inventors: Joel Rosenberg, Brookfield, CT (US); Steven Mason, Las Vegas, NV (US)

(73) Assignee: ROM Technologies, Inc., Brookfield, CT (US)

( * ) Notice: Subject to any disclaimer, the term of this patent is extended or adjusted under 35 U.S.C. 154(b) by 0 days.

(21) Appl. No.: 18/217,235

(22) Filed: Jun. 30, 2023

(65) Prior Publication Data
US 2023/0360765 A1 Nov. 9, 2023

Related U.S. Application Data

(63) Continuation-in-part of application No. 17/736,891, filed on May 4, 2022, which is a continuation-in-part
(Continued)

(51) Int. Cl.
*A63B 24/00* (2006.01)
*G16H 20/30* (2018.01)
*G16H 50/30* (2018.01)

(52) U.S. Cl.
CPC ......... *G16H 20/30* (2018.01); *A63B 24/0062* (2013.01); *G16H 50/30* (2018.01); *A63B 2024/0065* (2013.01)

(58) Field of Classification Search
CPC ........ G16H 20/30; G16H 40/67; G16H 10/60; G16H 15/00; G16H 20/40; G16H 30/20;
(Continued)

(56) References Cited

U.S. PATENT DOCUMENTS

| 823,712 A | 6/1906 | Uhlmann |
| 4,499,900 A | 2/1985 | Petrofsky et al. |

(Continued)

FOREIGN PATENT DOCUMENTS

| CA | 3193419 A1 | 3/2022 |
| CN | 2885238 Y | 4/2007 |

(Continued)

OTHER PUBLICATIONS

HCL Fitness, HCl Fitness PhysioTrainer Pro, 2017, retrieved on Aug. 19, 2021, 7 pages, https://www.amazon.com/HCl-Fitness-Physio Trainer-Electronically-Controlled/dp/B0759YMW78/.
(Continued)

*Primary Examiner* — George Manuel
(74) *Attorney, Agent, or Firm* — Dickinson Wright PLLC; Stephen A. Mason; Jonathan H. Harder

(57) ABSTRACT

Computer-implemented systems, computer-implemented methods, and tangible, non-transitory computer-readable media for detecting abnormal heart rhythms of a user performing treatment plan with an electromechanical machine. The system includes, in one embodiment, an electromechanical machine, one or more sensors, and one or more processing devices. The electromechanical machine is configured to be manipulated by a user while the user is performing a treatment plan. The one or more sensors are configured to determine one or more measurements associated with the user. The one or more processing devices are configured to receive, from the one or more sensors while the user performs the treatment plan, the one or more measurements associated with the user. The one or more processing devices also configured to determine, using one or more machine learning models, a probability that the one or more measurements indicate that the user satisfies a threshold for a condition associated with an abnormal heart
(Continued)

rhythm. The one or more processing devices are further configured to perform one or more preventative actions responsive to determining that the one or more measurements indicate the user satisfies the threshold for the condition associated with the abnormal heart rhythm. The one or more preventative actions are determined using the one or more machine learning models.

20 Claims, 36 Drawing Sheets

Related U.S. Application Data of application No. 17/379,542, filed on Jul. 19, 2021, now Pat. No. 11,328,807, which is a continuation of application No. 17/146,705, filed on Jan. 12, 2021, which is a continuation-in-part of application No. 17/021,895, filed on Sep. 15, 2020, now Pat. No. 11,071,597.

(60) Provisional application No. 63/407,049, filed on Sep. 15, 2022, provisional application No. 63/113,484, filed on Nov. 13, 2020, provisional application No. 62/910,232, filed on Oct. 3, 2019.

(58) Field of Classification Search
CPC ........ G16H 40/40; G16H 40/63; G16H 50/20; G16H 50/30; G16H 50/70; G16H 80/00; A63B 2071/0625; A63B 2071/063; A63B 2071/0675; A63B 2071/068; A63B 22/0605; A63B 2220/10; A63B 2220/17; A63B 2220/20; A63B 2220/30; A63B 2220/40; A63B 2220/51; A63B 2220/52; A63B 2220/80; A63B 2220/806; A63B 2220/808; A63B 2220/833; A63B 2225/09; A63B 2225/20; A63B 2225/50; A63B 71/0622; A63B 2022/0094; A63B 2022/0623; A63B 2024/0065; A63B 2071/0638; A63B 2071/0655; A63B 2071/0677; A63B 22/0694; A63B 2220/16; A63B 2220/56; A63B 2220/801; A63B 2220/803; A63B 2220/805; A63B 2220/836; A63B 2225/093; A63B 2230/06; A63B 2230/207; A63B 2230/30; A63B 2230/42; A63B 2230/50; A63B 23/0476; A63B 24/0062
See application file for complete search history.

(56) References Cited

U.S. PATENT DOCUMENTS

| | | |
|---|---|---|
| 4,822,032 A | 4/1989 | Whitmore et al. |
| 4,860,763 A | 8/1989 | Schminke |
| 4,869,497 A | 9/1989 | Stewart et al. |
| 4,932,650 A | 6/1990 | Bingham et al. |
| 5,137,501 A | 8/1992 | Mertesdorf |
| 5,161,430 A | 11/1992 | Febey |
| 5,202,794 A | 4/1993 | Schnee et al. |
| 5,240,417 A | 8/1993 | Smithson et al. |
| 5,247,853 A | 9/1993 | Dalebout |
| 5,256,117 A | 10/1993 | Potts et al. |
| D342,299 S | 12/1993 | Birrell et al. |
| 5,282,748 A | 2/1994 | Little |
| 5,284,131 A | 2/1994 | Gray |
| 5,316,532 A | 5/1994 | Butler |
| 5,318,487 A | 6/1994 | Golen |
| 5,324,241 A | 6/1994 | Artigues et al. |
| 5,336,147 A | 8/1994 | Sweeney, III |
| 5,338,272 A | 8/1994 | Sweeney, III |
| 5,361,649 A | 11/1994 | Slocum, Jr. |
| 5,429,140 A | 7/1995 | Burdea et al. |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |
| 5,860,941 A | 1/1999 | Saringer et al. |
| 5,950,813 A | 9/1999 | Hoskins et al. |
| 6,007,459 A | 12/1999 | Burgess |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,162,189 A | 12/2000 | Girone et al. |
| 6,182,029 B1 | 1/2001 | Friedman |
| D438,580 S | 3/2001 | Shaw |
| 6,253,638 B1 | 7/2001 | Bermudez |
| 6,267,735 B1 | 7/2001 | Blanchard et al. |
| 6,273,863 B1 | 8/2001 | Avni et al. |
| D450,100 S | 11/2001 | Hsu |
| D450,101 S | 11/2001 | Hsu |
| D451,972 S | 12/2001 | Easley |
| D452,285 S | 12/2001 | Easley |
| D454,605 S | 3/2002 | Lee |
| 6,371,891 B1 | 4/2002 | Speas |
| D459,776 S | 7/2002 | Lee |
| 6,413,190 B1 | 7/2002 | Wood et al. |
| 6,430,436 B1 | 8/2002 | Richter |
| 6,436,058 B1 | 8/2002 | Krahner et al. |
| 6,450,923 B1 | 9/2002 | Vatti |
| 6,474,193 B1 | 11/2002 | Farney |
| 6,491,649 B1 | 12/2002 | Ombrellaro |
| 6,514,085 B2 | 2/2003 | Slattery et al. |
| 6,535,861 B1 | 3/2003 | OConnor et al. |
| 6,543,309 B2 | 4/2003 | Heim |
| 6,589,139 B1 | 7/2003 | Butterworth |
| 6,601,016 B1 | 7/2003 | Brown et al. |
| 6,602,191 B2 | 8/2003 | Quy |
| 6,613,000 B1 | 9/2003 | Reinkensmeyer et al. |
| 6,626,800 B1 | 9/2003 | Casler |
| 6,626,805 B1 | 9/2003 | Lightbody |
| 6,640,122 B2 | 10/2003 | Manoli |
| 6,640,662 B1 | 11/2003 | Baxter |
| 6,652,425 B1 | 11/2003 | Martin et al. |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 6,902,513 B1 | 6/2005 | McClure |
| 7,058,453 B2 | 6/2006 | Nelson et al. |
| 7,063,643 B2 | 6/2006 | Arai |
| 7,156,665 B1 | 1/2007 | OConnor et al. |
| 7,156,780 B1 | 1/2007 | Fuchs et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,406,003 B2 | 7/2008 | Burkhardt et al. |
| 7,507,188 B2 | 3/2009 | Nurre |
| 7,594,879 B2 | 9/2009 | Johnson |
| 7,628,730 B1 | 12/2009 | Watterson et al. |
| 7,778,851 B2 | 8/2010 | Schoenberg et al. |
| 7,809,601 B2 | 10/2010 | Shaya et al. |
| 7,833,135 B2 | 11/2010 | Radow et al. |
| 7,837,472 B1 | 11/2010 | Elsmore et al. |
| 7,955,219 B2 | 6/2011 | Birrell et al. |
| 7,969,315 B1 | 6/2011 | Ross et al. |
| 7,988,599 B2 | 8/2011 | Ainsworth et al. |
| 8,012,107 B2 | 9/2011 | Einav et al. |
| 8,021,270 B2 | 9/2011 | D'Eredita |
| 8,038,578 B2 | 10/2011 | Olrik et al. |
| 8,079,937 B2 | 12/2011 | Bedell |
| 8,113,991 B2 | 2/2012 | Kutliroff |
| 8,177,732 B2 | 5/2012 | Einav et al. |

(56) References Cited

U.S. PATENT DOCUMENTS

| | | |
|---|---|---|
| 8,287,434 B2 | 10/2012 | Zavadsky et al. |
| 8,298,123 B2 | 10/2012 | Hickman |
| 8,371,990 B2 | 2/2013 | Shea |
| 8,419,593 B2 | 4/2013 | Ainsworth et al. |
| 8,465,398 B2 | 6/2013 | Lee et al. |
| 8,506,458 B2 | 8/2013 | Dugan |
| 8,540,515 B2 | 9/2013 | Williams et al. |
| 8,540,516 B2 | 9/2013 | Williams et al. |
| 8,556,778 B1 | 10/2013 | Dugan |
| 8,607,465 B1 | 12/2013 | Edwards |
| 8,613,689 B2 | 12/2013 | Dyer et al. |
| 8,672,812 B2 | 3/2014 | Dugan |
| 8,751,264 B2 | 6/2014 | Beraja et al. |
| 8,784,273 B2 | 7/2014 | Dugan |
| 8,818,496 B2 | 8/2014 | Dziubinski et al. |
| 8,823,448 B1 | 9/2014 | Shen |
| 8,845,493 B2 | 9/2014 | Watterson et al. |
| 8,849,681 B2 | 9/2014 | Hargrove et al. |
| 8,864,628 B2 | 10/2014 | Boyette et al. |
| 8,893,287 B2 | 11/2014 | Gjonej et al. |
| 8,905,925 B2 | 12/2014 | Beck et al. |
| 8,979,711 B2 | 3/2015 | Dugan |
| 9,044,630 B1 | 6/2015 | Lampert et al. |
| 9,167,281 B2 | 10/2015 | Petrov et al. |
| D744,050 S | 11/2015 | Colburn |
| 9,177,106 B2 | 11/2015 | Smith et al. |
| 9,248,071 B1 | 2/2016 | Brenda |
| 9,272,185 B2 | 3/2016 | Dugan |
| 9,283,434 B1 | 3/2016 | Wu |
| 9,311,789 B1 | 4/2016 | Gwin |
| 9,312,907 B2 | 4/2016 | Auchinleck et al. |
| 9,367,668 B2 | 6/2016 | Flynt et al. |
| 9,409,054 B2 | 8/2016 | Dugan |
| 9,420,956 B2 | 8/2016 | Gopalakrishnan et al. |
| 9,443,205 B2 | 9/2016 | Wall |
| 9,474,935 B2 | 10/2016 | Abbondanza et al. |
| 9,480,873 B2 | 11/2016 | Chuang |
| 9,481,428 B2 | 11/2016 | Gros |
| 9,514,277 B2 | 12/2016 | Hassing et al. |
| 9,566,472 B2 | 2/2017 | Dugan |
| 9,579,056 B2 | 2/2017 | Rosenbek et al. |
| 9,629,558 B2 | 4/2017 | Yuen et al. |
| 9,640,057 B1 | 5/2017 | Ross |
| 9,707,147 B2 | 7/2017 | Levital et al. |
| 9,713,744 B2 | 7/2017 | Suzuki |
| D794,142 S | 8/2017 | Zhou |
| 9,717,947 B2 | 8/2017 | Lin |
| 9,737,761 B1 | 8/2017 | Govindarajan |
| 9,782,621 B2 | 10/2017 | Chiang et al. |
| 9,802,076 B2 | 10/2017 | Murray et al. |
| 9,802,081 B2 | 10/2017 | Ridgel et al. |
| 9,813,239 B2 | 11/2017 | Chee et al. |
| 9,826,908 B2 | 11/2017 | Wu |
| 9,827,445 B2 | 11/2017 | Marcos et al. |
| 9,849,337 B2 | 12/2017 | Roman et al. |
| 9,868,028 B2 | 1/2018 | Shin |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 9,977,587 B2 | 5/2018 | Mountain |
| 9,993,181 B2 | 6/2018 | Ross |
| 10,004,946 B2 | 6/2018 | Ross |
| 10,055,550 B2 | 8/2018 | Goetz |
| 10,058,473 B2 | 8/2018 | Oshima et al. |
| 10,074,148 B2 | 9/2018 | Cashman et al. |
| 10,089,443 B2 | 10/2018 | Miller et al. |
| 10,111,643 B2 | 10/2018 | Shulhauser et al. |
| 10,130,311 B1 | 11/2018 | De Sapio et al. |
| 10,137,328 B2 | 11/2018 | Baudhuin |
| 10,143,395 B2 | 12/2018 | Chakravarthy et al. |
| 10,155,134 B2 | 12/2018 | Dugan |
| 10,159,872 B2 | 12/2018 | Sasaki et al. |
| 10,173,094 B2 | 1/2019 | Gomberg et al. |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,182,726 B2 | 1/2019 | Ahmed et al. |
| 10,198,928 B1 | 2/2019 | Ross et al. |
| 10,226,663 B2 | 3/2019 | Gomberg et al. |
| 10,231,664 B2 | 3/2019 | Ganesh |
| 10,244,990 B2 | 4/2019 | Hu et al. |
| 10,325,070 B2 | 6/2019 | Beale et al. |
| 10,327,697 B1 | 6/2019 | Stein et al. |
| 10,369,021 B2 | 8/2019 | Zoss et al. |
| 10,380,866 B1 | 8/2019 | Ross et al. |
| 10,424,033 B2 | 9/2019 | Romeo |
| 10,430,552 B2 | 10/2019 | Mihai |
| D866,957 S | 11/2019 | Ross et al. |
| 10,468,131 B2 | 11/2019 | Macoviak et al. |
| 10,475,323 B1 | 11/2019 | Ross |
| 10,475,537 B2 | 11/2019 | Purdie et al. |
| 10,492,977 B2 | 12/2019 | Kapure et al. |
| 10,507,358 B2 | 12/2019 | Kinnunen et al. |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,777,200 B2 | 9/2020 | Will et al. |
| D899,605 S | 10/2020 | Ross et al. |
| 10,792,495 B2 | 10/2020 | Izvorski et al. |
| 10,867,695 B2 | 12/2020 | Neagle |
| 10,874,905 B2 | 12/2020 | Belson et al. |
| D907,143 S | 1/2021 | Ach et al. |
| 10,881,911 B2 | 1/2021 | Kwon et al. |
| 10,918,332 B2 | 2/2021 | Belson et al. |
| 10,931,643 B1 | 2/2021 | Neumann |
| 10,987,176 B2 | 4/2021 | Poltaretskyi et al. |
| 10,991,463 B2 | 4/2021 | Kutzko et al. |
| 11,000,735 B2 | 5/2021 | Orady et al. |
| 11,045,709 B2 | 6/2021 | Putnam |
| 11,065,170 B2 | 7/2021 | Yang et al. |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Arn et al. |
| D939,096 S | 12/2021 | Lee |
| D939,644 S | 12/2021 | Ach et al. |
| D940,797 S | 1/2022 | Ach et al. |
| D940,891 S | 1/2022 | Lee |
| 11,229,727 B2 | 1/2022 | Tatonetti |
| 11,270,795 B2 | 3/2022 | Mason et al. |
| 11,272,879 B2 | 3/2022 | Wiedenhoefer et al. |
| 11,278,766 B2 | 3/2022 | Lee |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,348,683 B2 | 5/2022 | Guaneri et al. |
| 11,404,150 B2 | 8/2022 | Guaneri et al. |
| 11,410,768 B2 | 8/2022 | Mason et al. |
| 11,422,841 B2 | 8/2022 | Jeong |
| 11,495,355 B2 | 11/2022 | McNutt et al. |

(56) References Cited

U.S. PATENT DOCUMENTS

| | | |
|---|---|---|
| 11,508,258 B2 | 11/2022 | Nakashima et al. |
| 11,524,210 B2 | 12/2022 | Kim et al. |
| 11,527,326 B2 | 12/2022 | McNair et al. |
| 11,532,402 B2 | 12/2022 | Farley et al. |
| 11,534,654 B2 | 12/2022 | Silcock et al. |
| D976,339 S | 1/2023 | Li |
| 11,636,944 B2 | 4/2023 | Hanrahan et al. |
| 11,663,673 B2 | 5/2023 | Pyles |
| 11,701,548 B2 | 7/2023 | Posnack et al. |
| 2002/0072452 A1 | 6/2002 | Torkelson |
| 2002/0143279 A1 | 10/2002 | Porter et al. |
| 2002/0160883 A1 | 10/2002 | Dugan |
| 2002/0183599 A1 | 12/2002 | Castellanos |
| 2003/0013072 A1 | 1/2003 | Thomas |
| 2003/0036683 A1 | 2/2003 | Kehr et al. |
| 2003/0064863 A1 | 4/2003 | Chen |
| 2003/0083596 A1 | 5/2003 | Kramer et al. |
| 2003/0092536 A1 | 5/2003 | Romanelli et al. |
| 2003/0181832 A1 | 9/2003 | Carnahan et al. |
| 2004/0102931 A1 | 5/2004 | Ellis et al. |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2004/0204959 A1 | 10/2004 | Moreano et al. |
| 2005/0015118 A1 | 1/2005 | Davis et al. |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |
| 2005/0274220 A1 | 12/2005 | Reboullet |
| 2006/0003871 A1 | 1/2006 | Houghton et al. |
| 2006/0046905 A1 | 3/2006 | Doody, Jr. et al. |
| 2006/0064329 A1 | 3/2006 | Abolfathi et al. |
| 2006/0199700 A1 | 9/2006 | LaStayo et al. |
| 2006/0247095 A1 | 11/2006 | Rummerfield |
| 2007/0042868 A1 | 2/2007 | Fisher et al. |
| 2007/0118389 A1 | 5/2007 | Shipon |
| 2007/0137307 A1 | 6/2007 | Gruben et al. |
| 2007/0173392 A1 | 7/2007 | Stanford |
| 2007/0194939 A1 | 8/2007 | Alvarez et al. |
| 2007/0287597 A1 | 12/2007 | Cameron |
| 2008/0021834 A1 | 1/2008 | Holla et al. |
| 2008/0082356 A1 | 4/2008 | Friedlander et al. |
| 2008/0096726 A1 | 4/2008 | Riley et al. |
| 2008/0153592 A1 | 6/2008 | James-Herbert |
| 2008/0161166 A1 | 7/2008 | Lo |
| 2008/0161733 A1 | 7/2008 | Einav et al. |
| 2008/0281633 A1 | 11/2008 | Burdea et al. |
| 2008/0300914 A1 | 12/2008 | Karkanias et al. |
| 2009/0011907 A1 | 1/2009 | Radow et al. |
| 2009/0058635 A1 | 3/2009 | LaLonde et al. |
| 2009/0070138 A1 | 3/2009 | Langheier et al. |
| 2009/0211395 A1 | 8/2009 | Mule |
| 2009/0270227 A1 | 10/2009 | Ashby et al. |
| 2009/0287503 A1 | 11/2009 | Angell et al. |
| 2009/0299766 A1 | 12/2009 | Friedlander et al. |
| 2010/0048358 A1 | 2/2010 | Tchao et al. |
| 2010/0076786 A1 | 3/2010 | Dalton et al. |
| 2010/0121160 A1 | 5/2010 | Stark et al. |
| 2010/0173747 A1 | 7/2010 | Chen et al. |
| 2010/0216168 A1 | 8/2010 | Heinzman et al. |
| 2010/0248899 A1 | 9/2010 | Bedell et al. |
| 2010/0248905 A1 | 9/2010 | Lu |
| 2010/0268304 A1 | 10/2010 | Matos |
| 2010/0298102 A1 | 11/2010 | Bosecker et al. |
| 2011/0010188 A1 | 1/2011 | Yoshikawa et al. |
| 2011/0047108 A1 | 2/2011 | Chakrabarty et al. |
| 2011/0119212 A1 | 5/2011 | De Bruin et al. |
| 2011/0172059 A1 | 7/2011 | Watterson et al. |
| 2011/0195819 A1 | 8/2011 | Shaw et al. |
| 2011/0218814 A1 | 9/2011 | Coats |
| 2011/0275483 A1 | 11/2011 | Dugan |
| 2011/0306846 A1 | 12/2011 | Osorio |
| 2012/0041771 A1 | 2/2012 | Cosentino et al. |
| 2012/0065987 A1 | 3/2012 | Farooq et al. |
| 2012/0116258 A1 | 5/2012 | Lee |
| 2012/0167709 A1 | 7/2012 | Chen et al. |
| 2012/0183939 A1 | 7/2012 | Aragones et al. |
| 2012/0190502 A1 | 7/2012 | Paulus et al. |
| 2012/0232438 A1 | 9/2012 | Cataldi et al. |
| 2012/0259648 A1 | 10/2012 | Mallon et al. |
| 2012/0295240 A1 | 11/2012 | Walker et al. |
| 2012/0296455 A1 | 11/2012 | Ohnemus et al. |
| 2012/0310667 A1 | 12/2012 | Altman et al. |
| 2013/0123071 A1 | 5/2013 | Rhea |
| 2013/0123667 A1 | 5/2013 | Komatireddy et al. |
| 2013/0137550 A1 | 5/2013 | Skinner et al. |
| 2013/0178334 A1 | 7/2013 | Brammer |
| 2013/0211281 A1 | 8/2013 | Ross et al. |
| 2013/0253943 A1 | 9/2013 | Lee et al. |
| 2013/0274069 A1 | 10/2013 | Watterson et al. |
| 2013/0296987 A1 | 11/2013 | Rogers et al. |
| 2013/0318027 A1 | 11/2013 | Almogy et al. |
| 2013/0332616 A1 | 12/2013 | Landwehr |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0073486 A1 | 3/2014 | Ahmed et al. |
| 2014/0089836 A1 | 3/2014 | Damani et al. |
| 2014/0113768 A1 | 4/2014 | Lin et al. |
| 2014/0155129 A1 | 6/2014 | Dugan |
| 2014/0172442 A1 | 6/2014 | Broderick |
| 2014/0172460 A1 | 6/2014 | Kohli |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0207264 A1 | 7/2014 | Quy |
| 2014/0207486 A1 | 7/2014 | Carty et al. |
| 2014/0228649 A1 | 8/2014 | Rayner et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0309083 A1 | 10/2014 | Dugan |
| 2014/0322686 A1 | 10/2014 | Kang |
| 2015/0025816 A1 | 1/2015 | Ross |
| 2015/0045700 A1 | 2/2015 | Cavanagh et al. |
| 2015/0088544 A1 | 3/2015 | Goldberg |
| 2015/0094192 A1 | 4/2015 | Skwortsow et al. |
| 2015/0099458 A1 | 4/2015 | Weisner et al. |
| 2015/0099952 A1 | 4/2015 | Lain et al. |
| 2015/0112230 A1 | 4/2015 | Iglesias |
| 2015/0130830 A1 | 5/2015 | Nagasaki |
| 2015/0141200 A1 | 5/2015 | Murray et al. |
| 2015/0149217 A1 | 5/2015 | Kaburagi |
| 2015/0151162 A1 | 6/2015 | Dugan |
| 2015/0161331 A1 | 6/2015 | Oleynik |
| 2015/0257679 A1 | 9/2015 | Ross |
| 2015/0265209 A1 | 9/2015 | Zhang |
| 2015/0290061 A1 | 10/2015 | Stafford et al. |
| 2015/0339442 A1 | 11/2015 | Oleynik |
| 2015/0341812 A1 | 11/2015 | Dion et al. |
| 2015/0351664 A1 | 12/2015 | Ross |
| 2015/0351665 A1 | 12/2015 | Ross |
| 2015/0360069 A1 | 12/2015 | Marti et al. |
| 2015/0379232 A1 | 12/2015 | Mainwaring et al. |
| 2015/0379430 A1 | 12/2015 | Dirac et al. |
| 2016/0007885 A1 | 1/2016 | Basta |
| 2016/0023081 A1 | 1/2016 | Popa-Simil et al. |
| 2016/0045170 A1 | 2/2016 | Migita |
| 2016/0096073 A1 | 4/2016 | Rahman et al. |
| 2016/0117471 A1 | 4/2016 | Belt et al. |
| 2016/0143593 A1 | 5/2016 | Fu et al. |
| 2016/0151670 A1 | 6/2016 | Dugan |
| 2016/0166833 A1 | 6/2016 | Bum |
| 2016/0166881 A1 | 6/2016 | Ridgel et al. |
| 2016/0193306 A1 | 7/2016 | Rabovsky et al. |
| 2016/0275259 A1 | 9/2016 | Nolan et al. |
| 2016/0287166 A1 | 10/2016 | Tran |
| 2016/0302721 A1 | 10/2016 | Wiedenhoefer et al. |
| 2016/0317869 A1 | 11/2016 | Dugan |

(56) References Cited

U.S. PATENT DOCUMENTS

| | | |
|---|---|---|
| 2016/0322078 A1 | 11/2016 | Bose et al. |
| 2016/0325140 A1 | 11/2016 | Wu |
| 2016/0332028 A1 | 11/2016 | Melnik |
| 2016/0361597 A1 | 12/2016 | Cole et al. |
| 2017/0004260 A1 | 1/2017 | Moturu et al. |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0095670 A1 | 4/2017 | Ghaffari et al. |
| 2017/0095692 A1 | 4/2017 | Chang et al. |
| 2017/0095693 A1 | 4/2017 | Chang et al. |
| 2017/0100637 A1 | 4/2017 | Princen et al. |
| 2017/0106242 A1 | 4/2017 | Dugan |
| 2017/0113092 A1 | 4/2017 | Johnson |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147752 A1 | 5/2017 | Toru |
| 2017/0147789 A1 | 5/2017 | Wiedenhoefer et al. |
| 2017/0148297 A1 | 5/2017 | Ross |
| 2017/0168555 A1 | 6/2017 | Munoz et al. |
| 2017/0181698 A1 | 6/2017 | Wiedenhoefer et al. |
| 2017/0190052 A1 | 7/2017 | Jaekel et al. |
| 2017/0209766 A1 | 7/2017 | Riley et al. |
| 2017/0235882 A1 | 8/2017 | Orlov et al. |
| 2017/0235906 A1 | 8/2017 | Dorris et al. |
| 2017/0243028 A1 | 8/2017 | LaFever et al. |
| 2017/0262604 A1 | 9/2017 | Francois |
| 2017/0265800 A1 | 9/2017 | Auchinleck et al. |
| 2017/0266501 A1 | 9/2017 | Sanders et al. |
| 2017/0278209 A1 | 9/2017 | Olsen et al. |
| 2017/0282015 A1 | 10/2017 | Wicks et al. |
| 2017/0283508 A1 | 10/2017 | Demopulos et al. |
| 2017/0300654 A1 | 10/2017 | Stein et al. |
| 2017/0312614 A1 | 11/2017 | Tran et al. |
| 2017/0323481 A1* | 11/2017 | Tran .................. H04N 23/611 |
| 2017/0329917 A1 | 11/2017 | McRaith et al. |
| 2017/0329933 A1 | 11/2017 | Brust |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 11/2017 | Duffy et al. |
| 2017/0347923 A1 | 12/2017 | Roh |
| 2017/0360586 A1 | 12/2017 | Dempers et al. |
| 2017/0368413 A1 | 12/2017 | Shavit |
| 2018/0017806 A1 | 1/2018 | Wang et al. |
| 2018/0036593 A1 | 2/2018 | Ridgel et al. |
| 2018/0052962 A1 | 2/2018 | Van Der Koijk et al. |
| 2018/0056104 A1 | 3/2018 | Cromie et al. |
| 2018/0060494 A1 | 3/2018 | Dias et al. |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0096111 A1 | 4/2018 | Wells et al. |
| 2018/0102190 A1 | 4/2018 | Hogue et al. |
| 2018/0116741 A1 | 5/2018 | Garcia Kilroy et al. |
| 2018/0140927 A1 | 5/2018 | Kito |
| 2018/0177612 A1 | 6/2018 | Trabish et al. |
| 2018/0178061 A1 | 6/2018 | O'larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0240552 A1 | 8/2018 | Tuyl et al. |
| 2018/0253991 A1 | 9/2018 | Tang et al. |
| 2018/0256079 A1 | 9/2018 | Yang et al. |
| 2018/0263530 A1 | 9/2018 | Jung |
| 2018/0263535 A1 | 9/2018 | Cramer |
| 2018/0263552 A1 | 9/2018 | Graman et al. |
| 2018/0264312 A1 | 9/2018 | Pompile et al. |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0290017 A1 | 10/2018 | Fung |
| 2018/0296143 A1 | 10/2018 | Anderson et al. |
| 2018/0296157 A1 | 10/2018 | Bleich et al. |
| 2018/0326243 A1 | 11/2018 | Badi et al. |
| 2018/0330058 A1 | 11/2018 | Bates |
| 2018/0330810 A1 | 11/2018 | Gamarnik |
| 2018/0330824 A1 | 11/2018 | Athey et al. |
| 2018/0353812 A1 | 12/2018 | Lannon et al. |
| 2018/0360340 A1 | 12/2018 | Rehse et al. |
| 2018/0373844 A1 | 12/2018 | Ferrandez-Escamez et al. |
| 2019/0009135 A1 | 1/2019 | Wu |
| 2019/0019163 A1 | 1/2019 | Batey et al. |
| 2019/0019573 A1 | 1/2019 | Lake et al. |
| 2019/0019578 A1 | 1/2019 | Vaccaro |
| 2019/0030415 A1 | 1/2019 | Volpe, Jr. |
| 2019/0031284 A1 | 1/2019 | Fuchs |
| 2019/0046794 A1 | 2/2019 | Goodall et al. |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0080802 A1 | 3/2019 | Ziobro et al. |
| 2019/0088356 A1 | 3/2019 | Oliver et al. |
| 2019/0090744 A1 | 3/2019 | Mahfouz |
| 2019/0111299 A1 | 4/2019 | Radcliffe et al. |
| 2019/0115097 A1 | 4/2019 | Macoviak et al. |
| 2019/0118038 A1 | 4/2019 | Tana et al. |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0200920 A1 | 7/2019 | Tien et al. |
| 2019/0209891 A1 | 7/2019 | Fung |
| 2019/0223797 A1 | 7/2019 | Tran |
| 2019/0228856 A1 | 7/2019 | Leifer |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0304584 A1 | 10/2019 | Savolainen |
| 2019/0307983 A1 | 10/2019 | Goldman |
| 2019/0314681 A1 | 10/2019 | Yang |
| 2019/0344123 A1 | 11/2019 | Rubin et al. |
| 2019/0354632 A1 | 11/2019 | Mital et al. |
| 2019/0362242 A1 | 11/2019 | Pillai et al. |
| 2019/0366146 A1 | 12/2019 | Tong et al. |
| 2019/0388728 A1 | 12/2019 | Wang et al. |
| 2020/0005928 A1 | 1/2020 | Daniel |
| 2020/0038703 A1 | 2/2020 | Cleary et al. |
| 2020/0051446 A1 | 2/2020 | Rubinstein et al. |
| 2020/0066390 A1 | 2/2020 | Svendrys et al. |
| 2020/0085300 A1 | 3/2020 | Kwatra et al. |
| 2020/0093418 A1 | 3/2020 | Kluger et al. |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0221975 A1 | 7/2020 | Basta et al. |
| 2020/0237291 A1 | 7/2020 | Raja |
| 2020/0267487 A1 | 8/2020 | Siva |
| 2020/0275886 A1 | 9/2020 | Mason |
| 2020/0289045 A1 | 9/2020 | Hacking et al. |

(56) References Cited

U.S. PATENT DOCUMENTS

| | | |
|---|---|---|
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0303063 A1 | 9/2020 | Sharma et al. |
| 2020/0334972 A1 | 10/2020 | Gopalakrishnan |
| 2020/0357299 A1 | 11/2020 | Patel et al. |
| 2020/0365256 A1 | 11/2020 | Hayashitani et al. |
| 2020/0395112 A1 | 12/2020 | Ronner |
| 2020/0401224 A1 | 12/2020 | Cotton |
| 2020/0411162 A1 | 12/2020 | Lien et al. |
| 2021/0005224 A1 | 1/2021 | Rothschild et al. |
| 2021/0005319 A1 | 1/2021 | Otsuki et al. |
| 2021/0035674 A1 | 2/2021 | Volosin et al. |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134428 A1 | 5/2021 | Mason et al. |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0202090 A1 | 7/2021 | ODonovan et al. |
| 2021/0202103 A1 | 7/2021 | Bostic et al. |
| 2021/0244998 A1 | 8/2021 | Hacking et al. |
| 2021/0245003 A1 | 8/2021 | Turner |
| 2021/0251562 A1 | 8/2021 | Jain |
| 2021/0272677 A1 | 9/2021 | Barbee |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0361514 A1 | 11/2021 | Choi et al. |
| 2021/0366587 A1 | 11/2021 | Mason et al. |
| 2021/0383909 A1 | 12/2021 | Mason et al. |
| 2021/0391091 A1 | 12/2021 | Mason |
| 2021/0398668 A1 | 12/2021 | Chock et al. |
| 2021/0407670 A1 | 12/2021 | Mason et al. |
| 2021/0407681 A1 | 12/2021 | Mason et al. |
| 2022/0000556 A1 | 1/2022 | Casey et al. |
| 2022/0015838 A1 | 1/2022 | Posnack et al. |
| 2022/0016480 A1 | 1/2022 | Bissonnette et al. |
| 2022/0016485 A1 | 1/2022 | Bissonnette et al. |
| 2022/0020469 A1 | 1/2022 | Tanner |
| 2022/0044806 A1 | 2/2022 | Sanders et al. |
| 2022/0047921 A1 | 2/2022 | Bissonnette et al. |
| 2022/0079690 A1 | 3/2022 | Mason et al. |
| 2022/0080256 A1 | 3/2022 | Arn et al. |
| 2022/0105384 A1 | 4/2022 | Hacking et al. |
| 2022/0105385 A1 | 4/2022 | Hacking et al. |
| 2022/0105390 A1 | 4/2022 | Yuasa |
| 2022/0115133 A1 | 4/2022 | Mason et al. |
| 2022/0118218 A1 | 4/2022 | Bense et al. |
| 2022/0126169 A1 | 4/2022 | Mason |
| 2022/0133576 A1 | 5/2022 | Choi et al. |
| 2022/0148725 A1 | 5/2022 | Mason et al. |
| 2022/0158916 A1 | 5/2022 | Mason et al. |
| 2022/0176039 A1 | 6/2022 | Lintereur et al. |
| 2022/0181004 A1 | 6/2022 | Zilca et al. |
| 2022/0193491 A1 | 6/2022 | Mason et al. |
| 2022/0230729 A1 | 7/2022 | Mason et al. |
| 2022/0238222 A1 | 7/2022 | Neuberg |
| 2022/0238223 A1 | 7/2022 | Mason et al. |
| 2022/0262483 A1 | 8/2022 | Rosenberg et al. |
| 2022/0262504 A1 | 8/2022 | Bratty et al. |
| 2022/0266094 A1 | 8/2022 | Mason et al. |
| 2022/0270738 A1 | 8/2022 | Mason et al. |
| 2022/0273985 A1 | 9/2022 | Jeong et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0300787 A1 | 9/2022 | Wall et al. |
| 2022/0304881 A1 | 9/2022 | Choi et al. |
| 2022/0304882 A1 | 9/2022 | Choi |
| 2022/0305328 A1 | 9/2022 | Choi et al. |
| 2022/0314075 A1 | 10/2022 | Mason et al. |
| 2022/0323826 A1 | 10/2022 | Khurana |
| 2022/0327714 A1 | 10/2022 | Cook et al. |
| 2022/0327807 A1 | 10/2022 | Cook et al. |
| 2022/0328181 A1 | 10/2022 | Mason et al. |
| 2022/0330823 A1 | 10/2022 | Janssen |
| 2022/0331663 A1 | 10/2022 | Mason |
| 2022/0338761 A1 | 10/2022 | Maddahi et al. |
| 2022/0339052 A1 | 10/2022 | Kim |
| 2022/0339501 A1 | 10/2022 | Mason et al. |
| 2022/0384012 A1 | 12/2022 | Mason |
| 2022/0392591 A1 | 12/2022 | Guaneri et al. |
| 2022/0395232 A1 | 12/2022 | Locke |
| 2022/0401783 A1 | 12/2022 | Choi |
| 2022/0415469 A1 | 12/2022 | Mason |
| 2022/0415471 A1 | 12/2022 | Mason |
| 2023/0001268 A1 | 1/2023 | Bissonnette et al. |
| 2023/0013530 A1 | 1/2023 | Mason |
| 2023/0014598 A1 | 1/2023 | Mason et al. |
| 2023/0029639 A1 | 2/2023 | Roy |
| 2023/0048040 A1 | 2/2023 | Hacking et al. |
| 2023/0051751 A1 | 2/2023 | Hacking et al. |
| 2023/0058605 A1 | 2/2023 | Mason |
| 2023/0060039 A1 | 2/2023 | Mason |
| 2023/0072368 A1 | 3/2023 | Mason |
| 2023/0078793 A1 | 3/2023 | Mason |
| 2023/0119461 A1 | 4/2023 | Mason |
| 2023/0190100 A1 | 6/2023 | Stump |
| 2023/0201656 A1 | 6/2023 | Hacking et al. |
| 2023/0207097 A1 | 6/2023 | Mason |
| 2023/0207124 A1 | 6/2023 | Walsh et al. |
| 2023/0215539 A1 | 7/2023 | Rosenberg et al. |
| 2023/0215552 A1 | 7/2023 | Khotilovich et al. |
| 2023/0245747 A1 | 8/2023 | Rosenberg et al. |
| 2023/0245748 A1 | 8/2023 | Rosenberg et al. |
| 2023/0245750 A1 | 8/2023 | Rosenberg et al. |
| 2023/0245751 A1 | 8/2023 | Rosenberg et al. |
| 2023/0253089 A1 | 8/2023 | Rosenberg et al. |
| 2023/0255555 A1 | 8/2023 | Sundaram et al. |
| 2023/0263428 A1 | 8/2023 | Hull et al. |
| 2023/0274813 A1 | 8/2023 | Rosenberg et al. |
| 2023/0282329 A1 | 9/2023 | Mason et al. |
| 2023/0364472 A1 | 11/2023 | Posnack |
| 2023/0368886 A1 | 11/2023 | Rosenberg |
| 2023/0377711 A1 | 11/2023 | Rosenberg |
| 2023/0377712 A1 | 11/2023 | Rosenberg |
| 2023/0386639 A1 | 11/2023 | Rosenberg |

(56) References Cited

U.S. PATENT DOCUMENTS

| | | |
|---|---|---|
| 2023/0395231 A1 | 12/2023 | Rosenberg |
| 2023/0395232 A1 | 12/2023 | Rosenberg |

FOREIGN PATENT DOCUMENTS

| | | |
|---|---|---|
| CN | 101964151 A | 2/2011 |
| CN | 201889024 U | 7/2011 |
| CN | 202220794 U | 5/2012 |
| CN | 102670381 A | 9/2012 |
| CN | 103263336 A | 8/2013 |
| CN | 103390357 A | 11/2013 |
| CN | 103473631 A | 12/2013 |
| CN | 103488880 A | 1/2014 |
| CN | 103501328 A | 1/2014 |
| CN | 103721343 A | 4/2014 |
| CN | 203677851 U | 7/2014 |
| CN | 104335211 A | 2/2015 |
| CN | 105620643 A | 6/2016 |
| CN | 105683977 A | 6/2016 |
| CN | 103136447 B | 8/2016 |
| CN | 105894088 A | 8/2016 |
| CN | 105930668 A | 9/2016 |
| CN | 205626871 U | 10/2016 |
| CN | 106127646 A | 11/2016 |
| CN | 106236502 A | 12/2016 |
| CN | 106510985 A | 3/2017 |
| CN | 106621195 A | 5/2017 |
| CN | 107025373 A | 8/2017 |
| CN | 107066819 A | 8/2017 |
| CN | 107430641 A | 12/2017 |
| CN | 107551475 A | 1/2018 |
| CN | 107736982 A | 2/2018 |
| CN | 107930021 A | 4/2018 |
| CN | 108078737 A | 5/2018 |
| CN | 207429102 U | 6/2018 |
| CN | 208224811 A | 12/2018 |
| CN | 109191954 A | 1/2019 |
| CN | 109248432 A | 1/2019 |
| CN | 109308940 A | 2/2019 |
| CN | 109363887 A | 2/2019 |
| CN | 109431742 A | 3/2019 |
| CN | 208573971 U | 3/2019 |
| CN | 110148472 A | 8/2019 |
| CN | 110201358 A | 9/2019 |
| CN | 110215188 A | 9/2019 |
| CN | 110322957 A | 10/2019 |
| CN | 110613585 A | 12/2019 |
| CN | 110721438 A | 1/2020 |
| CN | 110808092 A | 2/2020 |
| CN | 110931103 A | 3/2020 |
| CN | 110993057 A | 4/2020 |
| CN | 210384372 U | 4/2020 |
| CN | 111084618 A | 5/2020 |
| CN | 111105859 A | 5/2020 |
| CN | 111111110 A | 5/2020 |
| CN | 111199787 A | 5/2020 |
| CN | 210447971 U | 5/2020 |
| CN | 111329674 A | 6/2020 |
| CN | 111370088 A | 7/2020 |
| CN | 111460305 A | 7/2020 |
| CN | 111544834 A | 8/2020 |
| CN | 111714832 A | 9/2020 |
| CN | 111790111 A | 10/2020 |
| CN | 211635070 U | 10/2020 |
| CN | 211798556 U | 10/2020 |
| CN | 111973956 A | 11/2020 |
| CN | 212067582 U | 12/2020 |
| CN | 212141371 U | 12/2020 |
| CN | 112190440 A | 1/2021 |
| CN | 112289425 A | 1/2021 |
| CN | 212522890 U | 2/2021 |
| CN | 212624809 U | 2/2021 |
| CN | 212730865 U | 3/2021 |
| CN | 112603295 A | 4/2021 |
| CN | 213049207 U | 4/2021 |
| CN | 213077324 U | 4/2021 |
| CN | 213190965 U | 5/2021 |
| CN | 213220742 U | 5/2021 |
| CN | 213823322 U | 7/2021 |
| CN | 213851851 U | 8/2021 |
| CN | 213994716 U | 8/2021 |
| CN | 113384850 A | 9/2021 |
| CN | 113421642 A | 9/2021 |
| CN | 214232565 U | 9/2021 |
| CN | 113499572 A | 10/2021 |
| CN | 113521655 A | 10/2021 |
| CN | 214388673 U | 10/2021 |
| CN | 214763119 U | 11/2021 |
| CN | 214806540 U | 11/2021 |
| CN | 214913108 U | 11/2021 |
| CN | 215025723 U | 12/2021 |
| CN | 215084603 U | 12/2021 |
| CN | 215136488 U | 12/2021 |
| CN | 113885361 A | 1/2022 |
| CN | 114049961 A | 2/2022 |
| CN | 114203274 A | 3/2022 |
| CN | 216258145 U | 4/2022 |
| CN | 216366476 U | 4/2022 |
| CN | 216497237 U | 5/2022 |
| CN | 114632302 A | 6/2022 |
| CN | 114694824 A | 7/2022 |
| CN | 114898832 A | 8/2022 |
| CN | 217246501 U | 8/2022 |
| CN | 114983760 A | 9/2022 |
| CN | 114983761 A | 9/2022 |
| CN | 115006789 A | 9/2022 |
| CN | 115089917 A | 9/2022 |
| CN | 217472652 U | 9/2022 |
| CN | 110270062 B | 10/2022 |
| CN | 217612764 U | 10/2022 |
| CN | 115337599 A | 11/2022 |
| CN | 115382062 A | 11/2022 |
| CN | 115487042 A | 12/2022 |
| CN | 218187703 U | 1/2023 |
| CN | 218187717 U | 1/2023 |
| CN | 218420859 U | 2/2023 |
| CN | 115954081 A | 4/2023 |
| DE | 95019 C | 1/1897 |
| DE | 7628633 U1 | 12/1977 |
| DE | 8519150 U1 | 10/1985 |
| DE | 3732905 A1 | 7/1988 |
| DE | 19619820 A1 | 12/1996 |
| DE | 29620008 U1 | 2/1997 |
| DE | 19947926 A1 | 4/2001 |
| DE | 102007025664 A1 | 12/2008 |
| DE | 102018202497 A1 | 8/2018 |
| DE | 102018211212 A1 | 1/2019 |
| DE | 102019108425 B3 | 8/2020 |
| EP | 199600 A2 | 10/1986 |
| EP | 0383137 A2 | 8/1990 |
| EP | 634319 A2 | 1/1995 |
| EP | 1034817 A1 | 9/2000 |
| EP | 1159989 A1 | 12/2001 |
| EP | 1391179 A1 | 2/2004 |
| EP | 1968028 | 9/2008 |
| EP | 2564904 A1 | 3/2013 |
| EP | 1909730 B1 | 4/2014 |
| EP | 2815242 A4 | 12/2014 |
| EP | 2869805 A | 5/2015 |
| EP | 2997951 A1 | 3/2016 |
| EP | 2688472 B1 | 4/2016 |
| EP | 3264303 A1 | 1/2018 |
| EP | 3323473 A1 | 5/2018 |
| EP | 3627514 A1 | 3/2020 |
| EP | 3671700 A1 | 6/2020 |
| EP | 3688537 A1 | 8/2020 |
| EP | 3731733 A1 | 11/2020 |
| EP | 3984508 A1 | 4/2022 |
| EP | 3984509 A1 | 4/2022 |
| EP | 3984510 A1 | 4/2022 |
| EP | 3984511 A1 | 4/2022 |
| EP | 3984512 A1 | 4/2022 |
| EP | 3984513 A1 | 4/2022 |
| EP | 4054699 A1 | 9/2022 |

(56) References Cited

FOREIGN PATENT DOCUMENTS

| | | |
|---|---|---|
| EP | 4112033 A1 | 1/2023 |
| FR | 2527541 A2 | 12/1983 |
| FR | 3127393 A1 | 3/2023 |
| GB | 141664 A | 11/1920 |
| GB | 2336140 A | 10/1999 |
| GB | 2372459 A | 8/2002 |
| GB | 2512431 A | 10/2014 |
| GB | 2591542 B | 3/2022 |
| IN | 23/2009 | 5/2009 |
| IN | 201811043670 A | 7/2018 |
| JP | 2000005339 A | 1/2000 |
| JP | 2003225875 A | 8/2003 |
| JP | 2005227928 A | 8/2005 |
| JP | 2005227928 A1 | 8/2005 |
| JP | 2009112336 A | 5/2009 |
| JP | 2013515995 A | 5/2013 |
| JP | 3193662 U | 10/2014 |
| JP | 3198173 U | 6/2015 |
| JP | 5804063 B2 | 11/2015 |
| JP | 6454071 B2 | 1/2019 |
| JP | 2019028647 A | 2/2019 |
| JP | 2019134909 A | 8/2019 |
| JP | 6573739 B1 | 9/2019 |
| JP | 6659831 B2 | 3/2020 |
| JP | 6710357 B1 | 6/2020 |
| JP | 6775757 B1 | 10/2020 |
| JP | 2021027917 A | 2/2021 |
| JP | 2021040882 A | 3/2021 |
| JP | 6871379 B2 | 5/2021 |
| JP | 2022521378 A | 4/2022 |
| JP | 3238491 U | 7/2022 |
| JP | 7198364 B2 | 12/2022 |
| JP | 7202474 B2 | 1/2023 |
| JP | 7231750 B2 | 3/2023 |
| JP | 7231751 B2 | 3/2023 |
| JP | 7231752 B2 | 3/2023 |
| KR | 20020009724 A | 2/2002 |
| KR | 200276919 Y1 | 5/2002 |
| KR | 20020065253 A | 8/2002 |
| KR | 20040082259 A | 9/2004 |
| KR | 100582596 B1 | 5/2006 |
| KR | 101042258 B1 | 6/2011 |
| KR | 101258250 B1 | 4/2013 |
| KR | 101325581 B1 | 11/2013 |
| KR | 20140128630 A | 11/2014 |
| KR | 20150017693 A | 2/2015 |
| KR | 20150078191 A | 7/2015 |
| KR | 101580071 B1 | 12/2015 |
| KR | 101647620 B1 | 8/2016 |
| KR | 20160093990 A | 8/2016 |
| KR | 20170038837 A | 4/2017 |
| KR | 20170086922 A | 7/2017 |
| KR | 20180004928 A | 1/2018 |
| KR | 20190016727 A | 2/2019 |
| KR | 20190029175 A | 3/2019 |
| KR | 20190056116 A | 5/2019 |
| KR | 101988167 B1 | 6/2019 |
| KR | 101969392 B1 | 8/2019 |
| KR | 102038055 B1 | 10/2019 |
| KR | 102043239 B1 | 11/2019 |
| KR | 102055279 B1 | 12/2019 |
| KR | 102088333 B1 | 3/2020 |
| KR | 20200025290 A | 3/2020 |
| KR | 20200029180 A | 3/2020 |
| KR | 102116664 B1 | 5/2020 |
| KR | 102116968 B1 | 5/2020 |
| KR | 20200056233 A | 5/2020 |
| KR | 102120828 B1 | 6/2020 |
| KR | 102121586 B1 | 6/2020 |
| KR | 102142713 B1 | 8/2020 |
| KR | 102162522 B1 | 10/2020 |
| KR | 20200119665 A | 10/2020 |
| KR | 102173553 B1 | 11/2020 |
| KR | 102180079 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102224618 B1 | 3/2021 |
| KR | 102246049 B1 | 4/2021 |
| KR | 102246050 B1 | 4/2021 |
| KR | 102246051 B1 | 4/2021 |
| KR | 102246052 B1 | 4/2021 |
| KR | 20210052028 A | 5/2021 |
| KR | 102264498 B1 | 6/2021 |
| KR | 102352602 B1 | 1/2022 |
| KR | 102352603 B1 | 1/2022 |
| KR | 102352604 B1 | 1/2022 |
| KR | 20220004639 A | 1/2022 |
| KR | 102387577 B1 | 4/2022 |
| KR | 102421437 B1 | 7/2022 |
| KR | 20220102207 A | 7/2022 |
| KR | 102427545 B1 | 8/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20220145989 A | 11/2022 |
| KR | 20220156134 A | 11/2022 |
| KR | 102502744 B1 | 2/2023 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 | 3/2023 |
| KR | 20230050506 A | 4/2023 |
| KR | 20230056118 A | 4/2023 |
| KR | 102528503 B1 | 5/2023 |
| KR | 102531930 B1 | 5/2023 |
| KR | 102532766 B1 | 5/2023 |
| KR | 102539190 B1 | 6/2023 |
| PL | P.401020 | 4/2014 |
| RU | 2154460 C2 | 8/2000 |
| RU | 2014131288 A | 2/2016 |
| RU | 2738571 C1 | 12/2020 |
| TW | M474545 U | 3/2014 |
| TW | I442956 B | 7/2014 |
| TW | M638437 U | 3/2023 |
| WO | 1998009687 A1 | 3/1998 |
| WO | 9912468 | 3/1999 |
| WO | 0149235 A2 | 7/2001 |
| WO | 0151083 A2 | 7/2001 |
| WO | 2001050387 A1 | 7/2001 |
| WO | 2001056465 A1 | 8/2001 |
| WO | 02062211 A2 | 8/2002 |
| WO | 02093312 A2 | 11/2002 |
| WO | 2003043494 A1 | 5/2003 |
| WO | 2005018453 A1 | 3/2005 |
| WO | 2006004430 A2 | 1/2006 |
| WO | 2006012694 A1 | 2/2006 |
| WO | 2007102709 A1 | 9/2007 |
| WO | 2008114291 A1 | 9/2008 |
| WO | 2009008968 A1 | 1/2009 |
| WO | 2011025322 A2 | 3/2011 |
| WO | 2012128801 A1 | 9/2012 |
| WO | 2013002568 A2 | 1/2013 |
| WO | 2023164292 A1 | 3/2013 |
| WO | 2013122839 A1 | 8/2013 |
| WO | 2014011447 A1 | 1/2014 |
| WO | 2014039567 A1 | 3/2014 |
| WO | 2014163976 A1 | 10/2014 |
| WO | 2015026744 A1 | 2/2015 |
| WO | 2015065298 A1 | 5/2015 |
| WO | 2015082555 A1 | 6/2015 |
| WO | 2016154318 A1 | 9/2016 |
| WO | 2017030781 A1 | 2/2017 |
| WO | 2017166074 A1 | 5/2017 |
| WO | 2017091691 A1 | 6/2017 |
| WO | 2017165238 A1 | 9/2017 |
| WO | 2018081795 A1 | 5/2018 |
| WO | 2018171853 A1 | 9/2018 |
| WO | 2019022706 A1 | 1/2019 |
| WO | 2019143940 A1 | 7/2019 |
| WO | 2020075190 A1 | 4/2020 |

(56) References Cited

FOREIGN PATENT DOCUMENTS

| | | | |
|---|---|---|---|
| WO | 2020130979 | A1 | 6/2020 |
| WO | 2020149815 | A2 | 7/2020 |
| WO | 2020158904 | A1 | 8/2020 |
| WO | 2020229705 | A1 | 11/2020 |
| WO | 2020245727 | A1 | 12/2020 |
| WO | 2020249855 | A1 | 12/2020 |
| WO | 2020252599 | A1 | 12/2020 |
| WO | 2020256577 | A1 | 12/2020 |
| WO | 2021021447 | A1 | 2/2021 |
| WO | 2021022003 | A1 | 2/2021 |
| WO | 2021038980 | A1 | 3/2021 |
| WO | 2021055427 | A1 | 3/2021 |
| WO | 2021061061 | A1 | 4/2021 |
| WO | 2021090267 | A1 | 5/2021 |
| WO | 2021138620 | A1 | 7/2021 |
| WO | 2022047006 | A1 | 3/2022 |
| WO | 2022092493 | A1 | 5/2022 |
| WO | 2022092494 | A1 | 5/2022 |
| WO | 2022212883 | A1 | 10/2022 |
| WO | 2022212921 | A1 | 10/2022 |
| WO | 2022216498 | A1 | 10/2022 |
| WO | 2022251420 | A1 | 12/2022 |
| WO | 2023008680 | A1 | 2/2023 |
| WO | 2023008681 | A1 | 2/2023 |
| WO | 2023022319 | A1 | 2/2023 |
| WO | 2023022320 | A1 | 2/2023 |
| WO | 2023052695 | A1 | 4/2023 |
| WO | 2023091496 | A1 | 5/2023 |
| WO | 2023215155 | A1 | 11/2023 |
| WO | 2023230075 | A1 | 11/2023 |

OTHER PUBLICATIONS

International Searching Authority, International Preliminary Report on Patentability of International Application No. PCT/US2017/50895, dated Dec. 11, 2018, 52 pages.

International Searching Authority, Search Report and Written Opinion for International Application No. PCT/US2017/50895, dated Jan. 12, 2018, 6 pages.

International Searching Authority, Search Report and Written Opinion for International Application No. PCT/US2020/021876, dated May 28, 2020, 8 pages.

International Searching Authority, Search Report and Written Opinion for International Application No. PCT/US2020/051008, dated Dec. 10, 2020, 9 pages.

International Searching Authority, Search Report and Written Opinion for International Application No. PCT/US2020/056661, dated Feb. 12, 2021, 12 pages.

International Searching Authority, Search Report and Written Opinion for International Application No. PCT/US2021/032807, dated Sep. 6, 2021, 11 pages.

Matrix, R3xm Recumbent Cycle, retrieved on Aug. 4, 2020, 7 pages, https://www.matrixfitness.com/en/cardio/cycles/r3xm-recumbent.

ROM3 Rehab, ROM3 Rehab System, Apr. 20, 2015, retrieved on Aug. 31, 2018, 12 pages, https://vimeo.com/125438463.

International Search Report and Written Opinion for PCT/US2023/014137, dated Jun. 9, 2023, 13 pages.

Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.

Abedtash, "An Interoperable Electronic Medical Record-Based Platform for Personalized Predictive Analytics", ProQuest LLC, Jul. 2017, 185 pages.

Jeong et al., "Computer-assisted upper extremity training using interactive biking exercise (iBikE) platform," Sep. 2012, pp. 1-5, 34th Annual International Conference of the IEEE EMBS.

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Barrett et al., "Artificial intelligence supported patient self-care in chronic heart failure: a paradigm shift from reactive to predictive, preventive and personalised care," EPMA Journal (2019), pp. 445-464.

Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.

Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.

Thomas et al., "Home-Based Cardiac Rehabilitation," Circulation, 2019, pp. e69-e89, vol. 140.

Thomas et al., "Home-Based Cardiac Rehabilitation," Journal of the American College of Cardiology, Nov. 1, 2019, pp. 133-153, vol. 74.

Thomas et al., "Home-Based Cardiac Rehabilitation," HHS Public Access, Oct. 2, 2020, pp. 1-39.

Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.

Chen et al., "Home-based cardiac rehabilitation improves quality of life, aerobic capacity, and readmission rates in patients with chronic heart failure," Medicine, 2018, pp. 1-5 vol. 97:4.

Lima de Melo Ghisi et al., "A systematic review of patient education in cardiac patients: Do they increase knowledge and promote health behavior change?," Patient Education and Counseling, 2014, pp. 1-15.

Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.

Beene et al., "AI and Care Delivery: Emerging Opportunities for Artificial Intelligence to Transform How Care Is Delivered," Nov. 2019, American Hospital Association, pp. 1-12.

Website for "Pedal Exerciser", p. 1, retrieved on Sep. 9, 2022 from https://www.vivehealth.com/collections/physical-therapy-equipment/products/pedalexerciser.

Website for "Functional Knee Brace with ROM", p. 1, retrieved on Sep. 9, 2022 from http://medicalbrace.gr/en/product/functional-knee-brace-with-goniometer-mbtelescopicknee/.

(56) References Cited

OTHER PUBLICATIONS

Website for "ComfySplints Goniometer Knee", pp. 1-5, retrieved on Sep. 9, 2022 from https://www.comfysplints.com/product/knee-splints/.
Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.
Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.
Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.
Ahmed et al., "Artificial intelligence with multi-functional machine learning platform development for better healthcare and precision medicine," Database, 2020, pp. 1-35.
Davenport et al., "The potential for artificial intelligence in healthcare," Digital Technology, Future Healthcare Journal, 2019, pp. 1-5, vol. 6, No. 2.
Website for "OxeFit XS1", pp. 1-3, retrieved on Sep. 9, 2022 from https://www.oxefit.com/xs1.
Website for "Preva Mobile", pp. 1-6, retrieved on Sep. 9, 2022 from https://www.precor.com/en-us/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.
Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.
Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.
Androutsou et al., "A Smartphone Application Designed to Engage the Elderly in Home-Based Rehabilitation," Frontiers in Digital Health, Sep. 2020, vol. 2, Article 15, 13 pages.
Silva et al., "SapoFitness: A mobile health application for dietary evaluation," 2011 IEEE 13th International Conference on U e-Health Networking, Applications and Services, Columbia, MO, USA, 2011, 6 pages.
Wang et al., "Interactive wearable systems for upper body rehabilitation: a systematic review," Journal of NeuroEngineering and Rehabilitation, 2017, 21 pages.
Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.
Nijjar et al., "Randomized Trial of Mindfulness-Based Stress Reduction in Cardiac Patients Eligible for Cardiac Rehabilitation," Scientific Reports, 2019, 12 pages.
Lara et al., "Human-Robot Sensor Interface for Cardiac Rehabilitation," IEEE International Conference on Rehabilitation Robotics, Jul. 2017, 8 pages.
Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.
Zakari et al., "Are There Limitations to Exercise Benefits in Peripheral Arterial Disease?," Frontiers in Cardiovascular Medicine, Nov. 2018, vol. 5, Article 173, 12 pages.
You et al., "Including Blood Vasculature into a Game—Theoretic Model of Cancer Dynamics," Games 2019, 10, 13, 22 pages.
Jeong et al., "Computer-assisted upper extremity training using interactive biking exercise (iBikE) platform," Sep. 2012, 34th Annual International Conference of the IEEE EMBS, 5 pages.
Gerbild et al., "Physical Activity to Improve Erectile Dysfunction: A Systematic Review of Intervention Studies," Sexual Medicine, 2018, 15 pages.

\* cited by examiner

SYSTEMS AND METHODS FOR USING ARTIFICIAL INTELLIGENCE AND MACHINE LEARNING TO DETECT ABNORMAL HEART RHYTHMS OF A USER PERFORMING A TREATMENT PLAN WITH AN ELECTROMECHANICAL MACHINE

CROSS-REFERENCES TO RELATED APPLICATIONS

This application is a continuation-in-part of and claims priority to and the benefit of U.S. patent application Ser. No. 17/736,891, filed May 4, 2022, titled "Systems and Methods for Using Artificial Intelligence to Implement a Cardio Protocol via a Relay-Based System," which is a continuation-in-part of and claims priority to and the benefit of U.S. patent application Ser. No. 17/379,542, filed Jul. 19, 2021, titled "System and Method for Using Artificial Intelligence in Telemedicine-Enabled Hardware to Optimize Rehabilitative Routines Capable of Enabling Remote Rehabilitative Compliance" (now U.S. Pat. No. 11,328,807, issued May 10, 2022), which is a continuation of and claims priority to and the benefit of U.S. patent application Ser. No. 17/146,705, filed Jan. 12, 2021, titled "System and Method for Using Artificial Intelligence in Telemedicine-Enabled Hardware to Optimize Rehabilitative Routines Capable of Enabling Remote Rehabilitative Compliance," which is a continuation-in-part of and claims priority to and the benefit of U.S. patent application Ser. No. 17/021,895, filed Sep. 15, 2020, titled "Telemedicine for Orthopedic Treatment" (now U.S. Pat. No. 11,071,597, issued Jul. 27, 2021), which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes. The application U.S. patent application Ser. No. 17/146,705 also claims priority to and the benefit of U.S. Provisional Patent Application Ser. No. 63/113,484, filed Nov. 13, 2020, titled "System and Method for Use of Artificial Intelligence in Telemedicine-Enabled Hardware to Optimize Rehabilitative Routines for Enabling Remote Rehabilitative Compliance," the entire disclosures of which are hereby incorporated by reference for all purposes.

This application also claims priority to and the benefit of U.S. Provisional Patent Application Ser. No. 63/407,049 filed Sep. 15, 2022, titled "Systems and Methods for Using Artificial Intelligence and an Electromechanical Machine to Aid Rehabilitation in Various Patient Markets," the entire disclosure of which is hereby incorporated by reference for all purposes.

BACKGROUND

Remote medical assistance, also referred to, inter alia, as remote medicine, telemedicine, telemed, telmed, tel-med, or telehealth, is an at least two-way communication between a healthcare professional or providers, such as a physician or a physical therapist, and a patient using audio and/or audiovisual and/or other sensorial or perceptive (e.g., tactile, gustatory, haptic, pressure-sensing-based or electromagnetic (e.g., neurostimulation) communications (e.g., via a computer, a smartphone, or a tablet). Telemedicine may aid a patient in performing various aspects of a rehabilitation regimen for a body part. The patient may use a patient interface in communication with an assistant interface for receiving the remote medical assistance via audio, visual, audiovisual, or other communications described elsewhere herein. Any reference herein to any particular sensorial modality shall be understood to include and to disclose by implication a different one or more sensory modalities.

Telemedicine is an option for healthcare professionals to communicate with patients and provide patient care when the patients do not want to or cannot easily go to the healthcare professionals' offices. Telemedicine, however, has substantive limitations as the healthcare professionals cannot conduct physical examinations of the patients. Rather, the healthcare professionals must rely on verbal communication and/or limited remote observation of the patients.

Cardiovascular health refers to the health of the heart and blood vessels of an individual. Cardiovascular diseases or cardiovascular health issues include a group of diseases of the heart and blood vessels, including coronary heart disease, stroke, heart failure, heart arrhythmias, and heart valve problems. It is generally known that exercise and a healthy diet can improve cardiovascular health and reduce the chance or impact of cardiovascular disease.

Various other markets are related to health conditions associated with other portions and/or systems of a human body. For example, other prevalent health conditions pertain to pulmonary health, bariatric health, oncologic health, prostate health, and the like. There is a large portion of the population who are affected by one or more of these health conditions. Treatment and/or rehabilitation for the health conditions, as currently provided, is not adequate to satisfy the massive demand prevalent in the population worldwide.

SUMMARY

The present disclosure provides a computer-implemented system including, in one embodiment, an electromechanical machine, one or more sensors, and one or more processing devices. The electromechanical machine is configured to be manipulated by a user while the user is performing a treatment plan. The one or more sensors are configured to determine one or more measurements associated with the user. The one or more processing devices are configured to receive, from the one or more sensors while the user performs the treatment plan, the one or more measurements associated with the user. The one or more processing devices also configured to determine, using one or more machine learning models, a probability that the one or more measurements indicate that the user satisfies a threshold for a condition associated with an abnormal heart rhythm. The one or more processing devices are further configured to perform one or more preventative actions responsive to determining that the one or more measurements indicate the user satisfies the threshold for the condition associated with the abnormal heart rhythm. The one or more preventative actions are determined using the one or more machine learning models. The one or more preventative actions include at least one preventative action selected from the group consisting of initiating a telecommunications transmission, stopping operation of the electromechanical machine, and modifying one or more parameters associated with the operation of the electromechanical machine.

The present disclosure also provides a computer-implemented method. The method includes receiving, from one or more sensors while a user performs a treatment plan on an electromechanical machine, one or more measurements associated with the user. The method also includes determining, using one or more machine learning models, a probability that the one or more measurements indicate that the user satisfies a threshold for a condition associated with an abnormal heart rhythm. The method further includes performing one or more preventative actions responsive to determining that the one or more measurements indicate the user satisfies the threshold for the condition associated with the abnormal heart rhythm. The one or more preventative actions are determined using the one or more machine learning models. The one or more preventative actions include at least one preventative action selected from the group consisting of initiating a telecommunications transmission, stopping operation of the electromechanical machine, and modifying one or more parameters associated with the operation of the electromechanical machine.

The present disclosure further provides one or more tangible, non-transitory computer-readable media storing instructions that, when executed, cause one or more processing devices to receive, from one or more sensors while a user performs a treatment plan on an electromechanical machine, one or more measurements associated with the user. The instructions also cause one or more processing devices to determine, using one or more machine learning models, a probability that the one or more measurements indicate that the user satisfies a threshold for a condition associated with an abnormal heart rhythm. The instructions further cause the one or more processing devices to perform one or more preventative actions responsive to determining that the one or more measurements indicate the user satisfies the threshold for the condition associated with the abnormal heart rhythm. The one or more preventative actions are determined using the one or more machine learning models. The one or more preventative actions include at least one preventative action selected from the group consisting of initiating a telecommunications transmission, stopping operation of the electromechanical machine, and modifying one or more parameters associated with the operation of the electromechanical machine.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

For a detailed description of example embodiments, reference will now be made to the accompanying drawings in which.

NOTATION AND NOMENCLATURE

Figure 1:
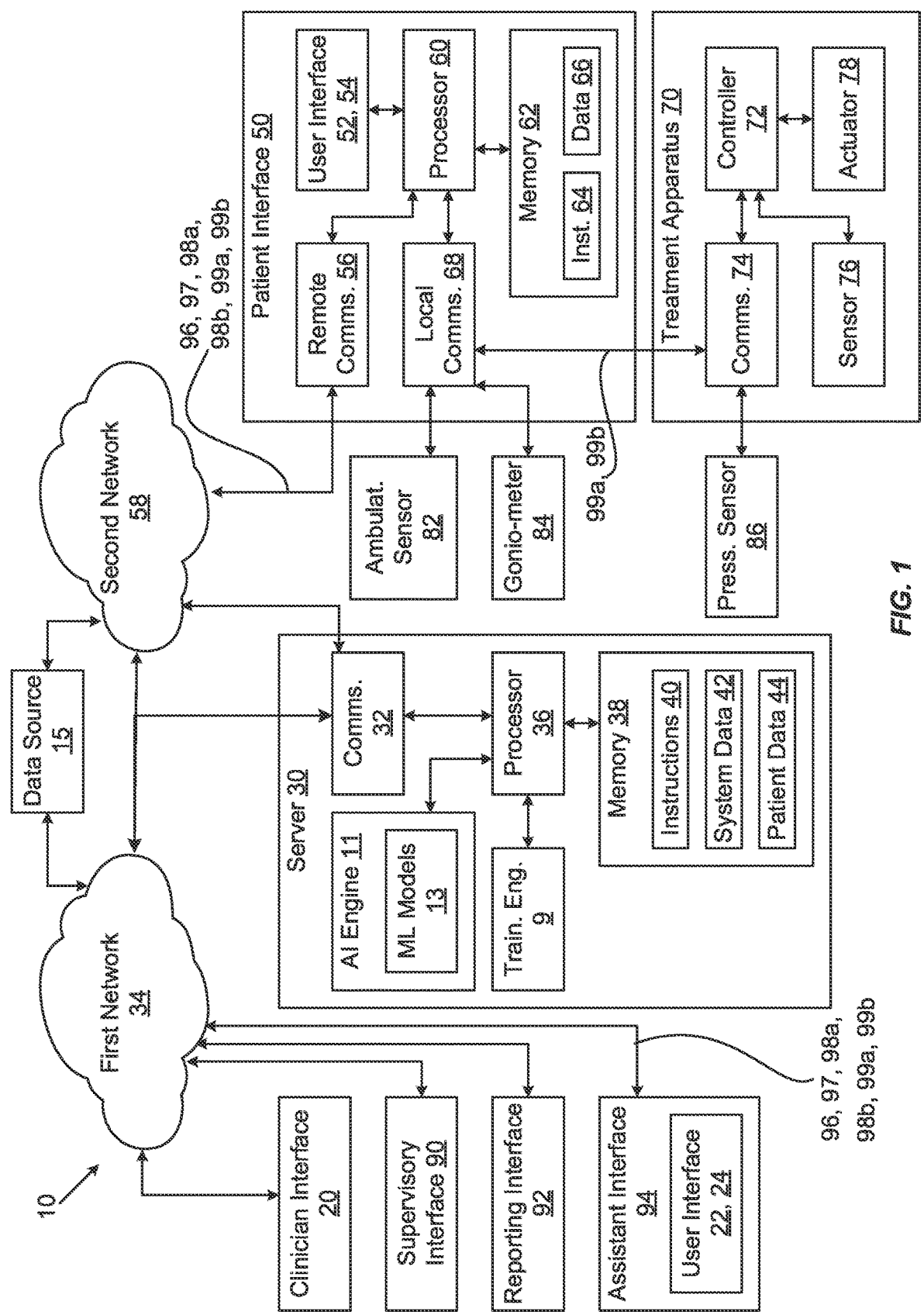
FIG. 1 generally illustrates a block diagram of an embodiment of a computer implemented system for managing a treatment plan according to the principles of the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," "the," and "said" may be intended to include the plural forms as well, unless the context clearly indicates otherwise. The terms "a," "an," "the," and "said" as used herein in connection with any type of processing component configured to perform various functions may refer to one processing component configured to perform each and every function, or a plurality of processing components collectively configured to perform each of the various functions. By way of example, "A processor" configured to perform actions A, B, and C may refer to one processor configured to perform actions A, B, and C. In addition, "A processor" configured to perform actions A, B, and C may also refer to a first processor configured to perform actions A and B, and a second processor configured to perform action C. Further, "A processor" configured to perform actions A, B, and C may also refer to a first processor configured to perform action A, a second processor configured to perform action B, and a third processor configured to perform action C. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols or exercise regimens, and each treatment protocol or exercise regimen may include one or more treatment sessions or one or more exercise sessions. Each treatment session or exercise session may comprise one or more session periods or exercise periods, where each session period or exercise period may include at least one exercise for treating the body part of the patient. In some embodiments, exercises that improve the cardiovascular health of the user are included in each session. For each session, exercises may be selected to enable the user to perform at different exertion levels. The exertion level for each session may be based at least on a cardiovascular health issue of the user and/or a standardized measure comprising a degree, characterization or other quantitative or qualitative description of exertion. The cardiovascular health issues may include, without limitation, heart surgery performed on the user, a heart transplant performed on the user, a heart arrhythmia of the user, an atrial fibrillation of the user, tachycardia, bradycardia, supraventricular tachycardia, congestive heart failure, heart valve disease, arteriosclerosis, atherosclerosis, pericardial disease, pericarditis, myocardial disease, myocarditis, cardiomyopathy, congenital heart disease, or some combination thereof. The cardiovascular health issues may also include, without limitation, diagnoses, diagnostic codes, symptoms, life consequences, comorbidities, risk factors to health, life, etc. The exertion levels may progressively increase between each session. For example, an exertion level may be low for a first session, medium for a second session, and high for a third session. The exertion levels may change dynamically during performance of a treatment plan based on at least cardiovascular data received from one or more sensors, the cardiovascular health issue, and/or the standardized measure comprising a degree, characterization or other quantitative or qualitative description of exertion. Any suitable exercise (e.g., muscular, weight lifting, cardiovascular, therapeutic, neuromuscular, neurocognitive, meditating, yoga, stretching, etc.) may be included in a session period or an exercise period. For example, a treatment plan for post-operative rehabilitation after a knee surgery may include an initial treatment protocol or exercise regimen with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment apparatus, a diet regimen for the patient, a medication regimen for the patient, a sleep regimen for the patient, additional regimens, or some combination thereof.

The terms telemedicine, telehealth, telemed, teletherapeutic, telemedicine, remote medicine, etc. may be used interchangeably herein.

The term "optimal treatment plan" may refer to optimizing a treatment plan based on a certain parameter or factors or combinations of more than one parameter or factor, such as, but not limited to, a measure of benefit which one or more exercise regimens provide to users, one or more probabilities of users complying with one or more exercise regimens, an amount, quality or other measure of sleep associated with the user, information pertaining to a diet of the user, information pertaining to an eating schedule of the user, information pertaining to an age of the user, information pertaining to a sex of the user, information pertaining to a gender of the user, an indication of a mental state of the user, information pertaining to a genetic condition of the user, information pertaining to a disease state of the user, an indication of an energy level of the user, information pertaining to a microbiome from one or more locations on or in the user (e.g., skin, scalp, digestive tract, vascular system, etc.), or some combination thereof.

As used herein, the term healthcare professional may include a medical professional (e.g., such as a doctor, a physician assistant, a nurse practitioner, a nurse, a therapist, and the like), an exercise professional (e.g., such as a coach, a trainer, a nutritionist, and the like), or another professional sharing at least one of medical and exercise attributes (e.g., such as an exercise physiologist, a physical therapist, a physical therapy technician, an occupational therapist, and the like). As used herein, and without limiting the foregoing, a "healthcare professional" may be a human being, a robot, a virtual assistant, a virtual assistant in virtual and/or augmented reality, or an artificially intelligent entity, such entity including a software program, integrated software and hardware, or hardware alone.

Real-time may refer to less than or equal to 2 seconds. Near real-time may refer to any interaction of a sufficiently short time to enable two individuals to engage in a dialogue via such user interface, and will preferably but not determinatively be less than 10 seconds but greater than 2 seconds.

Any of the systems and methods described in this disclosure may be used in connection with rehabilitation. Rehabilitation may be directed at cardiac rehabilitation, rehabilitation from stroke, multiple sclerosis, Parkinson's disease, myasthenia gravis, Alzheimer's disease, any other neurodegenerative or neuromuscular disease, a brain injury, a spinal cord injury, a spinal cord disease, a joint injury, a joint disease, post-surgical recovery, or the like. Rehabilitation can further involve muscular contraction in order to improve blood flow and lymphatic flow, engage the brain and nervous system to control and affect a traumatized area to increase the speed of healing, reverse or reduce pain (including arthralgias and myalgias), reverse or reduce stiffness, recover range of motion, encourage cardiovascular engagement to stimulate the release of pain-blocking hormones or to encourage highly oxygenated blood flow to aid in an overall feeling of well-being. Rehabilitation may be provided for individuals of average weight in reasonably good physical condition having no substantial deformities, as well as for individuals more typically in need of rehabilitation, such as those who are elderly, obese, subject to disease processes, injured and/or who have a severely limited range of motion. Unless expressly stated otherwise, is to be understood that rehabilitation includes prehabilitation (also referred to as "pre-habilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through, dissecting and/or harming numerous muscles and muscle groups in or about, without limitation, the skull or face, the abdomen, the ribs and/or the thoracic cavity, as well as in or about all joints and appendages. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. Performance of the one or more sets of exercises may be required in order to qualify for an elective surgery, such as a knee replacement. The patient may prepare an area of his or her body for the surgical procedure by performing the one or more sets of exercises, thereby strengthening muscle groups, improving existing muscle memory, reducing pain, reducing stiffness, establishing new muscle memory, enhancing mobility (i.e., improve range of motion), improving blood flow, and/or the like.

The phrase, and all permutations of the phrase, "respective measure of benefit with which one or more exercise regimens may provide the user" (e.g., "measure of benefit," "respective measures of benefit," "measures of benefit," "measure of exercise regimen benefit," "exercise regimen benefit measurement," etc.) may refer to one or more measures of benefit with which one or more exercise regimens may provide the user.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining a treatment plan for a patient having certain characteristics (e.g., vital-sign or other measurements; performance; demographic; psychographic; geographic; diagnostic; measurement- or test-based; medically historic; behavioral historic; cognitive; etiologic; cohort-associative; differentially diagnostic; surgical, physically therapeutic, microbiome related, pharmacologic and other treatment(s) recommended; arterial blood gas and/or oxygenation levels or percentages; glucose levels; blood oxygen levels; insulin levels; psychographics; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment apparatus, an amount of force exerted on a portion of the treatment apparatus, a range of motion achieved on the treatment apparatus, a movement speed of a portion of the treatment apparatus, a duration of use of the treatment apparatus, an indication of a plurality of pain levels using the treatment apparatus, or some combination thereof. The measurement information may include, e.g., a vital sign, a respiration rate, a heartrate, a temperature, a blood pressure, a glucose level, arterial blood gas and/or oxygenation levels or percentages, or other biomarker, or some combination thereof. It may be desirable to process and analyze the characteristics of a multitude of patients, the treatment plans performed for those patients, and the results of the treatment plans for those patients.

Further, another technical problem may involve distally treating, via a computing apparatus during a telemedicine session, a patient from a location different than a location at which the patient is located. An additional technical problem is controlling or enabling, from the different location, the control of a treatment apparatus used by the patient at the patient's location. Oftentimes, when a patient undergoes rehabilitative surgery (e.g., knee surgery), a healthcare professional may prescribe a treatment apparatus to the patient to use to perform a treatment protocol at their residence or at any mobile location or temporary domicile. A healthcare professional may refer to a doctor, physician assistant, nurse practitioner, nurse, chiropractor, dentist, physical therapist, acupuncturist, physical trainer, or the like. A healthcare professional may refer to any person with a credential, license, degree, or the like in the field of medicine, physical therapy, rehabilitation, or the like.

When the healthcare professional is located in a different location from the patient and the treatment apparatus, it may be technically challenging for the healthcare professional to monitor the patient's actual progress (as opposed to relying on the patient's word about their progress) in using the treatment apparatus, modify the treatment plan according to the patient's progress, adapt the treatment apparatus to the personal characteristics of the patient as the patient performs the treatment plan, and the like.

Additionally, or alternatively, a computer-implemented system may be used in connection with a treatment apparatus to treat the patient, for example, during a telemedicine session. For example, the treatment apparatus can be configured to be manipulated by a user while the user is performing a treatment plan. The system may include a patient interface that includes an output device configured to present telemedicine information associated with the telemedicine session. During the telemedicine session, the processing device can be configured to receive treatment data pertaining to the user. The treatment data may include one or more characteristics of the user. The processing device may be configured to determine, via one or more trained machine learning models, at least one respective measure of benefit which one or more exercise regimens provide the user. Determining the respective measure of benefit may be based on the treatment data. The processing device may be configured to determine, via the one or more trained machine learning models, one or more probabilities of the user complying with the one or more exercise regimens. The processing device may be configured to transmit the treatment plan, for example, to a computing device. The treatment plan can be generated based on the one or more probabilities and the respective measure of benefit which the one or more exercise regimens provide the user.

Accordingly, systems and methods, such as those described herein, that receive treatment data pertaining to the user of the treatment apparatus during telemedicine session, may be desirable.

In some embodiments, the systems and methods described herein may be configured to use a treatment apparatus configured to be manipulated by an individual while performing a treatment plan. The individual may include a user, patient, or other a person using the treatment apparatus to perform various exercises for prehabilitation, rehabilitation, stretch training, and the like. The systems and methods described herein may be configured to use and/or provide a patient interface comprising an output device configured to present telemedicine information associated with a telemedicine session.

In some embodiments, during an adaptive telemedicine session, the systems and methods described herein may be configured to use artificial intelligence and/or machine learning to assign patients to cohorts and to dynamically control a treatment apparatus based on the assignment. The term "adaptive telemedicine" may refer to a telemedicine session dynamically adapted based on one or more factors, criteria, parameters, characteristics, or the like. The one or more factors, criteria, parameters, characteristics, or the like may pertain to the user (e.g., heartrate, blood pressure, perspiration rate, pain level, or the like), the treatment apparatus (e.g., pressure, range of motion, speed of motor, etc.), details of the treatment plan, and so forth.

In some embodiments, numerous patients may be prescribed numerous treatment apparatuses because the numerous patients are recovering from the same medical procedure and/or suffering from the same injury. The numerous treatment apparatuses may be provided to the numerous patients. The treatment apparatuses may be used by the patients to perform treatment plans in their residences, at gyms, at rehabilitative centers, at hospitals, or at any suitable locations, including permanent or temporary domiciles.

In some embodiments, the treatment apparatuses may be communicatively coupled to a server. Characteristics of the patients, including the treatment data, may be collected before, during, and/or after the patients perform the treatment plans. For example, any or each of the personal information, the performance information, and the measurement information may be collected before, during, and/or after a patient performs the treatment plans. The results (e.g., improved performance or decreased performance) of performing each exercise may be collected from the treatment apparatus throughout the treatment plan and after the treatment plan is performed. The parameters, settings, configurations, etc. (e.g., position of pedal, amount of resistance, etc.) of the treatment apparatus may be collected before, during, and/or after the treatment plan is performed.

Each characteristic of the patient, each result, and each parameter, setting, configuration, etc. may be timestamped and may be correlated with a particular step or set of steps in the treatment plan. Such a technique may enable the determination of which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment apparatuses and/or any suitable computing device (e.g., computing devices where personal information is entered, such as the interface of the computing device described herein, a clinician interface, patient interface, or the like) over time as the patients use the treatment apparatuses to perform the various treatment plans. The data that may be collected may include the characteristics of the patients, the treatment plans performed by the patients, and the results of the treatment plans. Further, the data may include characteristics of the treatment apparatus. The characteristics of the treatment apparatus may include a make (e.g., identity of entity that designed, manufactured, etc. the treatment apparatus 70) of the treatment apparatus 70, a model (e.g., model number or other identifier of the model) of the treatment apparatus 70, a year (e.g., year the treatment apparatus was manufactured) of the treatment apparatus 70, operational parameters (e.g., engine temperature during operation, a respective status of each of one or more sensors included in or associated with the treatment apparatus 70, vibration measurements of the treatment apparatus 70 in operation, measurements of static and/or dynamic forces exerted internally or externally on the treatment apparatus 70, etc.) of the treatment apparatus 70, settings (e.g., range of motion setting, speed setting, required pedal force setting, etc.) of the treatment apparatus 70, and the like. The data collected from the treatment apparatuses, computing devices, characteristics of the user, characteristics of the treatment apparatus, and the like may be collectively referred to as "treatment data" herein.

In some embodiments, the data may be processed to group certain people into cohorts. The people may be grouped by people having certain or selected similar characteristics, treatment plans, and results of performing the treatment plans. For example, athletic people having no medical conditions who perform a treatment plan (e.g., use the treatment apparatus for 30 minutes a day 5 times a week for 3 weeks) and who fully recover may be grouped into a first cohort. Older people who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. In some embodiments, the artificial intelligence engine may be used to identify trends and/or patterns and to define new cohorts based on achieving desired results from the treatment plans and machine learning models associated therewith may be trained to identify such trends and/or patterns and to recommend and rank the desirability of the new cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment apparatus while the new patient uses the treatment apparatus to perform the treatment plan.

As may be appreciated, the characteristics of the new patient (e.g., a new user) may change as the new patient uses the treatment apparatus to perform the treatment plan. For example, the performance of the patient may improve quicker than expected for people in the cohort to which the new patient is currently assigned. Accordingly, the machine learning models may be trained to dynamically reassign, based on the changed characteristics, the new patient to a different cohort that includes people having characteristics similar to the now-changed characteristics as the new patient. For example, a clinically obese patient may lose weight and no longer meet the weight criterion for the initial cohort, result in the patient's being reassigned to a different cohort with a different weight criterion.

A different treatment plan may be selected for the new patient, and the treatment apparatus may be controlled, distally (e.g., which may be referred to as remotely) and based on the different treatment plan, the treatment apparatus while the new patient uses the treatment apparatus to perform the treatment plan. Such techniques may provide the technical solution of distally controlling a treatment apparatus.

Further, the systems and methods described herein may lead to faster recovery times and/or better results for the patients because the treatment plan that most accurately fits their characteristics is selected and implemented, in real-time, at any given moment. "Real-time" may also refer to near real-time, which may be less than 10 seconds or any reasonably proximate difference between two different times. As described herein, the term "results" may refer to medical results or medical outcomes. Results and outcomes may refer to responses to medical actions. The term "medical action(s)" may refer to any suitable action performed by the healthcare professional, and such action or actions may include diagnoses, prescription of treatment plans, prescription of treatment apparatuses, and the making, composing and/or executing of appointments, telemedicine sessions, prescription of medicines, telephone calls, emails, text messages, and the like.

Depending on what result is desired, the artificial intelligence engine may be trained to output several treatment plans. For example, one result may include recovering to a threshold level (e.g., 75% range of motion) in a fastest amount of time, while another result may include fully recovering (e.g., 100% range of motion) regardless of the amount of time. The data obtained from the patients and sorted into cohorts may indicate that a first treatment plan provides the first result for people with characteristics similar to the patient's, and that a second treatment plan provides the second result for people with characteristics similar to the patient.

Further, the artificial intelligence engine may be trained to output treatment plans that are not optimal i.e., sub-optimal, nonstandard, or otherwise excluded (all referred to, without limitation, as "excluded treatment plans") for the patient. For example, if a patient has high blood pressure, a particular exercise may not be approved or suitable for the patient as it may put the patient at unnecessary risk or even induce a hypertensive crisis and, accordingly, that exercise may be flagged in the excluded treatment plan for the patient. In some embodiments, the artificial intelligence engine may monitor the treatment data received while the patient (e.g., the user) with, for example, high blood pressure, uses the treatment apparatus to perform an appropriate treatment plan and may modify the appropriate treatment plan to include features of an excluded treatment plan that may provide beneficial results for the patient if the treatment data indicates the patient is handling the appropriate treatment plan without aggravating, for example, the high blood pressure condition of the patient. In some embodiments, the artificial intelligence engine may modify the treatment plan if the monitored data shows the plan to be inappropriate or counterproductive for the user.

In some embodiments, the treatment plans and/or excluded treatment plans may be presented, during a telemedicine or telehealth session, to a healthcare professional. The healthcare professional may select a particular treatment plan for the patient to cause that treatment plan to be transmitted to the patient and/or to control, based on the treatment plan, the treatment apparatus. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment apparatus.

In such cases, the recommended treatment plans and/or excluded treatment plans may be presented simultaneously with a video of the patient in real-time or near real-time during a telemedicine or telehealth session on a user interface of a computing apparatus of a healthcare professional. The video may also be accompanied by audio, text and other multimedia information and/or other sensorial or perceptive (e.g., tactile, gustatory, haptic, pressure-sensing-based or electromagnetic (e.g., neurostimulation). Real-time may refer to less than or equal to 2 seconds. Near real-time may refer to any interaction of a sufficiently short time to enable two individuals to engage in a dialogue via such user interface, and will generally be less than 10 seconds (or any suitably proximate difference or interval between two different times) but greater than 2 seconds. Presenting the treatment plans generated by the artificial intelligence engine concurrently with a presentation of the patient video may provide an enhanced user interface because the healthcare professional may continue to visually and/or otherwise communicate with the patient while also reviewing the treatment plans on the same user interface. The enhanced user interface may improve the healthcare professional's experience using the computing device and may encourage the healthcare professional to reuse the user interface. Such a technique may also reduce computing resources (e.g., processing, memory, network) because the healthcare professional does not have to switch to another user interface screen to enter a query for a treatment plan to recommend based on the characteristics of the patient. The artificial intelligence engine may be configured to provide, dynamically on the fly, the treatment plans and excluded treatment plans.

In some embodiments, the treatment plan may be modified by a healthcare professional. For example, certain procedures may be added, modified or removed. In the telehealth scenario, there are certain procedures that may not be performed due to the distal nature of a healthcare professional using a computing device in a different physical location than a patient.

A technical problem may relate to the information pertaining to the patient's medical condition being received in disparate formats. For example, a server may receive the information pertaining to a medical condition of the patient from one or more sources (e.g., from an electronic medical record (EMR) system, application programming interface (API), or any suitable system that has information pertaining to the medical condition of the patient). That is, some sources used by various healthcare professional entities may be installed on their local computing devices and, additionally and/or alternatively, may use proprietary formats. Accordingly, some embodiments of the present disclosure may use an API to obtain, via interfaces exposed by APIs used by the sources, the formats used by the sources. In some embodiments, when information is received from the sources, the API may map and convert the format used by the sources to a standardized (i.e., canonical) format, language and/or encoding ("format" as used herein will be inclusive of all of these terms) used by the artificial intelligence engine. Further, the information converted to the standardized format used by the artificial intelligence engine may be stored in a database accessed by the artificial intelligence engine when the artificial intelligence engine is performing any of the techniques disclosed herein. Using the information converted to a standardized format may enable a more accurate determination of the procedures to perform for the patient.

The various embodiments disclosed herein may provide a technical solution to the technical problem pertaining to the patient's medical condition information being received in disparate formats. For example, a server may receive the information pertaining to a medical condition of the patient from one or more sources (e.g., from an electronic medical record (EMR) system, application programming interface (API), or any suitable system that has information pertaining to the medical condition of the patient). The information may be converted from the format used by the sources to the standardized format used by the artificial intelligence engine. Further, the information converted to the standardized format used by the artificial intelligence engine may be stored in a database accessed by the artificial intelligence engine when performing any of the techniques disclosed herein. The standardized information may enable generating optimal treatment plans, where the generating is based on treatment plans associated with the standardized information. The optimal treatment plans may be provided in a standardized format that can be processed by various applications (e.g., telehealth) executing on various computing devices of healthcare professionals and/or patients.

A technical problem may include a challenge of generating treatment plans for users, such treatment plans comprising exercises that balance a measure of benefit which the exercise regimens provide to the user and the probability the user complies with the exercises (or the distinct probabilities the user complies with each of the one or more exercises). By selecting exercises having higher compliance probabilities for the user, more efficient treatment plans may be generated, and these may enable less frequent use of the treatment apparatus and therefore extend the lifetime or time between recommended maintenance of or needed repairs to the treatment apparatus. For example, if the user consistently quits a certain exercise but yet attempts to perform the exercise multiple times thereafter, the treatment apparatus may be used more times, and therefore suffer more "wear-and-tear" than if the user fully complies with the exercise regimen the first time. In some embodiments, a technical solution may include using trained machine learning models to generate treatment plans based on the measure of benefit exercise regimens provide users and the probabilities of the users associated with complying with the exercise regimens, such inclusion thereby leading to more time-efficient, cost-efficient, and maintenance-efficient use of the treatment apparatus.

In some embodiments, the treatment apparatus may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a healthcare professional may adapt, remotely during a telemedicine session, the treatment apparatus to the needs of the patient by causing a control instruction to be transmitted from a server to treatment apparatus. Such adaptive nature may improve the results of recovery for a patient, furthering the goals of personalized medicine, and enabling personalization of the treatment plan on a per-individual basis.

Center-based rehabilitation may be prescribed for certain patients that qualify and/or are eligible for cardiac rehabilitation. Further, the use of exercise equipment to stimulate blood flow and heart health may be beneficial for a plethora of other rehabilitation, in addition to cardiac rehabilitation, such as pulmonary rehabilitation, bariatric rehabilitation, cardio-oncologic rehabilitation, orthopedic rehabilitation, any other type of rehabilitation. However, center-based rehabilitation suffers from many disadvantages. For example, center-based access requires the patient to travel from their place of residence to the center to use the rehabilitation equipment. Traveling is a barrier to entry for some because not all people have vehicles or desire to spend money on gas to travel to a center. Further, center-based rehabilitation programs may not be individually tailored to a patient. That is, the center-based rehabilitation program may be one-size fits all based on a type of medical condition the patient underwent. In addition, center-based rehabilitation require the patient to adhere to a schedule of when the center is open, when the rehabilitation equipment is available, when the support staff is available, etc. In addition, center-based rehabilitation, due to the fact the rehabilitation is performed in a public center, lacks privacy. Center-based rehabilitation also suffers from weather constraints in that detrimental weather may prevent a patient from traveling to the center to comply with their rehabilitation program.

Accordingly, home-based rehabilitation may solve one or more of the issues related to center-based rehabilitation and provide various advantages over center-based rehabilitation. For example, home-based rehabilitation may require decreased days to enrollment, provide greater access for patients to engage in the rehabilitation, and provide individually tailored treatment plans based on one or more characteristics of the patient. Further, home-based rehabilitation provides greater flexibility in scheduling, as the rehabilitation may be performed at any time during the day when the user is at home and desires to perform the treatment plan. There is no transportation barrier for home-based rehabilitation since the treatment apparatus is located within the user's residence. Home-based rehabilitation provides greater privacy for the patient because the patient is performing the treatment plan within their own residence. To that end, the treatment plan implementing the rehabilitation may be easily integrated in to the patient's home routine. The home-based rehabilitation may be provided to more patients than center-based rehabilitation because the treatment apparatus may be delivered to rural regions. Additionally, home-based rehabilitation does not suffer from weather concerns.

This disclosure may refer, inter alia, to "cardiac conditions," "cardiac-related events" (also called "CREs" or "cardiac events"), "cardiac interventions" and "cardiac outcomes."

"Cardiac conditions," as used herein, may refer to medical, health or other characteristics or attributes associated with a cardiological or cardiovascular state. Cardiac conditions are descriptions, measurements, diagnoses, etc. which refer or relate to a state, attribute or explanation of a state pertaining to the cardiovascular system. For example, if one's heart is beating too fast for a given context, then the cardiac condition describing that is "tachycardia"; if one has had the left mitral valve of the heart replaced, then the cardiac condition is that of having a replaced mitral valve. If one has suffered a myocardial infarction, that term, too, is descriptive of a cardiac condition. A distinguishing essential point is that a cardiac condition reflects a state of a patient's cardiovascular system at a given point in time. It is, however, not an event or occurrence itself. Much as a needle can prick a balloon and burst the balloon, deflating it, the state or condition of the balloon is that it has been burst, while the event which caused that is entirely different, i.e., the needle pricking the balloon. Without limiting the foregoing, a cardiac condition may refer to an already existing cardiac condition, a change in state (e.g., an exacerbation or worsening) in or to an existing cardiac condition, and/or an appearance of a new cardiac condition. One or more cardiac conditions of a user may be used to describe the cardiac health of the user.

A "cardiac event," "cardiac-related event" or "CRE," on the other hand, is something that has occurred with respect to one's cardiovascular system and it may be a contributing, associated or precipitating cause of one or more cardiac conditions, but it is the causative reason for the one or more cardiac conditions or a contributing or associated reason for the one or more cardiac conditions. For example, if an angioplasty procedure results in a rupture of a blood vessel in the heart, the rupture is the CRE, while the underlying condition that caused the angioplasty to fail was the cardiac condition of having an aneurysm. The aneurysm is a cardiac condition, not a CRE. The rupture is the CRE. The angioplasty is the cause of the CRE (the rupture), but is not a cardiac condition (a heart cannot be "angioplastic"). The angioplasty procedure can also be deemed a CRE in and of itself, because it is an active, dynamic process, not a description of a state.

For example, and without limiting the foregoing, CREs may include cardiac-related medical conditions and events, and may also be a consequence of procedures or interventions (including, without limitation, cardiac interventions, as defined infra) that may negatively affect the health, performance, or predicted future performance of the cardiovascular system or of any physiological systems or health-related attributes of a patient where such systems or attributes are themselves affected by the performance of the patient's cardiovascular system. These CREs may render individuals, optionally with extant comorbidities, susceptible to a first comorbidity or additional comorbidities or independent medical problems such as, without limitation, congestive heart failure, fatigue issues, oxygenation issues, pulmonary issues, vascular issues, cardio-renal anemia syndrome (CRAS), muscle loss issues, endurance issues, strength issues, sexual performance issues (such as erectile dysfunction), ambulatory issues, obesity issues, reduction of lifespan issues, reduction of quality-of-life issues, and the like. "Issues," as used in the foregoing, may refer, without limitation, to exacerbations, reductions, mitigations, compromised functioning, elimination, or other directly or indirectly caused changes in an underlying condition or physiological organ or psychological characteristic of the individual or the sequelae of any such change, where the existence of at least one said issue may result in a diminution of the quality of life for the individual. The existence of such an at least one issue may itself be remediated by reversing, mitigating, controlling, or otherwise ameliorating the effects of said exacerbations, reductions, mitigations, compromised functionings, eliminations, or other directly or indirectly caused changes in an underlying condition or physiological organ or psychological characteristic of the individual or the sequelae of such change. In general, when an individual suffers a CRE, the individual's overall quality of life may become substantially degraded, compared to its prior state.

A "cardiac intervention" is a process, procedure, surgery, drug regimen or other medical intervention or action undertaken with the intent to minimize the negative effects of a CRE (or, if a CRE were to have positive effects, to maximize those positive effects) that has already occurred, that is about to occur or that is predicted to occur with some probability greater than zero, or to eliminate the negative effects altogether. A cardiac intervention may also be undertaken before a CRE occurs with the intent to avoid the CRE from occurring or to mitigate the negative consequences of the CRE should the CRE still occur.

A "cardiac outcome" may be the result of either a cardiac intervention or other treatment or the result of a CRE for which no cardiac intervention or other treatment has been performed. For example, if a patient dies from the CRE of a ruptured aorta due to the cardiac condition of an aneurysm, and the death occurs because of, in spite of, or without any cardiac interventions, then the cardiac outcome is the patient's death. On the other hand, if a patient has the cardiac conditions of atherosclerosis, hypertension, and dyspnea, and the cardiac intervention of a balloon angioplasty is performed to insert a stent to reduce the effects of arterial stenosis (another cardiac condition), then the cardiac outcome can be significantly improved cardiac health for the patient. Accordingly, a cardiac outcome may generally refer, in some examples, to both negative and positive outcomes.

To use an analogy of an automobile, an automotive condition may be dirty oil. If the oil is not changed, it may damage the engine. The engine damage is an automotive condition, but the time when the engine sustains damage due to the particulate matter in the oil is an "automotive-related event," the analogue to a CRE. If an automotive intervention is undertaken, the oil will be changed before it can damage the engine; or, if the engine has already been damaged, then an automotive intervention involving specific repairs to the engine will be undertaken. If ultimately the engine fails to work, then the automotive outcome is a broken engine; on the other hand, if the automotive interventions succeed, then the automotive outcome is that the automobile's performance is brought back to factory-standard or factory-acceptable level.

Despite the multifarious problems arising out of the foregoing quality-of-life issues, research has shown that exercise rehabilitation programs can substantially mitigate or ameliorate said issues as well as improve each affected individual's quality of life. In particular, such programs enable these improvements by enhancing aerobic exercise potential, increasing coronary perfusion, and decreasing both anxiety and depression (which, inter alia, may be present in patients suffering CREs). Moreover, participation in cardiac rehabilitation has resulted in demonstrated reductions in re-hospitalizations, in progressions of coronary vascular disease, and in negative cardiac outcomes (e.g., death).

Exercise rehabilitation programs are traditionally provided by in-person treatment centers. Unfortunately, studies involving hundreds of thousands of patients have demonstrated that, among all patients eligible to attend exercise rehabilitation programs, only approximately 25% of them actually engaged in the programs. Moreover, only approximately 6% of the patients who engaged in the programs actually completed them. This lack of engagement persists despite the high risk of CRE recurrence observed for non-participants as compared to the lowered risk observed for participants who complete the exercise rehabilitation programs. For example, for coronary artery disease patients, survival improved approximately 50% and the risk of a recurrent cardiac event decreased approximately 50%. Substantial improvements have also been observed in congestive heart failure patients and in patients that underwent cardiac surgical procedures.

The low attendance rates associated with treatment centers can be attributed to a variety of factors. In particular, treatment center visits are viewed by most individuals as an extension of their hospitalization, which, for understandable reasons, causes negative feelings toward attending the rehabilitation. Moreover, as a consequence of worldwide pandemics and shutdowns, any of which could recur in the future, many treatment centers closed down and have yet to reopen. Additionally, geographical limitations are a prominent issue in many areas. For example, in some areas, a visit to a treatment center requires a multi-hour round trip. Further, fragmentation of the organization of rehabilitation efforts between providers, hospitals, and other health centers—combined with individuals' fear of group exercising—negatively affects attendance at and compliance with exercise rehabilitation programs hosted by treatment centers. These limitations, in part or in sum, may severely inhibit the motivation for and/or actual ability of individuals to engage in and complete treatment plans. This is particularly unfortunate given that engagement in such treatment plans would, in all likelihood, substantially improve individuals' longevity and overall quality of life.

In view of the foregoing deficiencies, the embodiments described herein provide a system for enabling residentially-based (i.e., at home) rehabilitation (e.g., cardiac, pulmonary, oncologic, cardio-oncologic, bariatric, neurologic, etc.) programs that can provide a number of outcome-based and other benefits compared to those conferred by treatment center (i.e., in-person) rehabilitation programs. Advantages of residentially-based rehabilitation include a decrease in the average number of days required to enroll, unlimited access, individual tailoring of the programs, flexible scheduling, increased privacy, and ease of integration into home routines.

According to some embodiments, the residentially-based rehabilitation techniques discussed herein can involve a treatment apparatus—such as an interactive exercise component provided by ROMTech®, such as the ROMTech® PortableConnect®, CardiacConnect™ or other device—that has been optimized for use in one or more rehabilitation settings (e.g., cardiac, oncologic, cardio-oncologic, pulmonary, bariatric, etc.). Under this approach, the interactive exercise component can be adjusted so that the exercise regimen is customized for its user. For example, an interactive exercise bicycle can include regular pedals (i.e., pedals that do not require specialized "clip-in" bicycle shoes) and possess the ability to modify pedaling resistances in accordance with the patient's subjective assessment of the degree of difficulty.

In some embodiments, the interactive exercise component can be communicatively coupled to Mobile Cardiac Outpatient Telemetry (MCOT) equipment so that heart rate, respiratory rate, electrocardiogram (EKG), blood pressure, and/or other medical parameters of the patient can be obtained and evaluated. Such medical parameters can enable the interactive exercise component to alert the patient and/or a remote monitoring center to adjust (i.e., curtail, advance, or otherwise modify) exercise activity to optimize the patient's benefits through the exercise program. Notably, the techniques described herein are not limited to utilizing the foregoing devices/medical parameters: any device, configured to monitor any medical parameter of an individual, can be utilized consistent within the scope of this disclosure.

Additionally, the interactive exercise component can be configured to present patient-specific educational content that is identified and/or generated based on a variety of factors. Such factors can include, for example, the patient's physical characteristics, medical history, genetic predispositions (e.g., family medical history), environmental exposures, and so on. The educational content can be presented to the patient at appropriate times through the exercise rehabilitation program (also referred to as a treatment plan herein). For example, preliminary educational content can be provided to the patient prior to the patient's first engagement with the interactive exercise component. In turn, ongoing educational content can be provided to the patient throughout the course of the exercise rehabilitation program. For example, when the interactive exercise component detects that the patient has deviated from the recommended parameters of the exercise rehabilitation program, the interactive exercise component can be configured to display customized educational content directed to reorienting the patient. Finally, release/completion educational content can be provided to the patient upon their completion of the exercise rehabilitation program. For example, the educational content can promote an ongoing lifestyle that will mitigate risks that might otherwise arise were the patient to abandon or participate less often in the lifestyle that was implemented throughout the exercise rehabilitation program.

FIG. 1 shows a block diagram of a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients.

The system data store 42 may be configured to store optimal treatment plans generated based on one or more probabilities of users associated with complying with the exercise regimens, and the measure of benefit with which one or more exercise regimens provide the user. The system data store 42 may hold data pertaining to one or more exercises (e.g., a type of exercise, which body part the exercise affects, a duration of the exercise, which treatment apparatus to use to perform the exercise, repetitions of the exercise to perform, etc.). When any of the techniques described herein are being performed, or prior to or thereafter such performance, any of the data stored in the system data store 42 may be accessed by an artificial intelligence engine 11.

The server 30 may also be configured to store data regarding performance by a patient in following a treatment plan. For example, the memory 38 includes a patient data store 44 configured to hold patient data, such as data pertaining to the one or more patients, including data representing each patient's performance within the treatment plan. The patient data store 44 may hold treatment data pertaining to users over time, such that historical treatment data is accumulated in the patient data store 44. The patient data store 44 may hold data pertaining to measures of benefit one or more exercises provide to users, probabilities of the users complying with the exercise regimens, and the like. The exercise regimens may include any suitable number of exercises (e.g., shoulder raises, squats, cardiovascular exercises, sit-ups, curls, etc.) to be performed by the user. When any of the techniques described herein are being performed, or prior to or thereafter such performance, any of the data stored in the patient data store 44 may be accessed by an artificial intelligence engine 11.

In addition, the determination or identification of: the characteristics (e.g., personal, performance, measurement, etc.) of the users, the treatment plans followed by the users, the measure of benefits which exercise regimens provide to the users, the probabilities of the users associated with complying with exercise regimens, the level of compliance with the treatment plans (e.g., the user completed 4 out of 5 exercises in the treatment plans, the user completed 80% of an exercise in the treatment plan, etc.), and the results of the treatment plans may use correlations and other statistical or probabilistic measures to enable the partitioning of or to partition the treatment plans into different patient cohort-equivalent databases in the patient data store 44. For example, the data for a first cohort of first patients having a first determined measure of benefit provided by exercise regimens, a first determined probability of the user associated with complying with exercise regimens, a first similar injury, a first similar medical condition, a first similar medical procedure performed, a first treatment plan followed by the first patient, and/or a first result of the treatment plan, may be stored in a first patient database. The data for a second cohort of second patients having a second determined measure of benefit provided by exercise regimens, a second determined probability of the user associated with complying with exercise regimens, a second similar injury, a second similar medical condition, a second similar medical procedure performed, a second treatment plan followed by the second patient, and/or a second result of the treatment plan may be stored in a second patient database. Any single characteristic, any combination of characteristics, or any measures calculation therefrom or thereupon may be used to separate the patients into cohorts. In some embodiments, the different cohorts of patients may be stored in different partitions or volumes of the same database. There is no specific limit to the number of different cohorts of patients allowed, other than as limited by mathematical combinatoric and/or partition theory.

This measure of exercise benefit data, user compliance probability data, characteristic data, treatment plan data, and results data may be obtained from numerous treatment apparatuses and/or computing devices over time and stored in the database 44. The measure of exercise benefit data, user compliance probability data, characteristic data, treatment plan data, and results data may be correlated in the patient-cohort databases in the patient data store 44. The characteristics of the users may include personal information, performance information, and/or measurement information.

In addition to the historical treatment data, measure of exercise benefit data, and/or user compliance probability data about other users stored in the patient cohort-equivalent databases, real-time or near-real-time information based on the current patient's treatment data, measure of exercise benefit data, and/or user compliance probability data about a current patient being treated may be stored in an appropriate patient cohort-equivalent database. The treatment data, measure of exercise benefit data, and/or user compliance probability data of the patient may be determined to match or be similar to the treatment data, measure of exercise benefit data, and/or user compliance probability data of another person in a particular cohort (e.g., a first cohort "A", a second cohort "B" or a third cohort "C", etc.) and the patient may be assigned to the selected or associated cohort.

In some embodiments, the server 30 may execute the artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign users to certain cohorts based on their treatment data, generate treatment plans using real-time and historical data correlations involving patient cohort-equivalents, and control a treatment apparatus 70, among other things. The machine learning models 13 may be trained to generate, based on one or more probabilities of the user complying with one or more exercise regimens and/or a respective measure of benefit one or more exercise regimens provide the user, a treatment plan at least a subset of the one or more exercises for the user to perform. The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 9 may be cloud-based or a real-time software platform, and it may include privacy software or protocols, and/or security software or protocols.

To train the one or more machine learning models 13, the training engine 9 may use a training data set of a corpus of information (e.g., treatment data, measures of benefits of exercises provide to users, probabilities of users complying with the one or more exercise regimens, etc.) pertaining to users who performed treatment plans using the treatment apparatus 70, the details (e.g., treatment protocol including exercises, amount of time to perform the exercises, instructions for the patient to follow, how often to perform the exercises, a schedule of exercises, parameters/configurations/settings of the treatment apparatus 70 throughout each step of the treatment plan, etc.) of the treatment plans performed by the users using the treatment apparatus 70, and/or the results of the treatment plans performed by the users, etc.

The one or more machine learning models 13 may be trained to match patterns of treatment data of a user with treatment data of other users assigned to a particular cohort. The term "match" may refer to an exact match, a correlative match, a substantial match, a probabilistic match, etc. The one or more machine learning models 13 may be trained to receive the treatment data of a patient as input, map the treatment data to the treatment data of users assigned to a cohort, and determine a respective measure of benefit one or more exercise regimens provide to the user based on the measures of benefit the exercises provided to the users assigned to the cohort. The one or more machine learning models 13 may be trained to receive the treatment data of a patient as input, map the treatment data to treatment data of users assigned to a cohort, and determine one or more probabilities of the user associated with complying with the one or more exercise regimens based on the probabilities of the users in the cohort associated with complying with the one or more exercise regimens. The one or more machine learning models 13 may also be trained to receive various input (e.g., the respective measure of benefit which one or more exercise regimens provide the user; the one or more probabilities of the user complying with the one or more exercise regimens; an amount, quality or other measure of sleep associated with the user; information pertaining to a diet of the user, information pertaining to an eating schedule of the user; information pertaining to an age of the user, information pertaining to a sex of the user; information pertaining to a gender of the user; an indication of a mental state of the user; information pertaining to a genetic condition of the user; information pertaining to a disease state of the user; an indication of an energy level of the user; or some combination thereof), and to output a generated treatment plan for the patient.

The one or more machine learning models 13 may be trained to match patterns of a first set of parameters (e.g., treatment data, measures of benefits of exercises provided to users, probabilities of user compliance associated with the exercises, etc.) with a second set of parameters associated with an optimal treatment plan. The one or more machine learning models 13 may be trained to receive the first set of parameters as input, map the characteristics to the second set of parameters associated with the optimal treatment plan, and select the optimal treatment plan. The one or more machine learning models 13 may also be trained to control, based on the treatment plan, the treatment apparatus 70.

Using training data that includes training inputs and corresponding target outputs, the one or more machine learning models 13 may refer to model artifacts created by the training engine 9. The training engine 9 may find patterns in the training data wherein such patterns map the training input to the target output, and generate the machine learning models 13 that capture these patterns. In some embodiments, the artificial intelligence engine 11, the database 33, and/or the training engine 9 may reside on another component (e.g., assistant interface 94, clinician interface 20, etc.) depicted in FIG. 1.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

Further, in some embodiments, based on subsequent data (e.g., treatment data, measures of exercise benefit data, probabilities of user compliance data, treatment plan result data, etc.) received, the machine learning models 13 may be continuously or continually updated. For example, the machine learning models 13 may include one or more hidden layers, weights, nodes, parameters, and the like. As the subsequent data is received, the machine learning models 13 may be updated such that the one or more hidden layers, weights, nodes, parameters, and the like are updated to match or be computable from patterns found in the subsequent data. Accordingly, the machine learning models 13 may be re-trained on the fly as subsequent data is received, and therefore, the machine learning models 13 may continue to learn.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions and/or other sensorial or perceptive (e.g., tactile, gustatory, haptic, pressure-sensing-based or electromagnetic (e.g., neurostimulation) communication devices. The output device 54 may comprise one or more different display screens presenting various data and/or interfaces or controls for use by the patient. The output device 54 may include graphics, which may be presented by a web-based interface and/or by a computer program or application (App.). In some embodiments, the patient interface 50 may include functionality provided by or similar to existing voice-based assistants such as Siri by Apple, Alexa by Amazon, Google Assistant, or Bixby by Samsung.

In some embodiments, the output device 54 may present a user interface that may present a recommended treatment plan, excluded treatment plan, or the like to the patient. The user interface may include one or more graphical elements that enable the user to select which treatment plan to perform. Responsive to receiving a selection of a graphical element (e.g., "Start" button) associated with a treatment plan via the input device 54, the patient interface 50 may transmit a control signal to the controller 72 of the treatment apparatus, wherein the control signal causes the treatment apparatus 70 to begin execution of the selected treatment plan. As described below, the control signal may control, based on the selected treatment plan, the treatment apparatus 70 by causing actuation of the actuator 78 (e.g., cause a motor to drive rotation of pedals of the treatment apparatus at a certain speed), causing measurements to be obtained via the sensor 76, or the like. The patient interface 50 may transmit, via a local communication interface 68, the control signal to the treatment apparatus 70.

As shown in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The treatment apparatus 70 may be any suitable medical, rehabilitative, therapeutic, etc. apparatus configured to be controlled distally via another computing device to treat a patient and/or exercise the patient. The treatment apparatus 70 may be an electromechanical machine including one or more weights, an electromechanical bicycle, an electromechanical spinwheel, a smart-mirror, a treadmill, or the like. The body part may include, for example, a spine, a hand, a foot, a knee, or a shoulder. The body part may include a part of a joint, a bone, or a muscle group, such as one or more vertebrae, a tendon, or a ligament. As shown in FIG. 1, the treatment apparatus 70 includes a controller 72, which may include one or more processors, computer memory, and/or other components. The treatment apparatus 70 also includes a fourth communication interface 74 configured to communicate with the patient interface 50 via the local communication interface 68. The treatment apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment apparatus 70 such as, for example, a force, a position, a speed, a velocity, and/or an acceleration. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment apparatus 70.

The system 10 shown in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 shown in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 shown in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 shown in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 shown in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 for an assistant, such as a doctor, a nurse, a physical therapist, or a technician, to remotely communicate with the patient interface 50 and/or the treatment apparatus 70. Such remote communications may enable the assistant to provide assistance or guidance to a patient using the system 10. More specifically, the assistant interface 94 is configured to communicate a telemedicine signal 96, 97, 98a, 98b, 99a, 99b with the patient interface 50 via a network connection such as, for example, via the first network 34 and/or the second network 58. The telemedicine signal 96, 97, 98a, 98b, 99a, 99b comprises one of an audio signal 96, an audiovisual signal 97, an interface control signal 98a for controlling a function of the patient interface 50, an interface monitor signal 98b for monitoring a status of the patient interface 50, an apparatus control signal 99a for changing an operating parameter of the treatment apparatus 70, and/or an apparatus monitor signal 99b for monitoring a status of the treatment apparatus 70. In some embodiments, each of the control signals 98a, 99a may be unidirectional, conveying commands from the assistant interface 94 to the patient interface 50. In some embodiments, in response to successfully receiving a control signal 98a, 99a and/or to communicate successful and/or unsuccessful implementation of the requested control action, an acknowledgement message may be sent from the patient interface 50 to the assistant interface 94. In some embodiments, each of the monitor signals 98b, 99b may be unidirectional, status-information commands from the patient interface 50 to the assistant interface 94. In some embodiments, an acknowledgement message may be sent from the assistant interface 94 to the patient interface 50 in response to successfully receiving one of the monitor signals 98b, 99b.

In some embodiments, the patient interface 50 may be configured as a pass-through for the apparatus control signals 99a and the apparatus monitor signals 99b between the treatment apparatus 70 and one or more other devices, such as the assistant interface 94 and/or the server 30. For example, the patient interface 50 may be configured to transmit an apparatus control signal 99a to the treatment apparatus 70 in response to an apparatus control signal 99a within the telemedicine signal 96, 97, 98a, 98b, 99a, 99b from the assistant interface 94. In some embodiments, the assistant interface 94 transmits the apparatus control signal 99a (e.g., control instruction that causes an operating parameter of the treatment apparatus 70 to change) to the treatment apparatus 70 via any suitable network disclosed herein.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98a, 98b, 99a, 99b may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the assistant may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the assistant to speak to a patient via the patient interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the assistant. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the healthcare professional. In some embodiments, the system 10 may be configured to recognize and react to spoken requests or commands by the patient. For example, in response to a verbal command by the patient (which may be given in any one of several different languages), the system 10 may automatically initiate a telemedicine session.

In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate recommended treatment plans and/or excluded treatment plans for patients and generate the display screens including those recommended treatment plans and/or external treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network.

In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the treatment apparatus 70 may each operate from a patient location geographically separate from a location of the assistant interface 94. For example, the patient interface 50 and the treatment apparatus 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person may work as an assistant remotely from any conventional office infrastructure. Such remote work may be performed, for example, where the assistant interface 94 takes the form of a computer and/or telephone. This remote work functionality may allow for work-from-home arrangements that may include part time and/or flexible work hours for an assistant.

Figure 2:
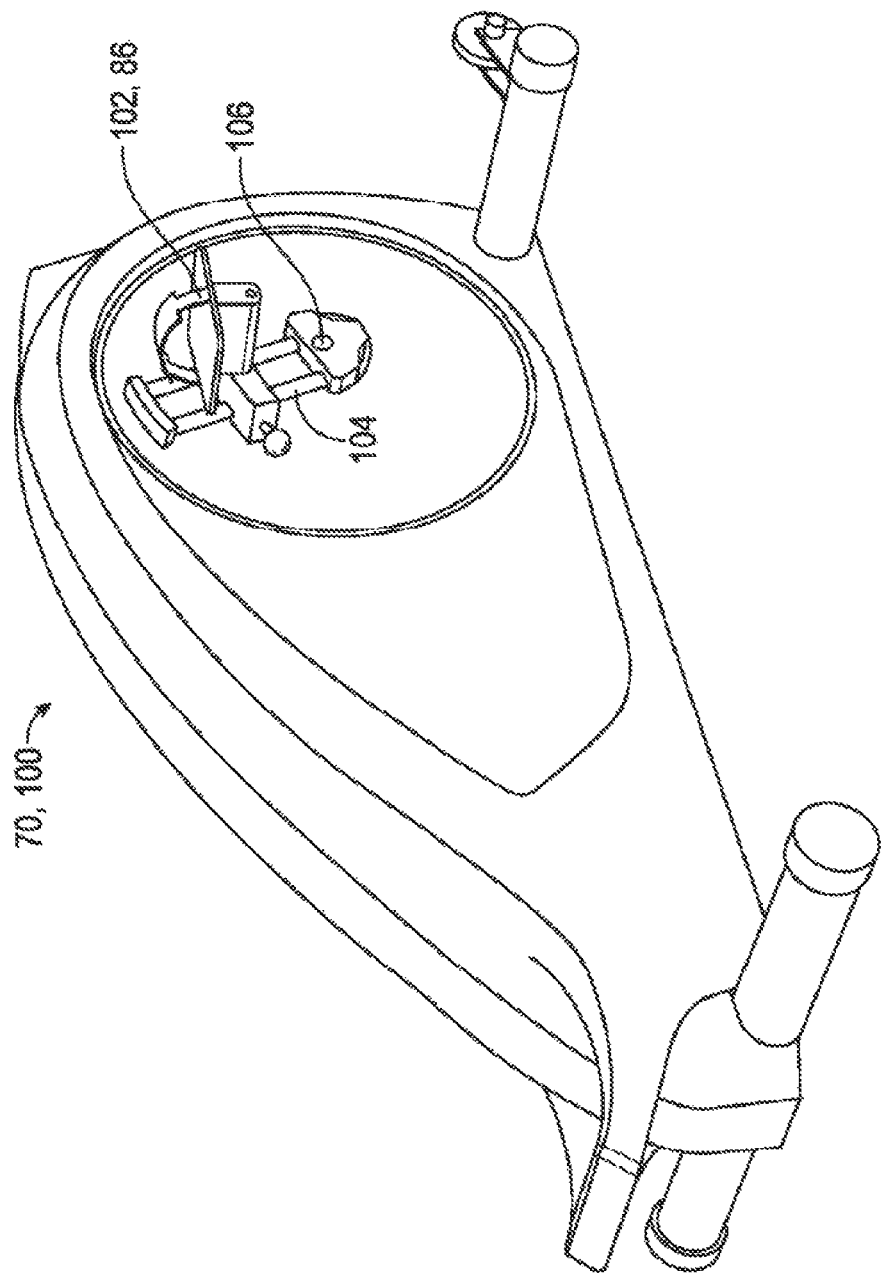
FIG. 2 generally illustrates a perspective view of an embodiment of a treatment apparatus according to the principles of the present disclosure.
Figure 3:
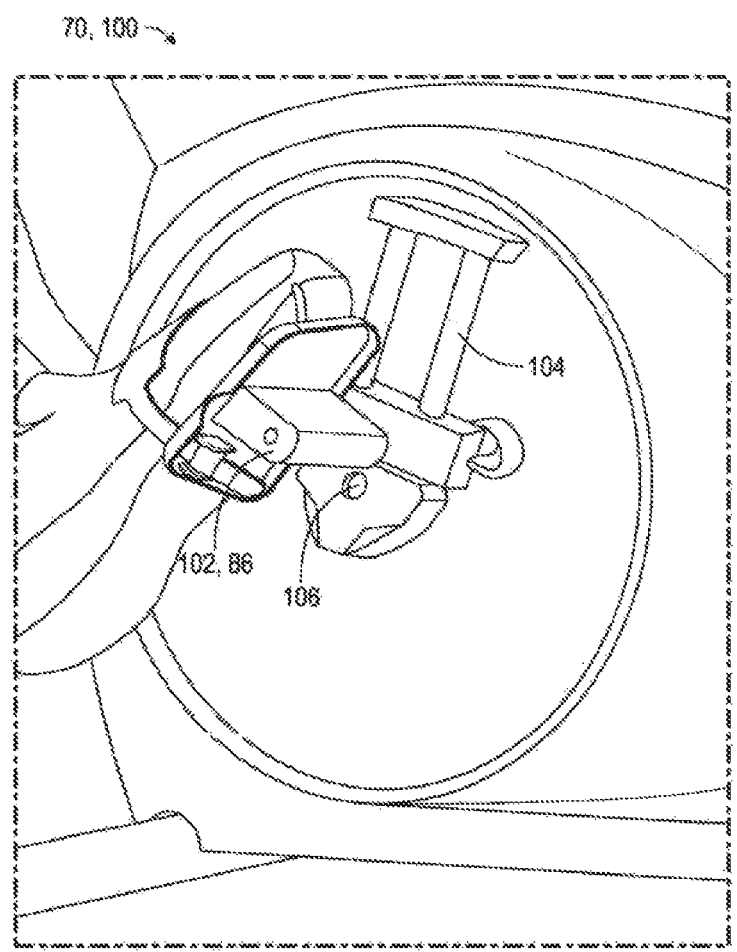
FIG. 3 generally illustrates a perspective view of a pedal of the treatment apparatus of FIG. 2 according to the principles of the present disclosure.

FIGS. 2-3 show an embodiment of a treatment apparatus 70. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one of the pedals 102 for measuring an amount of force applied by the patient on the pedal 102. The pressure sensor 86 may communicate wirelessly to the treatment apparatus 70 and/or to the patient interface 50.

Figure 4:
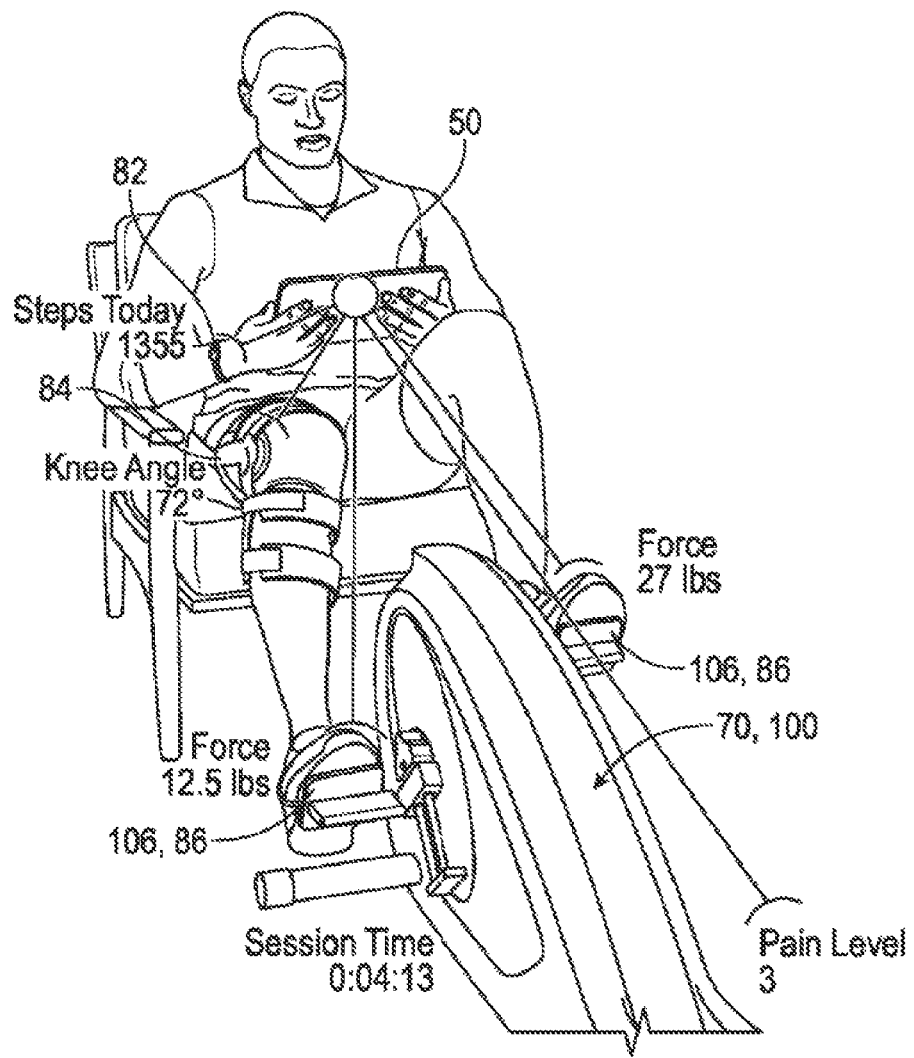
FIG. 4 generally illustrates a perspective view of a person using the treatment apparatus of FIG. 2 according to the principles of the present disclosure.

FIG. 4 shows a person (a patient) using the treatment apparatus of FIG. 2, and showing sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment apparatus 70. FIG. 4 shows the patient wearing the ambulation sensor 82 on his wrist, with a note showing "STEPS TODAY 1355", indicating that the ambulation sensor 82 has recorded and transmitted that step count to the patient interface 50. FIG. 4 also shows the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 102 with a pressure sensor 86 showing "FORCE 12.5 lbs.," indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also shows an indicator showing "PAIN LEVEL 3". Such a pain level may be obtained from the patent in response to a solicitation, such as a question, presented upon the patient interface 50.

Figure 5:
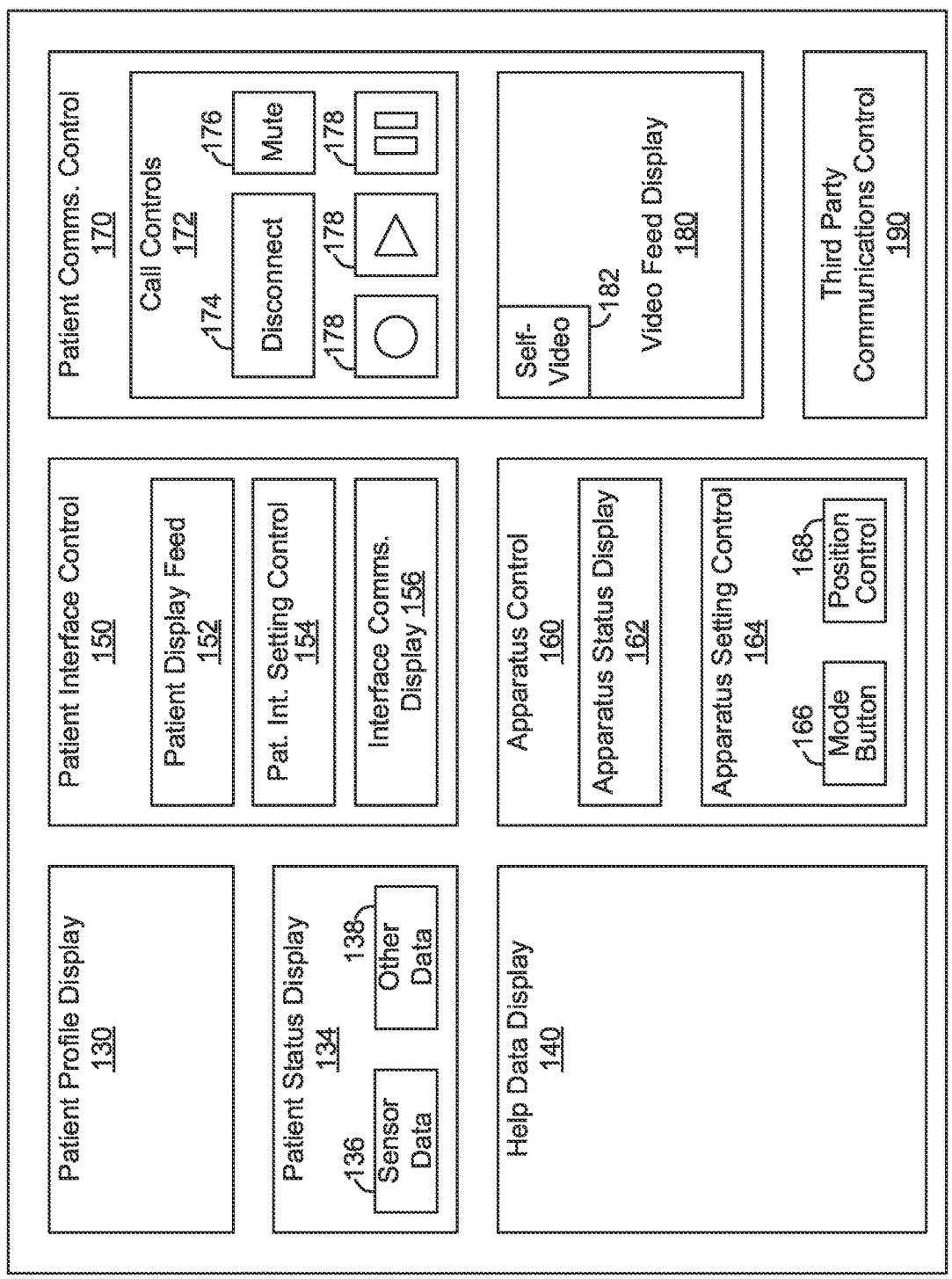
FIG. 5 generally illustrates an example embodiment of an overview display of an assistant interface according to the principles of the present disclosure.

FIG. 5 is an example embodiment of an overview display 120 of the assistant interface 94. Specifically, the overview display 120 presents several different controls and interfaces for the assistant to remotely assist a patient with using the patient interface 50 and/or the treatment apparatus 70. This remote assistance functionality may also be called telemedicine or telehealth.

Specifically, the overview display 120 includes a patient profile display 130 presenting biographical information regarding a patient using the treatment apparatus 70. The patient profile display 130 may take the form of a portion or region of the overview display 120, as shown in FIG. 5, although the patient profile display 130 may take other forms, such as a separate screen or a popup window. In some embodiments, the patient profile display 130 may include a limited subset of the patient's biographical information. More specifically, the data presented upon the patient profile display 130 may depend upon the assistant's need for that information. For example, a healthcare professional that is assisting the patient with a medical issue may be provided with medical history information regarding the patient, whereas a technician troubleshooting an issue with the treatment apparatus 70 may be provided with a much more limited set of information regarding the patient. The technician, for example, may be given only the patient's name. The patient profile display 130 may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the treatment apparatus 70. Such treatment plan information may be limited to an assistant who is a healthcare professional, such as a doctor or physical therapist. For example, a healthcare professional assisting the patient with an issue regarding the treatment regimen may be provided with treatment plan information, whereas a technician troubleshooting an issue with the treatment apparatus 70 may not be provided with any information regarding the patient's treatment plan.

In some embodiments, one or more recommended treatment plans and/or excluded treatment plans may be presented in the patient profile display 130 to the assistant. The one or more recommended treatment plans and/or excluded treatment plans may be generated by the artificial intelligence engine 11 of the server 30 and received from the server 30 in real-time during, inter alia, a telemedicine or telehealth session. An example of presenting the one or more recommended treatment plans and/or excluded treatment plans is described below with reference to FIG. 7.

The example overview display 120 shown in FIG. 5 also includes a patient status display 134 presenting status information regarding a patient using the treatment apparatus. The patient status display 134 may take the form of a portion or region of the overview display 120, as shown in FIG. 5, although the patient status display 134 may take other forms, such as a separate screen or a popup window. The patient status display 134 includes sensor data 136 from one or more of the external sensors 82, 84, 86, and/or from one or more internal sensors 76 of the treatment apparatus 70. In some embodiments, the patient status display 134 may include sensor data from one or more sensors of one or more wearable devices worn by the patient while using the treatment device 70. The one or more wearable devices may include a watch, a bracelet, a necklace, a chest strap, and the like. The one or more wearable devices may be configured to monitor a heartrate, a temperature, a blood pressure, one or more vital signs, and the like of the patient while the patient is using the treatment device 70. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the assistant/user's need for and/or qualifications to view that information.

The example overview display 120 shown in FIG. 5 also includes a help data display 140 presenting information for the assistant to use in assisting the patient. The help data display 140 may take the form of a portion or region of the overview display 120, as shown in FIG. 5. The help data display 140 may take other forms, such as a separate screen or a popup window. The help data display 140 may include, for example, presenting answers to frequently asked questions regarding use of the patient interface 50 and/or the treatment apparatus 70. The help data display 140 may also include research data or best practices. In some embodiments, the help data display 140 may present scripts for answers or explanations in response to patient questions. In some embodiments, the help data display 140 may present flow charts or walk-throughs for the assistant to use in determining a root cause and/or solution to a patient's problem. In some embodiments, the assistant interface 94 may present two or more help data displays 140, which may be the same or different, for simultaneous presentation of help data for use by the assistant. for example, a first help data display may be used to present a troubleshooting flowchart to determine the source of a patient's problem, and a second help data display may present script information for the assistant to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 shown in FIG. 5 also includes a patient interface control 150 presenting information regarding the patient interface 50, and/or to modify one or more settings of the patient interface 50. The patient interface control 150 may take the form of a portion or region of the overview display 120, as shown in FIG. 5. The patient interface control 150 may take other forms, such as a separate screen or a popup window. The patient interface control 150 may present information communicated to the assistant interface 94 via one or more of the interface monitor signals 98b. As shown in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the assistant to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the assistant to remotely view and/or control the patient interface 50. For example, the patient interface setting control 154 may enable the assistant to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the assistant to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the assistant to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the assistant to change the font size setting of the patient interface 50.

The example overview display 120 shown in FIG. 5 also includes an interface communications display 156 showing the status of communications between the patient interface 50 and one or more other devices 70, 82, 84, such as the treatment apparatus 70, the ambulation sensor 82, and/or the goniometer 84. The interface communications display 156 may take the form of a portion or region of the overview display 120, as shown in FIG. 5. The interface communications display 156 may take other forms, such as a separate screen or a popup window. The interface communications display 156 may include controls for the assistant to remotely modify communications with one or more of the other devices 70, 82, 84. For example, the assistant may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 shown in FIG. 5 also includes an apparatus control 160 for the assistant to view and/or to control information regarding the treatment apparatus 70. The apparatus control 160 may take the form of a portion or region of the overview display 120, as shown in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99b. The apparatus status display 162 may indicate whether the treatment apparatus 70 is currently communicating with the patient interface 50. The apparatus status display 162 may present other current and/or historical information regarding the status of the treatment apparatus 70.

The apparatus control 160 may include an apparatus setting control 164 for the assistant to adjust or control one or more aspects of the treatment apparatus 70. The apparatus setting control 164 may cause the assistant interface 94 to generate and/or to transmit an apparatus control signal 99a for changing an operating parameter of the treatment apparatus 70, (e.g., a pedal radius setting, a resistance setting, a target RPM, other suitable characteristics of the treatment device 70, or a combination thereof).

The apparatus setting control 164 may include a mode button 166 and a position control 168, which may be used in conjunction for the assistant to place an actuator 78 of the treatment apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the assistant may change an operating parameter of the treatment apparatus 70, such as a pedal radius setting, while the patient is actively using the treatment apparatus 70. Such "on the fly" adjustment may or may not be available to the patient using the patient interface 50. In some embodiments, the apparatus setting control 164 may allow the assistant to change a setting that cannot be changed by the patient using the patient interface 50. For example, the patient interface 50 may be precluded from changing a preconfigured setting, such as a height or a tilt setting of the treatment apparatus 70, whereas the apparatus setting control 164 may provide for the assistant to change the height or tilt setting of the treatment apparatus 70.

The example overview display 120 shown in FIG. 5 also includes a patient communications control 170 for controlling an audio or an audiovisual communications session with the patient interface 50. The communications session with the patient interface 50 may comprise a live feed from the assistant interface 94 for presentation by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one. In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 5. The patient communications control 170 may take other forms, such as a separate screen or a popup window. The audio and/or audiovisual communications may be processed and/or directed by the assistant interface 94 and/or by another device or devices, such as a telephone system, or a videoconferencing system used by the assistant while the assistant uses the assistant interface 94. Alternatively or additionally, the audio and/or audiovisual communications may include communications with a third party. For example, the system 10 may enable the assistant to initiate a 3-way conversation regarding use of a particular piece of hardware or software, with the patient and a subject matter expert, such as a medical professional or a specialist. The example patient communications control 170 shown in FIG. 5 includes call controls 172 for the assistant to use in managing various aspects of the audio or audiovisual communications with the patient. The call controls 172 include a disconnect button 174 for the assistant to end the audio or audiovisual communications session. The call controls 172 also include a mute button 176 to temporarily silence an audio or audiovisual signal from the assistant interface 94. In some embodiments, the call controls 172 may include other features, such as a hold button (not shown). The call controls 172 also include one or more record/playback controls 178, such as record, play, and pause buttons to control, with the patient interface 50, recording and/or playback of audio and/or video from the teleconference session (e.g., which may be referred to herein as the virtual conference room). The call controls 172 also include a video feed display 180 for presenting still and/or video images from the patient interface 50, and a self-video display 182 showing the current image of the assistant using the assistant interface. The self-video display 182 may be presented as a picture-in-picture format, within a section of the video feed display 180, as shown in FIG. 5. Alternatively or additionally, the self-video display 182 may be presented separately and/or independently from the video feed display 180.

The example overview display 120 shown in FIG. 5 also includes a third-party communications control 190 for use in conducting audio and/or audiovisual communications with a third party. The third-party communications control 190 may take the form of a portion or region of the overview display 120, as shown in FIG. 5. The third-party communications control 190 may take other forms, such as a display on a separate screen or a popup window. The third-party communications control 190 may include one or more controls, such as a contact list and/or buttons or controls to contact a third party regarding use of a particular piece of hardware or software, e.g., a subject matter expert, such as a medical professional or a specialist. The third-party communications control 190 may include conference calling capability for the third party to simultaneously communicate with both the assistant via the assistant interface 94, and with the patient via the patient interface 50. For example, the system 10 may provide for the assistant to initiate a 3-way conversation with the patient and the third party.

Figure 6:
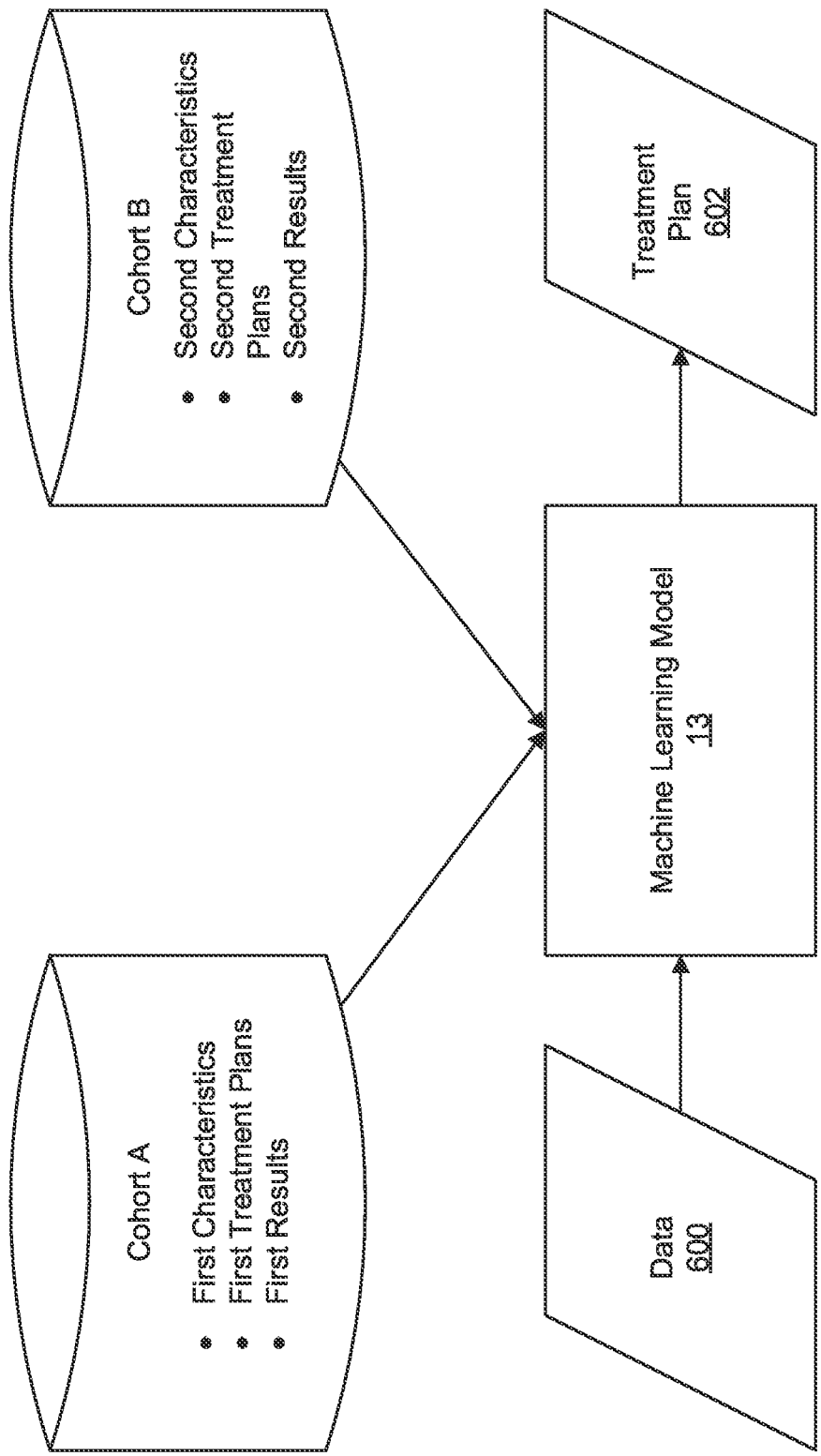
FIG. 6 generally illustrates an example block diagram of training a machine learning model to output, based on data pertaining to the patient, a treatment plan for the patient according to the principles of the present disclosure.

FIG. 6 shows an example block diagram of training a machine learning model 13 to output, based on data 600 pertaining to the patient, a treatment plan 602 for the patient according to the present disclosure. Data pertaining to other patients may be received by the server 30. The other patients may have used various treatment apparatuses to perform treatment plans. The data may include characteristics of the other patients, the details of the treatment plans performed by the other patients, and/or the results of performing the treatment plans (e.g., a percent of recovery of a portion of the patients' bodies, an amount of recovery of a portion of the patients' bodies, an amount of increase or decrease in muscle strength of a portion of patients' bodies, an amount of increase or decrease in range of motion of a portion of patients' bodies, etc.).

As depicted, the data has been assigned to different cohorts. Cohort A includes data for patients having similar first characteristics, first treatment plans, and first results. Cohort B includes data for patients having similar second characteristics, second treatment plans, and second results. For example, cohort A may include first characteristics of patients in their twenties without any medical conditions who underwent surgery for a broken limb; their treatment plans may include a certain treatment protocol (e.g., use the treatment apparatus 70 for 30 minutes 5 times a week for 3 weeks, wherein values for the properties, configurations, and/or settings of the treatment apparatus 70 are set to X (where X is a numerical value) for the first two weeks and to Y (where Y is a numerical value) for the last week).

Cohort A and cohort B may be included in a training dataset used to train the machine learning model 13. The machine learning model 13 may be trained to match a pattern between characteristics for each cohort and output the treatment plan that provides the result. Accordingly, when the data 600 for a new patient is input into the trained machine learning model 13, the trained machine learning model 13 may match the characteristics included in the data 600 with characteristics in either cohort A or cohort B and output the appropriate treatment plan 602. In some embodiments, the machine learning model 13 may be trained to output one or more excluded treatment plans that should not be performed by the new patient.

Figure 7:
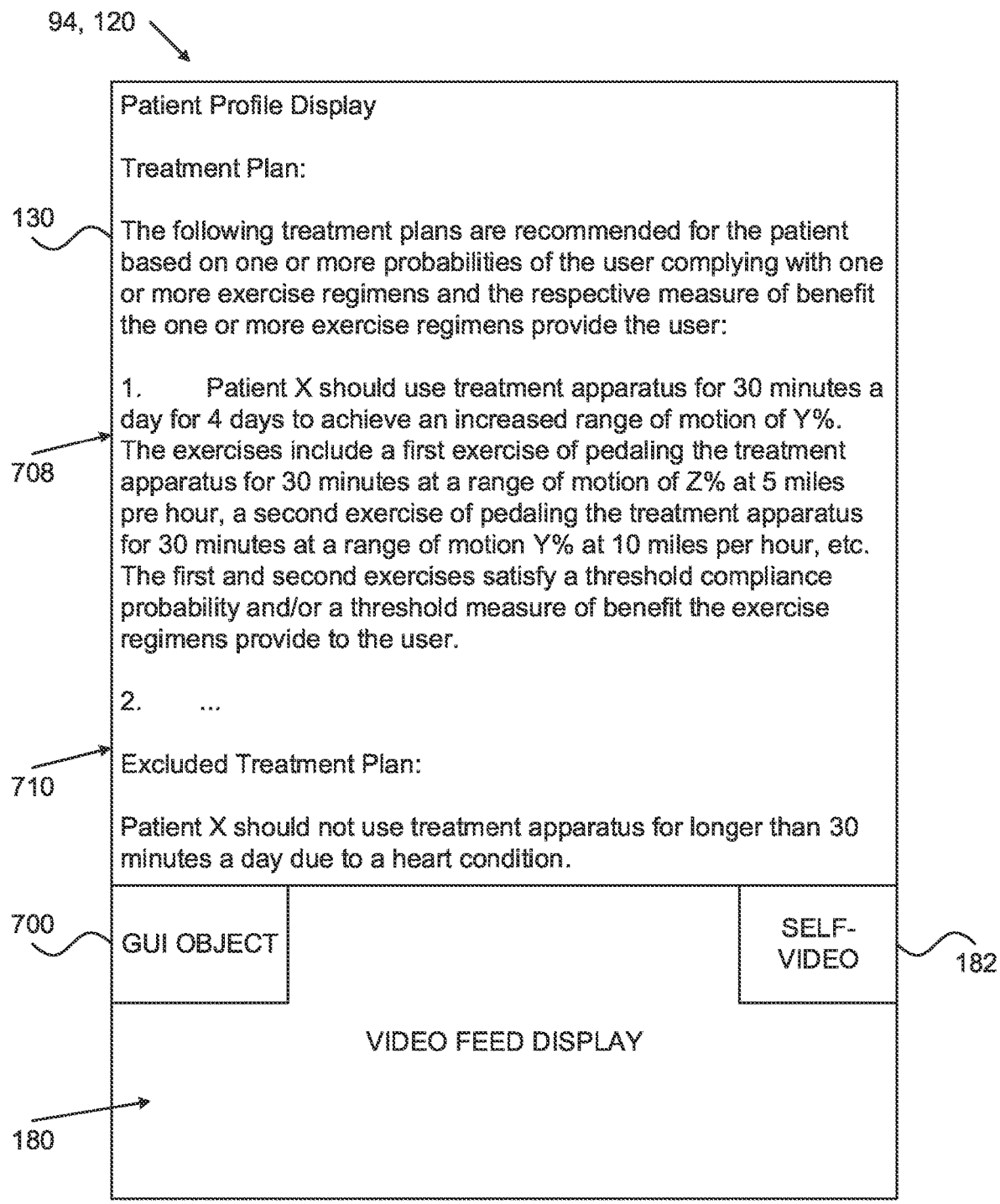
FIG. 7 generally illustrates an embodiment of an overview display of the assistant interface presenting recommended treatment plans and excluded treatment plans in real-time during a telemedicine session according to the principles of the present disclosure.

FIG. 7 shows an embodiment of an overview display 120 of the assistant interface 94 presenting recommended treatment plans and excluded treatment plans in real-time during a telemedicine session according to the present disclosure. As depicted, the overview display 120 only includes sections for the patient profile 130 and the video feed display 180, including the self-video display 182. Any suitable configuration of controls and interfaces of the overview display 120 described with reference to FIG. 5 may be presented in addition to or instead of the patient profile 130, the video feed display 180, and the self-video display 182.

The healthcare professional using the assistant interface 94 (e.g., computing device) during the telemedicine session may be presented in the self-video 182 in a portion of the overview display 120 (e.g., user interface presented on a display screen 24 of the assistant interface 94) that also presents a video from the patient in the video feed display 180. Further, the video feed display 180 may also include a graphical user interface (GUI) object 700 (e.g., a button) that enables the healthcare professional to share on the patient interface 50, in real-time or near real-time during the telemedicine session, the recommended treatment plans and/or the excluded treatment plans with the patient. The healthcare professional may select the GUI object 700 to share the recommended treatment plans and/or the excluded treatment plans. As depicted, another portion of the overview display 120 includes the patient profile display 130.

In FIG. 7, the patient profile display 130 is presenting two example recommended treatment plans 708 and one example excluded treatment plan 710. As described herein, the treatment plans may be recommended based on the one or more probabilities and the respective measure of benefit the one or more exercises provide the user. The trained machine learning models 13 may (i) use treatment data pertaining to a user to determine a respective measure of benefit which one or more exercise regimens provide the user, (ii) determine one or more probabilities of the user associated with complying with the one or more exercise regimens, and (iii) generate, using the one or more probabilities and the respective measure of benefit the one or more exercises provide to the user, the treatment plan. In some embodiments, the one or more trained machine learning models 13 may generate treatment plans including exercises associated with a certain threshold (e.g., any suitable percentage metric, value, percentage, number, indicator, probability, etc., which may be configurable) associated with the user complying with the one or more exercise regimens to enable achieving a higher user compliance with the treatment plan. In some embodiments, the one or more trained machine learning models 13 may generate treatment plans including exercises associated with a certain threshold (e.g., any suitable percentage metric, value, percentage, number, indicator, probability, etc., which may be configurable) associated with one or more measures of benefit the exercises provide to the user to enable achieving the benefits (e.g., strength, flexibility, range of motion, etc.) at a faster rate, at a greater proportion, etc. In some embodiments, when both the measures of benefit and the probability of compliance are considered by the trained machine learning models 13, each of the measures of benefit and the probability of compliance may be associated with a different weight, such different weight causing one to be more influential than the other. Such techniques may enable configuring which parameter (e.g., probability of compliance or measures of benefit) is more desirable to consider more heavily during generation of the treatment plan.

For example, as depicted, the patient profile display 130 presents "The following treatment plans are recommended for the patient based on one or more probabilities of the user complying with one or more exercise regimens and the respective measure of benefit the one or more exercises provide the user." Then, the patient profile display 130 presents a first recommended treatment plan.

As depicted, treatment plan "1" indicates "Patient X should use treatment apparatus for 30 minutes a day for 4 days to achieve an increased range of motion of Y %. The exercises include a first exercise of pedaling the treatment apparatus for 30 minutes at a range of motion of Z % at 5 miles per hour, a second exercise of pedaling the treatment apparatus for 30 minutes at a range of motion of Y % at 10 miles per hour, etc. The first and second exercise satisfy a threshold compliance probability and/or a threshold measure of benefit which the exercise regimens provide to the user." Accordingly, the treatment plan generated includes a first and second exercise, etc. that increase the range of motion of Y %. Further, in some embodiments, the exercises are indicated as satisfying a threshold compliance probability and/or a threshold measure of benefit which the exercise regimens provide to the user. Each of the exercises may specify any suitable parameter of the exercise and/or treatment apparatus 70 (e.g., duration of exercise, speed of motor of the treatment apparatus 70, range of motion setting of pedals, etc.). This specific example and all such examples elsewhere herein are not intended to limit in any way the generated treatment plan from recommending any suitable number and/or type of exercise.

Recommended treatment plan "2" may specify, based on a desired benefit, an indication of a probability of compliance, or some combination thereof, and different exercises for the user to perform.

As depicted, the patient profile display 130 may also present the excluded treatment plans 710. These types of treatment plans are shown to the assistant using the assistant interface 94 to alert the assistant not to recommend certain portions of a treatment plan to the patient. For example, the excluded treatment plan could specify the following: "Patient X should not use treatment apparatus for longer than 30 minutes a day due to a heart condition." Specifically, the excluded treatment plan points out a limitation of a treatment protocol where, due to a heart condition, Patient X should not exercise for more than 30 minutes a day. The excluded treatment plans may be based on treatment data (e.g., characteristics of the user, characteristics of the treatment apparatus 70, or the like).

The assistant may select the treatment plan for the patient on the overview display 120. For example, the assistant may use an input peripheral (e.g., mouse, touchscreen, microphone, keyboard, etc.) to select from the treatment plans 708 for the patient.

In any event, the assistant may select the treatment plan for the patient to follow to achieve a desired result. The selected treatment plan may be transmitted to the patient interface 50 for presentation. The patient may view the selected treatment plan on the patient interface 50. In some embodiments, the assistant and the patient may discuss during the telemedicine session the details (e.g., treatment protocol using treatment apparatus 70, diet regimen, medication regimen, etc.) in real-time or in near real-time. In some embodiments, as discussed further with reference to method 1000 of FIG. 10 below, the server 30 may control, based on the selected treatment plan and during the telemedicine session, the treatment apparatus 70 as the user uses the treatment apparatus 70.

Figure 8:
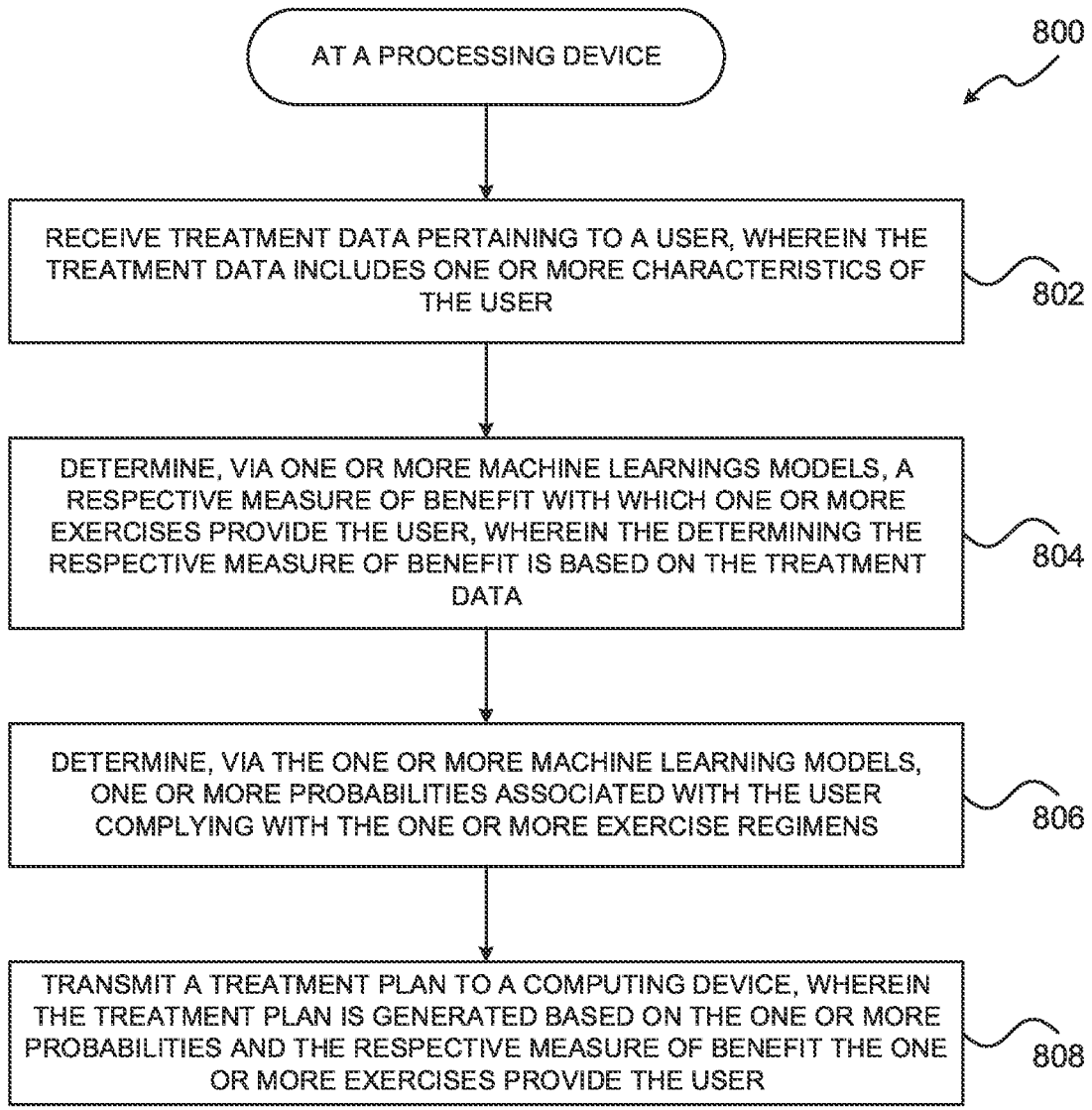
FIG. 8 generally illustrates an example embodiment of a method for optimizing a treatment plan for a user to increase a probability of the user complying with the treatment plan according to the principles of the present disclosure.

FIG. 8 shows an example embodiment of a method 800 for optimizing a treatment plan for a user to increase a probability of the user complying with the treatment plan according to the present disclosure. The method 800 is performed by processing logic that may include hardware (circuitry, dedicated logic, etc.), software (such as is run on a general-purpose computer system or a dedicated machine), or a combination of both. The method 800 and/or each of its individual functions, routines, other methods, scripts, subroutines, or operations may be performed by one or more processors of a computing device (e.g., any component of FIG. 1, such as server 30 executing the artificial intelligence engine 11). In certain implementations, the method 800 may be performed by a single processing thread. Alternatively, the method 800 may be performed by two or more processing threads, each thread implementing one or more individual functions or routines; or other methods, scripts, subroutines, or operations of the methods.

For simplicity of explanation, the method 800 is depicted and described as a series of operations. However, operations in accordance with this disclosure can occur in various orders and/or concurrently, and/or with other operations not presented and described herein. For example, the operations depicted in the method 800 may occur in combination with any other operation of any other method disclosed herein. Furthermore, not all illustrated operations may be required to implement the method 800 in accordance with the disclosed subject matter. In addition, those skilled in the art will understand and appreciate that the method 800 could alternatively be represented as a series of interrelated states via a state diagram, a directed graph, a deterministic finite state automaton, a non-deterministic finite state automaton, a Markov diagram, or event diagrams.

At 802, the processing device may receive treatment data pertaining to a user (e.g., patient, volunteer, trainee, assistant, healthcare professional, instructor, etc.). The treatment data may include one or more characteristics (e.g., vital-sign or other measurements; performance; demographic; psychographic; geographic; diagnostic; measurement- or test-based; medically historic; etiologic; cohort-associative; differentially diagnostic; surgical, physically therapeutic, pharmacologic and other treatment(s) recommended; arterial blood gas and/or oxygenation levels or percentages; psychographics; etc.) of the user. The treatment data may include one or more characteristics of the treatment apparatus 70. In some embodiments, the one or more characteristics of the treatment apparatus 70 may include a make (e.g., identity of entity that designed, manufactured, etc. the treatment apparatus 70) of the treatment apparatus 70, a model (e.g., model number or other identifier of the model) of the treatment apparatus 70, a year (e.g., year of manufacturing) of the treatment apparatus 70, operational parameters (e.g., motor temperature during operation; status of each sensor included in or associated with the treatment apparatus 70; the patient, or the environment; vibration measurements of the treatment apparatus 70 in operation; measurements of static and/or dynamic forces exerted on the treatment apparatus 70; etc.) of the treatment apparatus 70, settings (e.g., range of motion setting; speed setting; required pedal force setting; etc.) of the treatment apparatus 70, and the like. In some embodiments, the characteristics of the user and/or the characteristics of the treatment apparatus 70 may be tracked over time to obtain historical data pertaining to the characteristics of the user and/or the treatment apparatus 70. The foregoing embodiments shall also be deemed to include the use of any optional internal components or of any external components attachable to, but separate from the treatment apparatus itself. "Attachable" as used herein shall be physically, electronically, mechanically, virtually or in an augmented reality manner.

In some embodiments, when generating a treatment plan, the characteristics of the user and/or treatment apparatus 70 may be used. For example, certain exercises may be selected or excluded based on the characteristics of the user and/or treatment apparatus 70. For example, if the user has a heart condition, high intensity exercises may be excluded in a treatment plan. In another example, a characteristic of the treatment apparatus 70 may indicate the motor shudders, stalls or otherwise runs improperly at a certain number of revolutions per minute. In order to extend the lifetime of the treatment apparatus 70, the treatment plan may exclude exercises that include operating the motor at that certain revolutions per minute or at a prescribed manufacturing tolerance within those certain revolutions per minute.

At 804, the processing device may determine, via one or more trained machine learning models 13, a respective measure of benefit with which one or more exercises provide the user. In some embodiments, based on the treatment data, the processing device may execute the one or more trained machine learning models 13 to determine the respective measures of benefit. For example, the treatment data may include the characteristics of the user (e.g., heartrate, vital-sign, medical condition, injury, surgery, etc.), and the one or more trained machine learning models may receive the treatment data and output the respective measure of benefit with which one or more exercises provide the user. For example, if the user has a heart condition, a high intensity exercise may provide a negative benefit to the user, and thus, the trained machine learning model may output a negative measure of benefit for the high intensity exercise for the user. In another example, an exercise including pedaling at a certain range of motion may have a positive benefit for a user recovering from a certain surgery, and thus, the trained machine learning model may output a positive measure of benefit for the exercise regimen for the user.

At 806, the processing device may determine, via the one or more trained machine learning models 13, one or more probabilities associated with the user complying with the one or more exercise regimens. In some embodiments, the relationship between the one or more probabilities associated with the user complying with the one or more exercise regimens may be one to one, one to many, many to one, or many to many. The one or more probabilities of compliance may refer to a metric (e.g., value, percentage, number, indicator, probability, etc.) associated with a probability the user will comply with an exercise regimen. In some embodiments, the processing device may execute the one or more trained machine learning models 13 to determine the one or more probabilities based on (i) historical data pertaining to the user, another user, or both, (ii) received feedback from the user, another user, or both, (iii) received feedback from a treatment apparatus used by the user, or (iv) some combination thereof.

For example, historical data pertaining to the user may indicate a history of the user previously performing one or more of the exercises. In some instances, at a first time, the user may perform a first exercise to completion. At a second time, the user may terminate a second exercise prior to completion. Feedback data from the user and/or the treatment apparatus 70 may be obtained before, during, and after each exercise performed by the user. The trained machine learning model may use any combination of data (e.g., (i) historical data pertaining to the user, another user, or both, (ii) received feedback from the user, another user, or both, (iii) received feedback from a treatment apparatus used by the user) described above to learn a user compliance profile for each of the one or more exercises. The term "user compliance profile" may refer to a collection of histories of the user complying with the one or more exercise regimens. In some embodiments, the trained machine learning model may use the user compliance profile, among other data (e.g., characteristics of the treatment apparatus 70), to determine the one or more probabilities of the user complying with the one or more exercise regimens.

At 808, the processing device may transmit a treatment plan to a computing device. The computing device may be any suitable interface described herein. For example, the treatment plan may be transmitted to the assistant interface 94 for presentation to a healthcare professional, and/or to the patient interface 50 for presentation to the patient. The treatment plan may be generated based on the one or more probabilities and the respective measure of benefit the one or more exercises may provide to the user. In some embodiments, as described further below with reference to the method 1000 of FIG. 10, while the user uses the treatment apparatus 70, the processing device may control, based on the treatment plan, the treatment apparatus 70.

In some embodiments, the processing device may generate, using at least a subset of the one or more exercises, the treatment plan for the user to perform, wherein such performance uses the treatment apparatus 70. The processing device may execute the one or more trained machine learning models 13 to generate the treatment plan based on the respective measure of the benefit the one or more exercises provide to the user, the one or more probabilities associated with the user complying with each of the one or more exercise regimens, or some combination thereof. For example, the one or more trained machine learning models 13 may receive the respective measure of the benefit the one or more exercises provide to the user, the one or more probabilities of the user associated with complying with each of the one or more exercise regimens, or some combination thereof as input and output the treatment plan.

In some embodiments, during generation of the treatment plan, the processing device may more heavily or less heavily weight the probability of the user complying than the respective measure of benefit the one or more exercise regimens provide to the user. During generation of the treatment plan, such a technique may enable one of the factors (e.g., the probability of the user complying or the respective measure of benefit the one or more exercise regimens provide to the user) to become more important than the other factor. For example, if desirable to select exercises that the user is more likely to comply with in a treatment plan, then the one or more probabilities of the user associated with complying with each of the one or more exercise regimens may receive a higher weight than one or more measures of exercise benefit factors. In another example, if desirable to obtain certain benefits provided by exercises, then the measure of benefit an exercise regimen provides to a user may receive a higher weight than the user compliance probability factor. The weight may be any suitable value, number, modifier, percentage, probability, etc.

In some embodiments, the processing device may generate the treatment plan using a non-parametric model, a parametric model, or a combination of both a non-parametric model and a parametric model. In statistics, a parametric model or finite-dimensional model refers to probability distributions that have a finite number of parameters. Non-parametric models include model structures not specified a priori but instead determined from data. In some embodiments, the processing device may generate the treatment plan using a probability density function, a Bayesian prediction model, a Markovian prediction model, or any other suitable mathematically-based prediction model. A Bayesian prediction model is used in statistical inference where Bayes' theorem is used to update the probability for a hypothesis as more evidence or information becomes available. Bayes' theorem may describe the probability of an event, based on prior knowledge of conditions that might be related to the event. For example, as additional data (e.g., user compliance data for certain exercises, characteristics of users, characteristics of treatment apparatuses, and the like) are obtained, the probabilities of compliance for users for performing exercise regimens may be continuously updated. The trained machine learning models 13 may use the Bayesian prediction model and, in preferred embodiments, continuously, constantly or frequently be re-trained with additional data obtained by the artificial intelligence engine 11 to update the probabilities of compliance, and/or the respective measure of benefit one or more exercises may provide to a user.

In some embodiments, the processing device may generate the treatment plan based on a set of factors. In some embodiments, the set of factors may include an amount, quality or other quality of sleep associated with the user, information pertaining to a diet of the user, information pertaining to an eating schedule of the user, information pertaining to an age of the user, information pertaining to a sex of the user, information pertaining to a gender of the user, an indication of a mental state of the user, information pertaining to a genetic condition of the user, information pertaining to a disease state of the user, an indication of an energy level of the user, or some combination thereof. For example, the set of factors may be included in the training data used to train and/or re-train the one or more machine learning models 13. For example, the set of factors may be labeled as corresponding to treatment data indicative of certain measures of benefit one or more exercises provide to the user, probabilities of the user complying with the one or more exercise regimens, or both.

Figure 9:
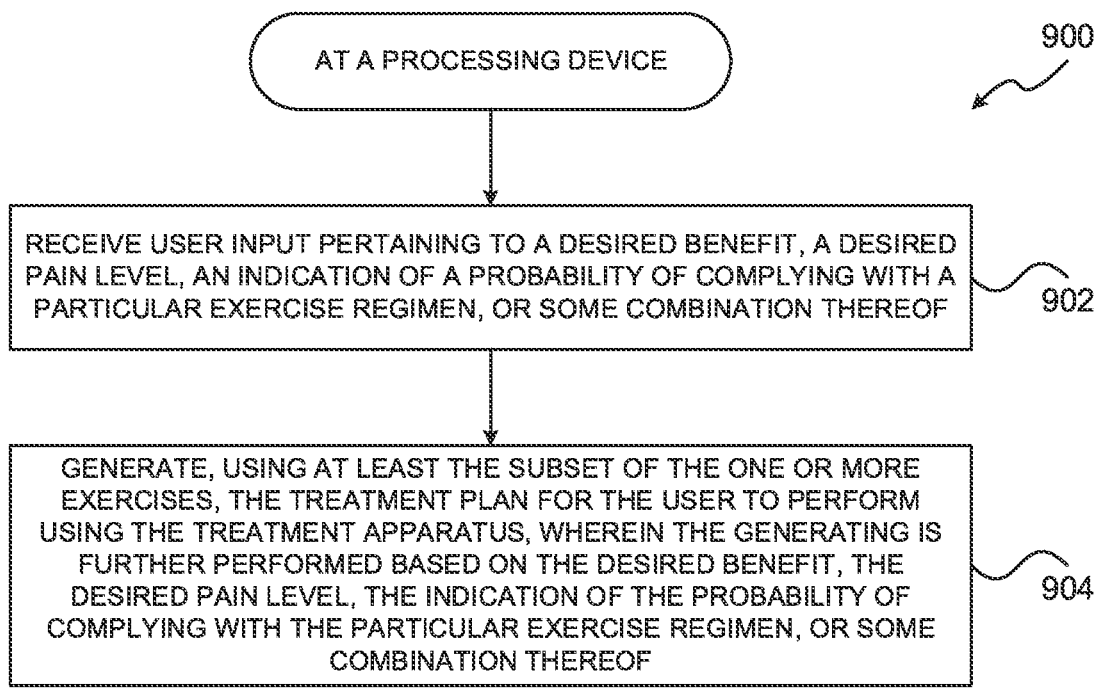
FIG. 9 generally illustrates an example embodiment of a method for generating a treatment plan based on a desired benefit, a desired pain level, an indication of probability of complying with a particular exercise regimen, or some combination thereof according to the principles of the present disclosure.

FIG. 9 shows an example embodiment of a method 900 for generating a treatment plan based on a desired benefit, a desired pain level, an indication of a probability associated with complying with the particular exercise regimen, or some combination thereof, according to some embodiments. Method 900 includes operations performed by processors of a computing device (e.g., any component of FIG. 1, such as server 30 executing the artificial intelligence engine 11). In some embodiments, one or more operations of the method 900 are implemented in computer instructions stored on a memory device and executed by a processing device. The method 900 may be performed in the same or a similar manner as described above in regard to method 800. The operations of the method 900 may be performed in some combination with any of the operations of any of the methods described herein.

At 902, the processing device may receive user input pertaining to a desired benefit, a desired pain level, an indication of a probability associated with complying with a particular exercise regimen, or some combination thereof. The user input may be received from the patient interface 50. That is, in some embodiments, the patient interface 50 may present a display including various graphical elements that enable the user to enter a desired benefit of performing an exercise, a desired pain level (e.g., on a scale ranging from 1-10, 1 being the lowest pain level and 10 being the highest pain level), an indication of a probability associated with complying with the particular exercise regimen, or some combination thereof. For example, the user may indicate he or she would not comply with certain exercises (e.g., one-arm push-ups) included in an exercise regimen due to a lack of ability to perform the exercise and/or a lack of desire to perform the exercise. The patient interface 50 may transmit the user input to the processing device (e.g., of the server 30, assistant interface 94, or any suitable interface described herein).

At 904, the processing device may generate, using at least a subset of the one or more exercises, the treatment plan for the user to perform wherein the performance uses the treatment apparatus 70. The processing device may generate the treatment plan based on the user input including the desired benefit, the desired pain level, the indication of the probability associated with complying with the particular exercise regimen, or some combination thereof. For example, if the user selected a desired benefit of improved range of motion of flexion and extension of their knee, then the one or more trained machine learning models 13 may identify, based on treatment data pertaining to the user, exercises that provide the desired benefit. Those identified exercises may be further filtered based on the probabilities of user compliance with the exercise regimens. Accordingly, the one or more machine learning models 13 may be interconnected, such that the output of one or more trained machine learning models that perform function(s) (e.g., determine measures of benefit exercises provide to user) may be provided as input to one or more other trained machine learning models that perform other functions(s) (e.g., determine probabilities of the user complying with the one or more exercise regimens, generate the treatment plan based on the measures of benefit and/or the probabilities of the user complying, etc.).

Figure 10:
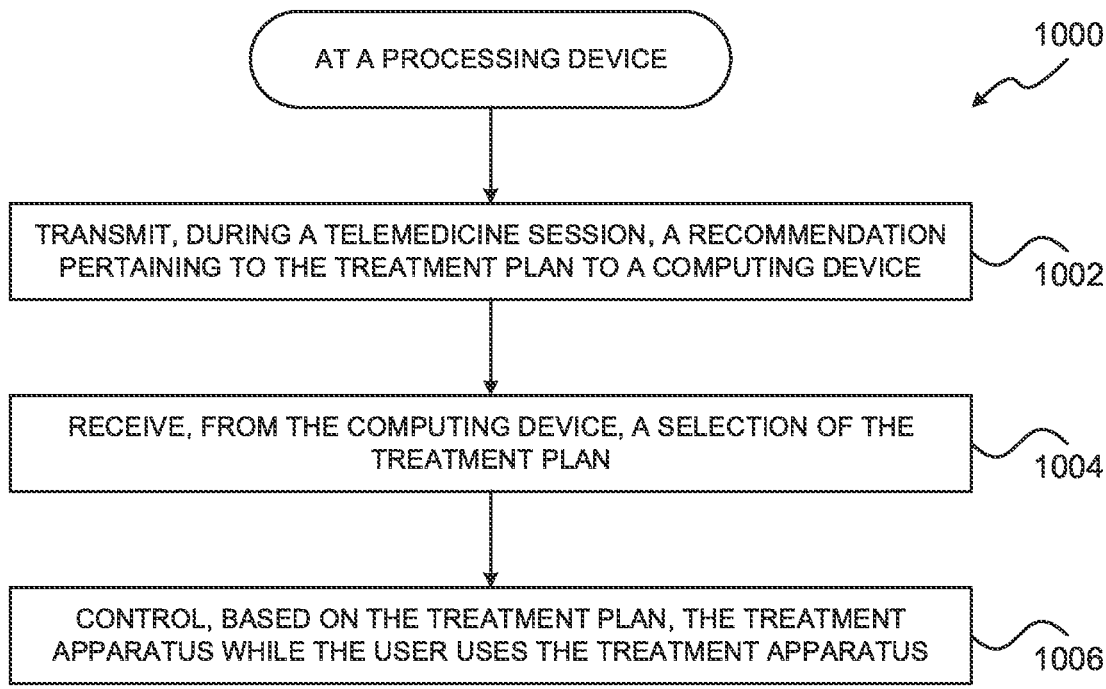
FIG. 10 generally illustrates an example embodiment of a method for controlling, based on a treatment plan, a treatment apparatus while a user uses the treatment apparatus according to the principles of the present disclosure.

FIG. 10 shows an example embodiment of a method 1000 for controlling, based on a treatment plan, a treatment apparatus 70 while a user uses the treatment apparatus 70, according to some embodiments. Method 1000 includes operations performed by processors of a computing device (e.g., any component of FIG. 1, such as server 30 executing the artificial intelligence engine 11). In some embodiments, one or more operations of the method 1000 are implemented in computer instructions stored on a memory device and executed by a processing device. The method 1000 may be performed in the same or a similar manner as described above in regard to method 800. The operations of the method 1000 may be performed in some combination with any of the operations of any of the methods described herein.

At 1002, the processing device may transmit, during a telemedicine or telehealth session, a recommendation pertaining to a treatment plan to a computing device (e.g., patient interface 50, assistant interface 94, or any suitable interface described herein). The recommendation may be presented on a display screen of the computing device in real-time (e.g., less than 2 seconds) in a portion of the display screen while another portion of the display screen presents video of a user (e.g., patient, healthcare professional, or any suitable user). The recommendation may also be presented on a display screen of the computing device in near time (e.g., preferably more than or equal to 2 seconds and less than or equal to 10 seconds) or with a suitable time delay necessary for the user of the display screen to be able to observe the display screen.

At 1004, the processing device may receive, from the computing device, a selection of the treatment plan. The user (e.g., patient, healthcare professional, assistant, etc.) may use any suitable input peripheral (e.g., mouse, keyboard, microphone, touchpad, etc.) to select the recommended treatment plan. The computing device may transmit the selection to the processing device of the server 30, which is configured to receive the selection. There may any suitable number of treatment plans presented on the display screen. Each of the treatment plans recommended may provide different results and the healthcare professional may consult, during the telemedicine session, with the user, to discuss which result the user desires. In some embodiments, the recommended treatment plans may only be presented on the computing device of the healthcare professional and not on the computing device of the user (patient interface 50). In some embodiments, the healthcare professional may choose an option presented on the assistant interface 94. The option may cause the treatment plans to be transmitted to the patient interface 50 for presentation. In this way, during the telemedicine session, the healthcare professional and the user may view the treatment plans at the same time in real-time or in near real-time, which may provide for an enhanced user experience for the patient and/or healthcare professional using the computing device.

After the selection of the treatment plan is received at the server 30, at 1006, while the user uses the treatment apparatus 70, the processing device may control, based on the selected treatment plan, the treatment apparatus 70. In some embodiments, controlling the treatment apparatus 70 may include the server 30 generating and transmitting control instructions to the treatment apparatus 70. In some embodiments, controlling the treatment apparatus 70 may include the server 30 generating and transmitting control instructions to the patient interface 50, and the patient interface 50 may transmit the control instructions to the treatment apparatus 70. The control instructions may cause an operating parameter (e.g., speed, orientation, required force, range of motion of pedals, etc.) to be dynamically changed according to the treatment plan (e.g., a range of motion may be changed to a certain setting based on the user achieving a certain range of motion for a certain period of time). The operating parameter may be dynamically changed while the patient uses the treatment apparatus 70 to perform an exercise. In some embodiments, during a telemedicine session between the patient interface 50 and the assistant interface 94, the operating parameter may be dynamically changed in real-time or near real-time.

Figure 11:
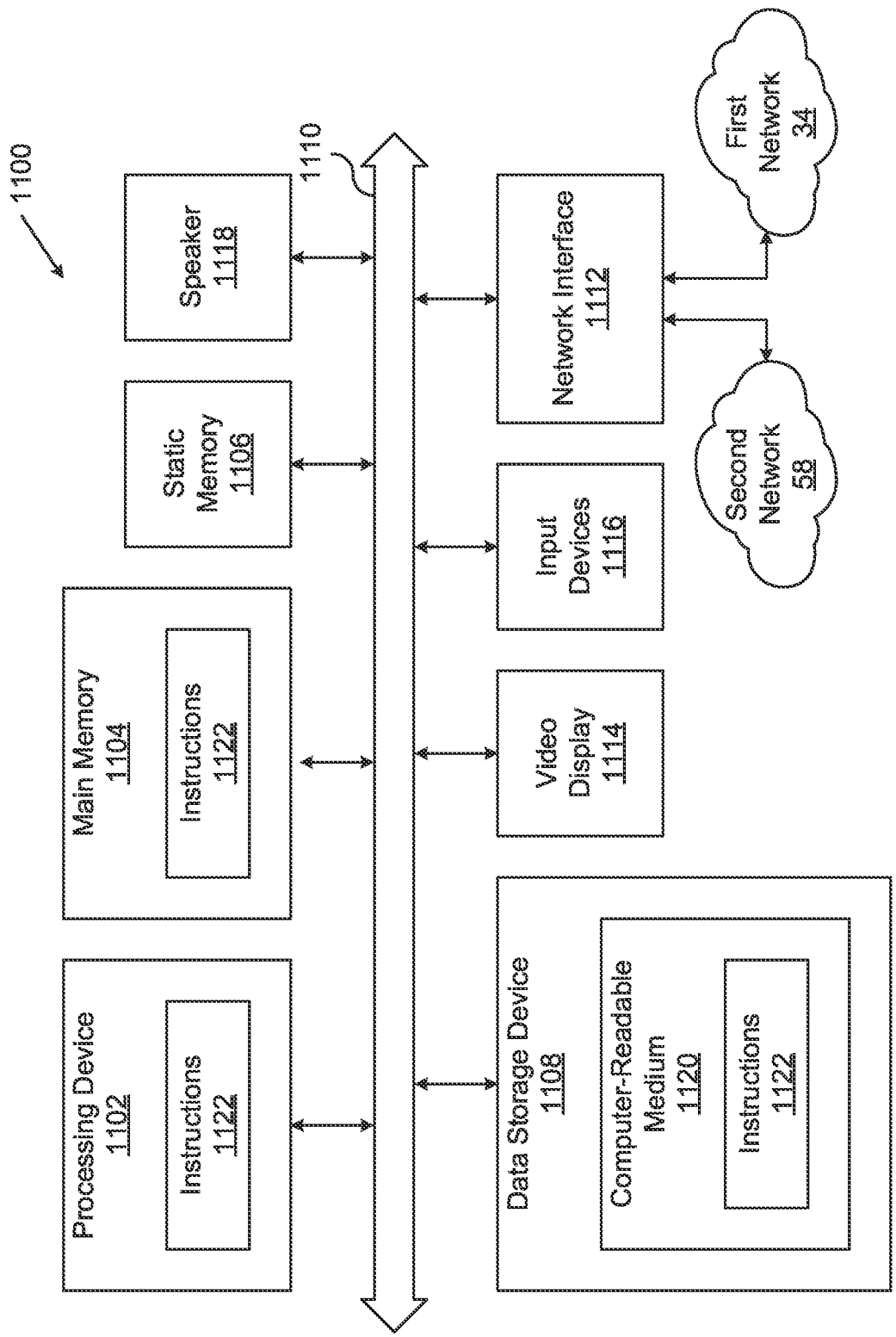
FIG. 11 generally illustrates an example computer system according to the principles of the present disclosure.

FIG. 11 shows an example computer system 1100 which can perform any one or more of the methods described herein, in accordance with one or more aspects of the present disclosure. In one example, computer system 1100 may include a computing device and correspond to the assistance interface 94, reporting interface 92, supervisory interface 90, clinician interface 20, server 30 (including the AI engine 11), patient interface 50, ambulatory sensor 82, goniometer 84, treatment apparatus 70, pressure sensor 86, or any suitable component of FIG. 1, further the computer system 1100 may include the computing device 1200 of FIG. 12. The computer system 1100 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1100 includes a processing device 1102, a main memory 1104 (e.g., read-only memory (ROM), flash memory, solid state drives (SSDs), dynamic random-access memory (DRAM) such as synchronous DRAM (SDRAM)), a static memory 1106 (e.g., flash memory, solid state drives (SSDs), static random access memory (SRAM)), and a data storage device 1108, which communicate with each other via a bus 1110.

Processing device 1102 represents one or more general-purpose processing devices such as a microprocessor, central processing unit, or the like. More particularly, the processing device 1102 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1102 may also be one or more special-purpose processing devices such as an application specific integrated circuit (ASIC), a system on a chip, a field programmable gate array (FPGA), a digital signal processor (DSP), network processor, or the like. The processing device 1102 is configured to execute instructions for performing any of the operations and steps discussed herein.

The computer system 1100 may further include a network interface device 1112. The computer system 1100 also may include a video display 1114 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1116 (e.g., a keyboard and/or a mouse or a gaming-like control), and one or more speakers 1118 (e.g., a speaker). In one illustrative example, the video display 1114 and the input device(s) 1116 may be combined into a single component or device (e.g., an LCD touch screen).

The data storage device 1116 may include a computer-readable medium 1120 on which the instructions 1122 embodying any one or more of the methods, operations, or functions described herein is stored. The instructions 1122 may also reside, completely or at least partially, within the main memory 1104 and/or within the processing device 1102 during execution thereof by the computer system 1100. As such, the main memory 1104 and the processing device 1102 also constitute computer-readable media. The instructions 1122 may further be transmitted or received over a network via the network interface device 1112.

While the computer-readable storage medium 1120 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Figure 12:
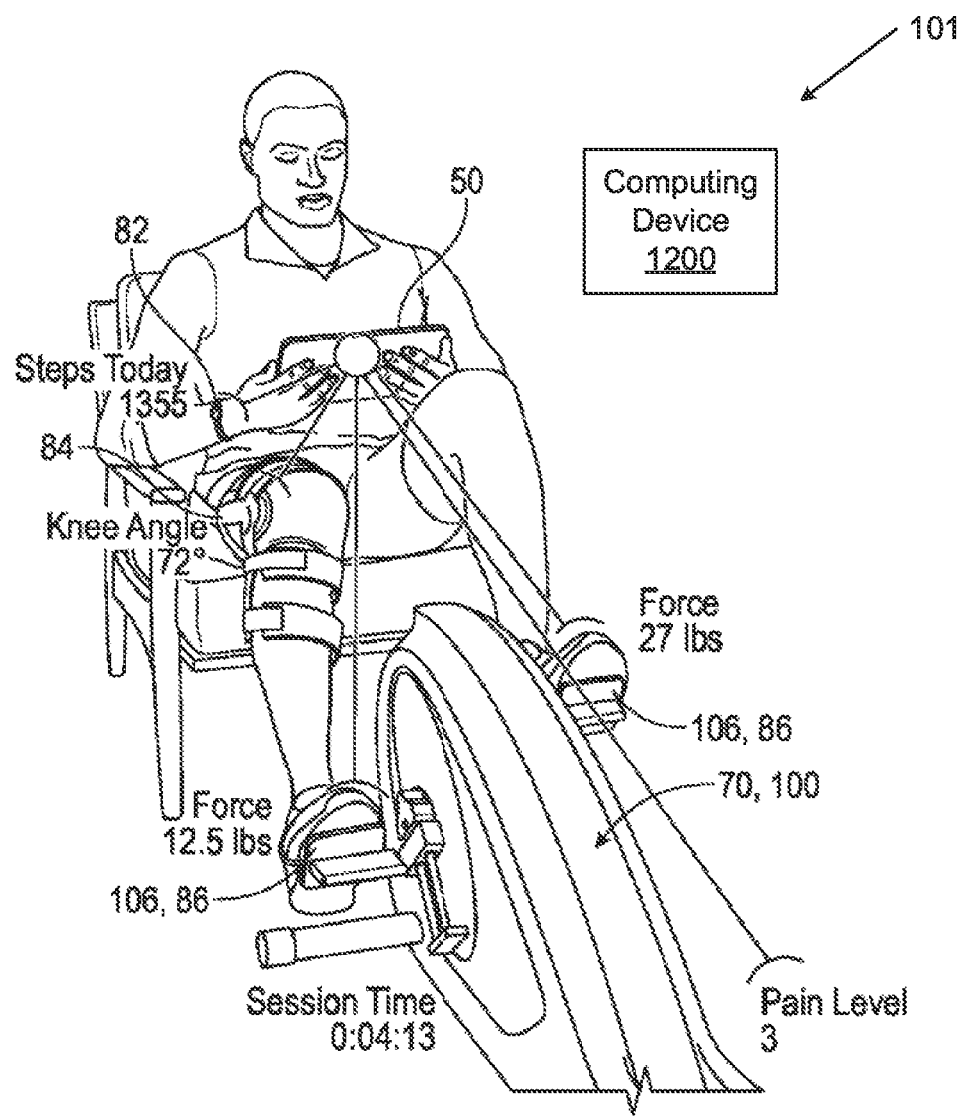
FIG. 12 generally illustrates a perspective view of a person using the treatment apparatus of FIG. 2, the patient interface 50, and a computing device according to the principles of the present disclosure.

FIG. 12 generally illustrates a perspective view of a person using the treatment apparatus 70, 100 of FIG. 2, the patient interface 50, and a computing device 1200 according to the principles of the present disclosure. In some embodiments, the patient interface 50 may not be able to communicate via a network to establish a telemedicine session with the assistant interface 94. In such an instance the computing device 1200 may be used as a relay to receive cardiovascular data from one or more sensors attached to the user and transmit the cardiovascular data to the patient interface 50 (e.g., via Bluetooth), the server 30, and/or the assistant interface 94. The computing device 1200 may be communicatively coupled to the one or more sensors via a short-range wireless protocol (e.g., Bluetooth). In some embodiments, the computing device 1200 may be connected to the assistant interface via a telemedicine session. Accordingly, the computing device 1200 may include a display configured to present video of the healthcare professional, to present instructional videos, to present treatment plans, etc. Further, the computing device 1200 may include a speaker configured to emit audio output, and a microphone configured to receive audio input (e.g., microphone).

In some embodiments, the computing device 1200 may be a smartphone capable of transmitting data via a cellular network and/or a wireless network. The computing device 1200 may include one or more memory devices storing instructions that, when executed, cause one or more processing devices to perform any of the methods described herein. The computing device 1200 may have the same or similar components as the computer system 1100 in FIG. 11.

In some embodiments, the treatment apparatus 70 may include one or more stands configured to secure the computing device 1200 and/or the patient interface 50, such that the user can exercise hands-free.

In some embodiments, the computing device 1200 functions as a relay between the one or more sensors and a second computing device (e.g., assistant interface 94) of a healthcare professional, and a third computing device (e.g., patient interface 50) is attached to the treatment apparatus and presents, on the display, information pertaining to a treatment plan.

Figure 13:
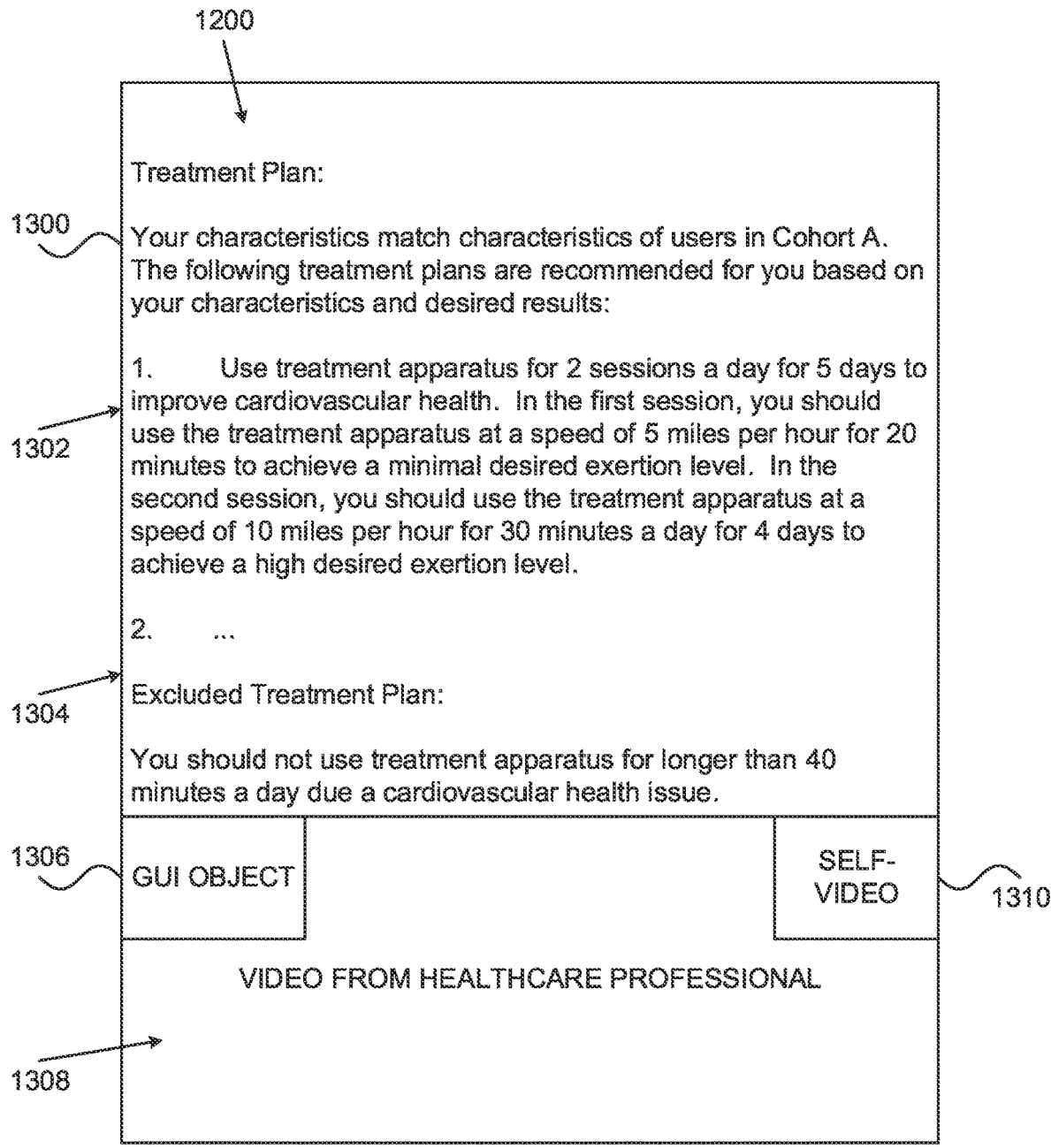
FIG. 13 generally illustrates a display of the computing device presenting a treatment plan designed to improve the user's cardiovascular health according to the principles of the present disclosure.

FIG. 13 generally illustrates a display 1300 of the computing device 1200, and the display presents a treatment plan 1302 designed to improve the user's cardiovascular health according to the principles of the present disclosure.

As depicted, the display 1300 only includes sections for the user profile 130 and the video feed display 1308, including the self-video display 1310. During a telemedicine session, the user may operate the computing device 1200 in connection with the assistant interface 94. The computing device 1200 may present a video of the user in the self-video 1310, wherein the presentation of the video of the user is in a portion of the display 1300 that also presents a video from the healthcare professional in the video feed display 1308. Further, the video feed display 1308 may also include a graphical user interface (GUI) object 1306 (e.g., a button) that enables the user to share with the healthcare professional on the assistant interface 94 in real-time or near real-time during the telemedicine session the recommended treatment plans and/or excluded treatment plans. The user may select the GUI object 1306 to select one of the recommended treatment plans. As depicted, another portion of the display 1300 may include the user profile display 1300.

In FIG. 13, the user profile display 1300 is presenting two example recommended treatment plans 1302 and one example excluded treatment plan 1304. As described herein, the treatment plans may be recommended based on a cardiovascular health issue of the user, a standardized measure comprising perceived exertion, cardiovascular data of the user, attribute data of the user, feedback data from the user, and the like. In some embodiments, the one or more trained machine learning models 13 may generate treatment plans that include exercises associated with increasing the user's cardiovascular health by a certain threshold (e.g., any suitable percentage metric, value, percentage, number, indicator, probability, etc., which may be configurable). The trained machine learning models 13 may match the user to a certain cohort based on a probability of likelihood that the user fits that cohort. A treatment plan associated with that particular cohort may be prescribed for the user, in some embodiments.

For example, as depicted, the user profile display 1300 presents "Your characteristics match characteristics of users in Cohort A. The following treatment plans are recommended for you based on your characteristics and desired results." Then, the user profile display 1300 presents a first recommended treatment plan. The treatment plans may include any suitable number of exercise sessions for a user. Each session may be associated with a different exertion level for the user to achieve or to maintain for a certain period of time. In some embodiments, more than one session may be associated with the same exertion level if having repeated sessions at the same exertion level are determined to enhance the user's cardiovascular health. The exertion levels may change dynamically between the exercise sessions based on data (e.g., the cardiovascular health issue of the user, the standardized measure of perceived exertion, cardiovascular data, attribute data, etc.) that indicates whether the user's cardiovascular health or some portion thereof is improving or deteriorating.

As depicted, treatment plan "1" indicates "Use treatment apparatus for 2 sessions a day for 5 days to improve cardiovascular health. In the first session, you should use the treatment apparatus at a speed of 5 miles per hour for 20 minutes to achieve a minimal desired exertion level. In the second session, you should use the treatment apparatus at a speed of 10 miles per hour 30 minutes a day for 4 days to achieve a high desired exertion level. The prescribed exercise includes pedaling in a circular motion profile." This specific example and all such examples elsewhere herein are not intended to limit in any way the generated treatment plan from recommending any suitable number of exercises and/or type(s) of exercise.

As depicted, the patient profile display 1300 may also present the excluded treatment plans 1304. These types of treatment plans are shown to the user by using the computing device 1200 to alert the user not to perform certain treatment plans that could potentially harm the user's cardiovascular health. For example, the excluded treatment plan could specify the following: "You should not use the treatment apparatus for longer than 40 minutes a day due to a cardiovascular health issue." Specifically, in this example, the excluded treatment plan points out a limitation of a treatment protocol where, due to a cardiovascular health issue, the user should not exercise for more than 40 minutes a day. Excluded treatment plans may be based on results from other users having a cardiovascular heart issue when performing the excluded treatment plans, other users' cardiovascular data, other users' attributes, the standardized measure of perceived exertion, or some combination thereof.

The user may select which treatment plan to initiate. For example, the user may use an input peripheral (e.g., mouse, touchscreen, microphone, keyboard, etc.) to select from the treatment plans 1302.

In some embodiments, the recommended treatment plans and excluded treatment plans may be presented on the display 120 of the assistant interface 94. The assistant may select the treatment plan for the user to follow to achieve a desired result. The selected treatment plan may be transmitted for presentation to the computing device 1200 and/or the patient interface 50. The patient may view the selected treatment plan on the computing device 1200 and/or patient interface 50. In some embodiments, the assistant and the patient may discuss the details (e.g., treatment protocol using treatment apparatus 70, diet regimen, medication regimen, etc.) during the telemedicine session in real-time or in near real-time. In some embodiments, as the user uses the treatment apparatus 70, as discussed further with reference to method 1000 of FIG. 10 above, the server 30 may control, based on the selected treatment plan and during the telemedicine session, the treatment apparatus 70.

Figure 14:
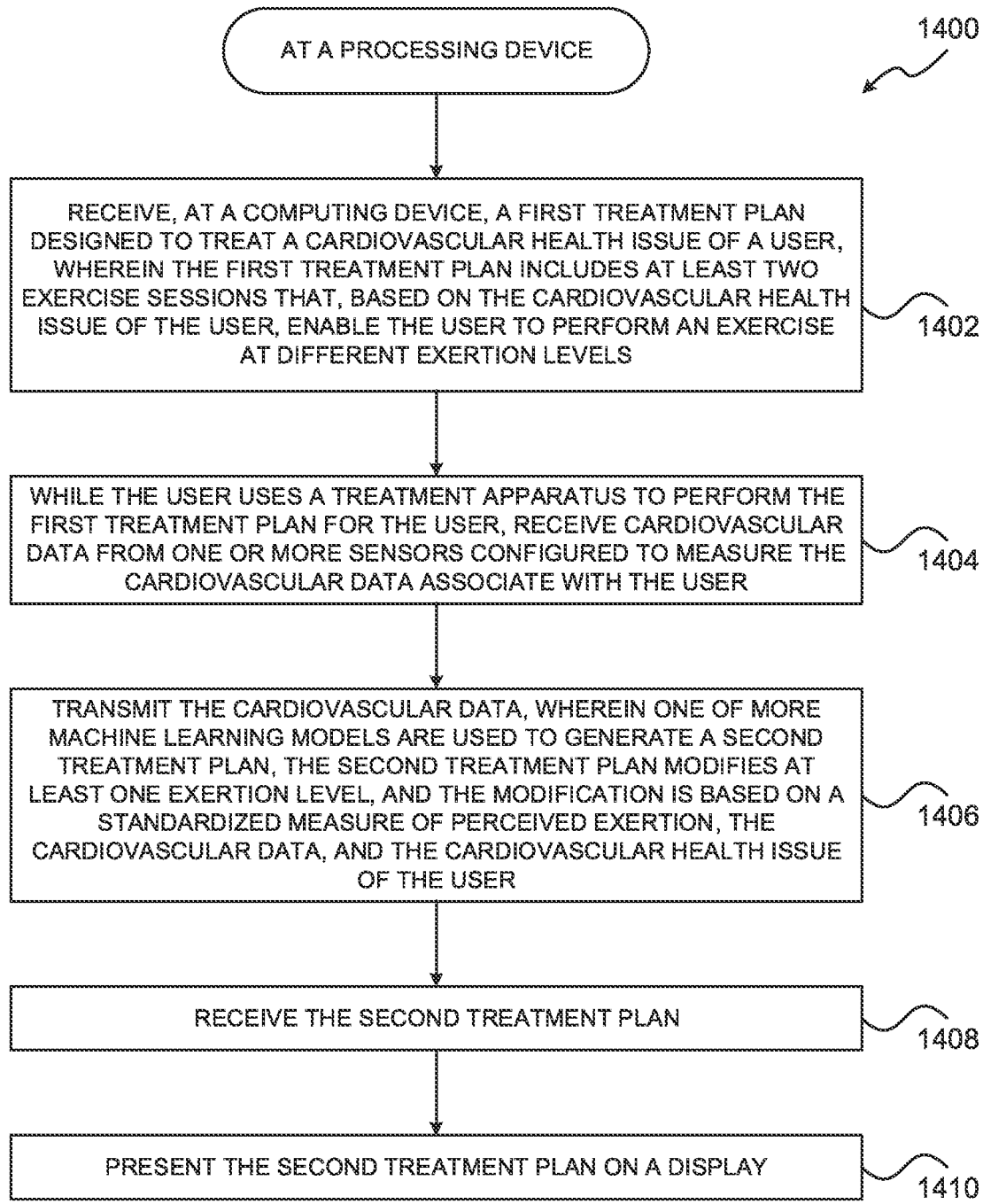
FIG. 14 generally illustrates an example embodiment of a method for generating treatment plans including sessions designed to enable a user to achieve a desired exertion level based on a standardized measure of perceived exertion according to the principles of the present disclosure.

FIG. 14 generally illustrates an example embodiment of a method 1400 for generating treatment plans, where such treatment plans may include sessions designed to enable a user, based on a standardized measure of perceived exertion, to achieve a desired exertion level according to the principles of the present disclosure. The method 1400 may be performed by processing logic that may include hardware (circuitry, dedicated logic, etc.), software, or a combination of both. The method 1400 and/or each of their individual functions, subroutines, or operations may be performed by one or more processors of a computing device (e.g., the computing device 1200 of FIG. 12 and/or the patient interface 50 of FIG. 1) implementing the method 1400. The method 1400 may be implemented as computer instructions stored on a memory device and executable by the one or more processors. In certain implementations, the method 1400 may be performed by a single processing thread. Alternatively, the method 1400 may be performed by two or more processing threads, each thread implementing one or more individual functions, routines, subroutines, or operations of the methods.

At block 1402, the processing device may receive, at a computing device 1200, a first treatment plan designed to treat a cardiovascular health issue of a user. The cardiovascular heart issue may include diagnoses, diagnostic codes, symptoms, life consequences, comorbidities, risk factors to health, risk factors to life, etc. The cardiovascular heart issue may include heart surgery performed on the user, a heart transplant performed on the user, a heart arrhythmia of the user, an atrial fibrillation of the user, tachycardia, bradycardia, supraventricular tachycardia, congestive heart failure, heart valve disease, arteriosclerosis, atherosclerosis, pericardial disease, pericarditis, myocardial disease, myocarditis, cardiomyopathy, congenital heart disease, or some combination thereof.

The first treatment plan may include at least two exercise sessions that provide different exertion levels based at least on the cardiovascular health issue of the user. For example, if the user recently underwent heart surgery, then the user may be at high risk for a complication if their heart is overexerted. Accordingly, a first exercise session may begin with a very mild desired exertion level, and a second exercise session may slightly increase the exertion level. There may any suitable number of exercise sessions in an exercise protocol associated with the treatment plan. The number of sessions may depend on the cardiovascular health issue of the user. For example, the person who recently underwent heart surgery may be prescribed a higher number of sessions (e.g., 36) than the number of sessions prescribed in a treatment plan to a person with a less severe cardiovascular health issue. The first treatment plan may be presented on the display 1300 of the computing device 1200.

In some embodiments, the first treatment plan may also be generated by accounting for a standardized measure comprising perceived exertion, such as a metabolic equivalent of task (MET) value and/or the Borg Rating of Perceived Exertion (RPE). The MET value refers to an objective measure of a ratio of the rate at which a person expends energy relative to the mass of that person while performing a physical activity compared to a reference (resting rate). In other words, MET may refer to a ratio of work metabolic rate to resting metabolic rate. One MET may be defined as 1 kcal/kg/hour and approximately the energy cost of sitting quietly. Alternatively, and without limitation, one MET may be defined as oxygen uptake in ml/kg/min where one MET is equal to the oxygen cost of sitting quietly (e.g., 3.5 ml/kg/min). In this example, 1 MET is the rate of energy expenditure at rest. A 5 MET activity expends 5 times the energy used when compared to the energy used for by a body at rest. Cycling may be a 6 MET activity. If a user cycles for 30 minutes, then that is equivalent to 180 MET activity (i.e., 6 MET x 30 minutes). Attaining certain values of MET may be beneficial or detrimental for people having certain cardiovascular health issues.

A database may store a table including MET values for activities correlated with treatment plans, cardiovascular results of users having certain cardiovascular health issues, and/or cardiovascular data. The database may be continuously and/or continually updated as data is obtained from users performing treatment plans. The database may be used to train the one or more machine learning models such that improved treatment plans with exercises having certain MET values are selected. The improved treatment plans may result in faster cardiovascular health recovery time and/or a better cardiovascular health outcome. The improved treatment plans may result in reduced use of the treatment apparatus, computing device 1200, patient interface 50, server 30, and/or assistant interface 94. Accordingly, the disclosed techniques may reduce the resources (e.g., processing, memory, network) consumed by the treatment apparatus, computing device 1200, patient interface 50, server 30, and/or assistant interface 94, thereby providing a technical improvement. Further, wear and tear of the treatment apparatus, computing device 1200, patient interface 50, server 30, and/or assistant interface 94 may be reduced, thereby improving their lifespan.

The Borg RPE is a standardized way to measure physical activity intensity level. Perceived exertion refers to how hard a person feels like their body is working. The Borg RPE may be used to estimate a user's actual heart rate during physical activity. The Borg RPE may be based on physical sensations a person experiences during physical activity, including increased heart rate, increased respiration or breathing rate, increased sweating, and/or muscle fatigue. The Borg rating scale may be from 6 (no exertion at all) to 20 (perceiving maximum exertion of effort). Similar to the MET table described above, the database may include a table that correlates the Borg values for activities with treatment plans, cardiovascular results of users having certain cardiovascular health issues, and/or cardiovascular data.

In some embodiments, the first treatment plan may be generated by one or more trained machine learning models. The machine learning models 13 may be trained by training engine 9. The one or more trained machine learning models may be trained using training data including labeled inputs of a standardized measure comprising perceived exertion, other users' cardiovascular data, attribute data of the user, and/or other users' cardiovascular health issues and a labeled output for a predicted treatment plan (e.g., the treatment plans may include details related to the number of exercise sessions, the exercises to perform at each session, the duration of the exercises, the exertion levels to maintain or achieve at each session, etc.). The attribute data may be received by the processing device and may include an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, of some combination thereof.

A mapping function may be used to map, using supervised learning, the labeled inputs to the labeled outputs, in some embodiments. In some embodiments, the machine learning models may be trained to output a probability that may be used to match to a treatment plan or match to a cohort of users that share characteristics similar to those of the user. If the user is matched to a cohort based on the probability, a treatment plan associated with that cohort may be prescribed to the user.

In some embodiments, the one or more machine learning models may include different layers of nodes that determine different outputs based on different data. For example, a first layer may determine, based on cardiovascular data of the user, a first probability of a predicted treatment plan. A second layer may receive the first probability and determine, based on the cardiovascular health issue of the user, a second probability of the predicted treatment plan. A third layer may receive the second probability and determine, based on the standardized measure of perceived exertion, a third probability of the predicted treatment plan. An activation function may combine the output from the third layer and output a final probability which may be used to prescribe the first treatment plan to the user.

In some embodiments, the first treatment plan may be designed and configured by a healthcare professional. In some embodiments, a hybrid approach may be used and the one or more machine learning models may recommend one or more treatment plans for the user and present them on the assistant interface 94. The healthcare professional may select one of the treatment plans, modify one of the treatment plans, or both, and the first treatment plan may be transmitted to the computing device 1200 and/or the patient interface 50.

At block 1404, while the user uses the treatment apparatus 70 to perform the first treatment plan for the user, the processing device may receive cardiovascular data from one or more sensors configured to measure the cardiovascular data associated with the user. In some embodiments, the treatment apparatus may include a cycling machine. The one or more sensors may include an electrocardiogram sensor, a pulse oximeter, a blood pressure sensor, a respiration rate sensor, a spirometry sensor, or some combination thereof. The electrocardiogram sensor may be a strap around the user's chest, the pulse oximeter may be clip on the user's finger, and the blood pressure sensor may be cuff on the user's arm. Each of the sensors may be communicatively coupled with the computing device 1200 via Bluetooth or a similar near field communication protocol. The cardiovascular data may include a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, or some combination thereof.

At block 1406, the processing device may transmit the cardiovascular data. In some embodiments, the cardiovascular data may be transmitted to the assistant interface 94 via the first network 34 and the second network 54. In some embodiments, the cardiovascular data may be transmitted to the server 30 via the second network 54. In some embodiments, cardiovascular data may be transmitted to the patient interface 50 (e.g., second computing device) which relays the cardiovascular data to the server 30 via the second network 58. In some embodiments, cardiovascular data may be transmitted to the patient interface 50 (e.g., second computing device) which relays the cardiovascular data to the assistant interface 94 (e.g., third computing device).

In some embodiments, one or more machine learning models 13 of the server 30 may be used to generate a second treatment plan. The second treatment plan may modify at least one of the exertion levels, and the modification may be based on a standardized measure of perceived exertion, the cardiovascular data, and the cardiovascular health issue of the user. In some embodiments, if the user is not able to meet or maintain the exertion level for a session, the one or more machine learning models 13 of the server 30 may modify the exertion level dynamically.

At block 1408, the processing device may receive the second treatment plan.

In some embodiments, the second treatment plan may include a modified parameter pertaining to the treatment apparatus 70. The modified parameter may include a resistance, a range of motion, a length of time, an angle of a component of the treatment apparatus, a speed, or some combination thereof. In some embodiments, while the user operates the treatment apparatus 70, the processing device may, based on the modified parameter in real-time or near real-time, cause the treatment apparatus 70 to be controlled.

In some embodiments, the one or more machine learning models may generate the second treatment plan by predicting exercises that will result in the desired exertion level for each session, and the one or more machine learning models may be trained using data pertaining to the standardized measure of perceived exertion, other users' cardiovascular data, and other users' cardiovascular health issues.

At block 1410, the processing device may present the second treatment plan on a display, such as the display 1300 of the computing device 1200.

In some embodiments, based on an operating parameter specified in the treatment plan, the second treatment plan, or both, the computing device 1200, the patient interface 50, the server 30, and/or the assistant interface 94 may send control instructions to control the treatment apparatus 70. The operating parameter may pertain to a speed of a motor of the treatment apparatus 70, a range of motion provided by one or more pedals of the treatment apparatus 70, an amount of resistance provided by the treatment apparatus 70, or the like.

Figure 15:
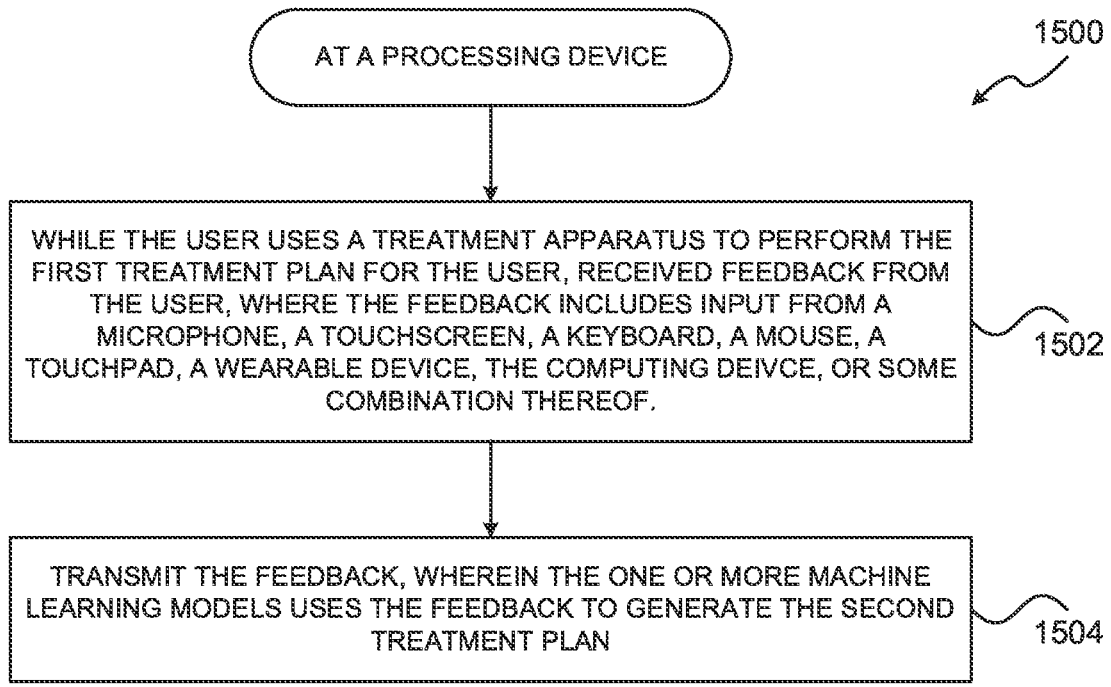
FIG. 15 generally illustrates an example embodiment of a method for receiving input from a user and transmitting the feedback to be used to generate a new treatment plan according to the principles of the present disclosure.

FIG. 15 generally illustrates an example embodiment of a method 1500 for receiving input from a user and transmitting the feedback to be used to generate a new treatment plan according to the principles of the present disclosure. The method 1500 may be performed by processing logic that may include hardware (circuitry, dedicated logic, etc.), software, or a combination of both. The method 1500 and/or each of their individual functions, subroutines, or operations may be performed by one or more processors of a computing device (e.g., the computing device 1200 of FIG. 12 and/or the patient interface 50 of FIG. 1) implementing the method 1500. The method 1500 may be implemented as computer instructions stored on a memory device and executable by the one or more processors. In certain implementations, the method 1500 may be performed by a single processing thread. Alternatively, the method 1500 may be performed by two or more processing threads, each thread implementing one or more individual functions, routines, subroutines, or operations of the methods.

At block 1502, while the user uses the treatment apparatus 70 to perform the first treatment plan for the user, the processing device may receive feedback from the user. The feedback may include input from a microphone, a touchscreen, a keyboard, a mouse, a touchpad, a wearable device, the computing device, or some combination thereof. In some embodiments, the feedback may pertain to whether or not the user is in pain, whether the exercise is too easy or too hard, whether or not to increase or decrease an operating parameter of the treatment apparatus 70, or some combination thereof.

At block 1504, the processing device may transmit the feedback to the server 30, wherein the one or more machine learning models uses the feedback to generate the second treatment plan.

Figure 16:
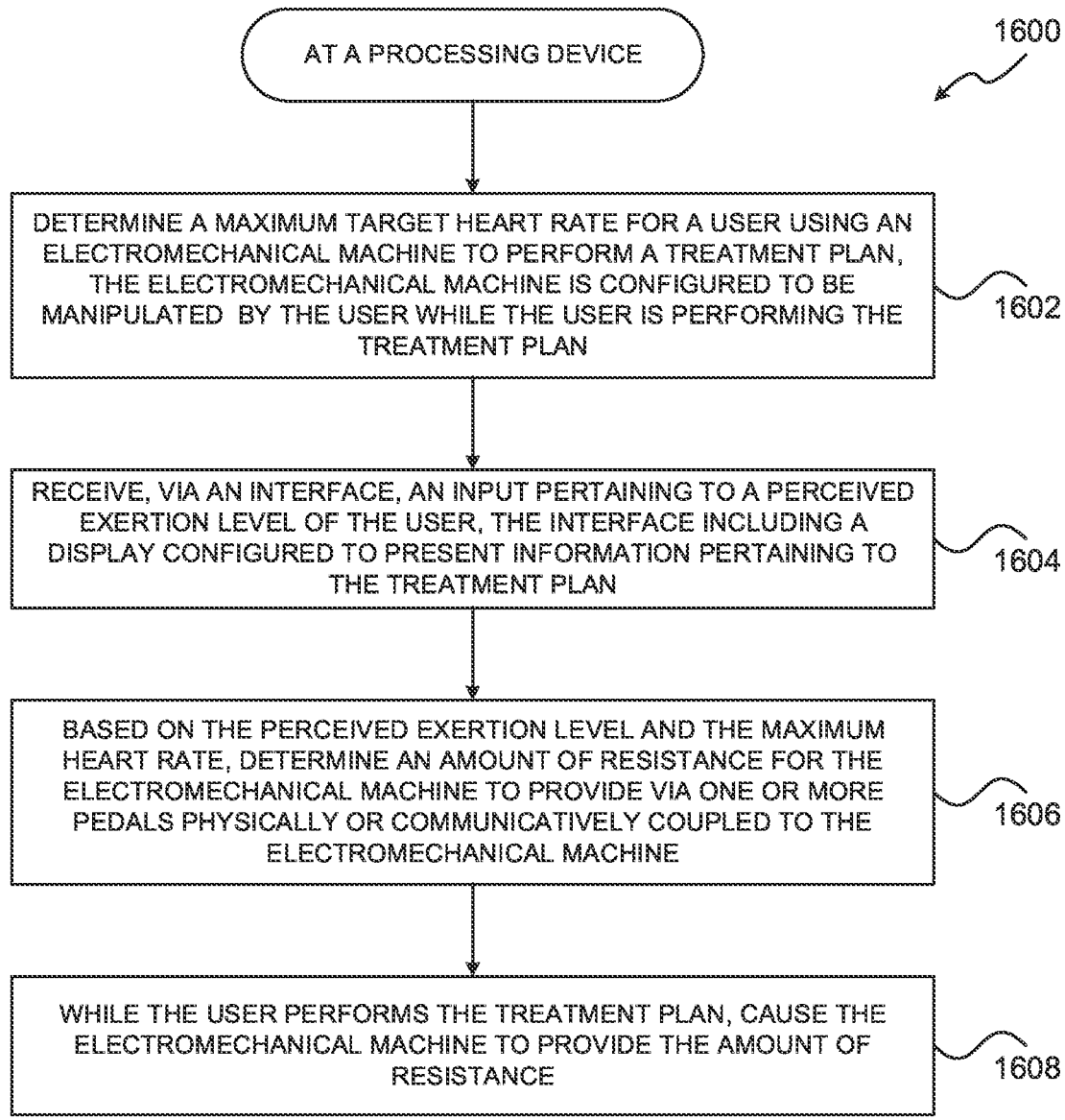
FIG. 16 generally illustrates an example embodiment of a method for implementing a cardiac rehabilitation protocol by using artificial intelligence and a standardized measurement according to the principles of the present disclosure.

Systems and Methods for Implementing a Cardiac Rehabilitation Protocol by Using Artificial Intelligence and a Standardized Measurement FIG. 16 generally illustrates an example embodiment of a method 1600 for implementing a cardiac rehabilitation protocol by using artificial intelligence and a standardized measurement according to the principles of the present disclosure. The method 1600 may be performed by processing logic that may include hardware (circuitry, dedicated logic, etc.), software, or a combination of both. The method 1600 and/or each of their individual functions, subroutines, or operations may be performed by one or more processing devices of a computing device (e.g., the computer system 1100 of FIG. 11) implementing the method 1600. The method 1600 may be implemented as computer instructions stored on a memory device and executable by the one or more processing devices. In certain implementations, the method 1600 may be performed by a single processing thread. Alternatively, the method 1600 may be performed by two or more processing threads, each thread implementing one or more individual functions, routines, subroutines, or operations of the methods.

In some embodiments, a system may be used to implement the method 1600. The system may include the treatment apparatus 70 (electromechanical machine) configured to be manipulated by a user while the user is performing a treatment plan, and an interface including a display configured to present information pertaining to the treatment plan. The system may include a processing device 1102 configured to execute instructions implemented the method 1600.

At block 1602, the processing device 1102 may determine a maximum target heart rate for a user using the electromechanical machine to perform the treatment plan. In some embodiments, the processing device 1102 may determine the maximum target heart rate by determining a heart rate reserve measure (HRRM) by subtracting from a maximum heart rate of the user a resting heart rate of the user.

At block 1604, the processing device 1102 may receive, via the interface (patient interface 50), an input pertaining to a perceived exertion level of the user. In some embodiments, the processing device 1102 may receive, via the interface, an input pertaining to a level of the user's anxiety, depression, pain, difficulty in performing the treatment plan, or some combination thereof. In some embodiments, the processing device 1102 may receive, via the interface, an input pertaining to a physical activity readiness (PAR) score, and the processing device 1102 may determine, based on the PAR score, an initiation point at which the user is to begin the treatment plan. The treatment plan may pertain to cardiac rehabilitation, bariatric rehabilitation, cardio-oncologic rehabilitation, oncologic rehabilitation, pulmonary rehabilitation, or some combination thereof.

In some embodiments, the processing device 1102 may receive, from one or more sensors, performance data related to the user's performance of the treatment plan. Based on the performance data, the input(s) received from the interface, or some combination thereof, the processing device 1102 may determine a state of the user.

At block 1606, based on the perceived exertion level and the maximum heart rate, the processing device 1102 may determine an amount of resistance for the electromechanical machine to provide via one or more pedals physically or communicatively coupled to the electromechanical machine. In some embodiments, the processing device 1102 may use one or more trained machine learning models that map one or more inputs to one or more outputs, wherein the mapping is to determine the amount of resistance the electromechanical machine is to provide via the one or more pedals. The one or more machine learning models 13 may be trained using a training dataset. The training dataset may include labeled inputs mapped to labeled outputs. The labeled inputs may pertain to one or more characteristics of one or more users (e.g., maximum target heart rates of users, perceived exertion levels of users during exercises using certain amounts of resistance, physiological data of users, health conditions of users, etc.) mapped to labeled outputs including amounts of resistance to provide by one or more pedals of an electromechanical machine.

At block 1608, while the user performs the treatment plan, the processing device 1102 may cause the electromechanical machine to provide the amount of resistance.

Further, in some embodiments, the processing device 1102 may transmit in real-time or near real-time one or more characteristic data of the user to a computing device used by a healthcare professional. The characteristic data may be transmitted to and presented on the computing device monitored by the healthcare professional. The characteristic data may include measurement data, performance data, and/or personal data pertaining to the user. For example, one or more wireless sensors may obtain the user's heart rate, blood pressure, blood oxygen level, and the like at a certain frequency (e.g., every 5 minutes, every 2 minutes, every 30 seconds, etc.) and transmit those measurements to the computing device 1200 or the patient interface 50. The computing device 1200 and/or patient interface 50 may relay the measurements to the server 30, which may transmit the measurements for real-time display on the assistant interface 94.

In some embodiments, the processing device 1102 may receive, via one or more wireless sensors (e.g., blood pressure cuff, electrocardiogram wireless sensor, blood oxygen level sensor, etc.), one or more measurements including a blood pressure, a heart rate, a respiration rate, a blood oxygen level, or some combination thereof, in real-time or near real-time. In some embodiments, based on the one or more measurements, the processing device 1102 may determine whether the user's heart rate is within a threshold relative to the maximum target heart rate. In some embodiments, if the one or more measurements exceed the threshold, the processing device 1102 may reduce the amount of resistance provided by the electromechanical machine. If the one or more measurements do not exceed the threshold, the processing device 1102 may maintain the amount of resistance provided by the electromechanical machine.

In some embodiments, the server 30 may be configured to enable communication detection between one or more devices and to perform one or more corrective actions. For example, the server 30 may determine whether one or more messages are received from at least one of an electromechanical machine, a sensor, and an interface. The electromechanical machine may include the treatment device 70 or other suitable electromechanical machine and may be configured to be manipulated by the user while the user is performing a treatment plan, such as one of the treatment plans described herein. The sensor may include any sensor described herein or any other suitable sense. The interface may include the patient interface 50 and/or any other suitable interface. The one or more messages may pertain to a user of the treatment device 70, a usage of the treatment device 70 by the user, or a combination thereof. The messages may comprise any suitable format and may include one or more text strings (e.g., including one or more alphanumeric characters, one or more special characters, and/or one or more of any other suitable characters or suitable text) or any other suitable information).

In some embodiments, the server 30 may, responsive to determining that the one or more messages have not been received, determine, using an artificial intelligence engine, such as the artificial intelligence engine 11, which may be configured to use one or more machine learning models, such as the machine learning model 13 and/or other suitable machine learning model, one or more preventative actions to perform.

Due to a telecommunications failure, a video communication failure, an audio communication failure, a data acquisition failure, any other suitable failure, or a combination thereof, the server 30 may not, under certain circumstances, receive the one or more messages.

The one or more preventative actions may include (i) causing at least one of a telecommunications transmission to be initiated, (ii) stopping the treatment device 70 from operating, (iii) modifying a speed at which the treatment device 70 operates, (iv) any other suitable preventative action (e.g., including any preventative action described herein), or (v) a combination thereof. In some embodiments, while the user uses the treatment device 70 to perform the treatment plan, the one or more messages may include information pertaining to a cardiac condition of the user. The server 30 may cause the one or more preventative actions to be performed (e.g., by a suitable processing device or other suitable mechanism associated with the telecommunications transmission and/or the treatment device 70).

In some embodiments, while the user uses the treatment device 70 to perform the treatment plan, the server 30 may determine a maximum target heart rate (e.g., as described herein) for the user. The server 30 may receive, via the patient interface 50, input pertaining to a perceived exertion level of the user. The server 30 may, based on the perceived exertion level and the maximum heart rate, determine an amount of resistance for the treatment device 70 to provide via one or more pedals of the treatment device 70. The server 30 may, while the user performs the treatment plan, cause, using a processing device or other suitable mechanism of the treatment device 70, the treatment device 70 to provide the amount of resistance.

In some embodiments, the server 30 may determine a condition associated with the user; and based on the condition and the determination that the one or more messages have not been received, further determine the one or more preventative actions. The condition may pertain to a cardiac rehabilitation, an oncologic rehabilitation, a cardio-oncologic rehabilitation, a rehabilitation from pathologies related to a prostate gland or a urogenital tract, a pulmonary rehabilitation, a bariatric rehabilitation, any other suitable rehabilitation or condition, or a combination thereof.

Clause 1.1 A computer-implemented system, comprising:
an electromechanical machine configured to be manipulated by a user while the user is performing a treatment plan;
an interface comprising a display configured to present information pertaining to the treatment plan; and
a processing device configured to:
determine a maximum target heart rate for a user using the electromechanical machine to perform the treatment plan;
receive, via the interface, an input pertaining to a perceived exertion level of the user;
based on the perceived exertion level and the maximum heart rate, determine an amount of resistance for the electromechanical machine to provide via one or more pedals physically or communicatively coupled to the electromechanical machine; and
while the user performs the treatment plan, cause the electromechanical machine to provide the amount of resistance.

Clause 2.1 The computer-implemented system of any clause herein, wherein the processing device is further to:

receive, via the interface, a second input pertaining to a level of the user's anxiety, depression, pain, difficulty in performing the treatment plan, or any combination thereof.

Clause 3.1 The computer-implemented system of any clause herein, wherein the processing device is further to:
receive, via the interface, a second input pertaining to a physical activity readiness (PAR) score; and
determine, based on the PAR, an initiation point at which the user is to begin the treatment plan, wherein the treatment plan pertains to cardiac rehabilitation.

Clause 4.1 The computer-implemented system of any clause herein, further comprising:
receiving, from one or more sensors, performance data related to the user's performance of the treatment plan; and
based on the performance data, the input, the second input, or some combination thereof, determining a state of the user.

Clause 5.1 The computer-implemented system of any clause herein, wherein the processing device is further to transmit in real-time or near real-time one or more characteristic data of the user to a computing device used by a healthcare professional, wherein the characteristic data is transmitted to and presented on the computing device monitored by the healthcare professional.

Clause 6.1 The computer-implemented system of any clause herein, wherein the processing device is further to determine the maximum target heart rate by:
determining a heart rate reserve measure (HRRM) by subtracting from a maximum heart rate of the user a resting heart rate of the user.

Clause 7.1 The computer-implemented system of any clause herein, wherein the processing device is further to use one or more trained machine learning models that map one or more inputs to one or more outputs, wherein the mapping is to determine the amount of resistance the electromechanical machine is to provide via the one or more pedals.

Clause 8.1 The computer-implemented system of any clause herein, wherein the processing device is further to:
receive, via one or more sensors, one or more measurements comprising a blood pressure, a heart rate, a respiration rate, a blood oxygen level, or some combination thereof, in real-time or near real-time;
based on the one or more measurements, determine whether the user's heart rate is within a threshold relative to the maximum target heart rate; and
if the one or more measurements exceed the threshold, reduce the amount of resistance provided by the electromechanical machine.

Clause 9.1 A computer-implemented method comprising:
determining a maximum target heart rate for a user using an electromechanical machine to perform a treatment plan, wherein the electromechanical machine is configured to be manipulated by the user while the user is performing the treatment plan;
receiving, via an interface, an input pertaining to a perceived exertion level of the user, wherein the interface comprises a display configured to present information pertaining to the treatment plan;
based on the perceived exertion level and the maximum heart rate, determining an amount of resistance for the electromechanical machine to provide via one or more pedals physically or communicatively coupled to the electromechanical machine; and while the user performs the treatment plan, causing the electromechanical machine to provide the amount of resistance.

Clause 10.1 The computer-implemented method of any clause herein, further comprising:
receiving, via the interface, a second input pertaining to a level of the user's anxiety, depression, pain, difficulty in performing the treatment plan, or any combination thereof.

Clause 11.1 The computer-implemented method of any clause herein, further comprising:
receiving, via the interface, a second input pertaining to a physical activity readiness (PAR) score; and
determining, based on the PAR, an initiation point at which the user is to begin the treatment plan, wherein the treatment plan pertains to cardiac rehabilitation.

Clause 12.1 The computer-implemented method of any clause herein, further comprising:
receiving, from one or more sensors, performance data related to the user's performance of the treatment plan; and
based on the performance data, the input, the second input, or some combination thereof, determining a state of the user.

Clause 13.1 The computer-implemented method of any clause herein, further comprising transmitting in real-time or near real-time one or more characteristic data of the user to a computing device used by a healthcare professional, wherein the characteristic data is transmitted to and presented on the computing device monitored by the healthcare professional.

Clause 14.1 The computer-implemented method of any clause herein, wherein determining the maximum target heart rate further comprises:
determining a heart rate reserve measure (HRRM) by subtracting from a maximum heart rate of the user a resting heart rate of the user.

Clause 15.1 The computer-implemented method of any clause herein, further comprising using one or more trained machine learning models that map one or more inputs to one or more outputs, wherein the mapping is to determine the amount of resistance the electromechanical machine is to provide via the one or more pedals.

Clause 16.1 The computer-implemented method of any clause herein, further comprising:
receiving, via one or more sensors, one or more measurements comprising a blood pressure, a heart rate, a respiration rate, a blood oxygen level, or some combination thereof, in real-time or near real-time;
based on the one or more measurements, determining whether the user's heart rate is within a threshold relative to the maximum target heart rate; and
if the one or more measurements exceed the threshold, reducing the amount of resistance provided by the electromechanical machine.

Clause 17.1 The computer-implemented method of any clause herein, further comprising:
receiving, via the interface, a second input pertaining to a level of the user's anxiety, depression, pain, difficulty in performing the treatment plan, or any combination thereof.

Clause 18.1 The computer-implemented method of any clause herein, further comprising:
receiving, via the interface, a second input pertaining to a physical activity readiness (PAR) score; and determining, based on the PAR, an initiation point at which the user is to begin the treatment plan, wherein the treatment plan pertains to cardiac rehabilitation.

Clause 19.1 A tangible, non-transitory computer-readable medium storing instructions that, when executed, cause a processing device to:
determine a maximum target heart rate for a user using an electromechanical machine to perform a treatment plan, wherein the electromechanical machine is configured to be manipulated by the user while the user is performing the treatment plan;
receive, via an interface, an input pertaining to a perceived exertion level of the user, wherein the interface comprises a display configured to present information pertaining to the treatment plan;
based on the perceived exertion level and the maximum heart rate, determine an amount of resistance for the electromechanical machine to provide via one or more pedals physically or communicatively coupled to the electromechanical machine; and
while the user performs the treatment plan, cause the electromechanical machine to provide the amount of resistance.

Clause 20.1 The computer-readable medium of any clause herein, wherein the processing device is further to:
receive, via the interface, a second input pertaining to a level of the user's anxiety, depression, pain, difficulty in performing the treatment plan, or any combination thereof.

Figure 17:
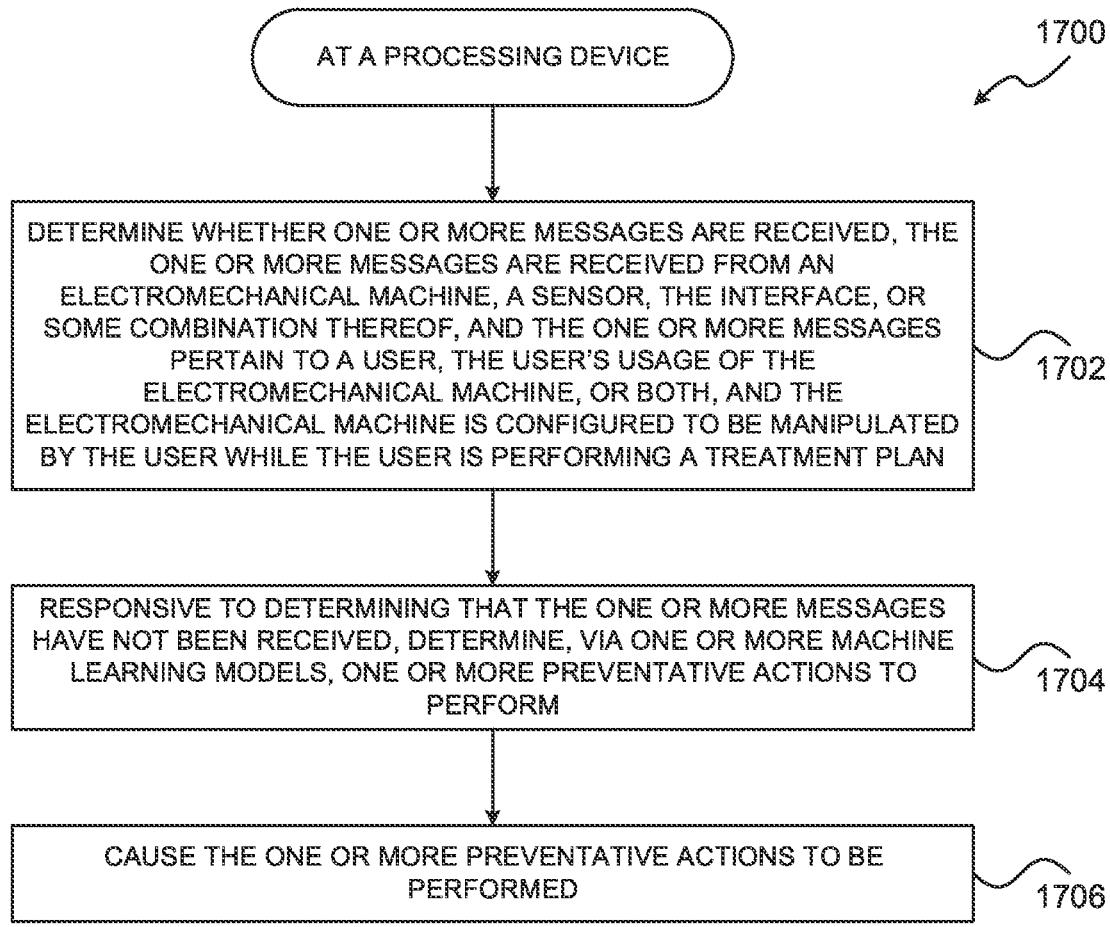
FIG. 17 generally illustrates an example embodiment of a method for enabling communication detection between devices and performance of a preventative action according to the principles of the present disclosure.

Systems and Methods to Enable Communication Detection Between Devices and Performance of a Preventative Action FIG. 17 generally illustrates a method 1700 for enabling communication detection between devices and performance of a preventative action according to the principles of the present disclosure. The method 1700 may be performed by processing logic that may include hardware (circuitry, dedicated logic, etc.), software, or a combination of both. The method 1700 and/or each of their individual functions, subroutines, or operations may be performed by one or more processing devices of a computing device (e.g., the computer system 1100 of FIG. 11) implementing the method 1700. The method 1700 may be implemented as computer instructions stored on a memory device and executable by the one or more processing devices. In certain implementations, the method 1700 may be performed by a single processing thread. Alternatively, the method 1700 may be performed by two or more processing threads, each thread implementing one or more individual functions, routines, subroutines, or operations of the methods.

In some embodiments, a system may be used to implement the method 1700. The system may include the treatment apparatus 70 (electromechanical machine) configured to be manipulated by a user while the user is performing a treatment plan, and an interface including a display configured to present information pertaining to the treatment plan. The system may include a processing device 1102 configured to execute instructions implemented the method 1700.

At block 1702, the processing device 1102 may determine whether one or more messages have been received. The one or more messages may be received from the electromechanical machine (e.g., the treatment device 70 or other suitable machine), one or more sensors, the patient interface 50, the computing device 1200, or a suitable combination thereof. The one or more messages may include information pertaining to the user, the usage of the electromechanical machine by the user, or both.

At block 1704, responsive to determining that the one or more messages have not been received, the processing device 1102 may determine, via the artificial intelligence engine 11, one or more machine learning models 13, or one or more preventative actions to perform. In some embodiments, the one or more messages not being received may pertain to a telecommunications failure, a video communication failure and/or a video communication being lost, an audio communication failure and/or an audio communication being lost, a data acquisition failure and/or a data acquisition being compromised, any other suitable failure, communication loss, or data compromise, or any combination thereof.

At block 1706, the processing device 1102 may cause the one or more preventative actions to be performed. In some embodiments, the one or more preventative actions may include causing a telecommunications transmission to be initiated (e.g., a phone call, a text message, a voice message, a video/multimedia message, an emergency service call, a beacon activation, a wireless communication of any kind, and/or the like), stopping the electromechanical machine from operating, modifying a speed at which the electromechanical machine operates, or any combination thereof.

In some embodiments, the one or more messages may include information pertaining to a cardiac condition of the user. The one or more messages may be sent by the treatment device 70, the computing device 1200, the patient interface 50, the sensors, any other suitable device, interface, sensor, or mechanism, or a combination thereof.

In some embodiments, while the user uses the treatment device 70 to perform the treatment plan, the processing device 1102 may determine a maximum target heart rate for a user. The processing device 1102 may receive, via the patient interface 50 (e.g., or any other suitable interface), an input pertaining to a perceived exertion level of the user. In some embodiments, based on the perceived exertion level and the maximum target heart rate, the processing device 1102 may determine an amount of resistance for the treatment device 70 to provide via one or more pedals of the treatment device 70. While the user performs the treatment plan (e.g., using the treatment device 70, any other suitable electromechanically machine, any other machine, and/or without a machine or device), the processing device 1102 may cause the treatment device 70 to provide the amount of resistance.

In some embodiments, the processing device 1102 may determine a condition associated with the user. The condition may pertain to cardiac rehabilitation, oncologic rehabilitation, cardio-oncologic rehabilitation, rehabilitation from pathologies related to the prostate gland or urogenital tract, pulmonary rehabilitation, bariatric rehabilitation, a wellness condition, a general state of the user based on vitals, physiologic data, measurements, or any combination thereof. Based on the condition associated with the user and the one or more messages not being received, the processing device 1102 may determine the one or more preventative actions. For example, if the one or more messages are not received and the user has a cardiac event, the preventative action may include stopping the treatment device 70 and/or contacting emergency services (e.g., calling an emergency service, such as 911 (US), 999 (UK) or other suitable emergency service).

Clause 1.2 A computer-implemented system, comprising: an electromechanical machine configured to be manipulated by a user while the user is performing a treatment plan; an interface comprising a display configured to present information pertaining to the treatment plan; and a processing device configured to: determine whether one or more messages, pertaining to at least one of the user and a usage of the electromechanically machine by the user, are received from at least one of the electromechanical machine, a sensor, and the interface; responsive to determining that the one or more messages have not been received, determining, via one or more machine learning models, one or more preventative actions to perform; and cause the one or more preventative actions to be performed.

2.2 The computer-implemented system of any clause herein, wherein the one or more preventative actions includes at least one of causing a telecommunications transmission to be initiated, stopping the electromechanical machine from operating, and modifying a speed at which the electromechanical machine operates.

3.2 The computer-implemented system of any clause herein, wherein the one or more messages not being received corresponds to at least one of a telecommunications failure, a video communication failure, an audio communication failure, and a data acquisition failure.

4.2 The computer-implemented system of any clause herein, wherein, while the user uses the electromechanical machine to perform the treatment plan, the one or more messages include information pertaining to a cardiac condition of the user.

5.2 The computer-implemented system of any clause herein, wherein the processing device is further configured to: determine a maximum target heart rate for the user while the user uses the electromechanical machine to perform the treatment plan; receive, via the interface, an input pertaining to a perceived exertion level of the user; based on the perceived exertion level and the maximum heart rate, determine an amount of resistance for the electromechanical machine to provide via one or more pedals; while the user performs the treatment plan, cause the electromechanical machine to provide the amount of resistance.

6.2 The computer-implemented system of any clause herein, wherein the processing device is further configured to: determine a condition associated with the user; and based on the condition and the one or more messages not being received, determine the one or more preventative actions.

7.2 The computer-implemented system of any clause herein, wherein the condition pertains to at least one of a cardiac rehabilitation, an oncology rehabilitation, a rehabilitation from pathologies related to a prostate gland or a urogenital tract, a pulmonary rehabilitation, and a bariatric rehabilitation.

8.2 A computer-implemented method comprising: determining whether one or more messages are received from at least one of an electromechanical machine, a sensor, and an interface, wherein the one or more messages pertain to at least one of a user and a usage of the electromechanical machine by the user, and wherein the electromechanical machine is configured to be manipulated by the user while the user is performing a treatment plan; responsive to determining that the one or more messages have not been received, determining, using one or more machine learning models, one or more preventative actions to perform; and causing the one or more preventative actions to be performed.

9.2 The computer-implemented method of any clause herein, wherein the one or more preventative actions comprise causing at least one of a telecommunications transmission to be initiated, stopping the electromechanical machine from operating, and modifying a speed at which the electromechanical machine operates.

10.2 The computer-implemented method of any clause herein, wherein the one or more messages not being received corresponds to at least one of a telecommunications failure, a video communication failure, an audio communication failure, and a data acquisition failure.

11.2 The computer-implemented method of any clause herein, wherein, while the user uses the electromechanical machine to perform the treatment plan, the one or more messages include information pertaining to a cardiac condition of the user.

12.2 The computer-implemented method of any clause herein, further comprising: determining a maximum target heart rate for the user while the user uses the electromechanical machine to perform the treatment plan; receiving, via the interface, an input pertaining to a perceived exertion level of the user; based on the perceived exertion level and the maximum heart rate, determining an amount of resistance for the electromechanical machine to provide via one or more pedals; while the user performs the treatment plan, causing the electromechanical machine to provide the amount of resistance.

13.2 The computer-implemented method of any clause herein, further comprising: determining a condition associated with the user; and based on the condition and the determination that the one or more messages have not been received, determining the one or more preventative actions.

14.2 The computer-implemented method of any clause herein, wherein the condition pertains to at least one of a cardiac rehabilitation, an oncology rehabilitation, a rehabilitation from pathologies related to a prostate gland or a urogenital tract, a pulmonary rehabilitation, and a bariatric rehabilitation.

15.2 A tangible, non-transitory computer-readable medium storing instructions that, when executed, cause a processing device to: determine whether one or more messages are received from at least one of an electromechanical machine, and a sensor, an interface, wherein the one or more messages pertain to at least one of a user and a use of the electromechanical machine by the user, and wherein the electromechanical machine is configured to be manipulated by a user while the user is performing a treatment plan; responsive to determining that the one or more messages have not been received, determine, via one or more machine learning models, one or more preventative actions to perform; and cause the one or more preventative actions to be performed.

16.2 The computer-readable medium of any clause herein, wherein the one or more preventative actions comprise causing at least one of a telecommunications transmission to be initiated, stopping the electromechanical machine from operating, and modifying a speed at which the electromechanical machine operates.

17.2 The computer-readable medium of any clause herein, wherein the one or more messages not being received pertains to at least one of a telecommunications failure, a video communication being lost, an audio communication being lost, and a data acquisition being compromised.

18.2 The computer-readable medium of any clause herein, wherein, while the user uses the electromechanical machine to perform the treatment plan, the one or more messages include information pertaining to a cardiac condition of the user.

19.2 The computer-readable medium of any clause herein, wherein the instructions further cause the processing device to: determine a maximum target heart rate for the user while the user uses the electromechanical machine to perform the treatment plan; receive, via an interface, an input pertaining to a perceived exertion level of the user; based on the perceived exertion level and the maximum heart rate, determine an amount of resistance for the electromechanical machine to provide via one or more pedals; while the user performs the treatment plan, cause the electromechanical machine to provide the amount of resistance.

20.2 The computer-readable medium of any clause herein, wherein the instructions further cause the processing device to: determine a condition associated with the user; and based on the condition associated with the user and the one or more messages not being received, determine the one or more preventative actions.

System and Method for Using AI/ML to Detect Abnormal Heart Rhythms of a User Performing a Treatment Plan with an Electromechanical Machine A heart arrhythmia is an abnormal (or irregular) heartbeat. Heart arrhythmias occur when the electrical signals that coordinate the beats of the heart do not work properly. The faulty signaling may cause the heart to beat too fast, too slow or irregularly. In general, heart arrhythmias are grouped by the speed of the heart rate. A fast resting heart rate (e.g., greater than 100 beats a minute) is tachycardia. Further, a slow resting heart rate (e.g., less than 60 beats a minute) is bradycardia. Atrial fibrillation (A-fib) is a type of tachycardia in which chaotic heart signaling causes a rapid, uncoordinated heart rate. A-fib may be temporary, but some A-fib episodes may not stop unless treated. A-fib is associated with serious complications such as stroke. Atrial flutter is another form of tachycardia that is similar to A-fib, but the heartbeats are more organized. Atrial flutter is also linked to stroke. Supraventricular tachycardia is a broad term that includes arrhythmias that start above the lower heart chambers. Supraventricular tachycardia causes episodes of a pounding heartbeat (e.g., palpitations) that begin and end abruptly. Ventricular fibrillation (V-fib) is another type of arrhythmia that occurs when rapid, chaotic electrical signals cause the lower heart chambers to quiver instead of contracting in a coordinated way that pumps blood to the rest of the body. Ventricular fibrillation can lead to death if a normal heart rhythm is not restored within minutes. Ventricular tachycardia is a rapid, regular heart rate that starts with faulty electrical signals in the ventricles. The rapid heart rate does not allow the ventricles to properly fill with blood. As a result, the heart cannot pump enough blood through the body. Ventricular tachycardia may not cause serious problems in some users with an otherwise healthy heart. However, in users with heart disease, ventricular tachycardia may be a medical emergency that requires immediate medical treatment.

Figure 18:
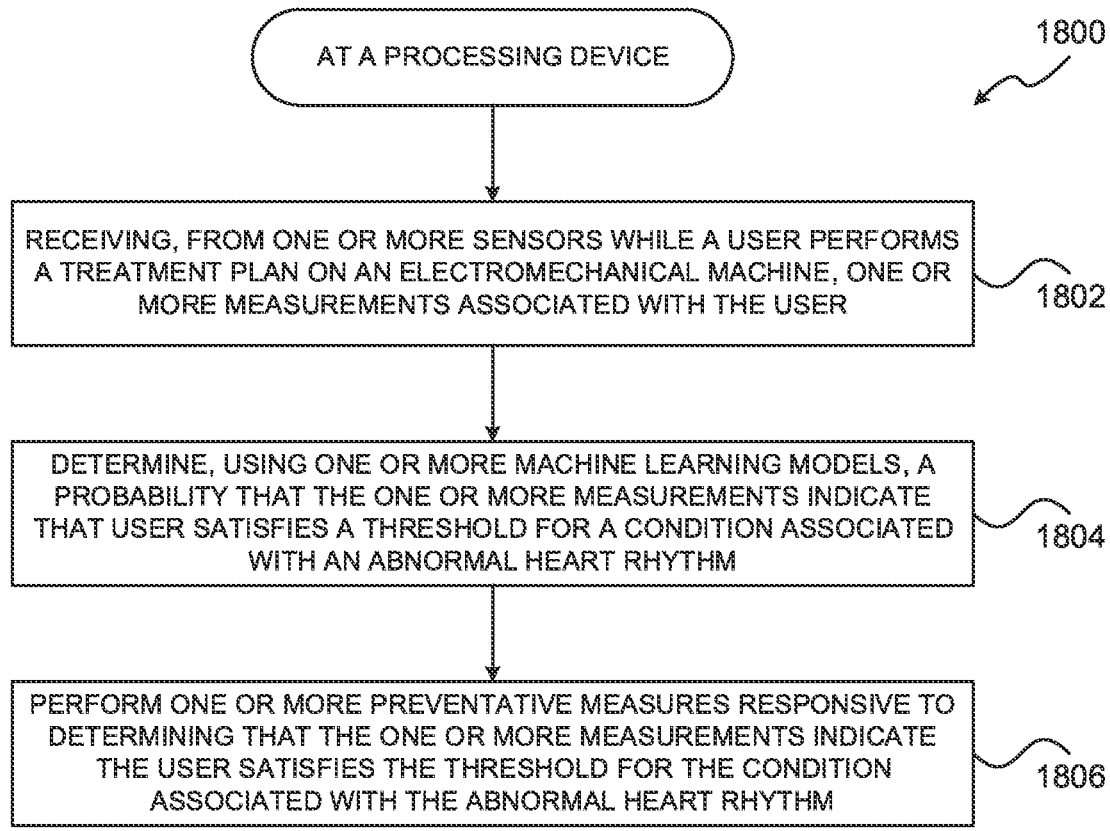
FIG. 18 generally illustrates an example embodiment of a method for using artificial intelligence and machine learning to detect abnormal heart rhythms of a user performing a treatment plan with an electromechanical machine according to the principles of the present disclosure.

As described above, while a user performs a treatment plan on the treatment apparatus 70 (an example of an "electromechanical machine"), one or more sensors determine measurements associated with the user. For example, the ambulation sensor 82 may track and store a number of steps taken by the user. Further, the goniometer 84 measures an angle of a body part of the user and the pressure sensor 86 measures an amount of pressure or weight applied by a body part of the user. In addition to determining the user's performance while performing the treatment plan, the measurements may be used to detect the possibility of conditions associated with an abnormal heart rhythm such as the conditions described above. FIG. 18 generally illustrates an example embodiment of a method 1800 for using artificial intelligence and machine learning to detect abnormal heart rhythms of a user performing a treatment plan with an electromechanical machine.

The method 1800 may be performed by processing logic that may include hardware (circuitry, dedicated logic, etc.), software, or a combination of both. The method 1800 and/or each of their individual functions (including "methods," as used in object-oriented programming), routines, subroutines, or operations may be performed by one or more processing devices of a computing device (e.g., computing device 1200 of FIG. 12). For example, the method 1800 may be implemented as computer instructions stored on one or more memory devices and executable by the one or more processing devices. In certain implementations, the method 1800 may be performed by a single processing thread. Alternatively, the method 1800 may be performed by two or more processing threads, each thread implementing one or more individual functions, routines, subroutines, or operations of the methods.

For simplicity of explanation, the method 1800 is depicted in FIG. 18 and described as a series of operations performed by the computing device 1200. However, operations in accordance with the present disclosure can occur in various orders and/or concurrently, and/or with other operations not presented and described herein. For example, the operations depicted in the method 1800 in FIG. 18 may occur in combination with any other operation of any other method disclosed herein. Furthermore, not all illustrated operations may be required to implement the method 1800 in accordance with the disclosed subject matter. In addition, those skilled in the art will understand and appreciate that the method 1800 could alternatively be represented as a series of interrelated states via a state diagram or event diagram.

At block 1802, the computing device 1200 may receive, from one or more sensors while a user performs a treatment plan on an electromechanical machine (e.g., the treatment apparatus 70 or the stationary cycling machine 100), one or more measurements associated with the user. In some embodiments, the one or more sensors may include a pulse oximeter, an electrocardiogram (ECG or EKG) sensor, a heart rate sensor, a blood pressure sensor, a temperature sensor, a force sensor (e.g., pressure sensor 86), a continuous glucose monitor (CGM) sensor, or some combination thereof. The pulse oximeter may be clipped on a finger of the user or to any other part of the body enabling a valid blood oxygen measurement. The electrocardiogram sensor may be attached to a strap positioned around the chest of the user. The heart rate sensor (e.g., an optical heart rate monitor) may be included in a wristband, a wristwatch, or a smartwatch worn by the user. The blood pressure sensor may be included in a cuff positioned around an arm of the user. The CGM sensor may be inserted under the skin of the user on the belly or arm of the user. Each of the sensors may be communicatively coupled with the computing device 1200 via Bluetooth or a similar near field communication (NFC) protocol. In some embodiments, the one or more measurements may include a blood oxygen level of the user, a heart rhythm of the user, a heart rate of the user, a blood pressure of the user, a respiration rate of the user, a temperature of the user, a glucose level of the user, another vital sign of the user, or some combination thereof.

At block 1804, the computing device 1200 may determine, using one or more machine learning models, a probability that the one or more measurements indicate the user satisfies a threshold for a condition associated with an abnormal heart rhythm. In some embodiments, the condition associated with an abnormal heart rhythm may include an arrhythmia that causes a form of tachycardia such as A-fib, atrial flutter, supraventricular tachycardia, ventricular fibrillation (V-fib), or ventricular tachycardia. In some embodiments, the one or more machine learning models may be trained to implement one or more photoplethysmography (PPG) algorithms approved by the Food and Drug Administration (FDA) to detect A-fib or another form of tachycardia. PPG algorithms use optical sensors to measure blood flow based on light levels reflected in the blood, turning the reflected light levels into heart rate and heart rhythm data. In some embodiments, the one or more machine learning models may be trained to implement one or more electrocardiogram (ECG) algorithms approved by the FDA to detect A-fib or another form of tachycardia. ECG algorithms use electrode sensors to track electrical activity and monitor cardiac muscle tissue activity. In some embodiments, the one or more machine learning models may be trained to implement PPG algorithms and/or ECG algorithms approved by a different governmental agency, regulatory agency, non-governmental organization (NGO) or standards body or organization.

In some embodiments, the one or more machine learning models may be trained with training data that includes labeled inputs (e.g., the one or more measurements associated with the user, personal information of the user, and/or performance information of the user, etc.) mapped to labeled outputs (e.g., conditions associated with an abnormal heart rhythm, preventative actions, customized treatment plans, etc.). Such training may be referred to as supervised learning. Additional types of training may be used, such as unsupervised learning where the training data is not labeled, and, where based on patterns, the machine learning models group clusters of the unlabeled training data. In addition, reinforcement learning may be used to train the one or more machine learning models, where a reward is associated with the ability of the models to correctly determine one or more probabilities for one or more characteristics (e.g., the one or more probabilities may be mapped to a curve that may be dynamically or statically adjusted to identify a dividing line that indicates the most likely correct probability for the one or more characteristics, or a range of probabilities for the one or more characteristics, but within a given error margin, standard deviation, range, variance, or other statistical or numerical measure), such that the machine learning models reinforce (e.g., adjust weights and/or parameters) selecting the one or more probabilities for those characteristics. In some embodiments, some combination of supervised learning, unsupervised learning, and/or reinforcement learning may be used to train the one or more machine learning models.

The one or more machine learning models may include one or more hidden layers that each determine a respective probability and wherein the one or more hidden layers are combined (e.g., summed, averaged, multiplied, etc.) in an activation function in a final layer of the one or more machine learning models. The hidden layers may receive the one or more measurements associated with the user. In some embodiments, the one or more machine learning models may also receive as input performance information of the user. The performance information may include an elapsed time of using the electromechanical machine, an amount of force exerted on a portion of the electromechanical machine, a range of motion achieved on the electromechanical machine, a rotational or traverse speed of a portion of the electromechanical machine, an indication of a plurality of pain levels of the user while using the electromechanical machine, or some combination thereof. In some embodiments, the one or more machine learning models may include personal information of the user as input. The personal information may include demographic, psychographic or other information, such as an age, a weight, a gender, a height, a body mass index, a medical condition, a familial medication history, an injury, a medical procedure, a medication prescribed, or some combination thereof.

The threshold condition may be satisfied when one or more of the measurements, alone or in combination, exceed a certain value. For example, if the heart rate of the user is outside of 60 to 100 beats per minute, the one or more machine learning models may determine that there is a high probability that the user may be experiencing a heart attack. Further, the one or more machine learning models may determine that, when the heart rate is above 100 beats per minute or below 60 beats per minute, there is a high probability of heart arrhythmia. Further, inputs received from the user may be used by the one or more machine learning models to determine whether the threshold has been satisfied. For example, the inputs from the user may relate to whether the user is experiencing a fluttering sensation in the chest area or a skipping of a heartbeat.

At block 1806, the computing device 1200 may perform one or more preventative actions responsive to determining that the one or more measurements indicate that the user satisfies the threshold for the condition associated with the abnormal heart rhythm. The one or more preventative actions may include initiating a telecommunications transmission. In some embodiments, the computing device 1200 may initiate a telecommunications transmission by initiating a call to an emergency service provider. For example, the computing device 1200 may initiate a call to a 911 operator when the one or more measurements indicate the user satisfies the threshold for A-fib. Alternatively, or in addition, the computing device 1200 may initiate a telecommunications transmission by initiating a telemedicine session with a computing device associated with a healthcare professional. For example, the computing device 1200 may initiate a telemedicine session with a doctor when the one or more measurements indicate that the user satisfies the threshold for atrial flutter.

The one or more preventative actions may also include stopping operation of the electromechanical machine. Further, the one or more preventative actions may include modifying one or more parameters associated with the operation of the electromechanical machine. For example, the computing device 1200 may reduce an amount of resistance provided by the treatment apparatus 70. In some implementations, the computing device 1200 may modify a parameter associated with the operation of the electromechanical machine by sending one or more control signals to the electromechanical machine. For example, the computing device 1200 may send a control signal to the treatment apparatus 70 that causes the controller 72 of the treatment apparatus 70 to reduce an amount of resistance provided by the treatment apparatus 70. Alternatively, or in addition, the computing device 1200 may modify a parameter associated with the operation of the electromechanical machine by displaying instructions for the user to manually adjust one or more settings of the electromechanical machine. For example, the patient interface 50 may display instructions for the user to rotate a resistance knob on the treatment apparatus 70 to reduce an amount of resistance provided by the treatment apparatus 70. The one or more preventative actions may also include displaying other types of instructions to the user. For example, when the one or more measurements indicate the user satisfies the threshold for tachycardia, the patient interface 50 may display instructions for the user to take action to lower their heart rate (e.g., lower the intensity of the treatment plan, take a short break from performing the treatment plan, etc.).

The computing device 1200 may determine the one or more preventative actions to perform using the one or more machine learning models. For example, when the one or more measurements indicate the user satisfies the threshold for ventricular tachycardia, the computing device 1200 may use the one or more machine learning models to determine whether the cardiac health of the user necessitates immediate or proximate medical treatment.

CLAUSES

Clause 1.3 A computer-implemented system, comprising:
an electromechanical machine configured to be manipulated by a user while the user is performing a treatment plan;
one or more sensors configured to determine one or more measurements associated with the user; and
one or more processing devices configured to:
receive, from the one or more sensors while the user performs the treatment plan, the one or more measurements associated with the user,
determine, using one or more machine learning models, a probability that the one or more measurements indicate that the user satisfies a threshold for a condition associated with an abnormal heart rhythm, and
perform one or more preventative actions responsive to determining that the one or more measurements indicate the user satisfies the threshold for the condition associated with the abnormal heart rhythm, wherein the one or more preventative actions are determined using the one or more machine learning models, and wherein the one or more preventative actions comprise at least one preventative action selected from the group consisting of initiating a telecommunications transmission, stopping operation of the electromechanical machine, and modifying one or more parameters associated with the operation of the electromechanical machine.

Clause 2.3 The computer-implemented system of any clause herein, wherein, to perform the one or more preventative actions, the one or more processing devices are further configured to initiate a call to an emergency service provider.

Clause 3.3 The computer-implemented system of any clause herein, wherein, to perform the one or more preventative actions, the one or more processing devices are further configured to initiate a telemedicine session with a computing device associated with a healthcare professional.

Clause 4.3 The computer-implemented system of any clause herein, further comprising a display, wherein, to perform the one or more preventative actions, the one or more processing devices are further configured to present, on the display, one or more instructions to modify usage of the electromechanical machine.

Clause 5.3 The computer-implemented system of any clause herein, wherein the condition associated with the abnormal heart rhythm comprises at least one condition selected from the group consisting of atrial fibrillation, atrial flutter, supraventricular tachycardia, ventricular fibrillation, and ventricular tachycardia.

Clause 6.3 The computer-implemented system of any clause herein, wherein the one or more sensors comprise at least one sensor selected from the group consisting of a pulse oximeter, an electrocardiogram sensor, a heart rate sensor, a blood pressure sensor, a temperature sensor, a force sensor, and a continuous glucose monitor sensor.

Clause 7.3 The computer-implemented system of any clause herein, wherein the one or more machine learning models are trained to implement a photoplethysmography algorithm or an electrocardiogram algorithm.

Clause 8.3 A computer-implemented method comprising:
receiving, from one or more sensors while a user performs a treatment plan on an electromechanical machine, one or more measurements associated with the user;
determining, using one or more machine learning models, a probability that the one or more measurements indicate that the user satisfies a threshold for a condition associated with an abnormal heart rhythm; and
performing one or more preventative actions responsive to determining that the one or more measurements indicate the user satisfies the threshold for the condition associated with the abnormal heart rhythm, wherein the one or more preventative actions are determined using the one or more machine learning models, and wherein the one or more preventative actions comprise at least one preventative action selected from the group consisting of initiating a telecommunications transmission, stopping operation of the electromechanical machine, and modifying one or more parameters associated with the operation of the electromechanical machine.

Clause 9.3 The computer-implemented method of any clause herein, wherein performing the one or more preventative actions comprising initiating the telecommunications transmission comprises initiating a call to an emergency service provider.

Clause 10.3 The computer-implemented method of any clause herein, wherein performing the one or more preventative actions comprising initiating a telemedicine session with a computing device associated with a healthcare professional.

Clause 11.3 The computer-implemented method of any clause herein, wherein performing the one or more preventative actions comprising presenting, on a display, one or more instructions to modify usage of the electromechanical machine.

Clause 12.3 The computer-implemented method of any clause herein, wherein the condition associated with the abnormal heart rhythm comprises at least one condition selected from the group consisting of atrial fibrillation, atrial flutter, supraventricular tachycardia, ventricular fibrillation, and ventricular tachycardia.

Clause 13.3 The computer-implemented method of any clause herein, wherein the one or more sensors comprise at least one sensor selected from the group consisting of a pulse oximeter, an electrocardiogram sensor, a heart rate sensor, a blood pressure sensor, a temperature sensor, a force sensor, and a continuous glucose monitor sensor.

Clause 14.3 The computer-implemented method of any clause herein, wherein the one or more machine learning models are trained to implement a photoplethysmography algorithm or an electrocardiogram algorithm.

Clause 15.3 One or more tangible, non-transitory computer-readable media storing instructions that, when executed, cause one or more processing devices to:
receive, from one or more sensors while a user performs a treatment plan on an electromechanical machine, one or more measurements associated with the user, determine, using one or more machine learning models, a probability that the one or more measurements indicate that the user satisfies a threshold for a condition associated with an abnormal heart rhythm, and perform one or more preventative actions responsive to determining that the one or more measurements indicate the user satisfies the threshold for the condition associated with the abnormal heart rhythm, wherein the one or more preventative actions are determined using the one or more machine learning models, and wherein the one or more preventative actions comprise at least one preventative action selected from the group consisting of initiating a telecommunications transmission, stopping operation of the electromechanical machine, and modifying one or more parameters associated with the operation of the electromechanical machine.

Clause 16.3 The one or more computer-readable media of any clause herein, wherein, to perform the one or more preventative actions, the instructions further cause the one or more processing devices to initiate a call to an emergency service provider or a telemedicine session with a computing device associated with a healthcare professional.

Clause 17.3 The one or more computer-readable media of any clause herein, wherein, to perform the one or more preventative actions, the instructions further cause the one or more processing devices to present, on a display, one or more instructions to modify usage of the electromechanical machine.

Clause 18.3 The one or more computer-readable media of any clause herein, wherein the condition associated with the abnormal heart rhythm comprises at least one condition selected from the group consisting of atrial fibrillation, atrial flutter, supraventricular tachycardia, ventricular fibrillation, and ventricular tachycardia.

Clause 19.3 The one or more computer-readable media of any clause herein, wherein the one or more sensors comprise at least one sensor selected from the group consisting of a pulse oximeter, an electrocardiogram sensor, a heart rate sensor, a blood pressure sensor, a temperature sensor, a force sensor, and a continuous glucose monitor sensor.

Clause 20.3 The one or more computer-readable media of any clause herein, wherein the one or more machine learning models are trained to implement a photoplethysmography algorithm or an electrocardiogram algorithm.

Figure 19:
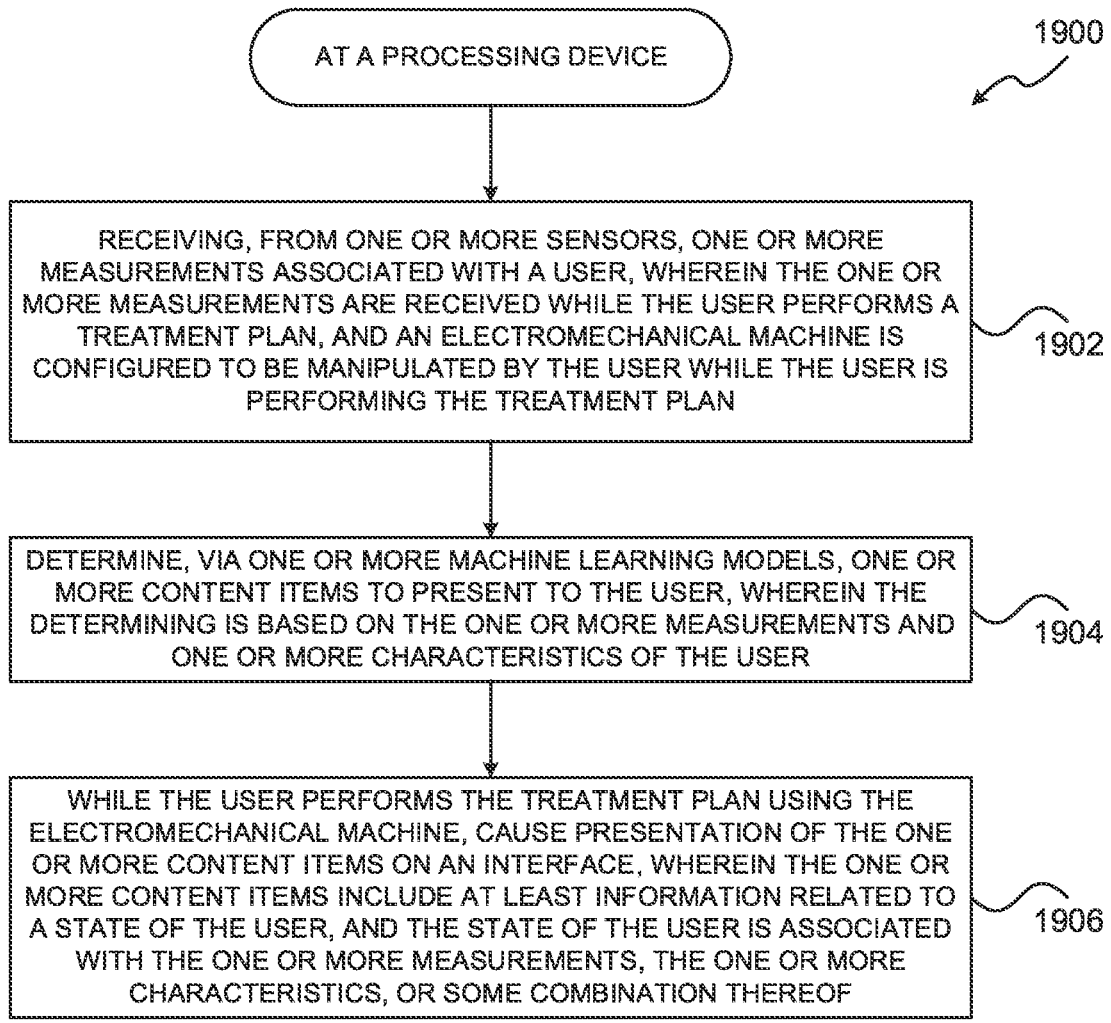
FIG. 19 generally illustrates an example embodiment of a method for residentially-based cardiac rehabilitation by using an electromechanical machine and educational content to mitigate risk factors and optimize user behavior according to the principles of the present disclosure.

System and Method for Residentially-Based Cardiac Rehabilitation by Using an Electromechanical Machine and Educational Content to Mitigate Risk Factors and Optimize User Behavior FIG. 19A illustrates a block diagram of a system 1900 for implementing residentially-based cardiac rehabilitation by using an electromechanical machine and educational content to mitigate risk factors and optimize user behavior, according to some embodiments. As shown in FIG. 19A, the system 1900 may include a data source 1902, a server 1904, a patient interface 1916, and a treatment apparatus 1922. Notwithstanding the specific illustrations in FIG. 19A, the number and/or organization of the various devices illustrated in FIG. 19A are not meant to be limiting. To the contrary, the system 1900 may be adapted to omit and/or combine a subset of the devices illustrated in FIG. 19A, or to include additional devices not illustrated in FIG. 19A, consistent with the scope of this disclosure.

According to some embodiments, the data source 1902 illustrated in FIG. 19A may represent one or more data sources from which patient records may be obtained, which is represented in FIG. 19A as patient records 1903. According to some embodiments, the patient records 1903 may include, for each patient, occupational characteristics of the patient, health-related characteristics of the patient, familial-related characteristics of the patient, cohort-related characteristics of the patient, medical history-related characteristics of the patient, demographic characteristics of the patient, psychographic characteristics of the patient, and/or the like.

According to some embodiments, the occupational characteristics for a given patient may include historical information about the patient's employment experiences, travel experiences, environmental exposures, social interactions, and the like. According to some embodiments, the health-related characteristics of the patient may include historical information about the patient's health, including a history of the patient's interactions with medical professionals; diagnoses received; medical test results received (e.g., blood tests, histologic tests, biopsies, radiologic images, etc.) prescriptions, OTC medications, and nutraceuticals prescribed or recommended; surgical procedures undertaken; past and/or ongoing medical conditions; dietary needs and/or habits; and the like. According to some embodiments, the demographic characteristics for a given patient may include information pertaining to the age, sex, gender, marital status, geographic location of residence, income or net worth, ethnicity, weight, height, etc., of the patient. Additionally, and according to some embodiments, the psychographic characteristics of the patient characteristics for a given patient may include information relating to the attitudes, interests, opinions, beliefs, activities, overt behaviors, motivating behaviors, etc., of the patient.

The foregoing types of patient records (occupational, health-related, demographic, psychographic, etc.) are merely exemplary and not meant to be limiting; further, any type of patient record—such as those previously discussed herein—may be stored by the data source 1902 consistent with the scope of this disclosure.

According to some embodiments, the server 1904 illustrated in FIG. 19A may represent one or more computing devices configured to implement all or part of the different techniques set forth herein. According to some embodiments, the server 1904 may generate customized treatment plans 1908 by using the various machine-learning functionalities described herein. For example, the server 1904 may utilize AI engines, the machine learning models, training engines, etc.—which are collectively represented in FIG. 19A as an assessment utility 1906—to generate the customized treatment plans 1908.

According to some embodiments, the assessment utility 1906 may be configured to receive data pertaining to patients who have performed customized treatment plans 1908 using different treatment apparatuses. In this regard, the data may include characteristics of the patients (e.g., patient records 1903), the details of the customized treatment plans 1908 performed by the patients, the results of performing the customized treatment plans 1908, and the like. The results may include, for example, feedback 1919/1925 received from the patient interface 1916/treatment apparatus 1922. The foregoing feedback sources are not meant to be limiting; further, the assessment utility 1906 may receive feedback/other information from any conceivable source/individual consistent with the scope of this disclosure.

According to some embodiments, the feedback may include changes requested by the patients (e.g., in relation to performing the customized treatment plans 1908) to the customized treatment plans 1908, survey answers provided by the patients regarding their overall experience related to the customized treatment plans 1908, information related to the patient's psychological and/or physical state during the treatment session (e.g., collected by sensors, by the patient, by a medical professional, etc.), information related to the patient's perceived exertion during the treatment session (e.g., using the Borg scale discussed herein), and the like.

Accordingly, the assessment utility 1906 may utilize the machine-learning techniques described herein to generate a customized treatment plan 1908 for a given patient. In some embodiments, one or more machine learning models may be trained using training data. The training data may include labeled inputs (e.g., patient data, feedback data, etc.) that are mapped to labeled outputs (e.g., customized treatment plans 1908). Such training may be referred to as supervised learning. Additional types of training may be used, such as unsupervised learning where the training data is not labeled, and, where based on patterns, the machine learning models group clusters of the unlabeled training data. In addition, reinforcement learning may be used to train the one or more machine learning models, where a reward is associated with the models correctly determining one or more probabilities for one or more characteristics (e.g., the one or more probabilities may be mapped to a curve that may be dynamically or statically adjusted to identify a dividing line that indicates the most likely correct probability for the one or more characteristics, or a range of probabilities for the one or more characteristics, but within a given error margin, standard deviation, range, variance, or other statistical or numerical measure), such that the machine learning models reinforces (e.g., adjusts weights and/or parameters) selecting the one or more probabilities for those characteristics. In some embodiments, some combination of supervised learning, unsupervised learning, and/or reinforcement learning may be used to train the one or more machine learning models.

According to some embodiments, and as shown in FIG. 19A, a customized treatment plan 1908 may include treatment apparatus parameters 1910 for configuring the treatment apparatus, content items 1912, and other parameters 1914. The treatment apparatus parameters 1910 may represent any information that can be utilized to optimize the user's experience and results. For example, the treatment apparatus parameters 1910 may include lighting parameters that specify the manner in which one or more light sources should be configured in order to optimize the patient's performance (e.g., energy) during the exercise sessions. Notably, the lighting parameters may enable one or more devices on which the customized treatment plan 1908 is being implemented—e.g., the patient interface 1916, the treatment apparatus 1922, etc. (hereinafter, "the recipient devices")—to identify light sources, if any, that are relevant to (i.e., nearby) the user and are at least partially configurable according to the lighting parameters. The configurational aspects may include, for example, the overall brightness of a light source, the color tone of a light source, and the like.

In another example, the treatment apparatus parameters 1910 may include sound parameters that specify the manner in which one or more sound sources should be configured in order to optimize the patient's performance during the exercise sessions. According to some embodiments, the sound parameters may enable one or more of the recipient devices to identify speakers (and/or amplifiers to which one or more speakers are connected), if any, that are near to the user and at least partially configurable according to the sound parameters. The configurational aspects may include, for example, an audio file and/or stream to play back, a volume at which to play back the audio file and/or stream, sound settings (e.g., bass, treble, balance, etc.), and the like. In one example, one of the recipient devices may be linked to one or more wired or wireless speakers, headphones, etc. located in a room in which the patient typically conducts the treatment sessions.

In yet another example, the treatment apparatus parameters 1910 may include environmental parameters that specify the manner in which one or more heating, ventilation, air purification, and air conditioning (HVAC) devices should be configured in order to optimize the patient's performance during the exercise sessions. According to some embodiments, the environmental parameters may enable one or more of the recipient devices to identify HVAC devices, if any, that are nearby the user and at least partially configurable according to the environmental parameters. The configurational aspects may include, for example, a temperature for the room, a humidity for the room, a fan speed for the room, an air purification setting (e.g., a highest level of purification), and the like.

In yet another example, the treatment apparatus parameters 1910 may include notification parameters that specify the manner in which one or more nearby computing devices should be configured in order to minimize the patient's distractions during the exercise sessions. More specifically, the notification parameters may enable one or more of the recipient devices to adjust their own (or other devices') notification settings. In one example, this may include updating configurations to suppress at least one of audible, visual, haptic, or physical alerts, to minimize distractions to the patient during the treatment session. This may also include updating a configuration to cause one or more of the recipient devices to transmit all electronic communications directly to an alternative target comprising one of voicemail, text, email, or other alternative electronic receiver or software application.

In a further example, the treatment apparatus parameters 1910 may include augmented reality parameters that specify the manner in which one or more of the recipient devices should configured in order to optimize the patient's performance during the exercise sessions. This may include, for example, updating a virtual background displayed on respective display devices communicatively coupled to the recipient devices. The techniques set forth herein are not limited to augmented reality but may also apply to virtual (or other) reality implementations. For example, the augmented reality parameters may include information enabling a patient to participate in a treatment session by using a virtual reality headset configured in accordance with one or more of the lighting parameters, sound parameters, notification parameters, augmented reality parameters, or other parameters. Further, any suitable immersive reality shall be deemed to be within the scope of the disclosure.

The foregoing types of parameters (lighting, sound, notification, augmented reality, other, etc.) are merely exemplary and not meant to be limiting; further, any type of parameter-such as those previously discussed herein—may be adjusted consistent with the scope of this disclosure.

According to some embodiments, the assessment utility 1906 can identify and/or generate, via one or more machine learning models, content items 1912 to present to the user. According to some embodiments, the content items 1912 may include any information necessary to facilitate a treatment session as described herein, e.g., pre-recorded content, interactive content, overarching treatment plan information, and so on. According to some embodiments, the content items 1912 can be based on obtained exercise measurements (e.g., via feedback 1919/1925), obtained characteristics of the user (e.g., obtained using the patient records 1903), and the like.

The content items 1912 can represent any information that can be presented to the user with the goal of maximizing the benefits of the user's engagement in the exercise rehabilitation program. For example, the content items 1912 can include educational materials that inform the user about the medical event(s) they have experienced, as well as the salience of engaging in exercise. The content items 1912 can also include educational materials about exercise commitments that are needed to effectively avoid subsequent medical events and/or improve ongoing medical conditions. For example, the educational materials can include custom-tailored exercise guidance to help ensure the user remains within acceptable exertion boundaries when utilizing the treatment apparatus 1922. The educational materials can also include custom-tailored lifestyle guidance, such as ways to influence modifiable risk factors including cholesterol levels, blood pressure levels, weight levels, stress levels, drug use levels (e.g., intake of alcohol, tobacco, etc.), diabetes levels, and the like. The educational materials can also include custom-tailored nutritional guidance. It is noted that the content items 1912 discussed herein are merely exemplary and not meant to be limiting, and that the content items 1912 can be based on any conceivable information that can be associated with the user, consistent with the scope of this disclosure.

FIG. 19B provides a conceptual user interface 1930 that displays a content item 1912-1, according to some embodiments. The content item 1912-1 can be displayed, for example, on a display device that is communicatively coupled to any of the recipient devices (e.g., the patient interface 1916). According to some embodiments, the content item 1912-1 can be generated by the assessment utility 1906 in accordance with the various techniques described herein. For example, the assessment utility 1906 can determine, based on patient records 1903 associated with the user, that the user has not yet engaged in any exercise rehabilitation program, such that it is appropriate to display educational information about the most optimal way to engage in the first session of the exercise rehabilitation program.

Additionally, the assessment utility 1906 can tailor the content item 1912-1 based on any information that is accessible to the assessment utility 1906 and relevant to the user's exercise rehabilitation program. For example, the assessment utility 1906 can identify, based on the user's medical history, demographic information, etc., appropriate parameters (e.g., warm-up time, exercise time, etc.) for the first exercise session. The appropriate parameters can also be based on medical research information to which the assessment utility 1906 has access, including regimens that proved successful for similar users, research information, and so on.

Additionally, the assessment utility 1906 can identify, based on various sensors (e.g., located on the patient interface 1916 and/or the treatment apparatus 1922), that the present environmental conditions of the room are not optimal for exercise. For example, in response to determining that the room is dim and warm (e.g., above eighty degrees), that the humidity is non-optimal, that there is no airflow, and that there is no music playing, the assessment utility 1906 can include in the content item 1912-1 information that encourages the user to activate all lights, to lower the room temperature, to increase or decrease the humidity, to activate any available fans, and to play upbeat music, in order to establish an environment that is conducive to energetic exercise.

FIG. 19C provides a conceptual user interface 1932 that displays a content item 1912-2, according to some embodiments. Here, the content item 1912-2 is generated by the assessment utility 1906 in response to determining that the user has successfully completed the first exercise session. As shown in FIG. 19C, the content item 1912-2 includes information about the Borg scale discussed herein, and the conceptual user interface 1932 enables the user to input a selection 1933 of the user's perceived difficulty of the first exercise. In turn, when the user submits their answer, the patient records 1903 for the user can be updated so that the assessment utility 1906 may generate and provide appropriate content items 1912 to the user prior to their next exercise session.

FIG. 19D provides a conceptual user interface 1934 that displays a content item 1912-3, according to some embodiments. As shown in FIG. 19D, the assessment utility 1906 determines, based on the selection 1943 discussed above in conjunction with FIG. 19C, that the user previously exceeded an exertion limit that should apply to the user. Accordingly, the content item 1912-3 includes information that informs the user of the overexertion. The content item 1912-3 also includes information about what the user can expect during their next exercise.

It is noted that the recipient devices can display useful information to the user during the exercise when relevant. For example, if the assessment utility 1906 determines that, during the second exercise session, the user is outputting similar amounts of energy to the first exercise (where the exertion level was exceeded), then the assessment utility 1906 can generate one or more content items 1912 that warn the user of the repeated overexertion. In this manner, the user can effectively adjust their exertion levels during the exercise and obtain a better understanding of how to manage their exertion.

FIG. 19E provides a conceptual user interface 1936 that displays a content item 1912-4, according to some embodiments. As shown in FIG. 19E, the assessment utility 1906 may determine, based on the selection 1943 discussed above in conjunction with FIG. 19C, that the user exceeded an exertion limit during their prior exercise. Accordingly, the content item 1912-4 includes information that reminds/informs the user of the overexertion, as well as providing guidance to achieve the optimal level of exertion for the user during the imminent exercise.

FIG. 19F provides a conceptual user interface 1938 that displays a content item 1912-5, according to some embodiments. As shown in FIG. 19F, the assessment utility 1906 determines that the user has completed the second exercise session. In turn, the assessment utility 1906 generates the content item 1912-5—which, as shown in FIG. 19F, includes a dietary plan tailored to the user.

Notably, the assessment utility 1906 can perform the tailoring based on any information accessible to the assessment utility 1906 and relevant to the user's exercise rehabilitation program. In one example, if the assessment utility 1906 determines that the user reports a similar perceived exertion despite outputting a lower amount of energy during the exercise, then it may be prudent to adjust the dietary recommendations in a manner that will improve the user's energy levels during the next exercise. For example, if the assessment utility 1906 determines that the user engaged in the first two exercise sessions immediately after lunch (where energy levels typically drop), then the assessment utility 1906 can generate content items 1912 that recommend both consuming a light snack and/or exercising prior to lunch.

Additionally, FIG. 19G generally illustrates an example embodiment of a method 1950 for enabling residentially-based cardiac rehabilitation by using an electromechanical machine and educational content to mitigate risk factors and optimize user behavior according to the principles of the present disclosure.

According to some embodiments, the method 1950 may be performed by processing logic that may include hardware (circuitry, dedicated logic, etc.), software, or a combination of both. The method 1950 and/or each of their individual functions, subroutines, or operations may be performed by one or more processing devices of a computing device (e.g., the computer system 1100 of FIG. 11) implementing the method 1950. The method 1950 may be implemented as computer instructions stored on a memory device and executable by the one or more processing devices. In certain implementations, the method 1950 may be performed by a single processing thread. Alternatively, the method 1950 may be performed by two or more processing threads, each thread implementing one or more individual functions, routines, subroutines, or operations of the techniques described herein.

In some embodiments, a system may be used to implement the method 1950. The system may include the treatment apparatus 1922 (electromechanical machine) configured to be manipulated by a user while the user is performing a treatment plan, and an interface including a display configured to present information pertaining to the treatment plan. The system may include a processing device configured to execute instructions implemented the method 1950.

At block 1952, the processing device may receive, from one or more sensors, one or more measurements associated with the user. The one or more measurements may be received while the user uses the electromechanical machine to perform the treatment plan. In some embodiments, the electromechanical machine may include at least one of a cycling machine, a rowing machine, a stair-climbing machine, a treadmill, and an elliptical machine.

At block 1954, the processing device may identify and/or generate, via one or more machine learning models, one or more content items to present to the user, wherein the identification and/or generation is based on the one or more measurements and one or more characteristics of the user. In some embodiments, the one or more content items can include digital brochures, digital videos, interactive user interfaces, and the like. In some embodiments, the one or more characteristics of the user may include both non-modifiable risk factors and modifiable risk factors, which are discussed below in greater detail.

In some embodiments, the one or more content items may pertain to cardiac rehabilitation, oncology rehabilitation, cardio-oncologic rehabilitation, neurologic rehabilitation, rehabilitation from pathologies related to the prostate gland or male or female urogenital tract or to male or female sexual reproduction, including pathologies related to the breast, pulmonary rehabilitation, bariatric rehabilitation, or some combination thereof. Notably, the rehabilitation categories discussed herein are not meant to be limiting, and the content items may pertain to any category of rehabilitation consistent with the scope of this disclosure. In some embodiments, the processing device may modify one or more risk factors of the user. The modifiable factors may relate to cholesterol levels, blood pressure levels, stress levels, drug use levels (e.g., intake of alcohol, tobacco, etc.), diabetes levels, or some combination thereof. Notably, the risk factors discussed herein are not meant to be limiting, and the risk factors may encompass any aspect of the user's medical profile consistent with the scope of this disclosure. For example, the risk factors may relate to medication compliance or noncompliance of the user. Unmodifiable risk factors may include age, gender, cardiac history, diabetes history, family history, prior environmental exposures, and so on.

At block 1956, while the user performs the treatment plan using the electromechanical machine, the processing device may cause presentation of the one or more content items on an interface. The one or more content items may include at least information related to a state of the user, and the state of the user may be associated with the one or more measurements, the one or more characteristics, or some combination thereof.

In some embodiments, the processing device may receive, from one or more peripheral devices, input from the user. The input from the user may include a request to view more details related to the information, a request to receive different information, a request to receive related or complementary information, a request to stop presentation of the information, or some combination thereof.

In some embodiments, based on the one or more content items, the processing device may modify one or more operating parameters of the electromechanical machine. Further, in some embodiments, based on usage of the electromechanical machine by the user, the processing device may modify, in real-time or near real-time, playback of the one or more content items. For example, if the user has used the electromechanical machine for more than a threshold period of time, for more than a threshold number of times, or the like, then the processing device may select content items that are more relevant to a physical, emotional, mental, etc. state of the user relative to the usage of the electromechanical machine. In other words, the processing device may select more content items including more advanced subject matter as the user progresses in the treatment plan.

CLAUSES

Clause 1.4 A computer-implemented system, comprising:
an electromechanical machine configured to be manipulated by a user while the user is performing a treatment plan;
an interface comprising a display configured to present information pertaining to the treatment plan; and
a processing device configured to:
receive, from one or more sensors, one or more measurements associated with the user, wherein the one or more measurements are received while the user performs the treatment plan;
determine, via one or more machine learning models, one or more content items to present to the user, wherein the determining is based on the one or more measurements and one or more characteristics of the user; and
while the user performs the treatment plan using the electromechanical machine, cause presentation of the one or more content items on the interface, wherein the one or more content items comprise at least information related to a state of the user, and the state of the user is associated with the one or more measurements, the one or more characteristics, or some combination thereof.

Clause 2.4 The computer-implemented system of any clause herein, wherein the one or more content items pertain to cardiac rehabilitation, oncology rehabilitation, cardio-oncologic rehabilitation, rehabilitation from pathologies related to the prostate gland or urogenital tract, pulmonary rehabilitation, bariatric rehabilitation, or some combination thereof.

Clause 3.4 The computer-implemented system of any clause herein, wherein the electromechanical machine is a cycling machine, a rowing machine, a stair-climbing machine, a treadmill, and/or an elliptical machine.

Clause 4.4 The computer-implemented system of any clause herein, wherein the processing device is further configured to modify one or more risk factors of the user by presenting the one or more content items.

Clause 5.5 The computer-implemented system of any clause herein, wherein the processing device is further configured to:
receive, from one or more peripheral devices, input from the user, wherein the input from the user comprises a request to view more details related to the information, a request to receive different information, a request to receive related or complementary information, a request to stop presentation of the information, or some combination thereof.

Clause 6.4 The computer-implemented system of any clause herein, wherein, based on the one or more content items, the processing device is further configured to modify one or more operating parameters of the electromechanical machine.

Clause 7.4 The computer-implemented system of any clause herein, wherein, based on usage of the electromechanical machine by the user, the processing device is further configured to modify in real-time or near real-time playback of the one or more content items.

Clause 8.4 A computer-implemented method comprising:
receiving, from one or more sensors, one or more measurements associated with a user, wherein the one or more measurements are received while the user performs a treatment plan, and an electromechanical machine is configured to be manipulated by the user while the user is performing the treatment plan;
determining, via one or more machine learning models, one or more content items to present to the user, wherein the determining is based on the one or more measurements and one or more characteristics of the user; and
while the user performs the treatment plan using the electromechanical machine, causing presentation of the one or more content items on an interface, wherein the one or more content items comprise at least information related to a state of the user, and the state of the user is associated with the one or more measurements, the one or more characteristics, or some combination thereof.

Clause 9.4 The computer-implemented method of any clause herein, wherein the one or more content items pertain to cardiac rehabilitation, oncology rehabilitation, cardio-oncologic rehabilitation, rehabilitation from pathologies related to the prostate gland or urogenital tract, pulmonary rehabilitation, bariatric rehabilitation, or some combination thereof.

Clause 10.4 The computer-implemented method of any clause herein, wherein the electromechanical machine is at least one of a cycling machine, a rowing machine, and a stair-climbing machine, a treadmill, and an elliptical machine.

Clause 11.4 The computer-implemented method of any clause herein, further comprising modifying one or more risk factors of the user by presenting the one or more content items.

Clause 12.4 The computer-implemented method of any clause herein, further comprising:
receiving, from one or more peripheral devices, input from the user, wherein the input from the user comprises a request to view more details related to the information, a request to receive different information, a request to receive related or complementary information, a request to stop presentation of the information, or some combination thereof.

Clause 13.4 The computer-implemented method of any clause herein, further comprising, based on the one or more content items, modifying one or more operating parameters of the electromechanical machine.

Clause 14.4 The computer-implemented method of any clause herein, further comprising, based on usage of the electromechanical machine by the user, modifying in real-time or near real-time playback of the one or more content items.

Clause 15. A tangible, non-transitory computer-readable medium storing instructions that, when executed, cause a processing device to:
receive, from one or more sensors, one or more measurements associated with a user, wherein the one or more measurements are received while the user performs a treatment plan, and an electromechanical machine is configured to be manipulated by the user while the user is performing the treatment plan;
determine, via one or more machine learning models, one or more content items to present to the user, wherein the determining is based on the one or more measurements and one or more characteristics of the user; and
while the user performs the treatment plan using the electromechanical machine, cause presentation of the one or more content items on an interface, wherein the one or more content items comprise at least information related to a state of the user, and the state of the user is associated with the one or more measurements, the one or more characteristics, or some combination thereof.

Clause 16.4 The computer-readable medium of any clause herein, wherein the one or more content items pertain to cardiac rehabilitation, oncology rehabilitation, cardio-oncologic rehabilitation, rehabilitation from pathologies related to the prostate gland or urogenital tract, pulmonary rehabilitation, bariatric rehabilitation, or some combination thereof.

Clause 17.4 The computer-readable medium of any clause herein, wherein the electromechanical machine is at least one of a cycling machine, a rowing machine, and a stair-climbing machine, a treadmill, and an elliptical machine.

Clause 18.4 The computer-readable medium of any clause herein, wherein the processing device is further caused to modify one or more risk factors of the user by presenting the one or more content items.

Clause 19.4 The computer-readable medium of any clause herein, wherein the processing device is further caused to:
receive, from one or more peripheral devices, input from the user, wherein the input from the user comprises a request to view more details related to the information, a request to receive different information, a request to receive related or complementary information, a request to stop presentation of the information, or some combination thereof.

Clause 20.4 The computer-readable medium of any clause herein, wherein, based on the one or more content items, the processing device is further caused to modify one or more operating parameters of the electromechanical machine.

Figure 20:
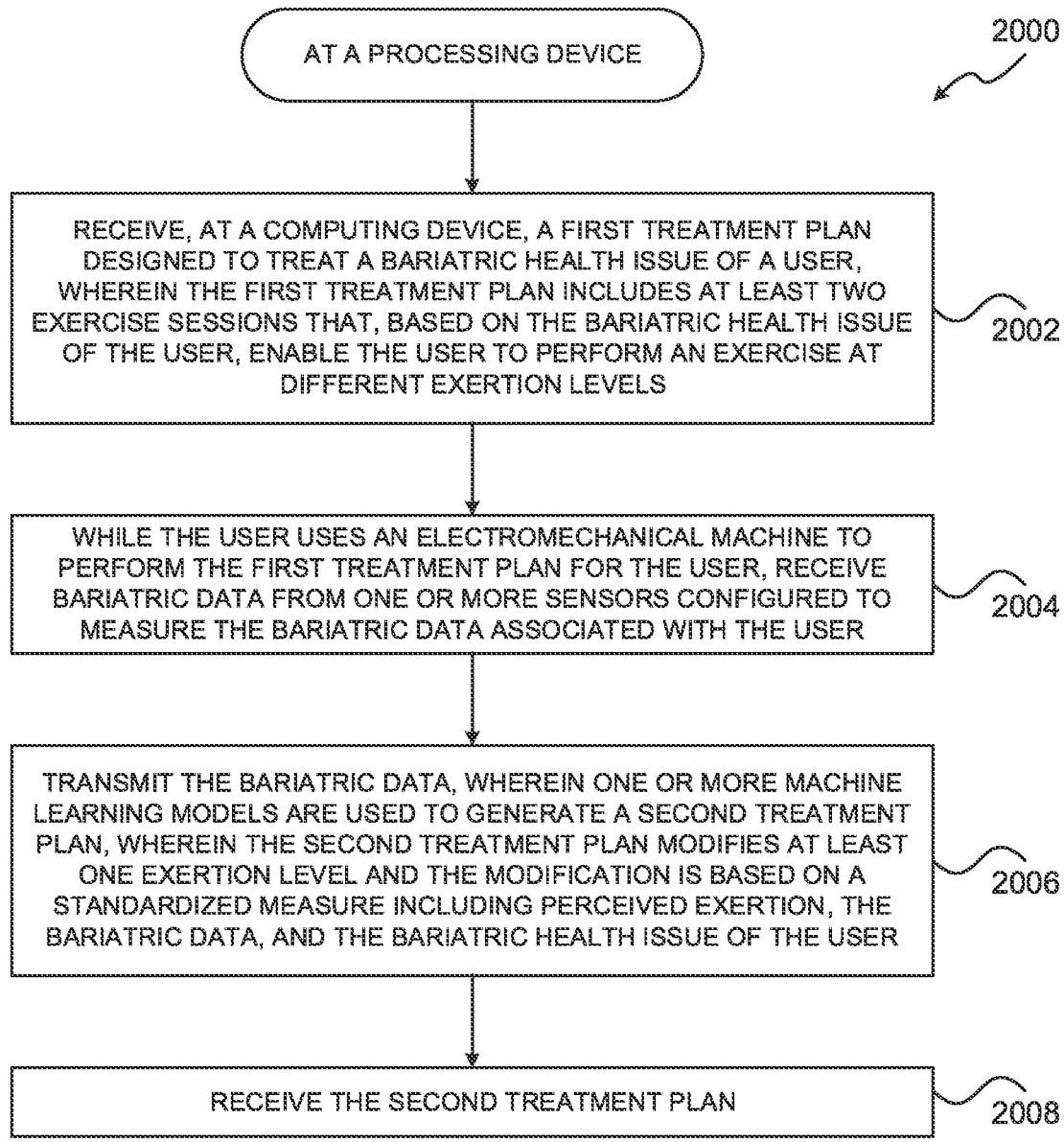
FIG. 20 generally illustrates an example embodiment of a method for using artificial intelligence and machine learning and telemedicine to perform bariatric rehabilitation via an electromechanical machine according to the principles of the present disclosure.

System and Method for Using AI/ML and Telemedicine to Perform Bariatric Rehabilitation Via an Electromechanical Machine FIG. 20 generally illustrates an example embodiment of a method 2000 for using artificial intelligence and machine learning and telemedicine to perform bariatric rehabilitation via an electromechanical machine according to the principles of the present disclosure. The method 2000 may be performed by processing logic that may include hardware (circuitry, dedicated logic, etc.), software, or a combination of both. The method 2000 and/or each of their individual functions, subroutines, or operations may be performed by one or more processing devices of a computing device (e.g., the computer system 1100 of FIG. 11) implementing the method 2000. The method 2000 may be implemented as computer instructions stored on a memory device and executable by the one or more processing devices. In certain implementations, the method 2000 may be performed by a single processing thread. Alternatively, the method 2000 may be performed by two or more processing threads, each thread implementing one or more individual functions, routines, subroutines, or operations of the methods.

In some embodiments, a system may be used to implement the method 2000. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 2000.

At block 2002, the processing device may receive, at a computing device, a first treatment plan designed to treat a bariatric health issue of a user. The first treatment plan may include at least two exercise sessions that, based on the bariatric health issue of the user, enable the user to perform an exercise at different exertion levels.

In some embodiments, the first treatment plan may be generated based on attribute data including an eating or drinking schedule of the user, information pertaining to an age of the user, information pertaining to a sex of the user, information pertaining to a weight of the user information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof. At block 2004, while the user uses an electromechanical machine to perform the first treatment plan for the user, the processing device may receive bariatric data from one or more sensors configured to measure the bariatric data associated with the user. In some embodiments, the bariatric data may include a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, a pulmonary diagnosis of the user, an oncologic diagnosis of the user, a bariatric diagnosis of the user, a pathological diagnosis related to a prostate gland or urogenital tract of the user, spirometry data related to the user, or some combination thereof.

At block 2006, the processing device may transmit the bariatric data. In some embodiments, one or more machine learning models 13 may be executed by the server 30 and the machine learning models 13 may be used to generate a second treatment plan based on the bariatric data. The second treatment plan may modify at least one exertion level, and the modification may be based on a standardized measure including perceived exertion, bariatric data, and the bariatric health issue of the user. In some embodiments, the standardized measure of perceived exertion may include a metabolic equivalent of tasks (MET) or a Borg rating of perceived exertion (RPE).

In some embodiments, the one or more machine learning models generate the second treatment plan by predicting exercises that will result in the desired exertion level for each session. The one or more machine learning models may be trained using data pertaining to the standardized measure of perceived exertion, other users' bariatric data, and other users' bariatric health issues as input data, and other users' exertion levels that led to desired results as output data. The input data and the output data may be labeled and mapped accordingly.

At block 2008, the processing device may receive the second treatment plan from the server 30. The processing device may implement at least a portion of the treatment plan to cause an operating parameter of the electromechanical machine to be modified in accordance with the modified exertion level set in the second treatment plan. To that end, in some embodiments, the second treatment plan may include a modified parameter pertaining to the electromechanical machine. The modified parameter may include a resistance, a range of motion, a length of time, an angle of a component of the electromechanical machine, a speed, or some combination thereof. The processing device may, based on the modified parameter, control the electromechanical machine.

In some embodiments, transmitting the bariatric data may include transmitting the bariatric data to a second computing device that relays the bariatric data to a third computing device that is associated with a healthcare professional.

CLAUSES

Clause 1.5 A computer-implemented system, comprising:
an electromechanical machine configured to be manipulated by a user while the user performs a treatment plan;
an interface comprising a display configured to present information pertaining to the treatment plan; and
a processing device configured to:
receive, at a computing device, a first treatment plan designed to treat a bariatric health issue of a user, wherein the first treatment plan comprises at least two exercise sessions that, based on the bariatric health issue of the user, enable the user to perform an exercise at different exertion levels;
while the user uses a treatment apparatus to perform the first treatment plan for the user, receive bariatric data from one or more sensors configured to measure the bariatric data associated with the user;

transmit the bariatric data, wherein one or more machine learning models are used to generate a second treatment plan, wherein the second treatment plan modifies at least one exertion level, and the modification is based on a standardized measure comprising perceived exertion, the bariatric data, and the bariatric health issue of the user; and receive the second treatment plan.

Clause 2.5 The computer-implemented system of any clause herein, wherein the second treatment plan comprises a modified parameter pertaining to the electromechanical machine, wherein the modified parameter comprises a resistance, a range of motion, a length of time, an angle of a component of the electromechanical machine, a speed, or some combination thereof, and the computer-implemented system further comprises:

based on the modified parameter, controlling the electromechanical machine.

Clause 3.5 The computer-implemented system of any clause herein, wherein the standardized measure of perceived exertion comprises a metabolic equivalent of tasks (MET) or a Borg rating of perceived exertion (RPE).

Clause 4.5 The computer-implemented system of any clause herein, wherein, by predicting exercises that will result in the desired exertion level for each session, the one or more machine learning models generate the second treatment plan, and the one or more machine learning models are trained using data pertaining to the standardized measure of perceived exertion, other users' bariatric data, and other users' bariatric health issues.

Clause 5.5 The computer-implemented system of any clause herein, wherein the first treatment plan is generated based on attribute data comprising an eating or drinking schedule of the user, information pertaining to an age of the user, information pertaining to a sex of the user, information pertaining to a weight of the user information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

Clause 6.5 The computer-implemented system of any clause herein, wherein the transmitting the bariatric data further comprises transmitting the bariatric data to a second computing device that relays the bariatric data to a third computing device that is associated with a healthcare professional.

Clause 7.5 The computer-implemented system of any clause herein, wherein the bariatric data comprises a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, a pulmonary diagnosis of the user, an oncologic diagnosis of the user, a bariatric diagnosis of the user, a pathological diagnosis related to a prostate gland or urogenital tract of the user, spirometry data related to the user, or some combination thereof.

Clause 8.5 A computer-implemented method comprising:

receiving, at a computing device, a first treatment plan designed to treat a bariatric health issue of a user, wherein the first treatment plan comprises at least two exercise sessions that, based on the bariatric health issue of the user, enable the user to perform an exercise at different exertion levels;

while the user uses an electromechanical machine to perform the first treatment plan for the user, receiving bariatric data from one or more sensors configured to measure the bariatric data associated with the user, wherein the electromechanical machine is configured to be manipulated by the user while the user performs the first treatment plan;

transmitting the bariatric data, wherein one or more machine learning models are used to generate a second treatment plan, wherein the second treatment plan modifies at least one exertion level, and the modification is based on a standardized measure comprising perceived exertion, the bariatric data, and the bariatric health issue of the user; and receiving the second treatment plan.

Clause 9.5 The computer-implemented method of any clause herein, wherein the second treatment plan comprises a modified parameter pertaining to the electromechanical machine, wherein the modified parameter comprises a resistance, a range of motion, a length of time, an angle of a component of the electromechanical machine, a speed, or some combination thereof, and the computer-implemented method further comprises:

based on the modified parameter, controlling the electromechanical machine.

Clause 10.5 The computer-implemented method of any clause herein, wherein the standardized measure of perceived exertion comprises a metabolic equivalent of tasks (MET) or a Borg rating of perceived exertion (RPE).

Clause 11.5 The computer-implemented method of any clause herein, wherein, by predicting exercises that will result in the desired exertion level for each session, the one or more machine learning models generate the second treatment plan, and the one or more machine learning models are trained using data pertaining to the standardized measure of perceived exertion, other users' bariatric data, and other users' bariatric health issues.

Clause 12.5 The computer-implemented method of any clause herein, wherein the first treatment plan is generated based on attribute data comprising an eating or drinking schedule of the user, information pertaining to an age of the user, information pertaining to a sex of the user, information pertaining to a weight of the user information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

Clause 13.5 The computer-implemented method of any clause herein, wherein the transmitting the bariatric data further comprises transmitting the bariatric data to a second computing device that relays the bariatric data to a third computing device that is associated with a healthcare professional.

Clause 14.5 The computer-implemented method of any clause herein, wherein the bariatric data comprises a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, a pulmonary diagnosis of the user, an oncologic diagnosis of the user, a bariatric diagnosis of the user, a pathological diagnosis related to a prostate gland or urogenital tract of the user, spirometry data related to the user, or some combination thereof.

Clause 15.5 A tangible, non-transitory computer-readable medium storing instructions that, when executed, cause a processing device to:
  receive a first treatment plan designed to treat a bariatric health issue of a user, wherein the first treatment plan comprises at least two exercise sessions that, based on the bariatric health issue of the user, enable the user to perform an exercise at different exertion levels;
  while the user uses an electromechanical machine to perform the first treatment plan for the user, receive bariatric data from one or more sensors configured to measure the bariatric data associated with the user, wherein the electromechanical machine is configured to be manipulated by the user while the user performs the first treatment plan;
  transmit the bariatric data, wherein one or more machine learning models are used to generate a second treatment plan, wherein the second treatment plan modifies at least one exertion level, and the modification is based on a standardized measure comprising perceived exertion, the bariatric data, and the bariatric health issue of the user; and
  receive the second treatment plan.

Clause 16.5 The computer-readable medium of any clause herein, wherein the second treatment plan comprises a modified parameter pertaining to the electromechanical machine, wherein the modified parameter comprises a resistance, a range of motion, a length of time, an angle of a component of the electromechanical machine, a speed, or some combination thereof, and the computer-implemented method further comprises:
  based on the modified parameter, controlling the electromechanical machine.

Clause 17.5 The computer-readable medium of any clause herein, wherein the standardized measure of perceived exertion comprises a metabolic equivalent of tasks (MET) or a Borg rating of perceived exertion (RPE).

Clause 18.5 The computer-readable medium of any clause herein, wherein, by predicting exercises that will result in the desired exertion level for each session, the one or more machine learning models generate the second treatment plan, and the one or more machine learning models are trained using data pertaining to the standardized measure of perceived exertion, other users' bariatric data, and other users' bariatric health issues.

Clause 19.5 The computer-readable medium of any clause herein, wherein the first treatment plan is generated based on attribute data comprising an eating or drinking schedule of the user, information pertaining to an age of the user, information pertaining to a sex of the user, information pertaining to a weight of the user information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

Clause 20.5 The computer-readable medium of any clause herein, wherein the transmitting the bariatric data further comprises transmitting the bariatric data to a second computing device that relays the bariatric data to a third computing device that is associated with a healthcare professional.

Figure 21:
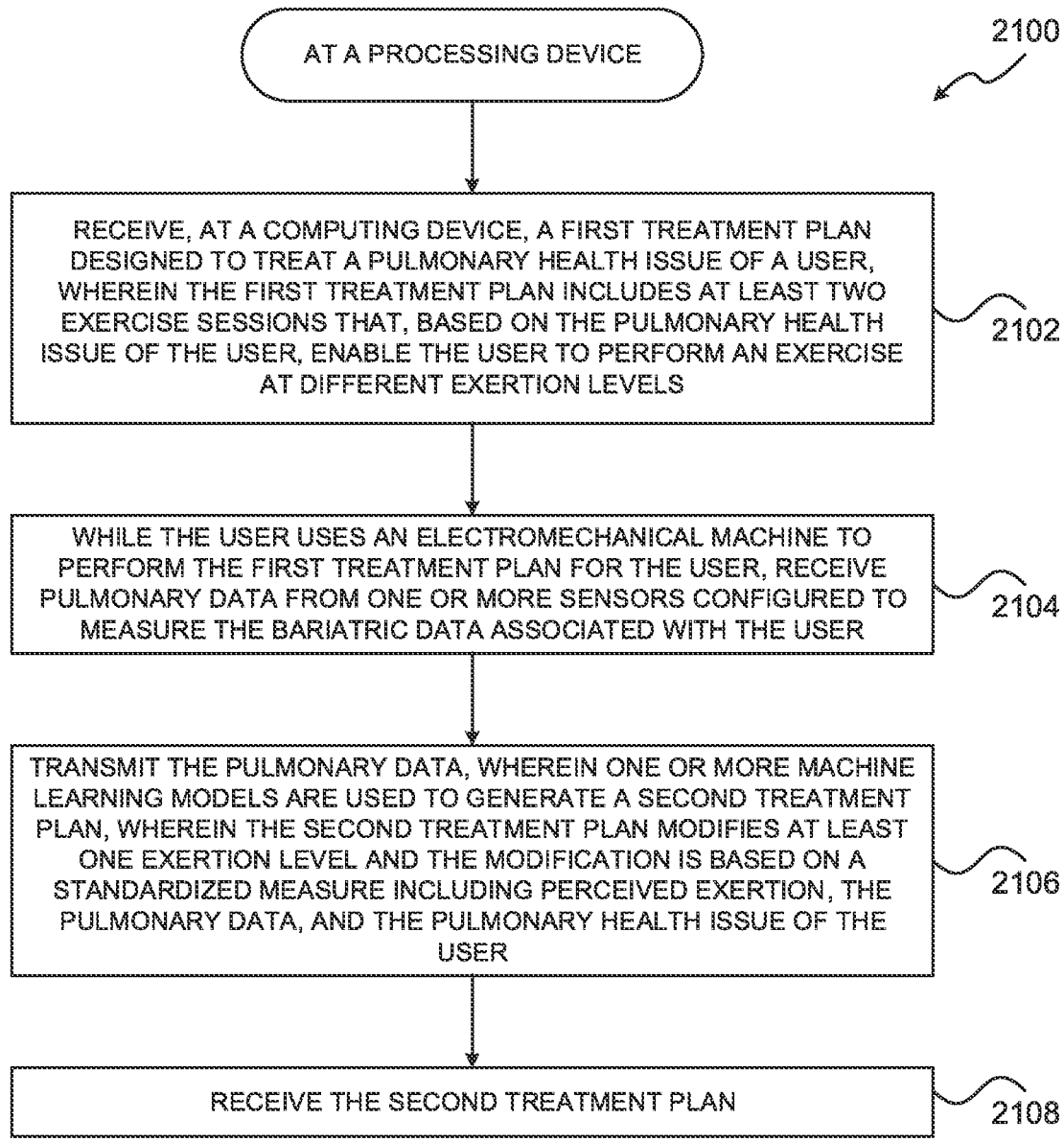
FIG. 21 generally illustrates an example embodiment of a method for using artificial intelligence and machine learning and telemedicine to perform pulmonary rehabilitation via an electromechanical machine according to the principles of the present disclosure.

System and Method for Using AI/ML and Telemedicine to Perform Pulmonary Rehabilitation Via an Electromechanical Machine FIG. 21 generally illustrates an example embodiment of a method 2100 for using artificial intelligence and machine learning and telemedicine to perform pulmonary rehabilitation via an electromechanical machine according to the principles of the present disclosure. The method 2100 may be performed by processing logic that may include hardware (circuitry, dedicated logic, etc.), software, or a combination of both. The method 2100 and/or each of their individual functions, subroutines, or operations may be performed by one or more processing devices of a computing device (e.g., the computer system 1100 of FIG. 11) implementing the method 2100. The method 2100 may be implemented as computer instructions stored on a memory device and executable by the one or more processing devices. In certain implementations, the method 2100 may be performed by a single processing thread. Alternatively, the method 2100 may be performed by two or more processing threads, each thread implementing one or more individual functions, routines, subroutines, or operations of the methods.

In some embodiments, a system may be used to implement the method 2100. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 2100.

At block 2102, the processing device may receive, at a computing device, a first treatment plan designed to treat a pulmonary health issue of a user. The first treatment plan may include at least two exercise sessions that, based on the pulmonary health issue of the user, enable the user to perform an exercise at different exertion levels.

In some embodiments, the first treatment plan may be generated based on attribute data including an eating or drinking schedule of the user, information pertaining to an age of the user, information pertaining to a sex of the user, information pertaining to a weight of the user information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

At block 2104, while the user uses an electromechanical machine to perform the first treatment plan for the user, the processing device may receive pulmonary data from one or more sensors configured to measure the pulmonary data associated with the user. In some embodiments, the pulmonary data may include a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, a pulmonary diagnosis of the user, an oncologic diagnosis of the user, a pulmonary diagnosis of the user, a pathological diagnosis related to a prostate gland or urogenital tract of the user, spirometry data related to the user, or some combination thereof.

At block 2106, the processing device may transmit the pulmonary data. In some embodiments, one or more machine learning models 13 may be executed by the server 30 and the machine learning models 13 may be used to generate a second treatment plan based on the pulmonary data. The second treatment plan may modify at least one exertion level, and the modification may be based on a standardized measure including perceived exertion, pulmonary data, and the pulmonary health issue of the user. In some embodiments, the standardized measure of perceived exertion may include a metabolic equivalent of tasks (MET) or a Borg rating of perceived exertion (RPE).

In some embodiments, the one or more machine learning models generate the second treatment plan by predicting exercises that will result in the desired exertion level for each session. The one or more machine learning models may be trained using data pertaining to the standardized measure of perceived exertion, other users' pulmonary data, and other users' pulmonary health issues as input data, and other users' exertion levels that led to desired results as output data. The input data and the output data may be labeled and mapped accordingly.

At block 2108, the processing device may receive the second treatment plan from the server 30. The processing device may implement at least a portion of the treatment plan to cause an operating parameter of the electromechanical machine to be modified in accordance with the modified exertion level set in the second treatment plan. To that end, in some embodiments, the second treatment plan may include a modified parameter pertaining to the electromechanical machine. The modified parameter may include a resistance, a range of motion, a length of time, an angle of a component of the electromechanical machine, a speed, a velocity, an angular velocity, an acceleration, a torque, or some combination thereof. The processing device may, based on the modified parameter, control the electromechanical machine.

In some embodiments, transmitting the pulmonary data may include transmitting the pulmonary data to a second computing device that relays the pulmonary data to a third computing device that is associated with a healthcare professional.

CLAUSES

Clause 1.6 A computer-implemented system, comprising:
an electromechanical machine configured to be manipulated by a user while the user performs a treatment plan;
an interface comprising a display configured to present information pertaining to the treatment plan; and
a processing device configured to:
receive, at a computing device, a first treatment plan designed to treat a pulmonary health issue of a user, wherein the first treatment plan comprises at least two exercise sessions that, based on the pulmonary health issue of the user, enable the user to perform an exercise at different exertion levels;
while the user uses an electromechanical machine to perform the first treatment plan for the user, receive pulmonary data from one or more sensors configured to measure the pulmonary data associated with the user;
transmit the pulmonary data, wherein one or more machine learning models are used to generate a second treatment plan; wherein the second treatment plan modifies at least one exertion level, and the modification is based on a standardized measure comprising perceived exertion; the pulmonary data; and the pulmonary health issue of the user; and
receive the second treatment plan.

Clause 2.6 The computer-implemented system of any clause herein, wherein the second treatment plan comprises a modified parameter pertaining to the electromechanical machine, wherein the modified parameter comprises a resistance, a range of motion, a length of time, an angle of a component of the electromechanical machine, a speed, or some combination thereof, and the computer-implemented system further comprises:
based on the modified parameter, controlling the electromechanical machine.

Clause 3.6 The computer-implemented system of any clause herein, wherein the standardized measure of perceived exertion comprises a metabolic equivalent of tasks (MET) or a Borg rating of perceived exertion (RPE).

Clause 4.6 The computer-implemented system of any clause herein, wherein, by predicting exercises that will result in the desired exertion level for each session, the one or more machine learning models generate the second treatment plan, and the one or more machine learning models are trained using data pertaining to the standardized measure of perceived exertion, other users' pulmonary data, and other users' pulmonary health issues.

Clause 5.6 The computer-implemented system of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

Clause 6.6 The computer-implemented system of any clause herein, wherein the transmitting the pulmonary data further comprises transmitting the pulmonary data to a second computing device that relays the pulmonary data to a third computing device associated with a healthcare professional.

Clause 7.6 The computer-implemented system of any clause herein, wherein the pulmonary data comprises a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, a pulmonary diagnosis of the user, an oncologic diagnosis of the user, a bariatric diagnosis of the user, a pathological diagnosis related to a prostate gland or urogenital tract of the user, or some combination thereof.

Clause 8.6 A computer-implemented method comprising:
  receiving, at a computing device, a first treatment plan designed to treat a pulmonary health issue of a user, wherein the first treatment plan comprises at least two exercise sessions that, based on the pulmonary health issue of the user, enable the user to perform an exercise at different exertion levels;
  while the user uses an electromechanical machine to perform the first treatment plan for the user, receiving pulmonary data from one or more sensors configured to measure the pulmonary data associated with the user, wherein the electromechanical machine is configured to be manipulated by a user while the user performs the first treatment plan;
  transmitting the pulmonary data, wherein one or more machine learning models are used to generate a second treatment plan; wherein the second treatment plan modifies at least one exertion level, and the modification is based on a standardized measure comprising perceived exertion; the pulmonary data; and the pulmonary health issue of the user; and
  receiving the second treatment plan.

Clause 9.6 The computer-implemented method of any clause herein, wherein the second treatment plan comprises a modified parameter pertaining to the electromechanical machine, wherein the modified parameter comprises a resistance, a range of motion, a length of time, an angle of a component of the electromechanical machine, a speed, or some combination thereof, and the computer-implemented system further comprises:
  based on the modified parameter, controlling the electromechanical machine.

Clause 10.6 The computer-implemented method of any clause herein, wherein the standardized measure of perceived exertion comprises a metabolic equivalent of tasks (MET) or a Borg rating of perceived exertion (RPE).

Clause 11.6 The computer-implemented method of any clause herein, wherein, by predicting exercises that will result in the desired exertion level for each session, the one or more machine learning models generate the second treatment plan, and the one or more machine learning models are trained using data pertaining to the standardized measure of perceived exertion, other users' pulmonary data, and other users' pulmonary health issues.

Clause 12.6 The computer-implemented method of any clause herein wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

Clause 13.6 The computer-implemented method of any clause herein, wherein the transmitting the pulmonary data further comprises transmitting the pulmonary data to a second computing device that relays the pulmonary data to a third computing device associated with a healthcare professional.

Clause 14.6 The computer-implemented method of any clause herein, wherein the pulmonary data comprises a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, a pulmonary diagnosis of the user, an oncologic diagnosis of the user, a bariatric diagnosis of the user, a pathological diagnosis related to a prostate gland or urogenital tract of the user, or some combination thereof.

Clause 15.6 A tangible, non-transitory computer-readable medium storing instructions that, when executed, cause a processing device to:
  receive a first treatment plan designed to treat a pulmonary health issue of a user, wherein the first treatment plan comprises at least two exercise sessions that, based on the pulmonary health issue of the user, enable the user to perform an exercise at different exertion levels;
  while the user uses an electromechanical machine to perform the first treatment plan for the user, receive pulmonary data from one or more sensors configured to measure the pulmonary data associated with the user, wherein the electromechanical machine is configured to be manipulated by a user while the user performs the first treatment plan;
  transmit the pulmonary data, wherein one or more machine learning models are used to generate a second treatment plan; wherein the second treatment plan modifies at least one exertion level, and the modification is based on a standardized measure comprising perceived exertion; the pulmonary data; and the pulmonary health issue of the user; and
  receive the second treatment plan.

Clause 16.6 The computer-readable medium of any clause herein, wherein the second treatment plan comprises a modified parameter pertaining to the electromechanical machine, wherein the modified parameter comprises a resistance, a range of motion, a length of time, an angle of a component of the electromechanical machine, a speed, or some combination thereof, and the computer-implemented system further comprises:

based on the modified parameter, controlling the electromechanical machine.

Clause 17.6 The computer-readable medium of any clause herein, wherein the standardized measure of perceived exertion comprises a metabolic equivalent of tasks (MET) or a Borg rating of perceived exertion (RPE).

Clause 18.6 The computer-readable medium of any clause herein, wherein, by predicting exercises that will result in the desired exertion level for each session, the one or more machine learning models generate the second treatment plan, and the one or more machine learning models are trained using data pertaining to the standardized measure of perceived exertion, other users' pulmonary data, and other users' pulmonary health issues.

Clause 19.6 The computer-readable medium of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

Clause 20.6 The computer-readable medium of any clause herein, wherein the transmitting the pulmonary data further comprises transmitting the pulmonary data to a second computing device that relays the pulmonary data to a third computing device associated with a healthcare professional.

Figure 22:
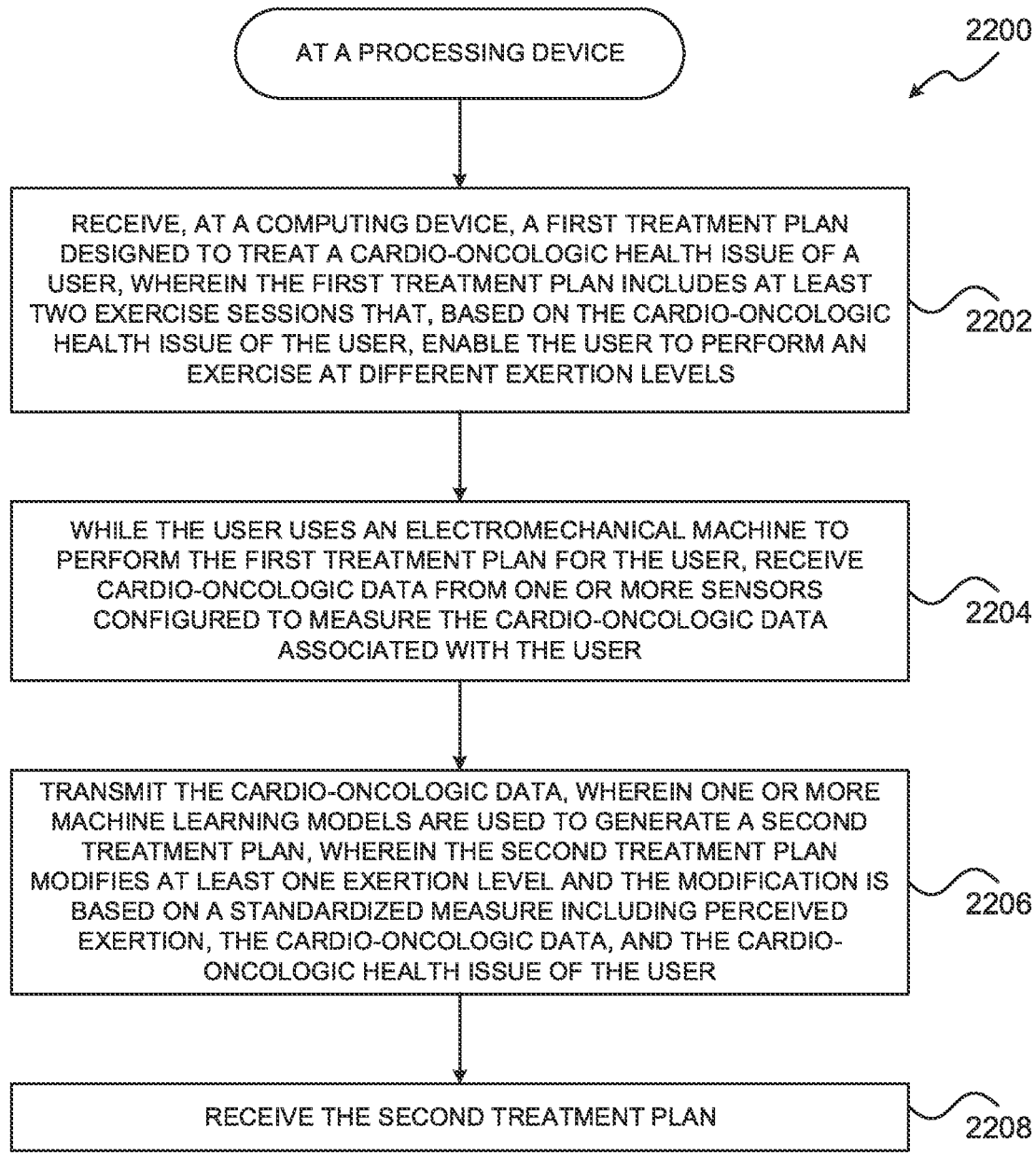
FIG. 22 generally illustrates an example embodiment of a method for using artificial intelligence and machine learning and telemedicine to perform cardio-oncologic rehabilitation via an electromechanical machine according to the principles of the present disclosure.

System and Method for Using AI/ML and Telemedicine for Cardio-Oncologic Rehabilitation Via an Electromechanical Machine FIG. 22 generally illustrates an example embodiment of a method 2200 for using artificial intelligence and machine learning and telemedicine to perform cardio-oncologic rehabilitation via an electromechanical machine according to the principles of the present disclosure. The method 2200 may be performed by processing logic that may include hardware (circuitry, dedicated logic, etc.), software, or a combination of both. The method 2200 and/or each of their individual functions, subroutines, or operations may be performed by one or more processing devices of a computing device (e.g., the computer system 1100 of FIG. 11) implementing the method 2200. The method 2200 may be implemented as computer instructions stored on a memory device and executable by the one or more processing devices. In certain implementations, the method 2200 may be performed by a single processing thread. Alternatively, the method 2200 may be performed by two or more processing threads, each thread implementing one or more individual functions, routines, subroutines, or operations of the methods.

In some embodiments, a system may be used to implement the method 2200. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 2200.

At block 2202, the processing device may receive, at a computing device, a first treatment plan designed to treat a cardio-oncologic health issue of a user. The first treatment plan may include at least two exercise sessions that, based on the cardio-oncologic health issue of the user, enable the user to perform an exercise at different exertion levels. In some embodiments, cardiac and/or oncologic information pertaining to the user may be received from an application programming interface associated with an electronic medical records system.

In some embodiments, the first treatment plan may be generated based on attribute data including an eating or drinking schedule of the user, information pertaining to an age of the user, information pertaining to a sex of the user, information pertaining to a weight of the user information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

At block 2204, while the user uses an electromechanical machine to perform the first treatment plan for the user, the processing device may receive cardio-oncologic data from one or more sensors configured to measure the cardio-oncologic data associated with the user. In some embodiments, the cardio-oncologic data may include a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, a cardio-oncologic diagnosis of the user, an oncologic diagnosis of the user, a cardio-oncologic diagnosis of the user, a pathological diagnosis related to a prostate gland or urogenital tract of the user, spirometry data related to the user, or some combination thereof.

At block 2206, the processing device may transmit the cardio-oncologic data. In some embodiments, one or more machine learning models 13 may be executed by the server 30 and the machine learning models 13 may be used to generate a second treatment plan based on the cardio-oncologic data. The second treatment plan may modify at least one exertion level, and the modification may be based on a standardized measure including perceived exertion, cardio-oncologic data, and the cardio-oncologic health issue of the user. In some embodiments, the standardized measure of perceived exertion may include a metabolic equivalent of tasks (MET) or a Borg rating of perceived exertion (RPE).

In some embodiments, the one or more machine learning models generate the second treatment plan by predicting exercises that will result in the desired exertion level for each session. The one or more machine learning models may be trained using data pertaining to the standardized measure of perceived exertion, other users' cardio-oncologic data, and other users' cardio-oncologic health issues as input data, and other users' exertion levels that led to desired results as output data. The input data and the output data may be labeled and mapped accordingly.

At block 2208, the processing device may receive the second treatment plan from the server 30. The processing device may implement at least a portion of the treatment plan to cause an operating parameter of the electromechanical machine to be modified in accordance with the modified exertion level set in the second treatment plan. To that end, in some embodiments, the second treatment plan may include a modified parameter pertaining to the electromechanical machine. The modified parameter may include a resistance, a range of motion, a length of time, an angle of a component of the electromechanical machine, a speed, a velocity, an angular velocity, an acceleration, a torque, or some combination thereof. The processing device may, based on the modified parameter, control the electromechanical machine.

In some embodiments, transmitting the cardio-oncologic data may include transmitting the cardio-oncologic data to a second computing device that relays the cardio-oncologic data to a third computing device that is associated with a healthcare professional.

CLAUSES

Clause 1.7 A computer-implemented system, comprising:
an electromechanical machine configured to be manipulated by a user while the user performs a treatment plan;
an interface comprising a display configured to present information pertaining to the treatment plan; and
a processing device configured to:
receive, at a computing device, a first treatment plan designed to treat a cardio-oncologic health issue of a user, wherein the first treatment plan comprises at least two exercise sessions that, based on the cardio-oncologic health issue of the user, enable the user to perform an exercise at different exertion levels;
while the user uses an electromechanical machine to perform the first treatment plan for the user, receive cardio-oncologic data from one or more sensors configured to measure the cardio-oncologic data associated with the user;
transmit the cardio-oncologic data, wherein one or more machine learning models are used to generate a second treatment plan; wherein the second treatment plan modifies at least one exertion level, and the modification is based on a standardized measure comprising perceived exertion; the cardio-oncologic data, and the cardio-oncologic health issue of the user; and
receive the second treatment plan.

Clause 2.7 The computer-implemented system of any clause herein, wherein the second treatment plan comprises a modified parameter pertaining to the electromechanical machine, wherein the modified parameter comprises a resistance, a range of motion, a length of time, an angle of a component of the electromechanical machine, a speed, or some combination thereof, and the computer-implemented system further comprises:
based on the modified parameter, controlling the electromechanical machine.

Clause 3.7 The computer-implemented system of any clause herein, wherein the standardized measure of perceived exertion comprises a metabolic equivalent of tasks (MET) or a Borg rating of perceived exertion (RPE).

Clause 4.7 The computer-implemented system of any clause herein, wherein the one or more machine learning models generate the second treatment plan by predicting exercises that will result in the desired exertion level for each session, and the one or more machine learning models are trained using data pertaining to the standardized measure of perceived exertion, other users' cardio-oncologic data, and other users' cardio-oncologic health issues.

Clause 5.7 The computer-implemented system of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

Clause 6.7 The computer-implemented system of any clause herein, wherein the transmitting the cardio-oncologic data further comprises transmitting the cardio-oncologic data to a second computing device that relays the cardio-oncologic data to a third computing device of a healthcare professional.

Clause 7.7 The computer-implemented system of any clause herein, wherein the cardio-oncologic data comprises a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, a pulmonary diagnosis of the user, an oncologic diagnosis of the user, a bariatric diagnosis of the user, a pathological diagnosis related to a prostate gland or urogenital tract of the user, or some combination thereof.

Clause 8.7 A computer-implemented method comprising:
receiving, at a computing device, a first treatment plan designed to treat a cardio-oncologic health issue of a user, wherein the first treatment plan comprises at least two exercise sessions that, based on the cardio-oncologic health issue of the user, enable the user to perform an exercise at different exertion levels;
while the user uses an electromechanical machine to perform the first treatment plan for the user, receiving cardio-oncologic data from one or more sensors configured to measure the cardio-oncologic data associated with the user, wherein the electromechanical machine is configured to be manipulated by the user while the user performs the first treatment plan;
transmitting the cardio-oncologic data, wherein one or more machine learning models are used to generate a second treatment plan; wherein the second treatment plan modifies at least one exertion level, and the modification is based on a standardized measure comprising perceived exertion; the cardio-oncologic data, and the cardio-oncologic health issue of the user; and receiving the second treatment plan.

Clause 9.7 The computer-implemented method of any clause herein, wherein the second treatment plan comprises a modified parameter pertaining to the electromechanical machine, wherein the modified parameter comprises a resistance, a range of motion, a length of time, an angle of a component of the electromechanical machine, a speed, or some combination thereof, and the computer-implemented system further comprises:

based on the modified parameter, controlling the electromechanical machine.

Clause 10.7 The computer-implemented method of any clause herein, wherein the standardized measure of perceived exertion comprises a metabolic equivalent of tasks (MET) or a Borg rating of perceived exertion (RPE).

Clause 11.7 The computer-implemented method of any clause herein, wherein the one or more machine learning models generate the second treatment plan by predicting exercises that will result in the desired exertion level for each session, and the one or more machine learning models are trained using data pertaining to the standardized measure of perceived exertion, other users' cardio-oncologic data, and other users' cardio-oncologic health issues.

Clause 12.7 The computer-implemented method of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

Clause 13.7 The computer-implemented method of any clause herein, wherein the transmitting the cardio-oncologic data further comprises transmitting the cardio-oncologic data to a second computing device that relays the cardio-oncologic data to a third computing device of a healthcare professional.

Clause 14.7 The computer-implemented method of any clause herein, wherein the cardio-oncologic data comprises a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, a pulmonary diagnosis of the user, an oncologic diagnosis of the user, a bariatric diagnosis of the user, a pathological diagnosis related to a prostate gland or urogenital tract of the user, or some combination thereof.

Clause 15.7 A tangible, computer-readable medium storing instructions that, when executed, cause a processing device to:

receive, at a computing device, a first treatment plan designed to treat a cardio-oncologic health issue of a user, wherein the first treatment plan comprises at least two exercise sessions that, based on the cardio-oncologic health issue of the user, enable the user to perform an exercise at different exertion levels;

while the user uses an electromechanical machine to perform the first treatment plan for the user, receive cardio-oncologic data from one or more sensors configured to measure the cardio-oncologic data associated with the user, wherein the electromechanical machine is configured to be manipulated by the user while the user performs the first treatment plan;

transmit the cardio-oncologic data, wherein one or more machine learning models are used to generate a second treatment plan; wherein the second treatment plan modifies at least one exertion level, and the modification is based on a standardized measure comprising perceived exertion; the cardio-oncologic data, and the cardio-oncologic health issue of the user; and receive the second treatment plan.

Clause 16.7 The computer-readable medium of any clause herein, wherein the second treatment plan comprises a modified parameter pertaining to the electromechanical machine, wherein the modified parameter comprises a resistance, a range of motion, a length of time, an angle of a component of the electromechanical machine, a speed, or some combination thereof, and the computer-implemented system further comprises:

based on the modified parameter, controlling the electromechanical machine.

Clause 17.7 The computer-readable medium of any clause herein, wherein the standardized measure of perceived exertion comprises a metabolic equivalent of tasks (MET) or a Borg rating of perceived exertion (RPE).

Clause 18.7 The computer-readable medium of any clause herein, wherein the one or more machine learning models generate the second treatment plan by predicting exercises that will result in the desired exertion level for each session, and the one or more machine learning models are trained using data pertaining to the standardized measure of perceived exertion, other users' cardio-oncologic data, and other users' cardio-oncologic health issues.

Clause 19.7 The computer-readable medium of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

Clause 20.7 The computer-readable medium of any clause herein, wherein the transmitting the cardio-oncologic data further comprises transmitting the cardio-oncologic data to a second computing device that relays the cardio-oncologic data to a third computing device of a healthcare professional.

Figure 23:
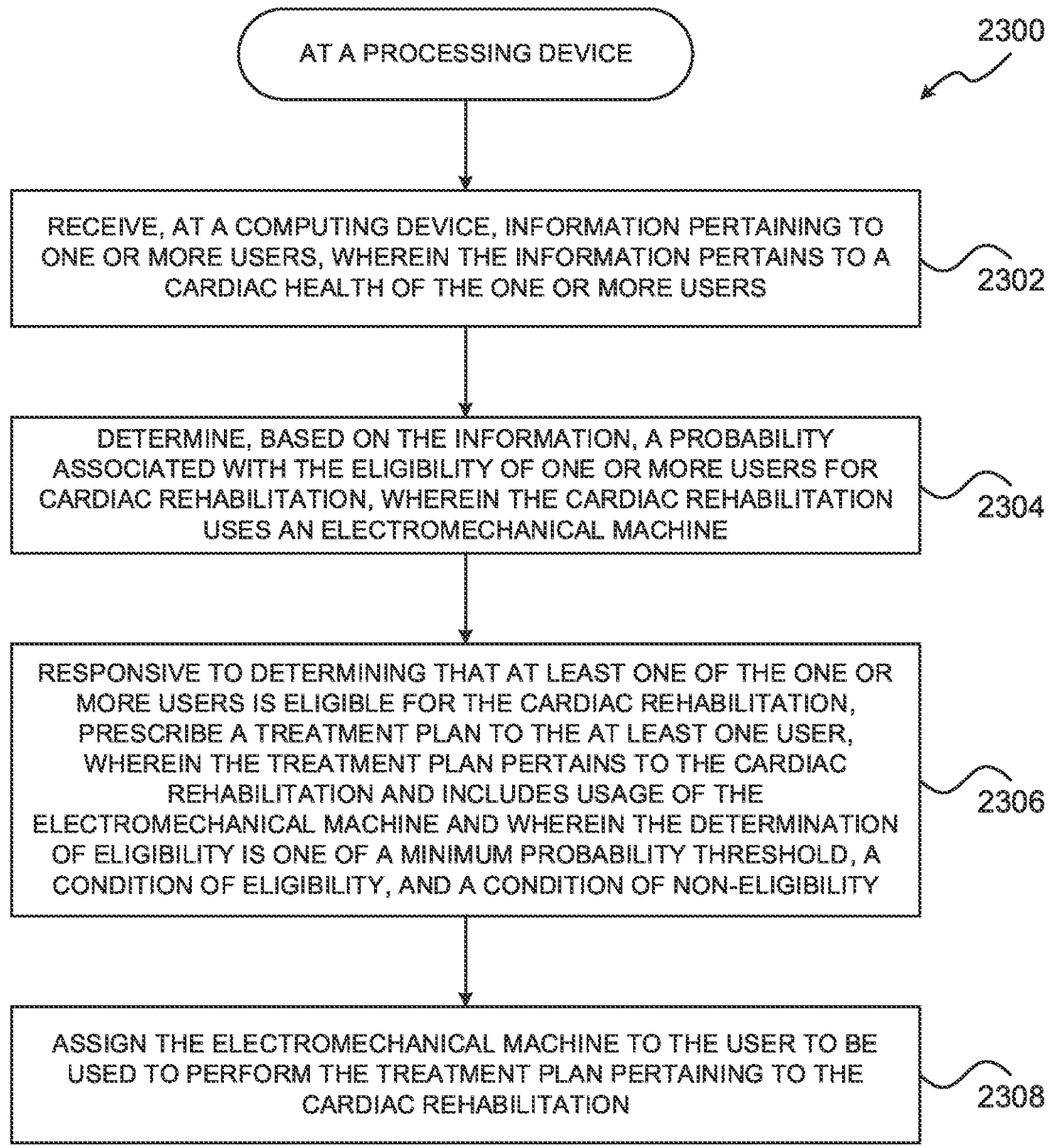
FIG. 23 generally illustrates an example embodiment of a method for identifying subgroups, determining cardiac rehabilitation eligibility, and prescribing a treatment plan for the eligible subgroups according to the principles of the present disclosure.

System and Method for Identifying Subgroups, Determining Cardiac Rehabilitation Eligibility, and Prescribing a Treatment Plan for the Eligible Subgroups FIG. 23 generally illustrates an example embodiment of a method 2300 for identifying subgroups, determining cardiac rehabilitation eligibility, and prescribing a treatment plan for the eligible subgroups according to the principles of the present disclosure. The method 2300 may be performed by processing logic that may include hardware (circuitry, dedicated logic, etc.), software, or a combination of both. The method 2300 and/or each of their individual functions, subroutines, or operations may be performed by one or more processing devices of a computing device (e.g., the computer system 1100 of FIG. 11) implementing the method 2300. The method 2300 may be implemented as computer instructions stored on a memory device and executable by the one or more processing devices. In certain implementations, the method 2300 may be performed by a single processing thread. Alternatively, the method 2300 may be performed by two or more processing threads, each thread implementing one or more individual functions, routines, subroutines, or operations of the methods.

In some embodiments, a system may be used to implement the method 2300. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 2300.

At block 2302, a processing device may receive, at a computing device, information pertaining to one or more users. The information may pertain to a cardiac health of the one or more users. In some embodiments, the information may be received from an electronic medical records source, a third-party source, or some combination thereof.

At block 2304, the processing device may determine, based on the information, a probability associated with the eligibility of the one or more users for cardiac rehabilitation. In some embodiments, the probability is either zero or one hundred percent. The cardiac rehabilitation may use an electromechanical machine. In some embodiments, the processing device may determine, based on the information, the eligibility of the one or more users for the cardiac rehabilitation using one or more machine learning models trained to map one or more inputs (e.g., characteristics of the user) to one or more outputs (e.g., eligibility of the user for cardiac rehabilitation). The cardiac rehabilitation may use the electromechanical machine.

At block 2306, responsive to determining that at least one of the one or more users is eligible for the cardiac rehabilitation, the processing device may prescribe a treatment plan to the at least one user. The treatment plan may pertain to the cardiac rehabilitation and may include usage of the electromechanical machine. In some embodiments, the determination of eligibility is one of a minimum probability threshold, a condition of eligibility, and/or a condition of non-eligibility. In some embodiments, the condition may pertain to the one or more users being included in one or more subgroups associated with a geographic region, having demographic or psychographic characteristics, being included in an underrepresented minority group, being a certain sex, being a certain nationality, having a certain cultural heritage, having a certain disability, having a certain sexual orientation, having certain genotypal or phenotypal characteristics, being a certain gender, having a certain risk level, having certain insurance characteristics, or some combination thereof. In some embodiments, the treatment plan may pertain to cardiac rehabilitation, oncology rehabilitation, rehabilitation from pathologies related to prostate gland or urogenital tract, pulmonary rehabilitation, bariatric rehabilitation, or some combination thereof.

In some embodiments, the processing device may generate the treatment plan using one or more trained machine learning models. The processing device may determine, via the one or more machine learning models 13, the treatment plan for the user based on one or more characteristics of the user, wherein the one or more characteristics include information pertaining the user's cardiac health, pulmonary health, oncologic health, bariatric health, or some combination thereof.

At block 2308, the processing device may assign the electromechanical machine to the user to be used to perform the treatment plan pertaining to the cardiac rehabilitation.

In some embodiments, the processing device may determine a number of users associated with treatment plans and may determine a geographic region in which the number of users resides. In some embodiments, based on the number of users, the processing device may deploy a calculated number of electromechanical machines to the geographic region to enable the users to execute the treatment plans.

CLAUSES

Clause 1.8 A computer-implemented method for facilitating cardiac rehabilitation among eligible users, the computer-implemented method comprising, at a computing device:
  receiving health information associated with one or more users;
  for each user of the one or more users:
  determining, based on health information associated with the user, a respective eligibility of the user for cardiac rehabilitation;
  determining, based on the respective eligibilities, that at least one user of the one or more users is eligible for cardiac rehabilitation;
  generating a treatment plan for the at least one user, wherein the treatment plan pertains to a cardiac rehabilitation that is specific to the at least one user; and
  assigning the treatment plan to at least one electromechanical machine to enable the user to perform the cardiac rehabilitation.

Clause 2.8 The computer-implemented method of claim 1, wherein the determination of eligibility of the at least one user is based on:
  the respective eligibility of the at least one user satisfying a threshold,
  the health information satisfying at least one condition of eligibility, or
  some combination thereof.

Clause 3.8 The computer-implemented method of claim 1, wherein the health information is received from an electronic medical records source, a third-party source, or some combination thereof.

Clause 4.8.1 The computer-implemented method of claim 1, wherein the cardiac rehabilitation is in response to a Cardiac-Related Event (CRE).

Clause 4.8.2 The computer-implemented method of claim 1, wherein, for a given user, the health information associated with the user indicates geographic region characteristics associated with the user, underrepresented minority group characteristics associated with the user, sex characteristics associated with the user, nationality characteristics associated with the user, cultural heritage characteristics associated with the user, disability characteristics associated with the user, sexual preference characteristics associated with the user, genotype characteristics associated with the user, phenotype characteristics associated with the user, gender characteristics associated with the user, risk level characteristics associated with the user, or some combination thereof.

Clause 5.8 The computer-implemented method of claim 1, wherein:
  treatment plan is based on one or more characteristics of the user, and the one or more characteristics comprise information pertaining to the at least one user's cardiac health, pulmonary health, oncologic health, bariatric health, or some combination thereof, and
  the treatment plan is generated using one or more machine learning models.

Clause 6.8 The computer-implemented method of claim 1, further comprising:
  determining a geographic location accessible to the at least one user; and
  causing an electromechanical machine to be deployed to the geographic location to enable the at least one user to perform the cardiac rehabilitation using the electromechanical machine.

Clause 7.8 The computer-implemented method of claim 1, wherein the treatment plan pertains to cardiac rehabilitation, oncology rehabilitation, rehabilitation from pathologies related to the prostate gland or urogenital tract, pulmonary rehabilitation, bariatric rehabilitation, or some combination thereof.

Clause 8.8 A computer-implemented system, comprising:
  a memory device storing instructions; and
  a processing device communicatively coupled to the memory device, wherein the processing device executes the instructions to:
  receive health information associated with one or more users;
  for each user of the one or more users:
  determine, based on health information associated with the user, a respective eligibility of the user for cardiac rehabilitation;
  determine, based on the respective eligibilities, that at least one user of the one or more users is eligible for cardiac rehabilitation;
  generate a treatment plan for the at least one user, wherein the treatment plan pertains to a cardiac rehabilitation that is specific to the at least one user; and
  assign the treatment plan to at least one electromechanical machine to enable the user to perform the cardiac rehabilitation.

Clause 9.8 The computer-implemented system of claim 8, wherein the determination of eligibility of the at least one user is based on:
  the respective eligibility of the at least one user satisfying a threshold,
  the health information satisfying at least one condition of eligibility, or
  some combination thereof.

Clause 10.8 The computer-implemented system of claim 8, wherein the health information is received from an electronic medical records source, a third-party source, or some combination thereof.

Clause 11.8.1 The computer-implemented system of claim 8, wherein the cardiac rehabilitation is in response to a Cardiac-Related Event (CRE).

Clause 11.8.2 The computer-implemented system of claim 8, wherein, for a given user, the health information associated with the user indicates geographic region characteristics associated with the user, underrepresented minority group characteristics associated with the user, sex characteristics associated with the user, nationality characteristics associated with the user, cultural heritage characteristics associated with the user, disability characteristics associated with the user, sexual preference characteristics associated with the user, genotype characteristics associated with the user, phenotype characteristics associated with the user, gender characteristics associated with the user, risk level characteristics associated with the user, or some combination thereof.

Clause 12.8 The computer-implemented system of claim 8, wherein:
  treatment plan is based on one or more characteristics of the user, and the one or more characteristics comprise information pertaining to the at least one user's cardiac health, pulmonary health, oncologic health, bariatric health, or some combination thereof, and
  the treatment plan is generated using one or more machine learning models.

Clause 13.8 The computer-implemented system of claim 8, wherein the processing device further executes the instructions to:
  determine a geographic location accessible to the at least one user; and
  cause an electromechanical machine to be deployed to the geographic location to enable the at least one user to perform the cardiac rehabilitation using the electromechanical machine.

Clause 14.8 The computer-implemented system of claim 8, wherein the treatment plan pertains to cardiac rehabilitation, oncology rehabilitation, rehabilitation from pathologies related to the prostate gland or urogenital tract, pulmonary rehabilitation, bariatric rehabilitation, or some combination thereof.

Clause 15.8 A tangible, non-transitory computer-readable medium storing instructions that, when executed, cause a processing device to:
  receive health information associated with one or more users;
  for each user of the one or more users:
  determine, based on health information associated with the user, a respective eligibility of the user for cardiac rehabilitation;
  determine, based on the respective eligibilities, that at least one user of the one or more users is eligible for cardiac rehabilitation;
  generate a treatment plan for the at least one user, wherein the treatment plan pertains to a cardiac rehabilitation that is specific to the at least one user; and
  assign the treatment plan to at least one electromechanical machine to enable the user to perform the cardiac rehabilitation.

Clause 16.8 The non-transitory computer-readable medium of claim 15, wherein the determination of eligibility of the at least one user is based on:

the respective eligibility of the at least one user satisfying a threshold,
the health information satisfying at least one condition of eligibility, or
some combination thereof.

Clause 17.8 The non-transitory computer-readable medium of claim 15, wherein the health information is received from an electronic medical records source, a third-party source, or some combination thereof.

Clause 18.8.1 The non-transitory computer-readable medium of claim 15, wherein the cardiac rehabilitation is in response to a Cardiac-Related Event (CRE).

Clause 18.8.2 The non-transitory computer-readable medium of claim 15, wherein, for a given user, the health information associated with the user indicates geographic region characteristics associated with the user, underrepresented minority group characteristics associated with the user, sex characteristics associated with the user, nationality characteristics associated with the user, cultural heritage characteristics associated with the user, disability characteristics associated with the user, sexual preference characteristics associated with the user, genotype characteristics associated with the user, phenotype characteristics associated with the user, gender characteristics associated with the user, risk level characteristics associated with the user, or some combination thereof.

Clause 19.8 The non-transitory computer-readable medium of claim 15, wherein:
treatment plan is based on one or more characteristics of the user, and the one or more characteristics comprise information pertaining to the at least one user's cardiac health, pulmonary health, oncologic health, bariatric health, or some combination thereof, and
the treatment plan is generated using one or more machine learning models.

Clause 20.8 The non-transitory computer-readable medium of claim 15, wherein the instructions, when executed, further cause the processing device to:
determine a geographic location accessible to the at least one user; and
cause an electromechanical machine to be deployed to the geographic location to enable the at least one user to perform the cardiac rehabilitation using the electromechanical machine.

Figure 24:
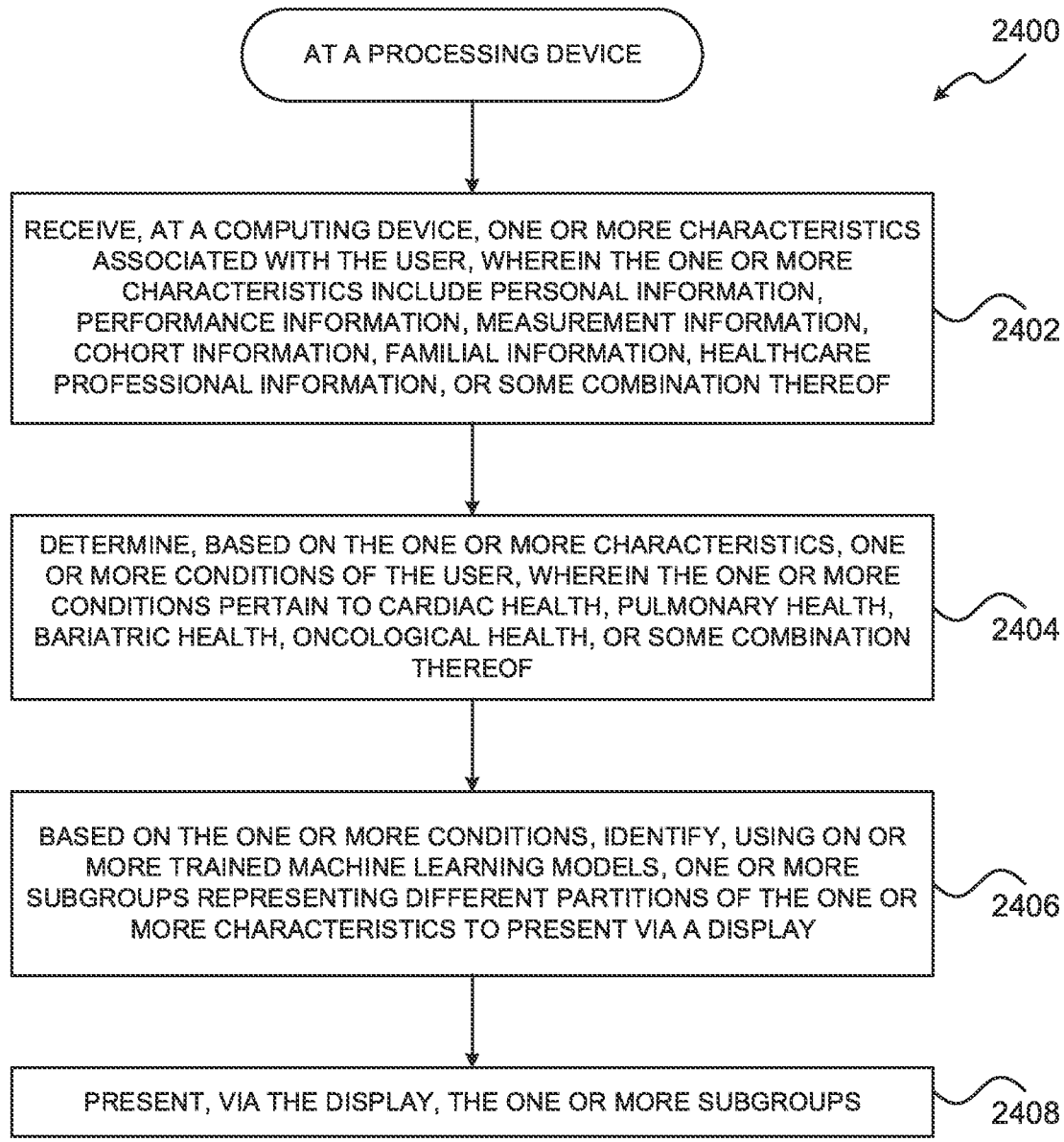
FIG. 24 generally illustrates an example embodiment of a method for using artificial intelligence and machine learning to provide an enhanced user interface presenting data pertaining to cardiac health, bariatric health, pulmonary health, and/or cardio-oncologic health for the purpose of performing preventative actions according to the principles of the present disclosure.

System and Method for Using AI/ML to Provide an Enhanced User Interface Presenting Data Pertaining to Cardiac Health, Bariatric Health, Pulmonary Health, and/or Cardio-Oncologic Health for the Purpose of Performing Preventative Actions FIG. 24 generally illustrates an example embodiment of a method 2400 for using artificial intelligence and machine learning to provide an enhanced user interface presenting data pertaining to cardiac health, bariatric health, pulmonary health, and/or cardio-oncologic health for the purpose of performing preventative actions according to the principles of the present disclosure. The method 2400 may be performed by processing logic that may include hardware (circuitry, dedicated logic, etc.), software, or a combination of both. The method 2400 and/or each of their individual functions, subroutines, or operations may be performed by one or more processing devices of a computing device (e.g., the computer system 1100 of FIG. 11) implementing the method 2400. The method 2400 may be implemented as computer instructions stored on a memory device and executable by the one or more processing devices. In certain implementations, the method 2400 may be performed by a single processing thread. Alternatively, the method 2400 may be performed by two or more processing threads, each thread implementing one or more individual functions, routines, subroutines, or operations of the methods.

In some embodiments, a system may be used to implement the method 2400. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 2400.

At block 2402, the processing device may receive, at a computing device, one or more characteristics associated with the user. The one or more characteristics may include personal information, performance information, measurement information, cohort information, familial information, healthcare professional information, or some combination thereof.

At block 2404, the processing device may determine, based on the one or more characteristics, one or more conditions of the user. The one or more conditions may pertain to cardiac health, pulmonary health, bariatric health, oncologic health, or some combination thereof.

At block 2406, based on the one or more conditions, the processing device may identify, using one or more trained machine learning models, one or more subgroups representing different partitions of the one or more characteristics to present via the display.

At block 2408, the processing device may present, via the display, the one or more subgroups. In some embodiments, the processing device may present one or more graphical elements associated with the one or more subgroups. The one or more graphical elements may be arranged based on a priority, a severity, or both of the one or more subgroups. The one or more graphical elements may include at least one input mechanism that enables performing a preventative action. The one or more preventative actions may include modifying an operating parameter of the electromechanical machine, initiating a telecommunications transmission, contacting a computing device associated with the user, or some combination thereof.

In some embodiments, the processing device may contact a second computing device of a healthcare professional if a portion of the one or more subgroups is presented on the display for a threshold period of time, if the portion of the one or more subgroups exceeds a threshold level, or both.

In some embodiments, the processing device may verify an identity of a healthcare professional prior to presenting the one or more subgroups on the display. The verifying the identity of the healthcare professional may include verifying biometric data associated with the healthcare professional, two-factor authentication (2FA) methods used by the healthcare professional, credential authentication of the healthcare professional, or other authenticable methods consistent with regulatory requirements.

CLAUSES

Clause 1.9 A computer-implemented system, comprising:
an electromechanical machine configured to be manipulated by a user while the user performs a treatment plan;
an interface comprising a display configured to present information pertaining to the user, treatment plan, or both; and a processing device configured to:
receive, at a computing device, one or more characteristics associated with the user, wherein the one or more characteristics comprise personal information, performance information, measurement information, cohort information, familial information, healthcare professional information, or some combination thereof;
determine, based on the one or more characteristics, one or more conditions of the user, wherein the one or more conditions pertain to cardiac health, pulmonary health, bariatric health, oncologic health, or some combination thereof;
based on the one or more conditions, identify, using one or more trained machine learning models, one or more subgroups representing different partitions of the one or more characteristics to present via the display; and
present, via the display, the one or more subgroups.

Clause 2.9 The computer-implemented system of any clause herein, wherein the processing device is further to present one or more graphical elements associated with the one or more subgroups.

Clause 3.9 The computer-implemented system of any clause herein, wherein the one or more graphical elements are arranged based on a priority, a severity, or both of the one or more subgroups.

Clause 4.9 The computer-implemented system of any clause herein, wherein the one or more graphical elements comprise at least one input mechanism that enables performing a preventative action.

Clause 5.9 The computer-implemented system of any clause herein, wherein the preventative action comprises modifying an operating parameter of the electromechanical machine, initiating a telecommunications transmission, contacting a computing device associated with the user, or some combination thereof.

Clause 6.9 The computer-implemented system of any clause herein, wherein the processing device is further to contact a second computing device of a healthcare professional if a portion of the one or more subgroups is presented on the display for a threshold period of time, if the portion of the one or more subgroups exceeds a threshold level, or both.

Clause 7.9 The computer-implemented system of any clause herein, wherein the processing device is configured to verify an identity of a healthcare professional prior to presenting the one or more subgroups on the display, wherein verifying the identity of the healthcare professional comprises verifying biometric data associated with the healthcare professional, two-factor authentication (2FA) methods used by the healthcare professional, or other authenticable methods consistent with regulatory requirements.

Clause 8.9 A computer-implemented method comprising:
receiving, at a computing device, one or more characteristics associated with the user, wherein the one or more characteristics comprise personal information, performance information, measurement information, cohort information, familial information, healthcare professional information, or some combination thereof;
determining, based on the one or more characteristics, one or more conditions of the user, wherein the one or more conditions pertain to cardiac health, pulmonary health, bariatric health, oncologic health, or some combination thereof;
based on the one or more conditions, identifying, using one or more trained machine learning models, one or more subgroups representing different partitions of the one or more characteristics to present via a display; and
presenting, via the display, the one or more subgroups.

Clause 9.9 The computer-implemented method of any clause herein, further comprising presenting one or more graphical elements associated with the one or more subgroups.

Clause 10.9 The computer-implemented method of any clause herein, wherein the one or more graphical elements are arranged based on a priority, a severity, or both of the one or more subgroups.

Clause 11.9 The computer-implemented method of any clause herein, wherein the one or more graphical elements comprise at least one input mechanism that enables performing a preventative action.

Clause 12.9 The computer-implemented method of any clause herein, wherein the preventative action comprises modifying an operating parameter of the electromechanical machine, contacting an emergency service, contacting a computing device associated with the user, or some combination thereof.

Clause 13.9 The computer-implemented method of any clause herein, further comprising contacting a second computing device of a healthcare professional if a portion of the one or more subgroups is presented on the display for a threshold period of time, if the portion of the one or more subgroups exceeds a threshold level, or both.

Clause 14.9 The computer-implemented method of any clause herein, wherein the processing device is configured to verify an identity of a healthcare professional prior to presenting the one or more subgroups on the display, wherein verifying the identity of the healthcare professional comprises verifying biometric data associated with the healthcare professional, two-factor authentication (2FA) methods used by the healthcare professional, or other authenticable methods consistent with regulatory requirements.

Clause 15.9 A tangible, non-transitory computer-readable medium storing instructions that, when executed, cause a processing device to:
receive one or more characteristics associated with the user, wherein the one or more characteristics comprise personal information, performance information, measurement information, cohort information, familial information, healthcare professional information, or some combination thereof;
determine, based on the one or more characteristics, one or more conditions of the user, wherein the one or more conditions pertain to cardiac health, pulmonary health, bariatric health, oncologic health, or some combination thereof;
based on the one or more conditions, identify, using one or more trained machine learning models, one or more subgroups representing different partitions of the one or more characteristics to present via a display; and
present, via the display, the one or more subgroups.

Clause 16.9 The computer-readable medium of any clause herein, wherein the processing device is to present one or more graphical elements associated with the one or more subgroups.

Clause 17.9 The computer-readable medium of any clause herein, wherein the one or more graphical elements are arranged based on a priority, a severity, or both of the one or more subgroups.

Clause 18.9 The computer-readable medium of any clause herein, wherein the one or more graphical elements comprise at least one input mechanism that enables performing a preventative action.

Clause 19.9 The computer-readable medium of any clause herein, wherein the preventative action comprises modifying an operating parameter of the electromechanical machine, contacting an emergency service, contacting a computing device associated with the user, or some combination thereof.

Clause 20.9 The computer-readable medium of any clause herein, further comprising contacting a second computing device of a healthcare professional if a portion of the one or more subgroups is presented on the display for a threshold period of time, if the portion of the one or more subgroups exceeds a threshold level, or both.

Figure 25:
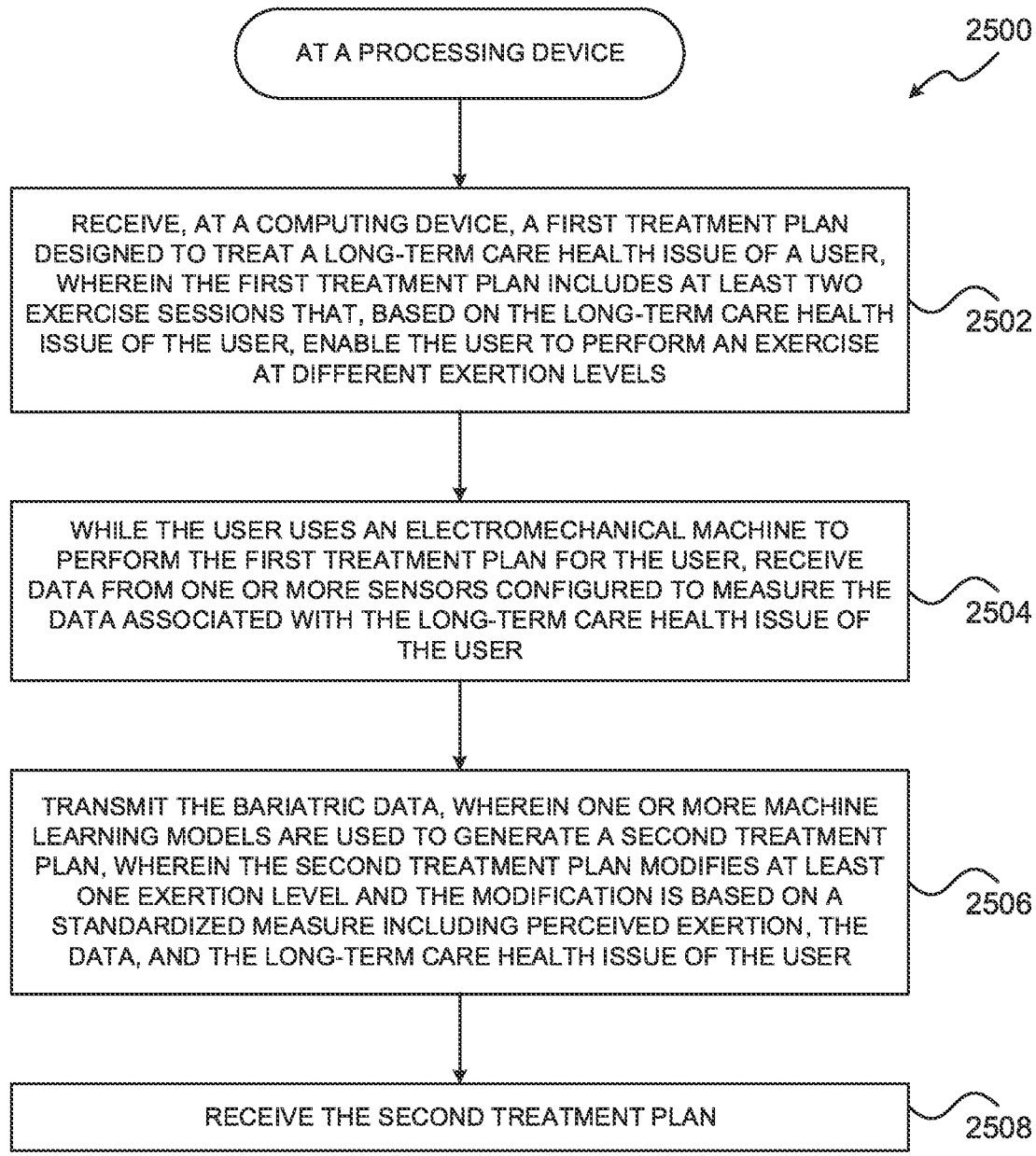
FIG. 25 generally illustrates an example embodiment of a method for using artificial intelligence and machine learning and telemedicine for long-term care via an electromechanical machine according to the principles of the present disclosure.

System and Method for Using AI/ML and Telemedicine for Long-Term Care Via an Electromechanical Machine FIG. 25 generally illustrates an example embodiment of a method 2500 for using artificial intelligence and machine learning and telemedicine for long-term care via an electromechanical machine according to the principles of the present disclosure. The method 2500 may be performed by processing logic that may include hardware (circuitry, dedicated logic, etc.), software, or a combination of both. The method 2500 and/or each of their individual functions, subroutines, or operations may be performed by one or more processing devices of a computing device (e.g., the computer system 1100 of FIG. 11) implementing the method 2500. The method 2500 may be implemented as computer instructions stored on a memory device and executable by the one or more processing devices. In certain implementations, the method 2500 may be performed by a single processing thread. Alternatively, the method 2500 may be performed by two or more processing threads, each thread implementing one or more individual functions, routines, subroutines, or operations of the methods.

In some embodiments, a system may be used to implement the method 2500. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 2500.

At block 2502, the processing device may receive, at a computing device, a first treatment plan designed to treat a long-term care health issue of a user. The first treatment plan may include at least two exercise sessions that, based on the long-term care health issue of the user, enable the user to perform an exercise at different exertion levels. In some embodiments, information pertaining to the user's long-term care health issue may be received from an application programming interface associated with an electronic medical records system.

In some embodiments, the first treatment plan may be generated based on attribute data including an eating or drinking schedule of the user, information pertaining to an age of the user, information pertaining to a sex of the user, information pertaining to a weight of the user information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

At block 2504, while the user uses an electromechanical machine to perform the first treatment plan for the user, the processing device may receive data from one or more sensors configured to measure the data associated with the long-term care health issue of the user. In some embodiments, the data may include a procedure performed on the user, an electronic medical record associated with the user, a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, a pulmonary diagnosis of the user, an oncologic diagnosis of the user, a bariatric diagnosis of the user, a pathological diagnosis related to a prostate gland or urogenital tract of the user, or some combination thereof.

At block 2506, the processing device may transmit the data. In some embodiments, one or more machine learning models 13 may be executed by the server 30 and the machine learning models 13 may be used to generate a second treatment plan based on the data and/or the long-term care health issues of users. The second treatment plan may modify at least one exertion level, and the modification may be based on a standardized measure including perceived exertion, the data, and the long-term care health issue of the user. In some embodiments, the standardized measure of perceived exertion may include a metabolic equivalent of tasks (MET) or a Borg rating of perceived exertion (RPE).

In some embodiments, the one or more machine learning models generate the second treatment plan by predicting exercises that will result in the desired exertion level for each session. The one or more machine learning models may be trained using data pertaining to the standardized measure of perceived exertion, other users' data, and other users' long-term care health issues as input data, and other users' exertion levels that led to desired results as output data. The input data and the output data may be labeled and mapped accordingly.

At block 2508, the processing device may receive the second treatment plan from the server 30. The processing device may implement at least a portion of the treatment plan to cause an operating parameter of the electromechanical machine to be modified in accordance with the modified exertion level set in the second treatment plan. To that end, in some embodiments, the second treatment plan may include a modified parameter pertaining to the electromechanical machine. The modified parameter may include a resistance, a range of motion, a length of time, an angle of a component of the electromechanical machine, a speed, a velocity, an angular velocity, an acceleration, a torque, or some combination thereof. The processing device may, based on the modified parameter, control the electromechanical machine.

In some embodiments, transmitting the data may include transmitting the data to a second computing device that relays the long-term care health issue data to a third computing device that is associated with a healthcare professional.

CLAUSES

Clause 1.10 A computer-implemented system, comprising:
  an electromechanical machine configured to be manipulated by a user while performing a treatment plan;
  an interface comprising a display configured to present information pertaining to the treatment plan; and
  a processing device configured to:
    receive, at a computing device, a first treatment plan designed to treat a long-term care health issue of a user, wherein the first treatment plan comprises at least two exercise sessions that, based on the long-term care health issue of the user, enable the user to perform one or more exercises at respectively different exertion levels;
    while the user uses an electromechanical machine to perform the first treatment plan for the user, receive data from one or more sensors configured to measure the data associated with the long-term care health issue of the user;
    transmit the data, wherein one or more machine learning models are used to generate a second treatment plan, wherein the second treatment plan modifies at least one exertion level, and the modification is based on a standardized measure comprising perceived exertion, the data, and the long-term care health issue of the user; and
    receive the second treatment plan.

Clause 2.10 The computer-implemented system of any clause herein, wherein the second treatment plan comprises a modified parameter pertaining to the electromechanical machine, wherein the modified parameter comprises a resistance, a range of motion, a length of time, an angle of a component of the electromechanical machine, a speed, a velocity, an angular velocity, an acceleration, a torque, or some combination thereof, and the computer-implemented system further comprises:
  controlling the electromechanical machine based on the modified parameter.

Clause 3.10 The computer-implemented system of any clause herein, wherein the standardized measure of perceived exertion comprises a metabolic equivalent of tasks (MET) or a Borg rating of perceived exertion (RPE).

Clause 4.10 The computer-implemented system of any clause herein, wherein the one or more machine learning models generate the second treatment plan by predicting exercises that will result in the desired exertion level for each session, and the one or more machine learning models are trained using data pertaining to the standardized measure of perceived exertion, other users' data, and other users' long-term care health issues.

Clause 5.10 The computer-implemented system of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, information pertaining to long term care health issues of other users, or some combination thereof.

Clause 6.10 The computer-implemented system of any clause herein, wherein the transmitting the data further comprises transmitting the data to a second computing device that relays the data to a third computing device of a healthcare professional.

Clause 7.10 The computer-implemented system of any clause herein, wherein the data comprises a procedure performed on the user, an electronic medical record associated with the user, a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, a pulmonary diagnosis of the user, an oncologic diagnosis of the user, a bariatric diagnosis of the user, a pathological diagnosis related to a prostate gland or urogenital tract of the user, or some combination thereof.

Clause 8.10 A computer-implemented method comprising:
  receiving, at a computing device, a first treatment plan designed to treat a long-term care health issue of a user, wherein the first treatment plan comprises at least two exercise sessions that, based on the long-term care health issue of the user, enable the user to perform one or more exercises at respectively different exertion levels;
  while the user uses an electromechanical machine to perform the first treatment plan for the user, receiving data from one or more sensors configured to measure the data associated with the long-term care health issue of the user, wherein the electromechanical machine is configured to be manipulated by the user while performing the first treatment plan;
  transmitting the data, wherein one or more machine learning models are used to generate a second treatment plan, wherein the second treatment plan modifies at least one exertion level, and the modification is based on a standardized measure comprising perceived exertion, the data, and the long-term care health issue of the user; and
  receiving the second treatment plan.

Clause 9.10 The computer-implemented method of any clause herein, wherein the second treatment plan comprises a modified parameter pertaining to the electromechanical machine, wherein the modified parameter comprises a resistance, a range of motion, a length of time, an angle of a component of the electromechanical machine, a speed, a velocity, an angular velocity, an acceleration, a torque, or some combination thereof, and the computer-implemented system further comprises:
  controlling the electromechanical machine based on the modified parameter.

Clause 10.10 The computer-implemented method of any clause herein, wherein the standardized measure of perceived exertion comprises a metabolic equivalent of tasks (MET) or a Borg rating of perceived exertion (RPE).

Clause 11.10 The computer-implemented method of any clause herein, wherein the one or more machine learning models generate the second treatment plan by predicting exercises that will result in the desired exertion level for each session, and the one or more machine learning models are trained using data pertaining to the standardized measure of perceived exertion, other users' data, and other users' long-term care health issues.

Clause 12.10 The computer-implemented method of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, information pertaining to long term care health issues of other users, or some combination thereof.

Clause 13.10 The computer-implemented method of any clause herein, wherein the transmitting the data further comprises transmitting the data to a second computing device that relays the data to a third computing device of a healthcare professional.

Clause 14.10 The computer-implemented method of any clause herein, wherein the data comprises a procedure performed on the user, an electronic medical record associated with the user, a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, a pulmonary diagnosis of the user, an oncologic diagnosis of the user, a bariatric diagnosis of the user, a pathological diagnosis related to a prostate gland or urogenital tract of the user, or some combination thereof.

Clause 15.10 A tangible, non-transitory computer-readable medium storing instructions that, when executed, cause a processing device to:
receive a first treatment plan designed to treat a long-term care health issue of a user, wherein the first treatment plan comprises at least two exercise sessions that, based on the long-term care health issue of the user, enable the user to perform one or more exercises at respectively different exertion levels;
while the user uses an electromechanical machine to perform the first treatment plan for the user, receive data from one or more sensors configured to measure the data associated with the long-term care health issue of the user, wherein the electromechanical machine is configured to be manipulated by the user while performing the first treatment plan;
transmit the data, wherein one or more machine learning models are used to generate a second treatment plan, wherein the second treatment plan modifies at least one exertion level, and the modification is based on a standardized measure comprising perceived exertion, the data, and the long-term care health issue of the user; and
receive the second treatment plan.

Clause 16.10 The computer-readable medium of any clause herein, wherein the second treatment plan comprises a modified parameter pertaining to the electromechanical machine, wherein the modified parameter comprises a resistance, a range of motion, a length of time, an angle of a component of the electromechanical machine, a speed, a velocity, an angular velocity, an acceleration, a torque, or some combination thereof, and the computer-implemented system further comprises:
controlling the electromechanical machine based on the modified parameter.

Clause 17. The computer-readable medium of any clause herein, wherein the standardized measure of perceived exertion comprises a metabolic equivalent of tasks (MET) or a Borg rating of perceived exertion (RPE).

Clause 18.10 The computer-readable medium of any clause herein, wherein the one or more machine learning models generate the second treatment plan by predicting exercises that will result in the desired exertion level for each session, and the one or more machine learning models are trained using data pertaining to the standardized measure of perceived exertion, other users' data, and other users' long-term care health issues.

Clause 19.10 The computer-readable medium of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, information pertaining to long term care health issues of other users, or some combination thereof.

Clause 20.10 The computer-readable medium of any clause herein, wherein the transmitting the data further comprises transmitting the data to a second computing device that relays the data to a third computing device of a healthcare professional.

Figure 26:
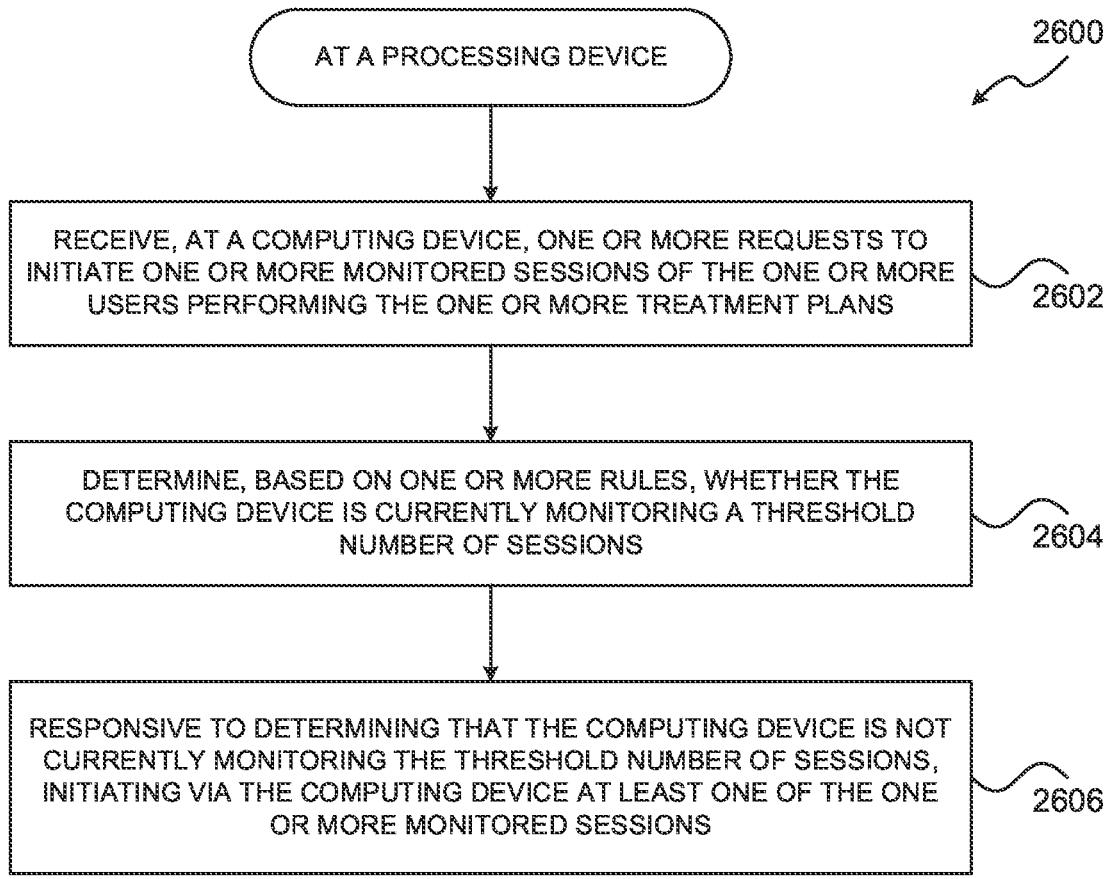
FIG. 26 generally illustrates an example embodiment of a method for assigning users to be monitored by observers where the assignment and monitoring are based on promulgated regulations according to the principles of the present disclosure.

System and Method for Assigning Users to be Monitored by Observers, where the Assignment and Monitoring are Based on Promulgated Regulations FIG. 26 generally illustrates an example embodiment of a method 2600 for assigning users to be monitored by observers where the assignment and monitoring are based on promulgated regulations according to the principles of the present disclosure. The method 2600 may be performed by processing logic that may include hardware (circuitry, dedicated logic, etc.), software, or a combination of both. The method 2600 and/or each of their individual functions, subroutines, or operations may be performed by one or more processing devices of a computing device (e.g., the computer system 1100 of FIG. 11) implementing the method 2600. The method 2600 may be implemented as computer instructions stored on a memory device and executable by the one or more processing devices. In certain implementations, the method 2600 may be performed by a single processing thread. Alternatively, the method 2600 may be performed by two or more processing threads, each thread implementing one or more individual functions, routines, subroutines, or operations of the methods.

In some embodiments, a system may be used to implement the method 2600. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 2600.

At block 2602, the processing device may receive, at a computing device, one or more requests to initiate one or more monitored sessions of the one or more users performing the one or more treatment plans. The computing device may be associated with a healthcare professional. The display of the interface may be presented on the computing device and the interface may enable the healthcare professional to privately communicate with each user being monitored in real-time or near real-time while performing the one or more treatment plans. In some embodiments, the one or more treatment plans may pertain to cardiac rehabilitation, pulmonary rehabilitation, bariatric rehabilitation, cardio-oncology rehabilitation, or some combination thereof.

At block 2604, the processing device may determine, based one or more rules, whether the computing device is currently monitoring a threshold number of sessions. The one or more rules may include a government agency regulation, a law, a protocol, or some combination thereof. For example, an FDA regulation may specify that up to 5 patients may be observed by 1 healthcare professional at any given time. That is, a healthcare professional may not concurrently or simultaneously observe more than 5 patients at any given moment in time.

At block 2606, responsive to determining that the computing device is not currently monitoring the threshold number of sessions, the processing device may initiate via the computing device at least one of the one or more monitored sessions.

In some embodiments, responsive to determining the computing device is currently monitoring the threshold number of sessions, the processing device may identify a second computing device. The second computing device may be associated with a second healthcare professional that is located proximate (e.g., a physician working for the same practice as the healthcare professional) or remote (e.g., a physician located in another city or state or country). The processing device may determine, based on the one or more rules, whether the second computing device is currently monitoring the threshold number of sessions. Responsive to determining the second computing device is not currently monitoring the threshold number of sessions, the processing device may initiate at least one of the one or more monitored sessions via the second computing device.

Further, in some embodiments, when the computing device is monitoring the threshold number of sessions, the processing device may identify a second computing device, and the identification may be performed without considering a geographical location of the second computing device relative to a geographical location of the electromechanical machine.

In some embodiments, the processing device may use one or more machine learning models trained to determine a prioritized order of users to initiate a monitored session. The one or more machine learning models may be trained to determine the priority based on one or more characteristics of the one or more users. For example, if a user has a familial history of cardiac disease or other similar life threatening disease, that user may be given a higher priority for a monitored session than a user that does not have that familial history. Accordingly, in some embodiments, the most at risk users in terms of health are given priority to engage in monitored sessions with healthcare professionals during their rehabilitation. In some embodiments, the prioritization may be adjusted based on other factors, such as compensation. For example, if a user desires to receive prioritized treatment, they may pay a certain amount of money to be advanced in priority for monitored sessions during their rehabilitation.

CLAUSES

Clause 1.11 A computer-implemented system, comprising:
one or more electromechanical machines configured to be manipulated by one or more users while the users are performing one or more treatment plans;
an interface comprising a display configured to present information pertaining to the treatment plan; and
a processing device configured to:
receive, at a computing device, one or more requests to initiate one or more monitored sessions of the one or more users performing the one or more treatment plans;
determine, based on one or more rules, whether the computing device is currently monitoring a threshold number of sessions; and
responsive to determining that the computing device is not currently monitoring the threshold number of sessions, initiate via the computing device at least one of the one or more monitored sessions.

Clause 2.11 The computer-implemented system of any clause herein, wherein the processing device is further configured to:
responsive to determining the computing device is currently monitoring the threshold number of sessions, identify a second computing device;
determine, based on the one or more rules, whether the second computing device is currently monitoring the threshold number of sessions; and
responsive to determining the second computing device is not currently monitoring the threshold number of sessions, initiate at least one of the one or more monitored sessions via the second computing device.

Clause 3.11 The computer-implemented system of any clause herein, wherein the one or more rules comprise a government agency regulation, a law, a protocol, or some combination thereof.

Clause 4.11 The computer-implemented system of any clause herein, wherein the computing device is associated with a healthcare professional, and the interface enables the healthcare professional to privately communicate with each user being monitored in real-time or near real-time while performing the one or more treatment plans.

Clause 5.11 The computer-implemented system of any clause herein, wherein the one or more treatment plans pertain to cardiac rehabilitation, pulmonary rehabilitation, bariatric rehabilitation, cardio-oncology rehabilitation, or some combination thereof.

Clause 6.11 The computer-implemented system of any clause herein, wherein, when the computing device is monitoring the threshold number of sessions, the processing device is further configured to identify a second computing device, and wherein the identification is performed without considering a geographical location of the second computing device relative to a geographical location the electromechanical machine.

Clause 7.11 The computer-implemented system of any clause herein, wherein the processing device is further configured to use one or more machine learning models to determine a prioritized order of users to initiate a monitored session, and the one or more machine learning models are trained to determine the priority based on one or more characteristics of the one or more users.

Clause 8.11 A computer-implemented method comprising:
  receiving, at a computing device, one or more requests to initiate one or more monitored sessions of the one or more users performing the one or more treatment plans;
  determining, based on one or more rules, whether the computing device is currently monitoring a threshold number of sessions; and
  responsive to determining that the computing device is not currently monitoring the threshold number of sessions, initiating via the computing device at least one of the one or more monitored sessions.

Clause 9.11 The computer-implemented method of any clause herein, further comprising:
  responsive to determining the computing device is currently monitoring the threshold number of sessions, identifying a second computing device;
  determining, based on the one or more rules, whether the second computing device is currently monitoring the threshold number of sessions; and
  responsive to determining the second computing device is not currently monitoring the threshold number of sessions, initiating at least one of the one or more monitored sessions via the second computing device.

Clause 10.11 The computer-implemented method of any clause herein, wherein the one or more rules comprise a government agency regulation, a law, a protocol, or some combination thereof.

Clause 11.11 The computer-implemented method of any clause herein, wherein the computing device is associated with a healthcare professional, and the interface enables the healthcare professional to privately communicate with each user being monitored in real-time or near real-time while performing the one or more treatment plans.

Clause 12.11 The computer-implemented method of any clause herein, wherein the one or more treatment plans pertain to cardiac rehabilitation, pulmonary rehabilitation, bariatric rehabilitation, cardio-oncology rehabilitation, or some combination thereof.

Clause 13.11 The computer-implemented method of any clause herein, wherein, when the computing device is monitoring the threshold number of sessions, the processing device is further configured to identify a second computing device, and wherein the identification is performed without considering a geographical location of the second computing device relative to a geographical location the electromechanical machine.

Clause 14.11 The computer-implemented method of any clause herein, further comprising using one or more machine learning models to determine a prioritized order of users to initiate a monitored session, and the one or more machine learning models are trained to determine the priority based on one or more characteristics of the one or more users.

Clause 15.11 A tangible, non-transitory computer-readable medium storing instructions that, when executed, cause a processing device to:
  receive, at a computing device, one or more requests to initiate one or more monitored sessions of the one or more users performing the one or more treatment plans;
  determine, based on one or more rules, whether the computing device is currently monitoring a threshold number of sessions; and
  responsive to determining that the computing device is not currently monitoring the threshold number of sessions, initiate via the computing device at least one of the one or more monitored sessions.

Clause 16.11 The computer-readable medium of any clause herein, wherein the processing device is to:
  responsive to determining the computing device is currently monitoring the threshold number of sessions, identify a second computing device;
  determine, based on the one or more rules, whether the second computing device is currently monitoring the threshold number of sessions; and
  responsive to determining the second computing device is not currently monitoring the threshold number of sessions, initiate at least one of the one or more monitored sessions via the second computing device.

Clause 17.11 The computer-readable medium of any clause herein, wherein the one or more rules comprise a government agency regulation, a law, a protocol, or some combination thereof.

Clause 18.11 The computer-readable medium of any clause herein, wherein the computing device is associated with a healthcare professional, and the interface enables the healthcare professional to privately communicate with each user being monitored in real-time or near real-time while performing the one or more treatment plans.

Clause 19.11 The computer-readable medium of any clause herein, wherein the one or more treatment plans pertain to cardiac rehabilitation, pulmonary rehabilitation, bariatric rehabilitation, cardio-oncology rehabilitation, or some combination thereof.

Clause 20.11 The computer-readable medium of any clause herein, wherein, when the computing device is monitoring the threshold number of sessions, the processing device is further configured to identify a second computing device, and wherein the identification is performed without considering a geographical location of the second computing device relative to a geographical location the electromechanical machine.

Figure 27:
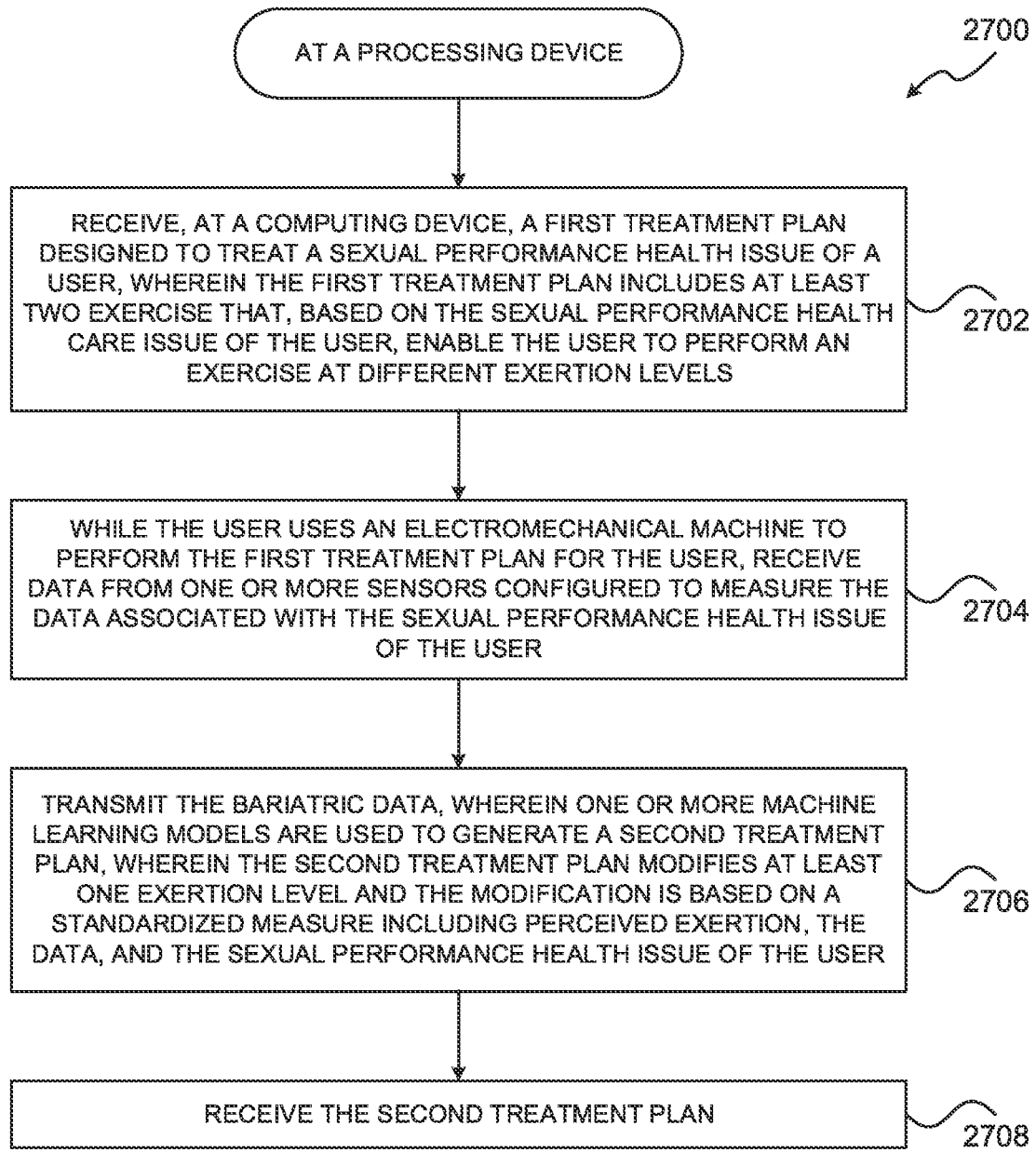
FIG. 27 generally illustrates an example embodiment of a method for using artificial intelligence and machine learning and telemedicine for cardiac and pulmonary treatment via an electromechanical machine of sexual performance according to the principles of the present disclosure.

System and Method for Using AI/ML and Telemedicine for Cardiac and Pulmonary Treatment Via an Electromechanical Machine of Sexual Performance FIG. 27 generally illustrates an example embodiment of a method 2700 for using artificial intelligence and machine learning and telemedicine for cardiac and pulmonary treatment via an electromechanical machine of sexual performance according to the principles of the present disclosure. The method 2700 may be performed by processing logic that may include hardware (circuitry, dedicated logic, etc.), software, or a combination of both. The method 2700 and/or each of their individual functions, subroutines, or operations may be performed by one or more processing devices of a computing device (e.g., the computer system 1100 of FIG. 11) implementing the method 2700. The method 2700 may be implemented as computer instructions stored on a memory device and executable by the one or more processing devices. In certain implementations, the method 2700 may be performed by a single processing thread. Alternatively, the method 2700 may be performed by two or more processing threads, each thread implementing one or more individual functions, routines, subroutines, or operations of the methods.

In some embodiments, a system may be used to implement the method 2700. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 2700.

At block 2702, the processing device may receive, at a computing device, a first treatment plan designed to treat a sexual performance health issue of a user. The first treatment plan may include at least two exercise sessions that, based on the sexual performance health issue of the user, enable the user to perform an exercise at different exertion levels. In some embodiments, sexual performance information pertaining to the user may be received from an application programming interface associated with an electronic medical records system. In some embodiments, the sexual performance health issue of the user may include erectile dysfunction, abnormally low or high testosterone levels, abnormally low or high estrogen levels, abnormally low or high progestin levels, diminished libido, health conditions associated with abnormal levels of any of the foregoing hormones or of other hormones, or some combination thereof.

In some embodiments, the first treatment plan may be generated based on attribute data including an eating or drinking schedule of the user, information pertaining to an age of the user, information pertaining to a sex of the user, information pertaining to a weight of the user information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

At block 2704, while the user uses an electromechanical machine to perform the first treatment plan for the user, the processing device may receive data from one or more sensors configured to measure the data associated with the sexual performance health issue of the user. In some embodiments, the data may include a procedure performed on the user, an electronic medical record associated with the user, a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, a pulmonary diagnosis of the user, an oncologic diagnosis of the user, a bariatric diagnosis of the user, a pathological diagnosis related to a prostate gland or urogenital tract of the user, or some combination thereof.

At block 2706, the processing device may transmit the data. In some embodiments, one or more machine learning models 13 may be executed by the server 30 and the machine learning models 13 may be used to generate a second treatment plan based on the data and/or the sexual performance health issues of users. The second treatment plan may modify at least one exertion level, and the modification may be based on a standardized measure including perceived exertion, the data, and the sexual performance health issue of the user. In some embodiments, the standardized measure of perceived exertion may include a metabolic equivalent of tasks (MET) or a Borg rating of perceived exertion (RPE).

In some embodiments, the one or more machine learning models generate the second treatment plan by predicting exercises that will result in the desired exertion level for each session. The one or more machine learning models may be trained using data pertaining to the standardized measure of perceived exertion, other users' data, and other users' sexual performance health issues as input data, and other users' exertion levels that led to desired results as output data. The input data and the output data may be labeled and mapped accordingly.

At block 2708, the processing device may receive the second treatment plan from the server 30. The processing device may implement at least a portion of the treatment plan to cause an operating parameter of the electromechanical machine to be modified in accordance with the modified exertion level set in the second treatment plan. To that end, in some embodiments, the second treatment plan may include a modified parameter pertaining to the electromechanical machine. The modified parameter may include a resistance, a range of motion, a length of time, an angle of a component of the electromechanical machine, a speed, a velocity, an angular velocity, an acceleration, a torque, or some combination thereof. The processing device may, based on the modified parameter, control the electromechanical machine.

In some embodiments, transmitting the data may include transmitting the data to a second computing device that relays the sexual performance health issue data to a third computing device that is associated with a healthcare professional.

CLAUSES

Clause 1.12 A computer-implemented system, comprising:
an electromechanical machine configured to be manipulated by a user while the user performs a treatment plan;
an interface comprising a display configured to present information pertaining to the treatment plan; and
a processing device configured to:
receive, at a computing device, a first treatment plan designed to treat a sexual performance health issue of a user, wherein the first treatment plan comprises at least two exercise sessions that, based on the sexual performance health issue of the user, enable the user to perform an exercise at different exertion levels;
while the user uses an electromechanical machine to perform the first treatment plan for the user, receive data from one or more sensors configured to measure the data associated with the sexual performance health issue of the user;

transmit the data, wherein one or more machine learning models are used to generate a second treatment plan, wherein the second treatment plan modifies at least one exertion level, and the modification is based on a standardized measure comprising perceived exertion, the data, and the sexual performance health issue of the user; and receive the second treatment plan.

Clause 2.12 The computer-implemented system of any clause herein, wherein the data comprises information pertaining to cardiac health of the user, oncologic health of the user, pulmonary health of the user, bariatric health of the user, rehabilitation from pathologies related to a prostate gland or urogenital tract, or some combination thereof.

Clause 3.12 The computer-implemented system of any clause herein, wherein the second treatment plan comprises a modified parameter pertaining to the electromechanical machine, wherein the modified parameter comprises a resistance, a range of motion, a length of time, an angle of a component of the electromechanical machine, a speed, a velocity, an angular velocity, an acceleration, a torque, or some combination thereof or some combination thereof, and the computer-implemented system further comprises:

controlling the electromechanical machine based on the modified parameter.

Clause 4.12 The computer-implemented system of any clause herein, wherein the standardized measure of perceived exertion comprises a metabolic equivalent of tasks (MET) or a Borg rating of perceived exertion (RPE).

Clause 5.12 The computer-implemented system of any clause herein, wherein, by predicting exercises that will result in the desired exertion level for each session, the one or more machine learning models generate the second treatment plan, and the one or more machine learning models are trained using data pertaining to the standardized measure of perceived exertion, other users' data, and other users' sexual performance health issues.

Clause 6.12 The computer-implemented system of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, information pertaining to sexual performance health issues of other users, or some combination thereof.

Clause 7.12 The computer-implemented system of any clause herein, wherein the transmitting the data further comprises transmitting the data to a second computing device that relays the data to a third computing device of a healthcare professional.

Clause 8.12 The computer-implemented system of any clause herein, wherein the data comprises a procedure performed on the user, an electronic medical record associated with the user, a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, a pulmonary diagnosis of the user, an oncologic diagnosis of the user, a bariatric diagnosis of the user, a pathological diagnosis related to a prostate gland or urogenital tract of the user, or some combination thereof.

Clause 9.12 The computer-implemented system of any clause herein, wherein the sexual performance health issue of the user comprises erectile dysfunction, abnormally low or high testosterone levels, abnormally low or high estrogen levels, abnormally low or high progestin levels, diminished libido, health conditions associated with abnormal levels of any of the foregoing hormones or of other hormones, or some combination thereof.

Clause 10.12 A computer-implemented method comprising:

receive, at a computing device, a first treatment plan designed to treat a sexual performance health issue of a user, wherein the first treatment plan comprises at least two exercise sessions that, based on the sexual performance health issue of the user, enable the user to perform an exercise at different exertion levels;

while the user uses an electromechanical machine to perform the first treatment plan for the user, receive data from one or more sensors configured to measure the data associated with the sexual performance health issue of the user, wherein the electromechanical machine is configured to be manipulated by the user while the user performs the first treatment plan;

transmit the data, wherein one or more machine learning models are used to generate a second treatment plan, wherein the second treatment plan modifies at least one exertion level, and the modification is based on a standardized measure comprising perceived exertion, the data, and the sexual performance health issue of the user; and receive the second treatment plan.

Clause 11.12 The computer-implemented method of any clause herein, wherein the data comprises information pertaining to cardiac health of the user, oncologic health of the user, pulmonary health of the user, bariatric health of the user, rehabilitation from pathologies related to a prostate gland or urogenital tract, or some combination thereof.

Clause 12.12 The computer-implemented method of any clause herein, wherein the second treatment plan comprises a modified parameter pertaining to the electromechanical machine, wherein the modified parameter comprises a resistance, a range of motion, a length of time, an angle of a component of the electromechanical machine, a speed, a velocity, an angular velocity, an acceleration, a torque, or some combination thereof or some combination thereof, and the computer-implemented system further comprises:

controlling the electromechanical machine based on the modified parameter.

Clause 13.12 The computer-implemented method of any clause herein, wherein the standardized measure of perceived exertion comprises a metabolic equivalent of tasks (MET) or a Borg rating of perceived exertion (RPE).

Clause 14.12 The computer-implemented method of any clause herein, wherein, by predicting exercises that will result in the desired exertion level for each session, the one or more machine learning models generate the second treatment plan, and the one or more machine learning models are trained using data pertaining to the standardized measure of perceived exertion, other users' data, and other users' sexual performance health issues.

Clause 15.12 The computer-implemented method of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, information pertaining to sexual performance health issues of other users, or some combination thereof.

Clause 16.12 The computer-implemented method of any clause herein, wherein the transmitting the data further comprises transmitting the data to a second computing device that relays the data to a third computing device of a healthcare professional.

Clause 17.12 The computer-implemented method of any clause herein, wherein the data comprises a procedure performed on the user, an electronic medical record associated with the user, a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, a pulmonary diagnosis of the user, an oncologic diagnosis of the user, a bariatric diagnosis of the user, a pathological diagnosis related to a prostate gland or urogenital tract of the user, or some combination thereof.

Clause 18.12 The computer-implemented method of any clause herein, wherein the sexual performance health issue of the user comprises erectile dysfunction, abnormally low or high testosterone levels, abnormally low or high estrogen levels, abnormally low or high progestin levels, diminished libido, health conditions associated with abnormal levels of any of the foregoing hormones or of other hormones, or some combination thereof.

Clause 19.12 A tangible, non-transitory computer-readable medium storing instructions that, when executed, cause a processing device to:
  receive, at a computing device, a first treatment plan designed to treat a sexual performance health issue of a user, wherein the first treatment plan comprises at least two exercise sessions that, based on the sexual performance health issue of the user, enable the user to perform an exercise at different exertion levels;
  while the user uses an electromechanical machine to perform the first treatment plan for the user, receive data from one or more sensors configured to measure the data associated with the sexual performance health issue of the user, wherein the electromechanical machine is configured to be manipulated by the user while the user performs the first treatment plan;
  transmit the data, wherein one or more machine learning models are used to generate a second treatment plan, wherein the second treatment plan modifies at least one exertion level, and the modification is based on a standardized measure comprising perceived exertion, the data, and the sexual performance health issue of the user; and
  receive the second treatment plan.

Clause 20.12 The computer-readable medium of any clause herein, wherein the data comprises information pertaining to cardiac health of the user, oncologic health of the user, pulmonary health of the user, bariatric health of the user, rehabilitation from pathologies related to a prostate gland or urogenital tract, or some combination thereof.

Figure 28:
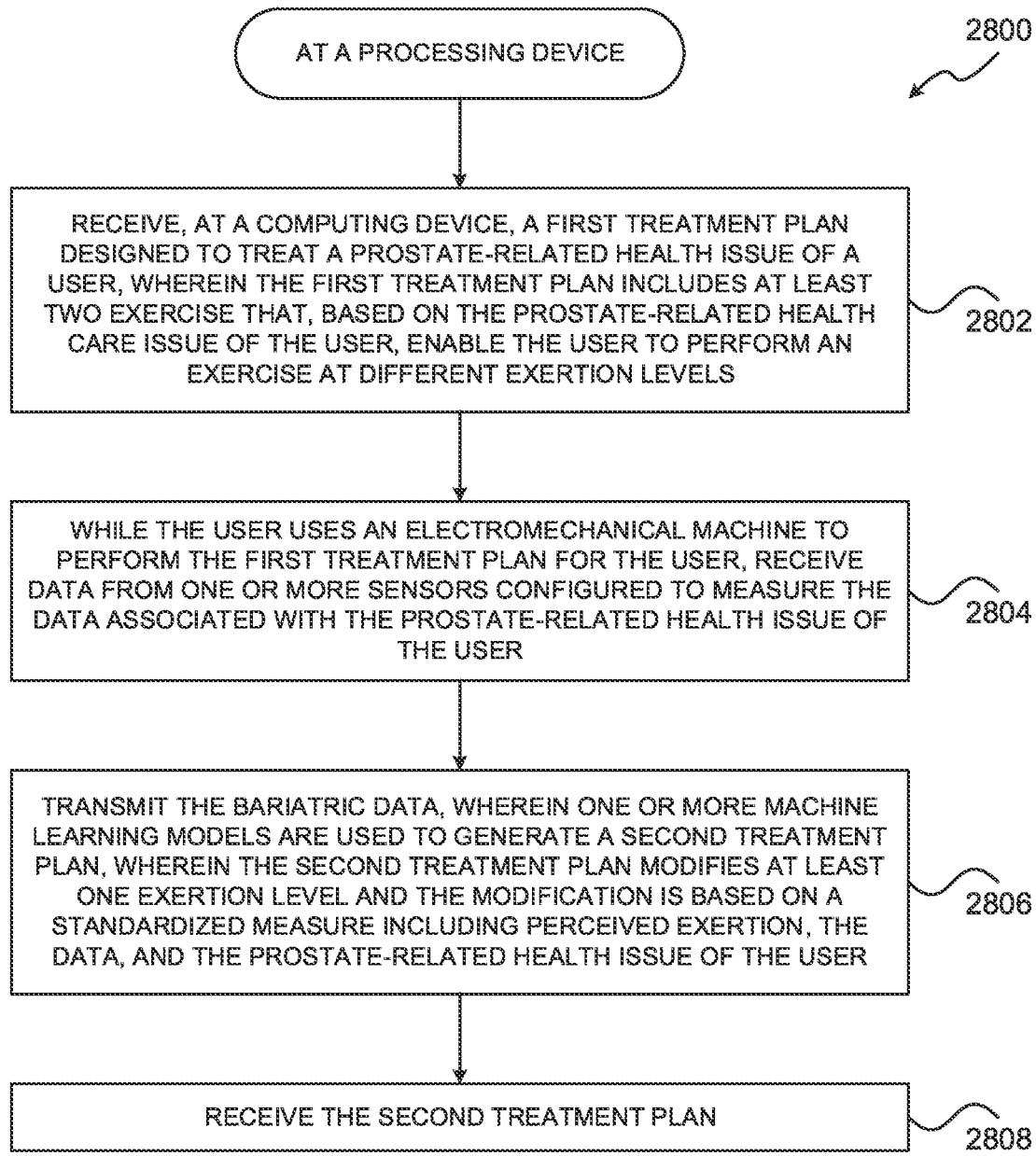
FIG. 28 generally illustrates an example embodiment of a method for using artificial intelligence and machine learning and telemedicine for prostate-related oncologic or other surgical treatment to determine a cardiac treatment plan that uses via an electromechanical machine, and where erectile dysfunction is secondary to the prostate treatment and/or condition according to the principles of the present disclosure.

System and Method for Using AI/ML and Telemedicine for Prostate-Related Oncologic or Other Surgical Treatment to Determine a Cardiac Treatment Plan that Uses Via an Electromechanical Machine, and where Erectile Dysfunction is Secondary to the Prostate Treatment and/or Condition FIG. 28 generally illustrates an example embodiment of a method 2800 for using artificial intelligence and machine learning and telemedicine for prostate-related oncologic or other surgical treatment to determine a cardiac treatment plan that uses via an electromechanical machine, and where erectile dysfunction is secondary to the prostate treatment and/or condition according to the principles of the present disclosure. The method 2800 may be performed by processing logic that may include hardware (circuitry, dedicated logic, etc.), software, or a combination of both. The method 2800 and/or each of their individual functions, subroutines, or operations may be performed by one or more processing devices of a computing device (e.g., the computer system 1100 of FIG. 11) implementing the method 2800. The method 2800 may be implemented as computer instructions stored on a memory device and executable by the one or more processing devices. In certain implementations, the method 2800 may be performed by a single processing thread. Alternatively, the method 2800 may be performed by two or more processing threads, each thread implementing one or more individual functions, routines, subroutines, or operations of the methods.

In some embodiments, a system may be used to implement the method 2800. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 2800.

At block 2802, the processing device may receive, at a computing device, a first treatment plan designed to treat a prostate-related health issue of a user. The first treatment plan may include at least two exercise sessions that, based on the prostate-related health issue of the user, enable the user to perform an exercise at different exertion levels. In some embodiments, prostate-related information pertaining to the user may be received from an application programming interface associated with an electronic medical records system. In some embodiments, the prostate-related health issue may include an oncologic health issue, another surgery-related health issue, or some combination thereof.

In some embodiments, the first treatment plan may be generated based on attribute data including an eating or drinking schedule of the user, information pertaining to an age of the user, information pertaining to a sex of the user, information pertaining to a weight of the user information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, or some combination thereof.

At block 2704, while the user uses an electromechanical machine to perform the first treatment plan for the user, the processing device may receive data from one or more sensors configured to measure the data associated with the prostate-related health issue of the user. In some embodiments, the data may include a procedure performed on the user, an electronic medical record associated with the user, a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a respiration rate of the user, spirometry data related to the user, a pulmonary diagnosis of the user, an oncologic diagnosis of the user, a bariatric diagnosis of the user, a pathological diagnosis related to a prostate gland or urogenital tract of the user, or some combination thereof. Further, the data may include information pertaining to cardiac health of the user, oncologic health of the user, pulmonary health of the user, bariatric health of the user, rehabilitation from pathologies related to a prostate gland or urogenital tract, or some combination thereof.

At block 2706, the processing device may transmit the data. In some embodiments, one or more machine learning models 13 may be executed by the server 30 and the machine learning models 13 may be used to generate a second treatment plan based on the data and/or the prostate-related health issues of users. The second treatment plan may modify at least one exertion level, and the modification may be based on a standardized measure including perceived exertion, the data, and the prostate-related health issue of the user. In some embodiments, the standardized measure of perceived exertion may include a metabolic equivalent of tasks (MET) or a Borg rating of perceived exertion (RPE).

In some embodiments, the one or more machine learning models generate the second treatment plan by predicting exercises that will result in the desired exertion level for each session. The one or more machine learning models may be trained using data pertaining to the standardized measure of perceived exertion, other users' data, and other users' prostate-related health issues as input data, and other users' exertion levels that led to desired results as output data. The input data and the output data may be labeled and mapped accordingly.

At block 2708, the processing device may receive the second treatment plan from the server 30. The processing device may implement at least a portion of the treatment plan to cause an operating parameter of the electromechanical machine to be modified in accordance with the modified exertion level set in the second treatment plan. To that end, in some embodiments, the second treatment plan may include a modified parameter pertaining to the electromechanical machine. The modified parameter may include a resistance, a range of motion, a length of time, an angle of a component of the electromechanical machine, a speed, a velocity, an angular velocity, an acceleration, a torque, or some combination thereof. The processing device may, based on the modified parameter, control the electromechanical machine.

In some embodiments, transmitting the data may include transmitting the data to a second computing device that relays the prostate-related health issue data to a third computing device that is associated with a healthcare professional.

CLAUSES

Clause 1.13 A computer-implemented system, comprising:
    an electromechanical machine configured to be manipulated by a user while the user performs a treatment plan;
    an interface comprising a display configured to present information pertaining to the treatment plan; and
    a processing device configured to:
    receive, at a computing device, a first treatment plan designed to treat a prostate-related health issue of a user, wherein the first treatment plan comprises at least two exercise sessions that, based on the prostate-related health issue of the user, enable the user to perform an exercise at different exertion levels;
    while the user uses an electromechanical machine to perform the first treatment plan for the user, receive data from one or more sensors configured to measure the data associated with the prostate-related health issue of the user;
    transmit the data, wherein one or more machine learning models are used to generate a second treatment plan, wherein the second treatment plan modifies at least one exertion level, and the modification is based on a standardized measure comprising perceived exertion, the data, and the prostate-related health issue of the user; and
    receive the second treatment plan.

Clause 2.13 The computer-implemented system of any clause herein, wherein the data comprises information pertaining to cardiac health of the user, oncologic health of the user, pulmonary health of the user, bariatric health of the user, rehabilitation from pathologies related to a prostate gland or urogenital tract, or some combination thereof.

Clause 3.13 The computer-implemented system of any clause herein, wherein the prostate-related health issue further comprises an oncologic health issue, another surgery-related health issue, or some combination thereof.

Clause 4.13 The computer-implemented system of any clause herein, wherein the second treatment plan comprises a modified parameter pertaining to the electromechanical machine, wherein the modified parameter comprises a resistance, a range of motion, a length of time, an angle of a component of the electromechanical machine, a speed, a velocity, an angular velocity, an acceleration, a torque, or some combination thereof, and the computer-implemented system further comprises:
    controlling the electromechanical machine based on the modified parameter.

Clause 5.13 The computer-implemented system of any clause herein, wherein the standardized measure of perceived exertion comprises a metabolic equivalent of tasks (MET) or a Borg rating of perceived exertion (RPE).

Clause 6.13 The computer-implemented system of any clause herein, wherein the one or more machine learning models generate the second treatment plan by predicting exercises that will result in the desired exertion level for each session, and the one or more machine learning models are trained using data pertaining to the standardized measure of perceived exertion, other users' data, and other users' prostate-related health issues.

Clause 7.13 The computer-implemented system of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, information pertaining to prostate-related health issues of other users, or some combination thereof.

Clause 8.13 The computer-implemented system of any clause herein, wherein the transmitting the data further comprises transmitting the data to a second computing device that relays the data to a third computing device of a healthcare professional.

Clause 9.13 The computer-implemented system of any clause herein, wherein the data comprises a procedure performed on the user, an electronic medical record associated with the user, a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a pulmonary diagnosis of the user, an oncologic diagnosis of the user, a respiration rate of the user, spirometry data related to the user, or some combination thereof.

Clause 10.13 A computer-implemented method comprising:
  receive, at a computing device, a first treatment plan designed to treat a prostate-related health issue of a user, wherein the first treatment plan comprises at least two exercise sessions that, based on the prostate-related health issue of the user, enable the user to perform an exercise at different exertion levels;
  while the user uses an electromechanical machine to perform the first treatment plan for the user, receive data from one or more sensors configured to measure the data associated with the prostate-related health issue of the user, wherein the electromechanical machine is configured to be used by the user while performing the first treatment plan;
  transmit the data, wherein one or more machine learning models are used to generate a second treatment plan, wherein the second treatment plan modifies at least one exertion level, and the modification is based on a standardized measure comprising perceived exertion, the data, and the prostate-related health issue of the user; and
  receive the second treatment plan.

Clause 11.13 The computer-implemented method of any clause herein, wherein the data comprises information pertaining to cardiac health of the user, oncologic health of the user, pulmonary health of the user, bariatric health of the user, rehabilitation from pathologies related to a prostate gland or urogenital tract, or some combination thereof.

Clause 12.13 The computer-implemented method of any clause herein, wherein the prostate-related health issue further comprises an oncologic health issue, another surgery-related health issue, or some combination thereof.

Clause 13.13 The computer-implemented method of any clause herein, wherein the second treatment plan comprises a modified parameter pertaining to the electromechanical machine, wherein the modified parameter comprises a resistance, a range of motion, a length of time, an angle of a component of the electromechanical machine, a speed, a velocity, an angular velocity, an acceleration, a torque, or some combination thereof, and the computer-implemented system further comprises:
  controlling the electromechanical machine based on the modified parameter.

Clause 14.13 The computer-implemented method of any clause herein, wherein the standardized measure of perceived exertion comprises a metabolic equivalent of tasks (MET) or a Borg rating of perceived exertion (RPE).

Clause 15.13 The computer-implemented method of any clause herein, wherein the one or more machine learning models generate the second treatment plan by predicting exercises that will result in the desired exertion level for each session, and the one or more machine learning models are trained using data pertaining to the standardized measure of perceived exertion, other users' data, and other users' prostate-related health issues.

Clause 16.13 The computer-implemented method of any clause herein, wherein the first treatment plan is generated based on attribute data comprising an eating or drinking schedule of the user, information pertaining to an age of the user, information pertaining to a sex of the user, information pertaining to a gender of the user, an indication of a mental state of the user, information pertaining to a genetic condition of the user, information pertaining to a disease state of the user, information pertaining to a microbiome from one or more locations on or in the user, an indication of an energy level of the user, information pertaining to a weight of the user, information pertaining to a height of the user, information pertaining to a body mass index (BMI) of the user, information pertaining to a family history of cardiovascular health issues of the user, information pertaining to comorbidities of the user, information pertaining to desired health outcomes of the user if the treatment plan is followed, information pertaining to predicted health outcomes of the user if the treatment plan is not followed, information pertaining to prostate-related health issues of other users, or some combination thereof.

Clause 17.13 The computer-implemented method of any clause herein, wherein the transmitting the data further comprises transmitting the data to a second computing device that relays the data to a third computing device of a healthcare professional.

Clause 18.13 The computer-implemented method of any clause herein, wherein the data comprises a procedure performed on the user, an electronic medical record associated with the user, a weight of the user, a cardiac output of the user, a heartrate of the user, a heart rhythm of the user, a blood pressure of the user, a blood oxygen level of the user, a cardiovascular diagnosis of the user, a non-cardiovascular diagnosis of the user, a pulmonary diagnosis of the user, an oncologic diagnosis of the user, a respiration rate of the user, spirometry data related to the user, or some combination thereof.

Clause 19.13 A tangible, non-transitory computer-readable medium storing instructions that, when executed, cause a processing device to:
  receive, at a computing device, a first treatment plan designed to treat a prostate-related health issue of a user, wherein the first treatment plan comprises at least two exercise sessions that, based on the prostate-related health issue of the user, enable the user to perform an exercise at different exertion levels;
  while the user uses an electromechanical machine to perform the first treatment plan for the user, receive data from one or more sensors configured to measure the data associated with the prostate-related health issue of the user, wherein the electromechanical machine is configured to be used by the user while performing the first treatment plan;
  transmit the data, wherein one or more machine learning models are used to generate a second treatment plan, wherein the second treatment plan modifies at least one exertion level, and the modification is based on a standardized measure comprising perceived exertion, the data, and the prostate-related health issue of the user; and
  receive the second treatment plan.

Clause 20.13 The computer-readable medium of any clause herein, wherein the data comprises information pertaining to cardiac health of the user, oncologic health of the user, pulmonary health of the user, bariatric health of the user, rehabilitation from pathologies related to a prostate gland or urogenital tract, or some combination thereof.

Figure 29:
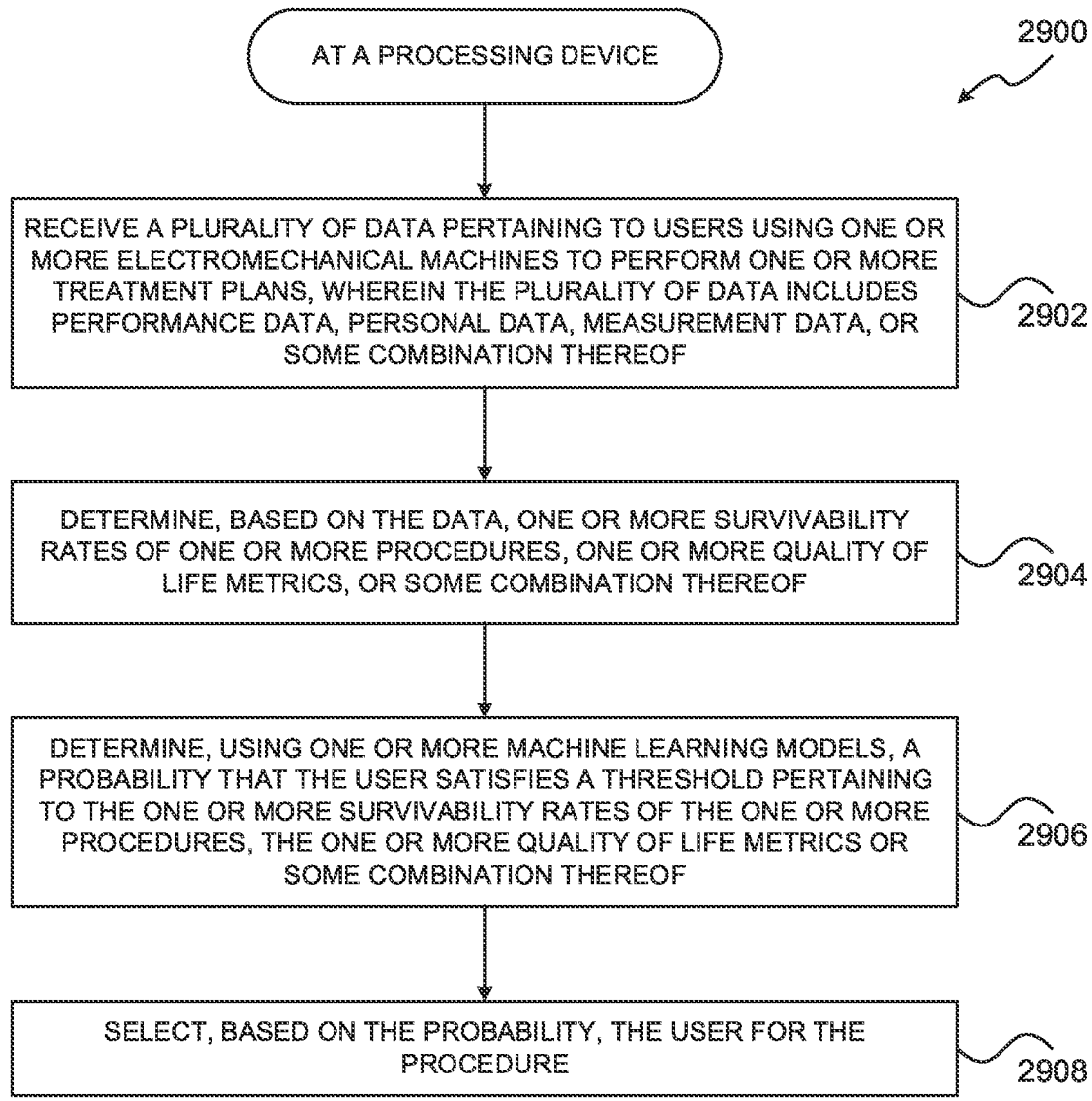
FIG. 29 generally illustrates an example embodiment of a method for determining, based on advanced metrics of actual performance on an electromechanical machine, medical procedure eligibility in order to ascertain survivability rates and measures of quality of life criteria according to the principles of the present disclosure.

System and Method for Determining, Based on Advanced Metrics of Actual Performance on an Electromechanical Machine, Medical Procedure Eligibility in Order to Ascertain Survivability Rates and Measures of Quality of Life Criteria FIG. 29 generally illustrates an example embodiment of a method 2900 for determining, based on advanced metrics of actual performance on an electromechanical machine, medical procedure eligibility in order to ascertain survivability rates and measures of quality of life criteria according to the principles of the present disclosure. The method 2900 may be performed by processing logic that may include hardware (circuitry, dedicated logic, etc.), software, or a combination of both. The method 2900 and/or each of their individual functions, subroutines, or operations may be performed by one or more processing devices of a computing device (e.g., the computer system 1100 of FIG. 11) implementing the method 2900. The method 2900 may be implemented as computer instructions stored on a memory device and executable by the one or more processing devices. In certain implementations, the method 2900 may be performed by a single processing thread. Alternatively, the method 2900 may be performed by two or more processing threads, each thread implementing one or more individual functions, routines, subroutines, or operations of the methods.

In some embodiments, a system may be used to implement the method 2900. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 2900.

At block 2902, the processing device may receive, a set of data pertaining to users using one or more electromechanical machines to perform one or more treatment plans. The set of data may include performance data, personal data, measurement data, or some combination thereof.

At block 2904, the processing device may determine, based on the data, one or more survivability rates of one or more procedures, one or more quality of life metrics, or some combination thereof.

At block 2906, the processing device may determine, using one or more machine learning models, a probability that the user satisfies a threshold pertaining to the one or more survivability rates of the one or more procedures, the one or more quality of life metrics, or some combination thereof. In some embodiments, the processing device may prescribe to the user the treatment plan associated with the one or more survivability rates, the one or more quality of life metrics, or some combination thereof. In some embodiments, the processing device may prescribe to the user the electromechanical machine associated with the treatment plan.

At block 2908, the processing device may select, based on the probability, the user for the one or more procedures.

In some embodiments, the processing device may initiate a telemedicine session while the user performs the treatment plan. The telemedicine session may include the processing device communicatively coupled to a processing device associated with a healthcare professional.

In some embodiments, the processing device may receive, via the patient interface 50, input pertaining to a perceived level of difficulty of an exercise associated with the treatment plan. The processing device may modify, based on the input, an operating parameter of the electromechanical machine. The processing device may receive input, via the patient interface 50, input pertaining to a level of the user's anxiety, depression, pain, difficulty in performing the treatment plan, or some combination thereof. This input may be used to adjust the treatment plan, determine an effectiveness of the treatment plan for users having similar characteristics, or the like. The input may be used to retrain the one or more machine learning models to determine subsequent treatment plans, survivability rates, quality of life metrics, or some combination thereof.

CLAUSES

Clause 1.14 A computer-implemented system, comprising:
  an electromechanical machine configured to be manipulated by a user while the user performs a treatment plan;
  an interface comprising a display configured to present information pertaining to the treatment plan; and
  a processing device configured to:
    receive a plurality of data pertaining to users using one or more electromechanical machines to perform one or more treatment plans, wherein the plurality of data comprises performance data, personal data, measurement data, or some combination thereof;
    determine, based on the data, one or more survivability rates of one or more procedures, one or more quality of life metrics, or some combination thereof;

determine, using one or more machine learning models, a probability that the user satisfies a threshold pertaining to the one or more survivability rates of the one or more procedures, the one or more quality of life metrics, or some combination thereof; and select, based on the probability, the user for the procedure.

Clause 2.14 The computer-implemented system of any clause herein, wherein the processing device is further configured to prescribe to the user the treatment plan associated with the one or more survivability rates, the one or more quality of life metrics, or some combination thereof.

Clause 3.14 The computer-implemented system of any clause herein, wherein the processing device is further configured to prescribe to the user the electromechanical machine associated with the treatment plan.

Clause 4.14 The computer-implemented system of any clause herein, wherein the processing device is further configured to initiate a telemedicine session while the user performs the treatment plan, wherein the telemedicine session comprises the processing device communicatively coupled to a processing device associated with a healthcare professional.

Clause 5.14 The computer-implemented system of any clause herein, wherein the interface is configured to receive input pertaining to a perceived level of difficulty of an exercise associated with the treatment plan.

Clause 6.14 The computer-implemented system of any clause herein, wherein the processing device is further configured to modify, based on the input, an operating parameter of the electromechanical machine.

Clause 7.14 The computer-implemented system of any clause herein, wherein the processing device is further configured to:

receive, via the interface, input pertaining to a level of the user's anxiety, depression, pain, difficulty in performing the treatment plan, or some combination thereof.

Clause 8.14 A computer-implemented method, comprising:

receiving a plurality of data pertaining to users using one or more electromechanical machines to perform one or more treatment plans, wherein the plurality of data comprises performance data, personal data, measurement data, or some combination thereof;

determining, based on the data, one or more survivability rates of one or more procedures, one or more quality of life metrics, or some combination thereof;

determining, using one or more machine learning models, a probability that the user satisfies a threshold pertaining to the one or more survivability rates of the one or more procedures, the one or more quality of life metrics, or some combination thereof; and selecting, based on the probability, the user for the procedure.

Clause 9.14 The computer-implemented method of any clause herein, further comprising prescribing to the user the treatment plan associated with the one or more survivability rates, the one or more quality of life metrics, or some combination thereof.

Clause 10.14 The computer-implemented method of any clause herein, further comprising prescribing to the user the electromechanical machine associated with the treatment plan.

Clause 11.14 The computer-implemented method of any clause herein, further comprising initiating a telemedicine session while the user performs the treatment plan, wherein the telemedicine session comprises the processing device communicatively coupled to a processing device associated with a healthcare professional.

Clause 12.14 The computer-implemented method of any clause herein, wherein the interface is configured to receive input pertaining to a perceived level of difficulty of an exercise associated with the treatment plan.

Clause 13.14 The computer-implemented method of any clause herein, further comprising modifying, based on the input, an operating parameter of the electromechanical machine.

Clause 14.14 The computer-implemented method of any clause herein, further comprising:

receiving, via the interface, input pertaining to a level of the user's anxiety, depression, pain, difficulty in performing the treatment plan, or some combination thereof.

Clause 15.14 A tangible, non-transitory computer-readable medium storing instructions that, when executed, cause a processing device to:

receive a plurality of data pertaining to users using one or more electromechanical machines to perform one or more treatment plans, wherein the plurality of data comprises performance data, personal data, measurement data, or some combination thereof;

determine, based on the data, one or more survivability rates of one or more procedures, one or more quality of life metrics, or some combination thereof;

determine, using one or more machine learning models, a probability that the user satisfies a threshold pertaining to the one or more survivability rates of the one or more procedures, the one or more quality of life metrics, or some combination thereof; and select, based on the probability, the user for the procedure.

Clause 16.14 The computer-readable medium of any clause herein, wherein the processing device is further configured to prescribe to the user the treatment plan associated with the one or more survivability rates, the one or more quality of life metrics, or some combination thereof.

Clause 17.14 The computer-readable medium of any clause herein, wherein the processing device is further configured to prescribe to the user the electromechanical machine associated with the treatment plan.

Clause 18.14 The computer-readable medium of any clause herein, wherein the processing device is further configured to initiate a telemedicine session while the user performs the treatment plan, wherein the telemedicine session comprises the processing device communicatively coupled to a processing device associated with a healthcare professional.

Clause 19.14 The computer-readable medium of any clause herein, wherein the interface is configured to receive input pertaining to a perceived level of difficulty of an exercise associated with the treatment plan.

Clause 20.14 The computer-readable medium of any clause herein, further comprising modifying, based on the input, an operating parameter of the electromechanical machine.

Figure 30:
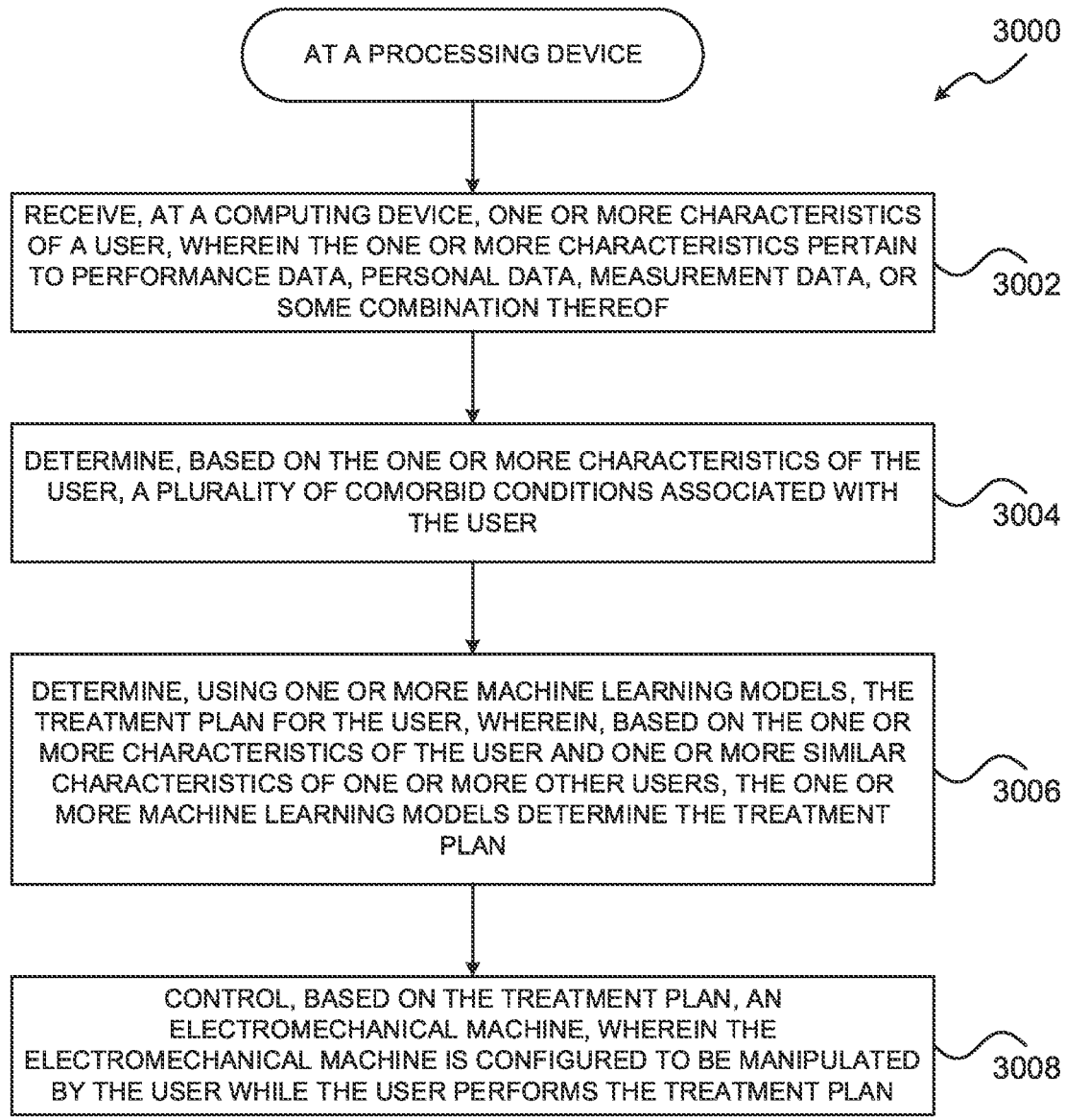
FIG. 30 generally illustrates an example embodiment of a method for using artificial intelligence and machine learning and telemedicine to integrate rehabilitation for a plurality of comorbid conditions according to the principles of the present disclosure.

System and Method for Using AI/ML and Telemedicine to Integrate Rehabilitation for a Plurality of Comorbid Conditions FIG. 30 generally illustrates an example embodiment of a method 3000 for using artificial intelligence and machine learning and telemedicine to integrate rehabilitation for a plurality of comorbid conditions according to the principles of the present disclosure. The method 3000 may be performed by processing logic that may include hardware (circuitry, dedicated logic, etc.), software, or a combination of both. The method 3000 and/or each of their individual functions, subroutines, or operations may be performed by one or more processing devices of a computing device (e.g., the computer system 1100 of FIG. 11) implementing the method 3000. The method 3000 may be implemented as computer instructions stored on a memory device and executable by the one or more processing devices. In certain implementations, the method 3000 may be performed by a single processing thread. Alternatively, the method 3000 may be performed by two or more processing threads, each thread implementing one or more individual functions, routines, subroutines, or operations of the methods.

In some embodiments, a system may be used to implement the method 3000. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 3000.

At block 3002, the processing device may receive, at a computing device, one or more characteristics of the user. The one or more characteristics of the user may pertain to performance data, personal data, measurement data, or some combination thereof. In some embodiments, a computing device associated with a healthcare professional may monitor the one or more characteristics of the user while the user performs the treatment plan in real-time or near real-time.

At block 3004, the processing device may determine, based on the one or more characteristics of the user, a set of comorbid conditions associated with the user. In some embodiments, the set of comorbid conditions may be related to cardiac, orthopedic, pulmonary, bariatric, oncologic, or some combination thereof.

At block 3006, the processing device may determine, using one or more machine learning models, the treatment plan for the user. Based on the one or more characteristics of the user and one or more similar characteristics of one or more other users, the one or more machine learning models determine the treatment plan.

At block 3008, the processing device may control, based on the treatment plan, the electromechanical machine.

In some embodiments, based on the one or more characteristics satisfying a threshold, the processing device may initiate a telemedicine session based on the one or more characteristics satisfying a threshold.

In some embodiments, the processing device may use the one or more machine learning models to determine one or more exercises to include in the treatment plan. The one or more exercises are determined based on a number of conditions they treat, based on whether the one or more exercises treat a most severe condition associated with the user, or based on some combination thereof.

In some embodiments, the processing device may receive, from the patient interface 50, input pertaining to a perceived level of difficulty of the user performing the treatment plan. The processing device may modify, based on the input, an operating parameter of the electromechanical machine.

CLAUSES

Clause 1.15 A computer-implemented system, comprising:
an electromechanical machine configured to be manipulated by a user while the user performs a treatment plan;
an interface comprising a display configured to present information pertaining to the treatment plan; and
a processing device configured to:
receive, at a computing device, one or more characteristics of the user, wherein the one or more characteristics pertain to performance data, personal data, measurement data, or some combination thereof;
determine, based on the one or more characteristics of the user, a plurality of comorbid conditions associated with the user;
determine, using one or more machine learning models, the treatment plan for the user, wherein, based on the one or more characteristics of the user and one or more similar characteristics of one or more other users, the one or more machine learning models determine the treatment plan; and
control, based on the treatment plan, the electromechanical machine.

Clause 2.15 The computer-implemented system of any preceding clause, wherein the plurality of comorbid conditions is related to cardiac, orthopedic, pulmonary, bariatric, oncologic, or some combination thereof.

Clause 3.15 The computer-implemented system of any preceding clause, wherein a computing device associated with a healthcare professional may monitor the one or more characteristics of the user while the user performs the treatment plan in real-time or near real-time.

Clause 4.15 The computer-implemented system of any preceding clause, wherein, based on the one or more characteristics satisfying a threshold, the processing device is further configured to initiate a telemedicine session based on the one or more characteristics satisfying a threshold.

Clause 5.15 The computer-implemented system of any preceding clause, wherein the processing device is further configured to use the one or more machine learning models to determine one or more exercises to include in the treatment plan, wherein the one or more exercises are determined based on a number of conditions they treat, based on whether the one or more exercises treat a most severe condition associated with the user, or based on some combination thereof.

Clause 6.15 The computer-implemented system of any preceding clause, wherein the processing device is further configured to receive input pertaining to a perceived level of difficulty of the user performing the treatment plan.

Clause 7.15 The computer-implemented system of any preceding clause, wherein the processing device is further configured to modify, based on the input, an operating parameter of the electromechanical machine.

Clause 8.15 A computer-implemented method comprising:
receiving, at a computing device, one or more characteristics of a user, wherein the one or more characteristics pertain to performance data, personal data, measurement data, or some combination thereof;
determining, based on the one or more characteristics of the user, a plurality of comorbid conditions associated with the user;
determining, using one or more machine learning models, the treatment plan for the user, wherein, based on the one or more characteristics of the user and one or more similar characteristics of one or more other users, the one or more machine learning models determine the treatment plan; and
controlling, based on the treatment plan, an electromechanical machine, wherein the electromechanical machine is configured to be manipulated by the user while the user performs the treatment plan.

Clause 9.15 The computer-implemented method of any preceding clause, wherein the plurality of comorbid conditions is related to cardiac, orthopedic, pulmonary, bariatric, oncologic, or some combination thereof.

Clause 10.15 The computer-implemented method of any preceding clause, wherein a computing device associated with a healthcare professional may monitor the one or more characteristics of the user while the user performs the treatment plan in real-time or near real-time.

Clause 11.15 The computer-implemented method of any preceding clause, wherein, based on the one or more characteristics satisfying a threshold, the processing device is further configured to initiate a telemedicine session based on the one or more characteristics satisfying a threshold.

Clause 12.15 The computer-implemented method of any preceding clause, further comprising using the one or more machine learning models to determine one or more exercises to include in the treatment plan, wherein the one or more exercises are determined based on a number of conditions they treat, based on whether the one or more exercises treat a most severe condition associated with the user, or based on some combination thereof.

Clause 13.15 The computer-implemented method of any preceding clause, further comprising receiving input pertaining to a perceived level of difficulty of the user performing the treatment plan.

Clause 14.15 The computer-implemented method of any preceding clause, further comprising modifying, based on the input, an operating parameter of the electromechanical machine.

Clause 15.15 A tangible, non-transitory computer-readable storing instructions that, when executed, cause a processing device to:
  receive, at a computing device, one or more characteristics of the user, wherein the one or more characteristics pertain to performance data, personal data, measurement data, or some combination thereof;
  determine, based on the one or more characteristics of the user, a plurality of comorbid conditions associated with the user;
  determine, using one or more machine learning models, the treatment plan for the user, wherein, based on the one or more characteristics of the user and one or more similar characteristics of one or more other users, the one or more machine learning models determine the treatment plan; and
  control, based on the treatment plan, an electromechanical machine, wherein the electromechanical machine is configured to be manipulated by a user while the user performs the treatment plan.

Clause 16.15 The computer-readable medium of any preceding clause, wherein the plurality of comorbid conditions is related to cardiac, orthopedic, pulmonary, bariatric, oncologic, or some combination thereof.

Clause 17.15 The computer-readable medium of any preceding clause, wherein a computing device associated with a healthcare professional may monitor the one or more characteristics of the user while the user performs the treatment plan in real-time or near real-time.

Clause 18.15 The computer-readable medium of any preceding clause, wherein, based on the one or more characteristics satisfying a threshold, the processing device is further configured to initiate a telemedicine session based on the one or more characteristics satisfying a threshold.

Clause 19.15 The computer-readable medium of any preceding clause, wherein the processing device is to use the one or more machine learning models to determine one or more exercises to include in the treatment plan, wherein the one or more exercises are determined based on a number of conditions they treat, based on whether the one or more exercises treat a most severe condition associated with the user, or based on some combination thereof.

Clause 20.15 The computer-readable medium of any preceding clause, wherein the processing device is to receive input pertaining to a perceived level of difficulty of the user performing the treatment plan.

Figure 31:
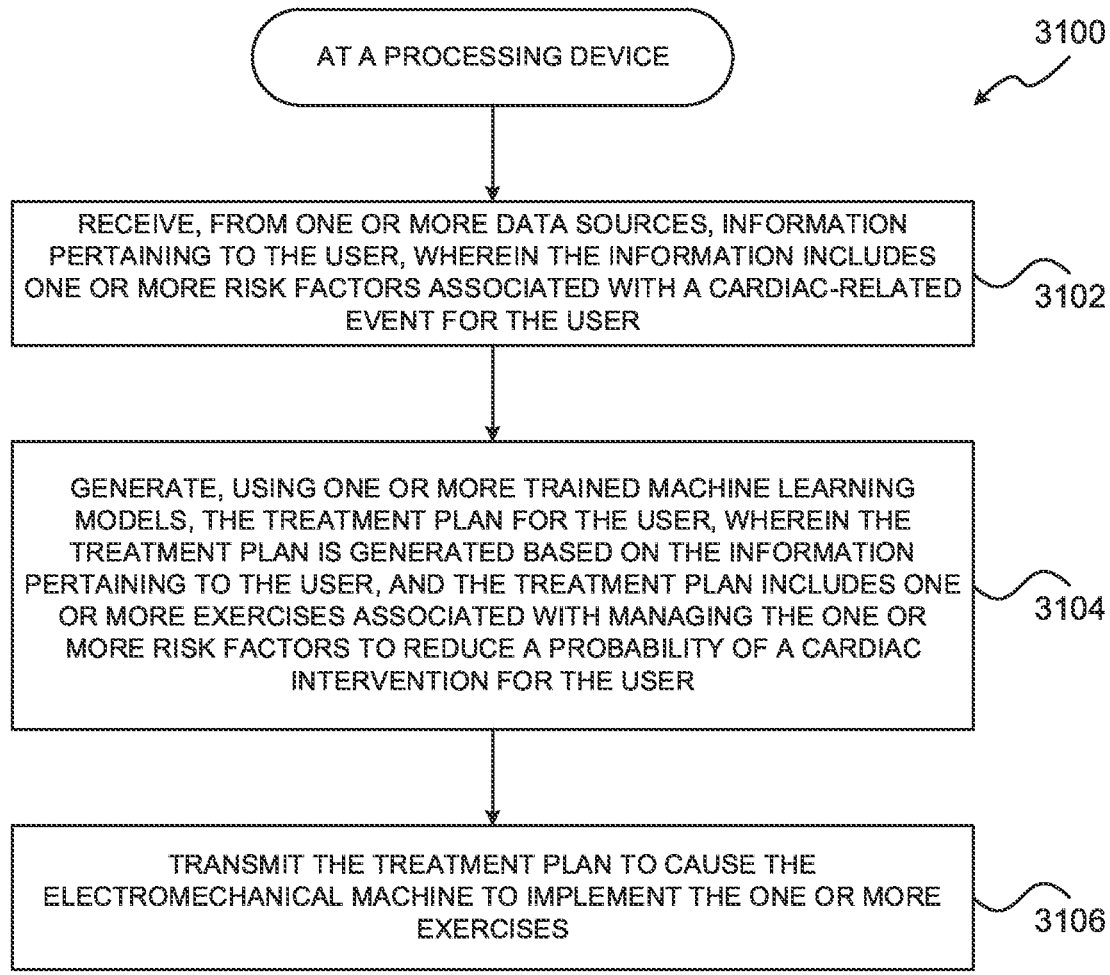
FIG. 31 generally illustrates an example embodiment of a method for using artificial intelligence and machine learning and generic risk factors to improve cardiovascular health such that the need for cardiac intervention is mitigated according to the principles of the present disclosure.

System and Method for Using AI/ML and Generic Risk Factors to Improve Cardiovascular Health Such that the Need for Additional Cardiac Interventions in Response to Cardiac-Related Events (CREs) is Mitigated FIG. 31 generally illustrates an example embodiment of a method 3100 for using artificial intelligence and machine learning and generic risk factors to improve cardiovascular health such that the need for cardiac intervention is mitigated according to the principles of the present disclosure. The method 3100 is configured to generate, provide, and/or adjust a treatment plan for a user who has experienced a cardiac-related event or who is likely, in a probabilistic sense or according to a probabilistic metric, whether parametric or non-parametric, to experience a cardiac-related event, including but not limited to CREs arising out of existing or incipient cardiac conditions. The method 3100 may be performed by processing logic that may include hardware (circuitry, dedicated logic, etc.), software, or a combination of both. The method 3100 and/or each of their individual functions, subroutines, or operations may be performed by one or more processing devices of a computing device (e.g., the system 10 of FIG. 1, the computer system 1100 of FIG. 11, etc.) implementing the method 3100. The method 3100 may be implemented as computer instructions stored on a memory device and executable by the one or more processing devices. In certain implementations, the method 3100 may be performed by a single processing thread. Alternatively, the method 3100 may be performed by two or more processing threads, each thread implementing one or more individual functions, routines, subroutines, or operations of the methods.

In some embodiments, a system may be used to implement the method 3100. The system may include the treatment apparatus 70 (e.g., an electromechanical machine) configured to be manipulated by a user while the user is performing a treatment plan, and an interface including a display configured to present information pertaining to the treatment plan. The system may include a processing device configured to execute instructions implemented the method 3100.

At block 3102, the processing device may receive, from one or more data sources, information pertaining to the user. The information may include one or more risk factors associated with a cardiac-related event for the user. In some embodiments, the one or more risk factors may include genetic history of the user, medical history of the user, familial medical history of the user, demographics of the user, a cohort or cohorts of the user, psychographics of the user, behavior history of the user, or some combination thereof. The one or more data sources may include an electronic medical record system, an application programming interface, a third-party application, a sensor, a website, or some combination thereof.

At block 3104, the processing device may generate, using one or more trained machine learning models, the treatment plan for the user. The treatment plan may be generated based on the information pertaining to the user, and the treatment plan may include one or more exercises associated with managing the one or more risk factors to reduce a probability of a cardiac intervention for the user.

At block 3106, the processing device may transmit the treatment plan to cause the electromechanical machine to implement the one or more exercises. In some embodiments, the processing device may modify an operating parameter of the electromechanical machine to case the electromechanical machine to implement the one or more exercises. In some embodiments, the processing device may initiate, while the user performs the treatment plan, a telemedicine session between a computing device of the user and a computing device of a healthcare professional.

In some embodiments, the processing device may receive, from one or more sensors, one or more measurements associated with the user. The one or more measurements may be received while the user performs the treatment plan. The processing device may determine, based on the one or more measurements, whether the one or more risk factors are being managed within a desired range. For example, the processing device determines whether characteristics (e.g., a heartrate) of the user while performing the treatment plan meet thresholds for addressing (e.g., improving, reducing, etc.) the risk factors. In some embodiments, a trained machine learning model 13 may be used to receive the measurements as input and to output a probability that one or more of the risk factors are being managed within a desired range or are not being managed within the desired range.

In some embodiments, responsive to determining the one or more risk factors are being managed within the desired range, the processing device is to control the electromechanical machine according to the treatment plan. In some embodiments, responsive to determining the one or more risk factors are not being managed within the desired range, the processing device may modify, using the one or more trained machine learning models, the treatment plan to generate a modified treatment plan including at least one modified exercise. In some embodiments, the processing device may transmit the modified treatment plan to cause the electromechanical machine to implement the at least one modified exercise.

CLAUSES

Clause 1.16 A computer-implemented system, comprising:
an electromechanical machine configured to be manipulated by a user while the user performs a treatment plan;
an interface comprising a display configured to present information associated with the treatment plan; and
a processing device configured to:
receive, from one or more data sources, information associated with the user, wherein the information comprises one or more risk factors associated with a cardiac-related event for the user;
generate, using one or more trained machine learning models, the treatment plan for the user, wherein the treatment plan is generated based on the information associated with the user, and the treatment plan comprises one or more exercises associated with managing the one or more risk factors to reduce a probability of a cardiac intervention for the user; and
transmit the treatment plan to cause the electromechanical machine to implement the one or more exercises.

Clause 2.16 The computer-implemented system of any clause herein, wherein the one or more risk factors comprise genetic history of the user, medical history of the user, familial medical history of the user, demographics of the user, psychographics of the user, behavior history of the user, or some combination thereof.

Clause 3.16 The computer-implemented system of any clause herein, wherein the processing device is further to:
receive, from one or more sensors, one or more measurements associated with the user, wherein the one or more measurements are received while the user performs the treatment plan; and
determine, based on the one or more measurements, whether the one or more risk factors are being managed within a desired range.

Clause 4.16 The computer-implemented system of any clause herein, wherein, responsive to determining the one or more risk factors are being managed within the desired range, the processing device is to control the electromechanical device according to the treatment plan.

Clause 5.16 The computer-implemented system of any clause herein, wherein, responsive to determining the one or more risk factors are not being managed within the desired range, the processing device is to:
modify, using the one or more trained machine learning models, the treatment plan to generate a modified treatment plan comprising at least one modified exercise, and
transmit the modified treatment plan to cause the electromechanical machine to implement the at least one modified exercise.

Clause 6.16 The computer-implemented system of any clause herein, wherein the one or more data sources comprise an electronic medical record system, an application programming interface, a third-party application, a sensor, a website, or some combination thereof.

Clause 7.16 The computer-implemented system of any clause herein, wherein the processing device is to modify an operating parameter of the electromechanical machine to cause the electromechanical machine to implement the one or more exercises.

Clause 8.16 The computer-implemented system of any clause herein, wherein the processing device is to initiate, while the user performs the treatment plan, a telemedicine session between a computing device of the user and a computing device of a healthcare professional.

Clause 9.16 A computer-implemented method, comprising:
receiving, from one or more data sources, information associated with a user, wherein the information comprises one or more risk factors associated with a cardiac-related event for the user;
generating, using one or more trained machine learning models, a treatment plan for the user, wherein the treatment plan is generated based on the information associated with the user, and the treatment plan comprises one or more exercises associated with managing the one or more risk factors to reduce a probability of a cardiac intervention for the user; and
transmitting the treatment plan to cause an electromechanical machine to implement the one or more exercises, the electromechanical machine configured to be manipulated by the user while the user performs the treatment plan.

Clause 10.16 The computer-implemented method of any clause herein, wherein the one or more risk factors comprise genetic history of the user, medical history of the user, familial medical history of the user, demographics of the user, psychographics of the user, behavior history of the user, or some combination thereof.

Clause 11.16 The computer-implemented method of any clause herein, further comprising:
receiving, from one or more sensors, one or more measurements associated with the user, wherein the one or more measurements are received while the user performs the treatment plan; and
determining, based on the one or more measurements, whether the one or more risk factors are being managed within a desired range.

Clause 12.16 The computer-implemented method of any clause herein, wherein, responsive to determining the one or more risk factors are being managed within the desired range, the method further comprises controlling the electromechanical device according to the treatment plan.

Clause 13.16 The computer-implemented method of any clause herein, wherein, responsive to determining the one or more risk factors are not being managed within the desired range, the method further comprises:
modifying, using the one or more trained machine learning models, the treatment plan to generate a modified treatment plan comprising at least one modified exercise, and
transmitting the modified treatment plan to cause the electromechanical machine to implement the at least one modified exercise.

Clause 14.16 The computer-implemented method of any clause herein, wherein the one or more data sources comprise an electronic medical record system, an application programming interface, a third-party application, a sensor, a website, or some combination thereof.

Clause 15.16 The computer-implemented method of any clause herein, further comprising modifying an operating parameter of the electromechanical machine to cause the electromechanical machine to implement the one or more exercises.

Clause 16.16 The computer-implemented method of any clause herein, further comprising initiating, while the user performs the treatment plan, a telemedicine session between a computing device of the user and a computing device of a healthcare professional.

Clause 17.16 A tangible, non-transitory computer-readable medium storing instructions that, when executed, cause a processing device to:
receive, from one or more data sources, information associated with a user, wherein the information comprises one or more risk factors associated with a cardiac-related event;
generate, using one or more trained machine learning models, a treatment plan for the user, wherein the treatment plan is generated based on the information associated with the user, and the treatment plan comprises one or more exercises associated with managing the one or more risk factors to reduce a probability of a cardiac intervention for the user; and
transmit the treatment plan to cause an electromechanical machine to implement the one or more exercises, the electromechanical machine configured to be manipulated by the user while the user performs the treatment plan;

Clause 18.16 The computer-readable medium of any clause herein, wherein the one or more risk factors comprise genetic history of the user, medical history of the user, familial medical history of the user, demographics of the user, psychographics of the user, behavior history of the user, or some combination thereof.

Clause 19.16 The computer-readable medium of any clause herein, wherein the processing device is further to:
receive, from one or more sensors, one or more measurements associated with the user, wherein the one or more measurements are received while the user performs the treatment plan; and
determine, based on the one or more measurements, whether the one or more risk factors are being managed within a desired range.

Clause 20.16 The computer-readable medium of any clause herein, wherein, responsive to determining the one or more risk factors are being managed within the desired range, the processing device is further to control the electromechanical device according to the treatment plan.

Clause 21.16 A computer-implemented system, comprising:
a processing device configured to
receive a plurality of risk factors associated with a cardiac-related event for a user,
generate a selected set of the risk factors,
determine, based on the selected set of the risk factors, a probability that a cardiac intervention will occur, and
generate, based on the probability and the selected set of the risk factors, a treatment plan including one or more exercises directed to reducing the probability that the cardiac intervention will occur; and
a treatment apparatus configured to implement the treatment plan while the treatment apparatus is being manipulated by the user.

Clause 22.16 The computer-implemented system of any clause herein, wherein the processing device is configured to execute a risk factor model, and wherein, to generate the selected set of the risk factors, the risk factor model is configured to at least one of assign weights to the risk factors, rank the risk factors, and filter the risk factors.

Clause 23.16 The computer-implemented system of any clause herein, wherein the processing device is configured to execute a probability model, wherein the probability model is configured to determine the probability that the cardiac intervention will occur.

Clause 24.16 The computer-implemented system of any clause herein, wherein the probability model is configured to determine the probability based on respective probabilities associated with individual ones of the selected set of the risk factors.

Clause 25.16 The computer-implemented system of any clause herein, wherein the processing device is configured to execute a treatment plan model, wherein the treatment plan model is configured to generate the treatment plan based on individual probabilities of the cardiac intervention of respective ones of the selected set of the risk factors.

Clause 26.16 The computer-implemented system of any clause herein, wherein the treatment plan model is configured to generate the treatment plan based on an identified one of the selected set of the risk factors having a largest contribution to the probability that the cardiac intervention will occur.

Clause 27.16 The computer-implemented system of any clause herein, wherein, subsequent to implementing the treatment plan using the treatment apparatus, the processing device is configured to modify the treatment plan based on a determination of whether the treatment plan reduced either one of the probability that the cardiac intervention will occur and the identified one of the selected set of risk factors.

Clause 28.16 The computer-implemented system of any clause herein, wherein the processing device is configured to transmit the modified treatment plan to cause the treatment apparatus to implement at least one modified exercise of the modified treatment plan.

Clause 29.16 The computer-implemented system of any clause herein, wherein the cardiac intervention is for minimizing one or more negative effects of the cardiac-related event.

Clause 30.16 The computer-implemented system of any clause herein, wherein the processing device is configured to initiate, while the user performs the treatment plan, a telemedicine session between a computing device of the user and a computing device of a healthcare professional.

Clause 31.16 The computer-implemented system of any clause herein, wherein the one or more risk factors comprise modifiable risk factors and non-modifiable risk factors.

Clause 32.16 A computer-implemented method, comprising:
receiving a plurality of risk factors associated with a cardiac-related event for a user;
generating a selected set of the risk factors;
determining a probability that a cardiac intervention will occur based on the selected set of the risk factors;
generating, based on the probability and the selected set of the risk factors, a treatment plan including one or more exercises directed to reducing the probability that the cardiac intervention will occur; and
using a treatment apparatus to implement the treatment plan while the treatment apparatus being manipulated by the user.

Clause 33.16 The computer-implemented method of any clause herein, further comprising:
using a risk factor machine learning model to generate the selected set of the risk factors, wherein the risk factor model is configured to at least one of assign weights to the risk factors, rank the risk factors, and filter the risk factors; and
using a probability machine learning model to determine the probability that the cardiac intervention will occur.

Clause 34.16 The computer-implemented method of any clause herein, further comprising using the probability machine learning model to determine the probability based on respective probabilities associated with individual ones of the selected set of the risk factors.

Clause 35.16 The computer-implemented method of any clause herein, further comprising using a treatment plan machine learning model to generate the treatment plan based on individual probabilities of the cardiac intervention of respective ones of the selected set of the risk factors.

Clause 36.16 The computer-implemented method of any clause herein, further comprising generating the treatment plan based on an identified one of the selected set of the risk factors having a largest contribution to the probability that the cardiac intervention will occur.

Clause 37.16 The computer-implemented method of any clause herein, further comprising, subsequent to implementing the treatment plan using the treatment apparatus, modifying the treatment plan based on a determination of whether the treatment plan reduced either one of (i) the probability that the cardiac will occur and (ii) the identified one of the selected set of the risk factors.

Clause 38.16 The computer-implemented method of any clause herein, wherein the cardiac intervention is for minimizing one or more negative effects of the cardiac-related event.

Clause 39.16 The computer-implemented method of any clause herein, wherein the one or more risk factors comprise modifiable risk factors and non-modifiable risk factors.

Figure 32:
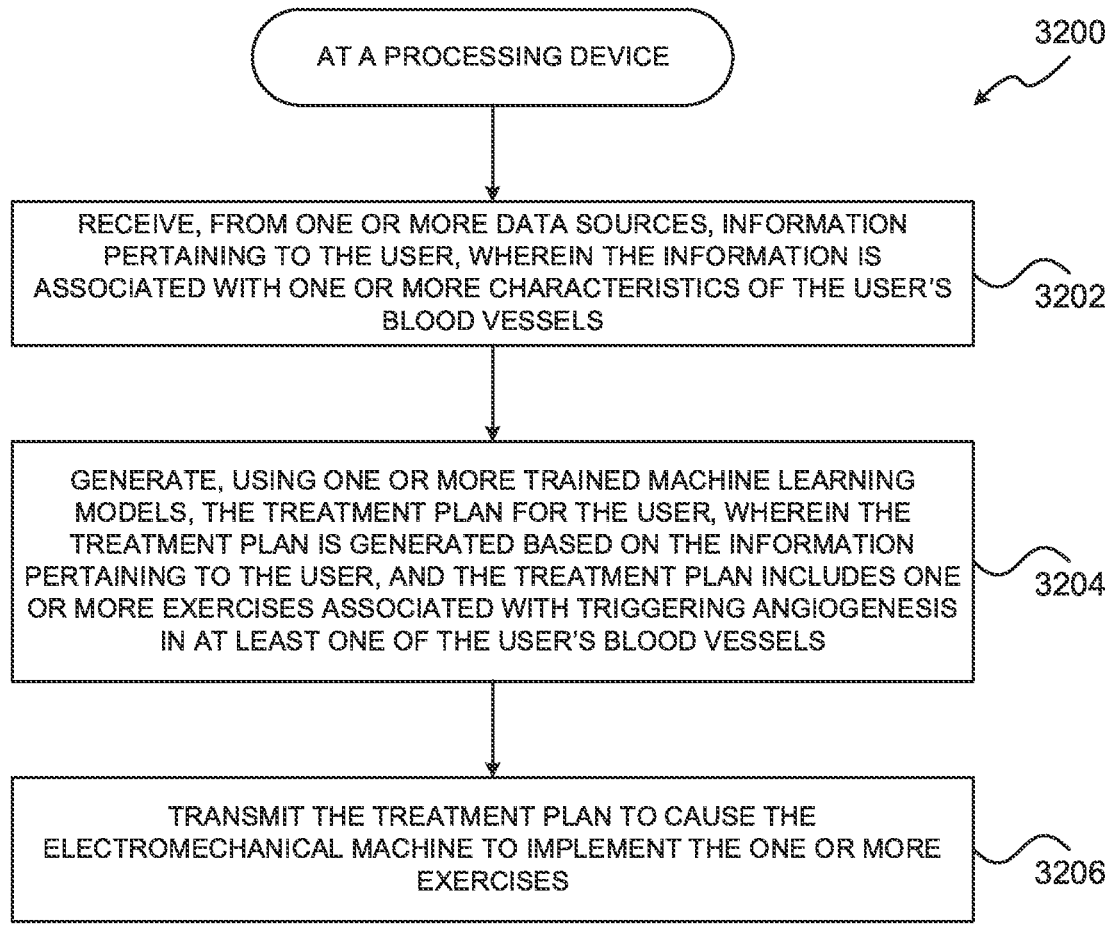
FIG. 32 generally illustrates an example embodiment of a method for using artificial intelligence and machine learning to generate treatment plans to stimulate preferred angiogenesis according to the principles of the present disclosure.

System and Method for Using AI/ML to Generate Treatment Plans to Stimulate Preferred Angiogenesis FIG. 32 generally illustrates an example embodiment of a method 3200 for using artificial intelligence and machine learning to generate treatment plans to stimulate preferred angiogenesis according to the principles of the present disclosure. The method 3200 may be performed by processing logic that may include hardware (circuitry, dedicated logic, etc.), software, or a combination of both. The method 3200 and/or each of their individual functions, subroutines, or operations may be performed by one or more processing devices of a computing device (e.g., the computer system 1100 of FIG. 11) implementing the method 3200. The method 3200 may be implemented as computer instructions stored on a memory device and executable by the one or more processing devices. In certain implementations, the method 3200 may be performed by a single processing thread. Alternatively, the method 3200 may be performed by two or more processing threads, each thread implementing one or more individual functions, routines, subroutines, or operations of the methods.

In some embodiments, a system may be used to implement the method 3200. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 3200.

At block 3202, the processing device may receive, from one or more data sources, information pertaining to the user. The information may be associated with one or more characteristics of the user's blood vessels. The information may pertain to blockage of at least one of the blood vessels of the user, familial history blood vessel disease of the user, heart rate of the user, blood pressure of the user, or some combination thereof. The one or more data sources may include an electronic medical record system, an application programming interface, a third-party application, or some combination thereof.

At block 3204, the processing device may generate, using one or more trained machine learning models, a treatment plan for the user. The treatment plan may be generated based on the information pertaining to the user, and the treatment plan includes one or more exercises associated with triggering angiogenesis in at least one of the user's blood vessels.

At block 3206, the processing device may transmit the treatment plan to cause the electromechanical machine to implement the one or more exercises. In some embodiments, the processing device may modify an operating parameter of the electromechanical machine to cause the electromechanical machine to implement the one or more exercises. In some embodiments, the processing device may initiate, while the user performs the treatment plan, a telemedicine session between a computing device of the user and a computing device of a healthcare professional.

In some embodiments, the processing device may receive, from one or more sensors, one or more measurements associated with the user. The one or more measurements may be received while the user performs the treatment plan. The processing device may determine, based on the one or more measurements, whether a predetermined criteria for the user's blood vessels is satisfied.

In some embodiments, responsive to determining the predetermined criteria for the user's blood vessels is satisfied, the processing device may control the electromechanical machine according to the treatment plan. Responsive to determining the predetermined criteria for the user's blood vessels is not satisfied, the processing device may modify, using the one or more trained machine learning models, the treatment plan to generate a modified treatment plan including at least one modified exercise. The processing device may transmit the modified treatment plan to cause the electromechanical machine to implement the at least one modified exercise.

CLAUSES

Clause 1.17 A computer-implemented system, comprising:
 an electromechanical machine configured to be manipulated by a user while performing a treatment plan;
 an interface comprising a display configured to present information pertaining to the treatment plan; and
 a processing device configured to:
  receive, from one or more data sources, information pertaining to the user, wherein the information is associated with one or more characteristics of the user's blood vessels;
  generate, using one or more trained machine learning models, a treatment plan for the user, wherein the treatment plan is generated based on the information pertaining to the user, and the treatment plan comprises one or more exercises associated with triggering angiogenesis in at least one of the user's blood vessels; and
  transmit the treatment plan to cause the electromechanical machine to implement the one or more exercises.

Clause 2.17 The computer-implemented system of any clause herein, wherein the information pertains to blockage of at least one of the blood vessels of the user, familial history blood vessel disease of the user, heart rate of the user, blood pressure of the user, or some combination thereof.

Clause 3.17 The computer-implemented system of any clause herein, wherein the processing device is further to:
 receive, from one or more sensors, one or more measurements associated with the user, wherein the one or more measurements are received while the user performs the treatment plan; and
 determine, based on the one or more measurements, whether a predetermined criteria for the user's blood vessels is satisfied.

Clause 4.17 The computer-implemented system of any clause herein, wherein, responsive to determining the predetermined criteria for the user's blood vessels is satisfied, the processing device is to control the electromechanical device according to the treatment plan.

Clause 5.17 The computer-implemented system of any clause herein, wherein, responsive to determining the predetermined criteria for the user's blood vessels is not satisfies, the processing device is to:
 modify, using the one or more trained machine learning models, the treatment plan to generate a modified treatment plan comprising at least one modified exercise, and
 transmit the modified treatment plan to cause the electromechanical machine to implement the at least one modified exercise.

Clause 6.17 The computer-implemented system of any clause herein, wherein the one or more data sources comprise an electronic medical record system, an application programming interface, a third-party application, or some combination thereof.

Clause 7.17 The computer-implemented system of any clause herein, wherein the processing device is to modify an operating parameter of the electromechanical machine to cause the electromechanical machine to implement the one or more exercises.

Clause 8.17 The computer-implemented system of any clause herein, wherein the processing device is to initiate, while the user performs the treatment plan, a telemedicine session between a computing device of the user and a computing device of a healthcare professional.

Clause 9.17 A computer-implemented method, comprising:
 receiving, from one or more data sources, information pertaining to the user, wherein the information is associated with one or more characteristics of the user's blood vessels;
 generating, using one or more trained machine learning models, a treatment plan for a user, wherein the treatment plan is generated based on the information pertaining to the user, and the treatment plan comprises one or more exercises associated with triggering angiogenesis in at least one of the user's blood vessels; and
 transmitting the treatment plan to cause an electromechanical machine to implement the one or more exercises.

Clause 10.17 The computer-implemented method of any clause herein, wherein the information pertains to blockage of at least one of the blood vessels of the user, familial history blood vessel disease of the user, heart rate of the user, blood pressure of the user, or some combination thereof.

Clause 11.17 The computer-implemented method of any clause herein, further comprising:
 receiving, from one or more sensors, one or more measurements associated with the user, wherein the one or more measurements are received while the user performs the treatment plan; and
 determining, based on the one or more measurements, whether a predetermined criteria for the user's blood vessels is satisfied.

Clause 12.17 The computer-implemented method of any clause herein, wherein, responsive to determining the predetermined criteria for the user's blood vessels is satisfied, the method further comprises controlling the electromechanical device according to the treatment plan.

Clause 13.17 The computer-implemented method of any clause herein, wherein, responsive to determining the predetermined criteria for the user's blood vessels is not satisfies, the method further comprises:
 modifying, using the one or more trained machine learning models, the treatment plan to generate a modified treatment plan comprising at least one modified exercise, and
 transmitting the modified treatment plan to cause the electromechanical machine to implement the at least one modified exercise.

Clause 14.17 The computer-implemented method of any clause herein, wherein the one or more data sources comprise an electronic medical record system, an application programming interface, a third-party application, or some combination thereof.

Clause 15.17 The computer-implemented method of any clause herein, wherein the processing device is to modify an operating parameter of the electromechanical machine to cause the electromechanical machine to implement the one or more exercises.

Clause 16.17 The computer-implemented method of any clause herein, further comprising initiating, while the user performs the treatment plan, a telemedicine session between a computing device of the user and a computing device of a healthcare professional.

Clause 17.17 A tangible, non-transitory computer-readable medium storing instructions that, when executed, cause a processing device to:
- receive, from one or more data sources, information pertaining to the user, wherein the information is associated with one or more characteristics of the user's blood vessels;
- generate, using one or more trained machine learning models, a treatment plan for a user, wherein the treatment plan is generated based on the information pertaining to the user, and the treatment plan comprises one or more exercises associated with triggering angiogenesis in at least one of the user's blood vessels; and
- transmit the treatment plan to cause an electromechanical machine to implement the one or more exercises.

Clause 18.17 The computer-readable medium of any clause herein, wherein the information pertains to blockage of at least one of the blood vessels of the user, familial history blood vessel disease of the user, heart rate of the user, blood pressure of the user, or some combination thereof.

Clause 19.17 The computer-readable medium of any clause herein, wherein the processing device is to:
- receive, from one or more sensors, one or more measurements associated with the user, wherein the one or more measurements are received while the user performs the treatment plan; and
- determine, based on the one or more measurements, whether a predetermined criteria for the user's blood vessels is satisfied.

Clause 20.17 The computer-readable medium of any clause herein, wherein, responsive to determining the predetermined criteria for the user's blood vessels is satisfied, the processing device controls the electromechanical device according to the treatment plan.

Figure 33:
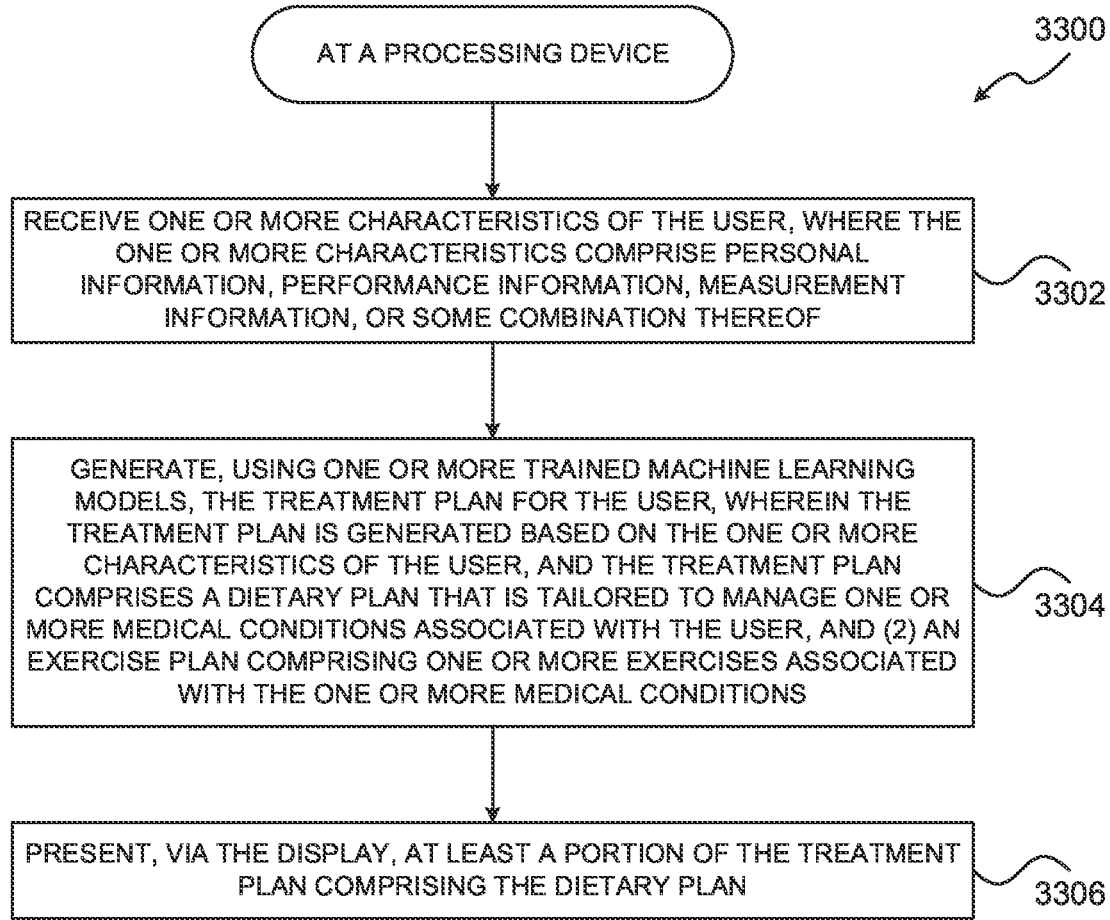
FIG. 33 generally illustrates an example embodiment of a method for using artificial intelligence and machine learning to generate treatment plans including tailored dietary plans for users according to the principles of the present disclosure.

System and Method for Using AI/ML to Generate Treatment Plans Including Tailored Dietary Plans for Users FIG. 33 generally illustrates an example embodiment of a method 3300 for using artificial intelligence and machine learning to generate treatment plans including tailored dietary plans for users according to the principles of the present disclosure. The method 3300 may be performed by processing logic that may include hardware (circuitry, dedicated logic, etc.), software, or a combination of both. The method 3300 and/or each of their individual functions, subroutines, or operations may be performed by one or more processing devices of a computing device (e.g., the computer system 1100 of FIG. 11) implementing the method 3300. The method 3300 may be implemented as computer instructions stored on a memory device and executable by the one or more processing devices. In certain implementations, the method 3300 may be performed by a single processing thread. Alternatively, the method 3300 may be performed by two or more processing threads, each thread implementing one or more individual functions, routines, subroutines, or operations of the methods.

In some embodiments, a system may be used to implement the method 3300. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 3300.

At block 3302, the processing device may receive one or more characteristics of the user. The one or more characteristics of the user may include personal information, performance information, measurement information, or some combination thereof.

At block 3304, the processing device may generate, using one or more trained machine learning models, the treatment plan for the user. The treatment plan may be generated based on the one or more characteristics of the user. The treatment plan may include a dietary plan tailored for the user to manage one or more medical conditions associated with the user, and an exercise plan including one or more exercises associated with the one or more medical conditions. In some embodiments, the one or more trained machine learning models may generate the treatment plan including the dietary plan based on at least a comorbidity of the user, a condition of the user, a demographic of the user, a psychographic of the user, or some combination thereof. In some embodiments, the one or more medical conditions pertain to cardiac health, pulmonary health, bariatric health, oncologic health, or some combination thereof.

At block 3306, the processing device may present, via the display, at least a portion of the treatment plan including the dietary plan. In some embodiments, the processing device modifies an operating parameter of the electromechanical machine to cause the electromechanical machine to implement the one or more exercises. In some embodiments the processing device may initiate, while the user performs the treatment plan, a telemedicine session between a computing device of the user and a computing device of a healthcare professional.

In some embodiments, the processing device may receive, from one or more sensors, one or more measurements associated with the user. The one or more measurements may be received while the user performs the treatment plan. The processing device may determine, based on the one or more measurements, whether a predetermined criteria for the dietary plan is satisfied. The predetermined criteria may relate to weight, heart rate, blood pressure, blood oxygen level, body mass index, blood sugar level, enzyme level, blood count level, blood vessel data, heart rhythm data, protein data, or some combination thereof.

Responsive to determining the predetermined criteria for the dietary plan is not satisfied, the processing device may maintain the dietary plan and control the electromechanical device according to the exercise plan. Responsive to determining the predetermined criteria for the dietary plan is not satisfied, the processing device may modify, using the one or more trained machine learning models, the treatment plan to generate a modified treatment plan including at least a modified dietary plan. The processing device may transmit the modified treatment plan to cause the display to present the modified dietary plan.

CLAUSES

Clause 1.18 A computer-implemented system, comprising:
    an electromechanical machine configured to be manipulated by a user while performing a treatment plan;
    an interface comprising a display configured to present information pertaining to the treatment plan; and
    a processing device configured to:
    receive one or more characteristics of the user, wherein the one or more characteristics comprise personal information, performance information, measurement information, or some combination thereof;
    generate, using one or more trained machine learning models, the treatment plan for the user, wherein the treatment plan is generated based on the one or more characteristics of the user, and the treatment plan comprises:
    a dietary plan tailored for the user to manage one or more medical conditions associated with the user, and
    an exercise plan comprises one or more exercises associated with the one or more medical conditions; and
    present, via the display, at least a portion of the treatment plan comprising the dietary plan.

Clause 2.18 The computer-implemented system of any clause herein, wherein the one or more trained machine learning models generates the treatment plan comprising the dietary plan based on at least a comorbidity of the user, a condition of the user, a demographic of the user, a psychographic of the user, or some combination thereof.

Clause 3.18 The computer-implemented system of any clause herein, wherein the one or more conditions pertain to cardiac health, pulmonary health, bariatric health, oncologic health, or some combination thereof.

Clause 4.18 The computer-implemented system of any clause herein, wherein the processing device is further to:
    receive, from one or more sensors, one or more measurements associated with the user, wherein the one or more measurements are received while the user performs the treatment plan; and
    determine, based on the one or more measurements, whether a predetermined criteria for the dietary plan is satisfied, wherein the predetermined criteria relates to:
    weight, heart rate, blood pressure, blood oxygen level, body mass index, blood sugar level, enzyme level, blood count level, blood vessel data, heart rhythm data, protein data, or some combination thereof.

Clause 5.18 The computer-implemented system of any clause herein, wherein, responsive to determining the predetermined criteria for the dietary plan is not satisfied, the processing device is to maintain the dietary plan and control the electromechanical device according to the exercise plan.

Clause 6.18 The computer-implemented system of any clause herein, wherein, responsive to determining the predetermined criteria for the dietary plan is not satisfied, the processing device is to:
    modify, using the one or more trained machine learning models, the treatment plan to generate a modified treatment plan comprising at least a modified dietary plan, and
    transmit the modified treatment plan to cause the display to present the modified dietary plan.

Clause 7.18 The computer-implemented system of any clause herein, wherein the processing device is to modify an operating parameter of the electromechanical machine to cause the electromechanical machine to implement the one or more exercises.

Clause 8.18 The computer-implemented system of any clause herein, wherein the processing device is to initiate, while the user performs the treatment plan, a telemedicine session between a computing device of the user and a computing device of a healthcare professional.

Clause 9.18 A computer-implemented method, comprising:
    receiving one or more characteristics of the user, wherein the one or more characteristics comprise personal information, performance information, measurement information, or some combination thereof;
    generating, using one or more trained machine learning models, the treatment plan for the user, wherein the treatment plan is generated based on the one or more characteristics of the user, and the treatment plan comprises:
    a dietary plan tailored for the user to manage one or more medical conditions associated with the user, and
    an exercise plan comprises one or more exercises associated with the one or more medical conditions; and
    presenting, via the display, at least a portion of the treatment plan comprising the dietary plan.

Clause 10.18 The computer-implemented method of any clause herein, wherein the one or more trained machine learning models generates the treatment plan comprising the dietary plan based on at least a comorbidity of the user, a condition of the user, a demographic of the user, a psychographic of the user, or some combination thereof.

Clause 11.18 The computer-implemented method of any clause herein, wherein the one or more conditions pertain to cardiac health, pulmonary health, bariatric health, oncologic health, or some combination thereof.

Clause 12.18 The computer-implemented method of any clause herein, further comprising:
    receiving, from one or more sensors, one or more measurements associated with the user, wherein the one or more measurements are received while the user performs the treatment plan; and
    determining, based on the one or more measurements, whether a predetermined criteria for the dietary plan is satisfied, wherein the predetermined criteria relates to:
    weight, heart rate, blood pressure, blood oxygen level, body mass index, blood sugar level, enzyme level, blood count level, blood vessel data, heart rhythm data, protein data, or some combination thereof.

Clause 13.18 The computer-implemented method of any clause herein, wherein, responsive to determining the predetermined criteria for the dietary plan is not satisfied, the method further comprises maintaining the dietary plan and control the electromechanical device according to the exercise plan.

Clause 14.18 The computer-implemented method of any clause herein, wherein, responsive to determining the predetermined criteria for the dietary plan is not satisfied, the method further comprises:
    modifying, using the one or more trained machine learning models, the treatment plan to generate a modified treatment plan comprising at least a modified dietary plan, and
    transmitting the modified treatment plan to cause the display to present the modified dietary plan.

Clause 15.18 The computer-implemented method of any clause herein, further comprising modifying an operating parameter of the electromechanical machine to cause the electromechanical machine to implement the one or more exercises.

Clause 16.18 The computer-implemented method of any clause herein, further comprising initiating, while the user performs the treatment plan, a telemedicine session between a computing device of the user and a computing device of a healthcare professional.

Clause 17.18 A tangible, non-transitory computer-readable medium storing instructions that, when executed, cause a processing device to:
  receive one or more characteristics of the user, wherein the one or more characteristics comprise personal information, performance information, measurement information, or some combination thereof;
  generate, using one or more trained machine learning models, the treatment plan for the user, wherein the treatment plan is generated based on the one or more characteristics of the user, and the treatment plan comprises:
  a dietary plan tailored for the user to manage one or more medical conditions associated with the user, and
  an exercise plan comprises one or more exercises associated with the one or more medical conditions; and
  present, via the display, at least a portion of the treatment plan comprising the dietary plan.

Clause 18.18 The computer-readable medium of any clause herein, wherein the one or more trained machine learning models generates the treatment plan comprising the dietary plan based on at least a comorbidity of the user, a condition of the user, a demographic of the user, a psychographic of the user, or some combination thereof.

Clause 19.18 The computer-readable medium of any clause herein, wherein the one or more conditions pertain to cardiac health, pulmonary health, bariatric health, oncologic health, or some combination thereof.

Clause 20.18 The computer-readable medium of any clause herein, wherein the processing device is further to:
  receiving, from one or more sensors, one or more measurements associated with the user, wherein the one or more measurements are received while the user performs the treatment plan; and
  determining, based on the one or more measurements, whether a predetermined criteria for the dietary plan is satisfied, wherein the predetermined criteria relates to: weight, heart rate, blood pressure, blood oxygen level, body mass index, blood sugar level, enzyme level, blood count level, blood vessel data, heart rhythm data, protein data, or some combination thereof.

Figure 34:
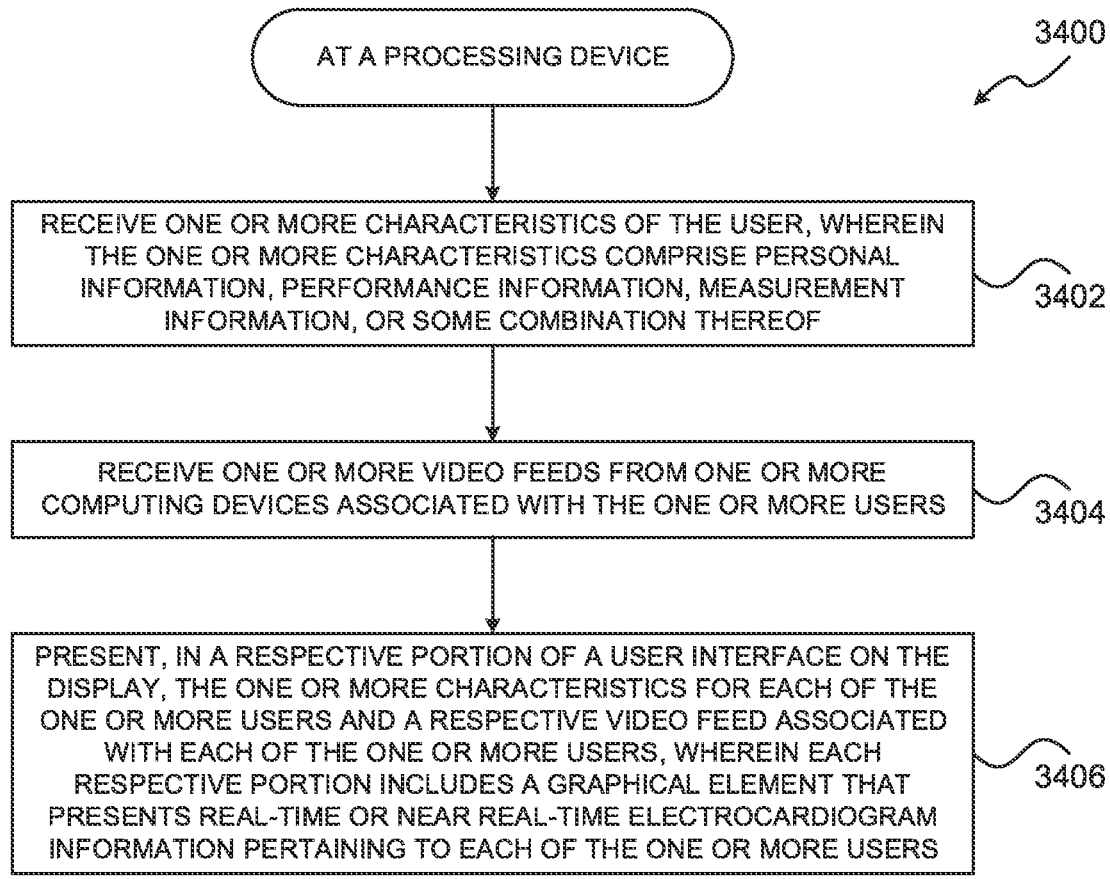
FIG. 34 generally illustrates an example embodiment of a method for presenting an enhanced healthcare professional user interface displaying measurement information for a plurality of users according to the principles of the present disclosure.

System and Method for an Enhanced Healthcare Professional User Interface Displaying Measurement Information for a Plurality of Users FIG. 34 generally illustrates an example embodiment of a method 3400 for presenting an enhanced healthcare professional user interface displaying measurement information for a plurality of users according to the principles of the present disclosure. The method 3400 may be performed by processing logic that may include hardware (circuitry, dedicated logic, etc.), software, or a combination of both. The method 3400 and/or each of their individual functions, subroutines, or operations may be performed by one or more processing devices of a computing device (e.g., the computer system 1100 of FIG. 11) implementing the method 3400. The method 3400 may be implemented as computer instructions stored on a memory device and executable by the one or more processing devices. In certain implementations, the method 3400 may be performed by a single processing thread. Alternatively, the method 3400 may be performed by two or more processing threads, each thread implementing one or more individual functions, routines, subroutines, or operations of the methods.

In some embodiments, a system may be used to implement the method 3400. The system may include the treatment apparatus 70 (electromechanical machine) configured to be manipulated by a user while the user is performing a treatment plan, and an interface including a display configured to present information pertaining to one or more users each using an electromechanical machine to perform a treatment plan. The system may include a processing device configured to execute instructions implemented the method 3400.

At block 3402, the processing device may receive one or more characteristics associated with each of one or more users. The one or more characteristics may include personal information, performance information, measurement information, or some combination thereof. In some embodiments, the measurement information and the performance information may be received via one or more wireless sensors associated with each of the one or more users.

At block 3404, the processing device may receive one or more video feeds from one or more computing devices associated with the one or more users. In some embodiments, the one or more video feeds may include real-time or near real-time video data of the user during a telemedicine session. In some embodiments, at least two video feeds are presented concurrently with at least two characteristics associated with at least two users.

At block 3406, the processing device may present, in a respective portion of a user interface on the display, the one or more characteristics for each of the one or more users and a respective video feed associated with each of the one or more users. Each respective portion may include a graphical element that presents real-time or near real-time electrocardiogram information pertaining to each of the one or more users.

In some embodiments, for each of the one or more users, the respective portion may include a set of graphical elements arranged in a row. The set of graphical elements may be associated with a blood pressure of the user, a blood oxygen level of the user, a heart rate of the user, the respective video feed, a means for communicating with the user, or some combination thereof.

In some embodiments, the processing device may present, via the user interface, a graphical element that enables initiating or terminating a telemedicine session with one or more computing devices of the one or more users. In some embodiments, the processing device may initiate at least two telemedicine sessions concurrently and present at least two video feeds of the user on the user interface at the same time.

In some embodiments, the processing device may control a refresh rate of the graphical element that presents real-time or near real-time electrocardiogram information pertaining to each of the one or more users, and the refresh rate may be controlled based on the electrocardiogram information satisfying a certain criteria (e.g., a heart rate above 100 beats per minute, a heart rate below 100 beats per minute, a heart rate with a range of 60-100 beats per minute, or the like).

CLAUSES

Clause 1.19 A computer-implemented system, comprising:
  an interface comprising a display configured to present information pertaining to one or more users, wherein the one or more users are each using an electromechanical machine to perform a treatment plan; and a processing device configured to:

receive one or more characteristics associated with each of the one or more users, wherein the one or more characteristics comprise personal information, performance information, measurement information, or some combination thereof;

receive one or more video feeds from one or more computing devices associated with the one or more users; and present, in a respective portion of a user interface on the display, the one or more characteristics for each of the one or more users and a respective video feed associated with each of the one or more users, wherein each respective portion comprises a graphical element that presents real-time or near real-time electrocardiogram information pertaining to each of the one or more users.

Clause 2.19 The computer-implemented system of any clause herein, wherein the one or more video feeds comprise real-time or near real-time video data of the user during a telemedicine session.

Clause 3.19 The computer-implemented system of any clause herein, wherein at least two video feeds are presented concurrently with at least two characteristics associated with at least two users.

Clause 4.19 The computer-implemented system of any clause herein, wherein, for each of the one or more users, the respective portion comprises a plurality of graphical elements arranged in a row, wherein the plurality of graphical elements are associated with a blood pressure of the user, a blood oxygen level of the user, a heart rate of the user, the respective video feed, a means for communicating with the user, or some combination thereof.

Clause 5.19 The computer-implemented system of any clause herein, wherein the processing device is to present, via the user interface, a graphical element that enables initiating or terminating a telemedicine session with one or more computing devices of the one or more users.

Clause 6.19 The computer-implemented system of any clause herein, wherein the processing device is to initiate at least two telemedicine sessions concurrently and present at least two video feeds of the user on the user interface at the same time.

Clause 7.19 The computer-implemented system of any clause herein, wherein the processing device controls a refresh rate of the graphical element that presents real-time or near real-time electrocardiogram information pertaining to each of the one or more users, and the refresh rate is controlled based on the electrocardiogram information satisfying a certain criteria.

Clause 8.19 The computer-implemented system of any clause herein, wherein the measurement information and the performance information is received via one or more wireless sensors associated with each of the one or more users.

Clause 9.19 A computer-implemented method, comprising:

receiving one or more characteristics associated with each of one or more users, wherein the one or more characteristics comprise personal information, performance information, measurement information, or some combination thereof, and wherein the one or more users are each using an electromechanical machine to perform a treatment plan;

receiving one or more video feeds from one or more computing devices associated with the one or more users; and presenting, in a respective portion of a user interface on a display of an interface, the one or more characteristics for each of the one or more users and a respective video feed associated with each of the one or more users, wherein each respective portion comprises a graphical element that presents real-time or near real-time electrocardiogram information pertaining to each of the one or more users.

Clause 10.19 The computer-implemented method of any clause herein, wherein the one or more video feeds comprise real-time or near real-time video data of the user during a telemedicine session.

Clause 11.19 The computer-implemented method of any clause herein, wherein at least two video feeds are presented concurrently with at least two characteristics associated with at least two users.

Clause 12.19 The computer-implemented method of any clause herein, wherein, for each of the one or more users, the respective portion comprises a plurality of graphical elements arranged in a row, wherein the plurality of graphical elements are associated with a blood pressure of the user, a blood oxygen level of the user, a heart rate of the user, the respective video feed, a means for communicating with the user, or some combination thereof.

Clause 13.19 The computer-implemented method of any clause herein, further comprising presenting, via the user interface, a graphical element that enables initiating or terminating a telemedicine session with one or more computing devices of the one or more users.

Clause 14.19 The computer-implemented method of any clause herein, further comprising initiating at least two telemedicine sessions concurrently and present at least two video feeds of the user on the user interface at the same time.

Clause 15.19 The computer-implemented method of any clause herein, further comprising controlling a refresh rate of the graphical element that presents real-time or near real-time electrocardiogram information pertaining to each of the one or more users, and the refresh rate is controlled based on the electrocardiogram information satisfying a certain criteria.

Clause 16.19 The computer-implemented method of any clause herein, wherein the measurement information and the performance information is received via one or more wireless sensors associated with each of the one or more users.

Clause 17.19 A tangible, non-transitory computer-readable medium storing instructions that, when executed, cause a processing device to:

receive one or more characteristics associated with each of one or more users, wherein the one or more characteristics comprise personal information, performance information, measurement information, or some combination thereof, and wherein the one or more users are each using an electromechanical machine to perform a treatment plan;

receive one or more video feeds from one or more computing devices associated with the one or more users; and present, in a respective portion of a user interface on a display of an interface, the one or more characteristics for each of the one or more users and a respective video feed associated with each of the one or more users, wherein each respective portion comprises a graphical element that presents real-time or near real-time electrocardiogram information pertaining to each of the one or more users.

Clause 18.19 The computer-readable medium of any clause herein, wherein the one or more video feeds comprise real-time or near real-time video data of the user during a telemedicine session.

Clause 19.19 The computer-readable medium of any clause herein, wherein at least two video feeds are presented concurrently with at least two characteristics associated with at least two users.

Clause 20.19 The computer-readable medium of any clause herein, wherein, for each of the one or more users, the respective portion comprises a plurality of graphical elements arranged in a row, wherein the plurality of graphical elements are associated with a blood pressure of the user, a blood oxygen level of the user, a heart rate of the user, the respective video feed, a means for communicating with the user, or some combination thereof.

Figure 35:
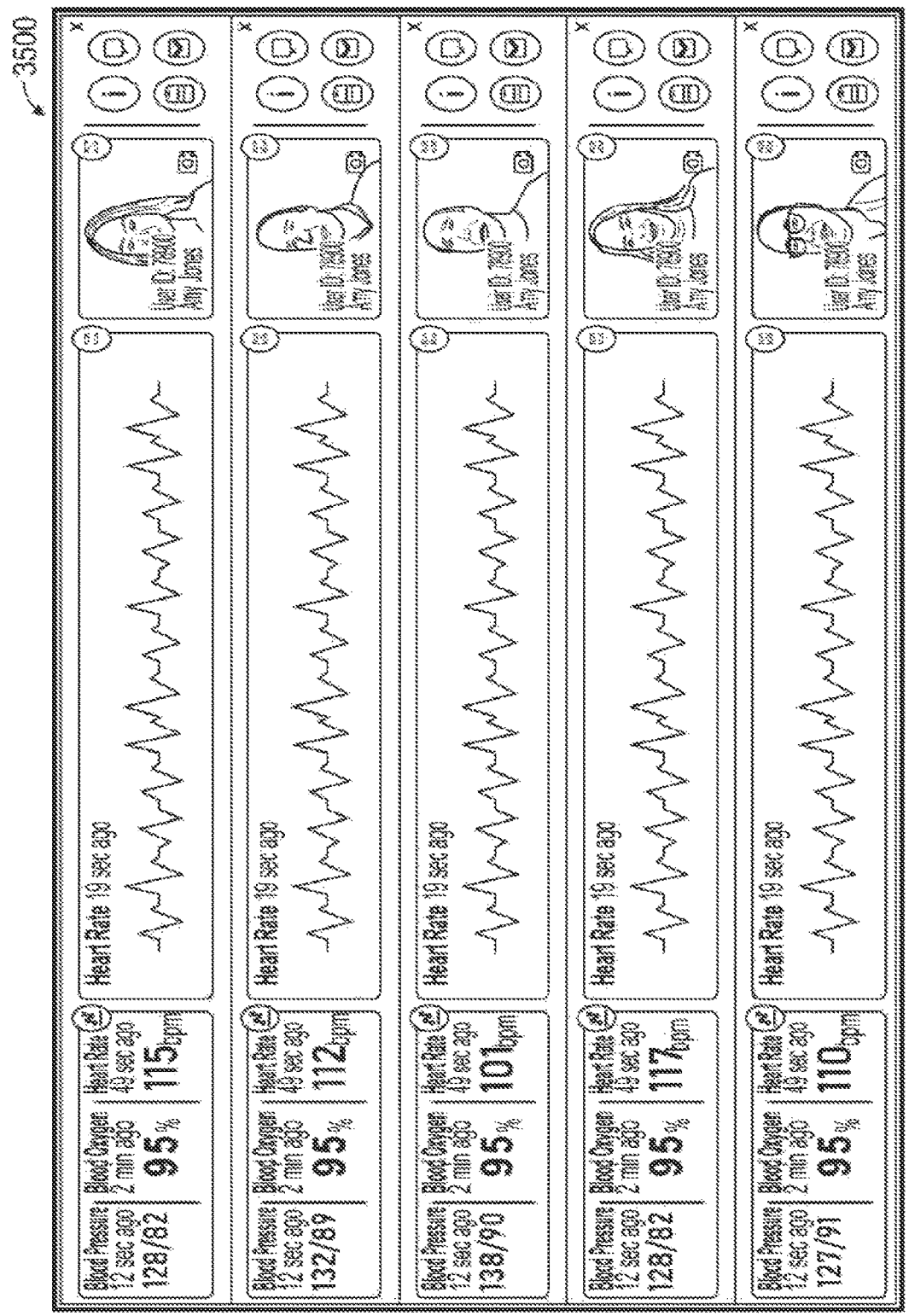
FIG. 35 generally illustrates an embodiment of an enhanced healthcare professional display of the assistant interface presenting measurement information for a plurality of patients concurrently engaged in telemedicine sessions with the healthcare professional according to the principles of the present disclosure.

FIG. 35 generally illustrates an embodiment of an enhanced healthcare professional display 3500 of the assistant interface presenting measurement information for a plurality of patients concurrently engaged in telemedicine sessions with the healthcare professional according to the principles of the present disclosure. As depicted, there are five patients that are actively engaged in a telemedicine session with a healthcare professional using the computing device presenting the healthcare professional display 3500. Each patient is associated with information represented by graphical elements arranged in a respective row. For example, each patient is assigned a row including graphical elements representing data pertaining to blood pressure, blood oxygen level, heart rate, a video feed of the patient during the telemedicine session, and various buttons to enable messaging, displaying information pertaining to the patient, scheduling appointment with the patient, etc. The enhanced graphical user interface displays the data related to the patients in a manner that may enhance the healthcare professional's experience using the computing device, thereby providing an improvement to technology. For example, the enhanced healthcare professional display 3500 arranges real-time or near real-time measurement data pertaining to each patient, as well as a video feed of the patient, that may be beneficial, especially on computing devices with a reduced screen size, such as a tablet. The number of patients that are allowed to initiate monitored telemedicine sessions concurrently may be controlled by a federal regulation, such as promulgated by the FDA. In some embodiments, the data received and displayed for each patient may be received from one or more wireless sensors, such as a wireless electrocardiogram sensor attached to a user's body.

Figure 36:
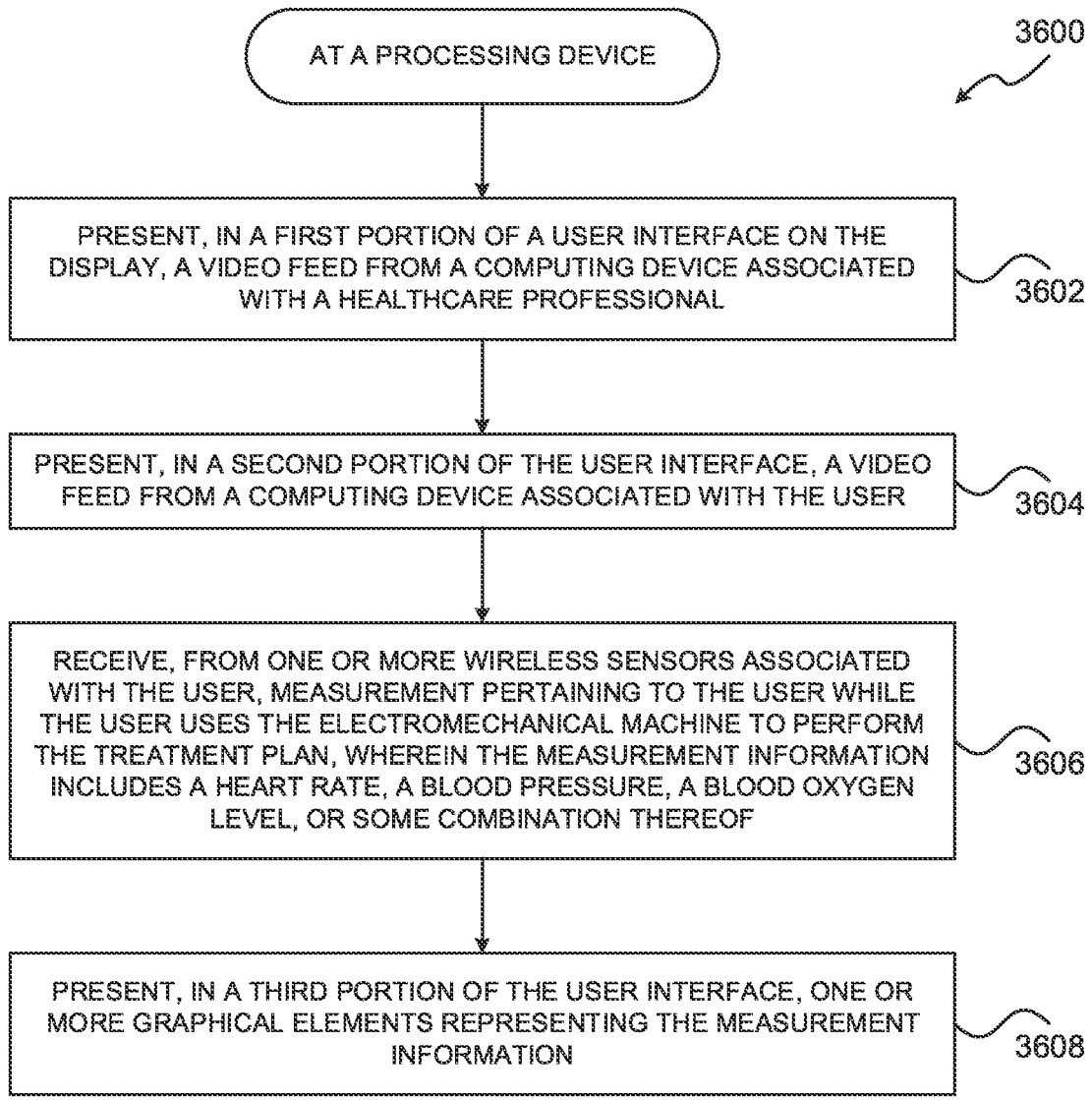
FIG. 36 generally illustrates an example embodiment of a method for presenting an enhanced patient user interface displaying real-time measurement information during a telemedicine session according to the principles of the present disclosure.

System and Method for an Enhanced Patient User Interface Displaying Real-Time Measurement Information During a Telemedicine Session FIG. 36 generally illustrates an example embodiment of a method 3600 for presenting an enhanced patient user interface displaying real-time measurement information during a telemedicine session according to the principles of the present disclosure. The method 3600 may be performed by processing logic that may include hardware (circuitry, dedicated logic, etc.), software, or a combination of both. The method 3600 and/or each of their individual functions, subroutines, or operations may be performed by one or more processing devices of a computing device (e.g., the computer system 1100 of FIG. 11) implementing the method 3600. The method 3600 may be implemented as computer instructions stored on a memory device and executable by the one or more processing devices. In certain implementations, the method 3600 may be performed by a single processing thread. Alternatively, the method 3600 may be performed by two or more processing threads, each thread implementing one or more individual functions, routines, subroutines, or operations of the methods.

In some embodiments, a system may be used to implement the method 3600. The system may include the treatment apparatus 70 (electromechanical machine) configured to be manipulated by a user while the user is performing a treatment plan, and an interface including a display configured to present information pertaining to the treatment plan. The system may include a processing device configured to execute instructions implemented the method 3600.

At block 3602, the processing device may present, in a first portion of a user interface on the display, a video feed from a computing device associated with a healthcare professional.

At block 3604, the processing device may present, in a second portion of the user interface, a video feed from a computing device associated with the user.

At block 3606, the processing device may receive, from one or more wireless sensors associated with the user, measurement information pertaining to the user while the user uses the electromechanical machine to perform the treatment plan. The measurement information may include a heart rate, a blood pressure, a blood oxygen level, or some combination thereof.

At block 3608, the processing device may present, in a third portion of the user interface, one or more graphical elements representing the measurement information. In some embodiments, the one or more graphical elements may be updated in real-time time or near real-time to reflect updated measurement information received from the one or more wireless sensors. In some embodiments, the one or more graphical elements may include heart rate information that is updated in real-time or near real-time and the heart rate information may be received from a wireless electrocardiogram sensor attached to the user's body.

In some embodiments, the processing device may present, in a further portion of the user interface, information pertaining to the treatment plan. The treatment plan may be generated by one or more machine learning models based on or more characteristics of the user. The one or more characteristics may pertain to the condition of the user. The condition may include cardiac health, pulmonary health, bariatric health, oncologic health, or some combination thereof. In some embodiments, the information may include at least an operating mode of the electromechanical machine. The operating mode may include an active mode, a passive mode, a resistive mode, an active-assistive mode, or some combination thereof.

In some embodiments, the processing device may control, based on the treatment plan, operation of the electromechanical machine.

CLAUSES

Clause 1.20 A computer-implemented system, comprising:
an electromechanical machine;
an interface comprising a display configured to present information pertaining to a user using the electromechanical machine to perform a treatment plan; and
a processing device configured to:
present, in a first portion of a user interface on the display, a video feed from a computing device associated with a healthcare professional;

present, in a second portion of the user interface, a video feed from a computing device associated with the user;

receiving, from one or more wireless sensors associated with the user, measurement information pertaining to the user while the user uses the electromechanical machine to perform the treatment plan, wherein the measurement information comprises a heart rate, a blood pressure, a blood oxygen level, or some combination thereof; and present, in a third portion of the user interface, one or more graphical elements representing the measurement information.

Clause 2.20 The computer-implemented system of any clause herein, wherein the one or more graphical elements are updated in real-time or near real-time to reflect updated measurement information received from the one or more wireless sensors.

Clause 3.20 The computer-implemented system of any clause herein, wherein the processing device is to present, in a further portion of the user interface, information pertaining to the treatment plan, wherein the treatment plan is generated by one or more machine learning models based on one or more characteristics of the user.

Clause 4.20 The computer-implemented system of any clause herein, wherein the one or more characteristics pertain to condition of the user, wherein the condition comprises cardiac health, pulmonary health, bariatric health, oncologic health, or some combination thereof.

Clause 5.20 The computer-implemented system of any clause herein, wherein the information comprises at least an operating mode of the electromechanical machine, wherein the operating mode comprises an active mode, a passive mode, a resistive mode, an active-assistive mode, or some combination thereof.

Clause 6.20 The computer-implemented system of any clause herein, wherein the processing device is to control, based on the treatment plan, operation of the electromechanical machine.

Clause 7.20 The computer-implemented system of any clause herein, wherein at least one of the one or more graphical elements comprises heart rate information that is updated in real-time or near real-time, and the heart rate information is received from a wireless electrocardiogram sensor attached to the user's body.

Clause 8.20 A computer-implemented method, comprising:

presenting, in a first portion of a user interface on a display, a video feed from a computing device associated with a healthcare professional;

presenting, in a second portion of the user interface, a video feed from a computing device associated with the user;

receiving, from one or more wireless sensors associated with the user, measurement information pertaining to the user while the user uses an electromechanical machine to perform a treatment plan, wherein the measurement information comprises a heart rate, a blood pressure, a blood oxygen level, or some combination thereof; and presenting, in a third portion of the user interface, one or more graphical elements representing the measurement information.

Clause 9.20 The computer-implemented method of any clause herein, wherein the one or more graphical elements are updated in real-time or near real-time to reflect updated measurement information received from the one or more wireless sensors.

Clause 10.20 The computer-implemented method of any clause herein, further comprising presenting, in a further portion of the user interface, information pertaining to the treatment plan, wherein the treatment plan is generated by one or more machine learning models based on one or more characteristics of the user.

Clause 11.20 The computer-implemented method of any clause herein, wherein the one or more characteristics pertain to condition of the user, wherein the condition comprises cardiac health, pulmonary health, bariatric health, oncologic health, or some combination thereof.

Clause 12.20 The computer-implemented method of any clause herein, wherein the information comprises at least an operating mode of the electromechanical machine, wherein the operating mode comprises an active mode, a passive mode, a resistive mode, an active-assistive mode, or some combination thereof.

Clause 13.20 The computer-implemented method of any clause herein, further comprising controlling, based on the treatment plan, operation of the electromechanical machine.

Clause 14.20 The computer-implemented method of any clause herein, wherein at least one of the one or more graphical elements comprises heart rate information that is updated in real-time or near real-time, and the heart rate information is received from a wireless electrocardiogram sensor attached to the user's body.

Clause 15.20 A tangible, non-transitory computer-readable medium storing instructions that, when executed, cause a processing device to:

present, in a first portion of a user interface on a display, a video feed from a computing device associated with a healthcare professional;

present, in a second portion of the user interface, a video feed from a computing device associated with the user;

receive, from one or more wireless sensors associated with the user, measurement information pertaining to the user while the user uses an electromechanical machine to perform a treatment plan, wherein the measurement information comprises a heart rate, a blood pressure, a blood oxygen level, or some combination thereof; and present, in a third portion of the user interface, one or more graphical elements representing the measurement information.

Clause 16.20 The computer-readable medium of any clause herein, wherein the one or more graphical elements are updated in real-time or near real-time to reflect updated measurement information received from the one or more wireless sensors.

Clause 17.20 The computer-readable medium of any clause herein, wherein the processing device is further to, in a further portion of the user interface, information pertaining to the treatment plan, wherein the treatment plan is generated by one or more machine learning models based on one or more characteristics of the user.

Clause 18.20 The computer-readable medium of any clause herein, wherein the one or more characteristics pertain to condition of the user, wherein the condition comprises cardiac health, pulmonary health, bariatric health, oncologic health, or some combination thereof.

Clause 19.20 The computer-readable medium of any clause herein, wherein the information comprises at least an operating mode of the electromechanical machine, wherein the operating mode comprises an active mode, a passive mode, a resistive mode, an active-assistive mode, or some combination thereof.

Clause 20.20 The computer-readable medium of any clause herein, wherein the processing device is further to, based on the treatment plan, operation of the electromechanical machine.

Figure 37:
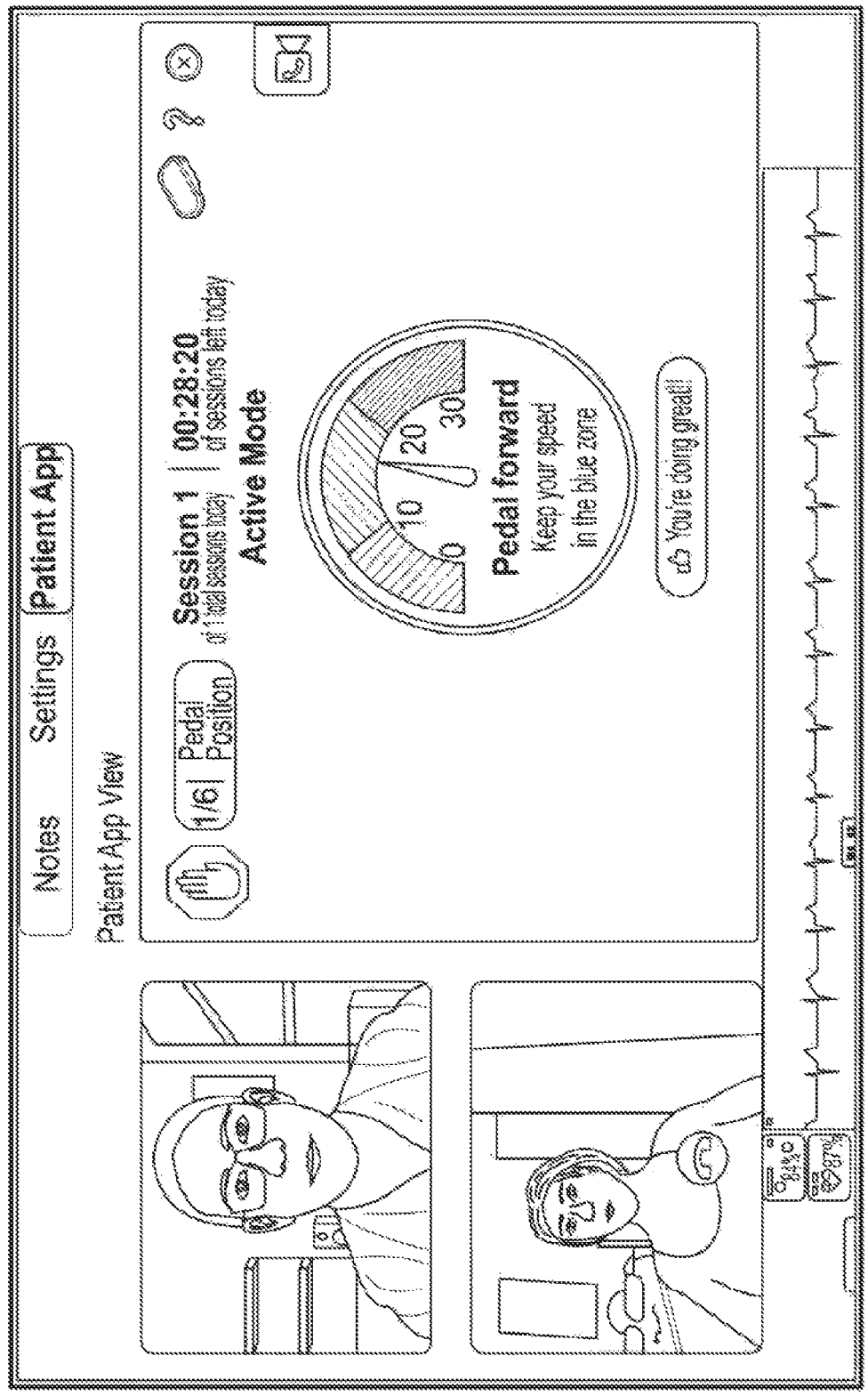
FIG. 37 generally illustrates an embodiment of an enhanced patient display of the patient interface presenting real-time measurement information during a telemedicine session according to the principles of the present disclosure.

FIG. 37 generally illustrates an embodiment of an enhanced patient display 3700 of the patient interface presenting real-time measurement information during a telemedicine session according to the principles of the present disclosure. As depicted, the enhanced patient display 3700 includes two graphical elements that represent two real-time or near real-time video feeds associated with the user and the healthcare professional (e.g., observer). Further, the enhanced patient display 3700 presents information pertaining to a treatment plan, such as a mode (Active Mode), a session number (Session 1), an amount of time remaining in the session (e.g., 00:28:20), and a graphical element speedometer that represents the speed at which the user is pedaling and provides instructions to the user.

Further, the enhanced patient display 3700 may include one or more graphical elements that present real-time or near real-time measurement data to the user. For example, as depicted, the graphical elements present blood pressure data, blood oxygen data, and heart rate data to the user and the data may be streaming live as the user is performing the treatment plan using the electromechanical machine. The enhanced patient display 3700 may arrange the video feeds, the treatment plan information, and the measurement information in such a manner that improves the user's experience using the computing device, thereby providing a technical improvement. For example, the layout of the patient display 3700 may be superior to other layouts, especially on a computing device with a reduced screen size, such as a tablet or smartphone.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A computer-implemented system, comprising:
an electromechanical machine configured to be manipulated by a user while the user is performing a treatment plan;
one or more sensors configured to determine one or more measurements associated with the user; and
one or more processing devices configured to:
receive, from the one or more sensors while the user performs the treatment plan, the one or more measurements associated with the user,
determine, using one or more machine learning models, a probability that the one or more measurements indicate that the user satisfies a threshold for a condition associated with an abnormal heart rhythm, and
perform one or more preventative actions responsive to determining that the one or more measurements indicate the user satisfies the threshold for the condition associated with the abnormal heart rhythm, wherein the one or more preventative actions are determined using the one or more machine learning models, and wherein the one or more preventative actions comprise at least one preventative action selected from the group consisting of initiating a telecommunications transmission, stopping operation of the electromechanical machine, and modifying one or more parameters associated with the operation of the electromechanical machine.

2. The computer-implemented system of claim 1, wherein, to perform the one or more preventative actions, the one or more processing devices are further configured to initiate a call to an emergency service provider.

3. The computer-implemented system of claim 1, wherein, to perform the one or more preventative actions, the one or more processing devices are further configured to initiate a telemedicine session with a computing device associated with a healthcare professional.

4. The computer-implemented system of claim 1, further comprising a display, wherein, to perform the one or more preventative actions, the one or more processing devices are further configured to present, on the display, one or more instructions to modify usage of the electromechanical machine.

5. The computer-implemented system of claim 1, wherein the condition associated with the abnormal heart rhythm comprises at least one condition selected from the group consisting of atrial fibrillation, atrial flutter, supraventricular tachycardia, ventricular fibrillation, and ventricular tachycardia.

6. The computer-implemented system of claim 1, wherein the one or more sensors comprise at least one sensor selected from the group consisting of a pulse oximeter, an electrocardiogram sensor, a heart rate sensor, a blood pressure sensor, a temperature sensor, a force sensor, and a continuous glucose monitor sensor.

7. The computer-implemented system of claim 1, wherein the one or more machine learning models are trained to implement a photoplethysmography algorithm or an electrocardiogram algorithm.

8. A computer-implemented method comprising:
receiving, from one or more sensors while a user performs a treatment plan on an electromechanical machine, one or more measurements associated with the user;
determining, using one or more machine learning models, a probability that the one or more measurements indicate that the user satisfies a threshold for a condition associated with an abnormal heart rhythm; and
performing one or more preventative actions responsive to determining that the one or more measurements indicate the user satisfies the threshold for the condition associated with the abnormal heart rhythm, wherein the one or more preventative actions are determined using the one or more machine learning models, and wherein the one or more preventative actions comprise at least one preventative action selected from the group consisting of initiating a telecommunications transmission, stopping operation of the electromechanical machine, and modifying one or more parameters associated with the operation of the electromechanical machine.

9. The computer-implemented method of claim 8, wherein performing the one or more preventative actions comprising initiating the telecommunications transmission comprises initiating a call to an emergency service provider.

10. The computer-implemented method of claim 8, wherein performing the one or more preventative actions comprising initiating a telemedicine session with a computing device associated with a healthcare professional.

11. The computer-implemented method of claim 8, wherein performing the one or more preventative actions comprising presenting, on a display, one or more instructions to modify usage of the electromechanical machine.

12. The computer-implemented method of claim 8, wherein the condition associated with the abnormal heart rhythm comprises at least one condition selected from the group consisting of atrial fibrillation, atrial flutter, supraventricular tachycardia, ventricular fibrillation, and ventricular tachycardia.

13. The computer-implemented method of claim 8, wherein the one or more sensors comprise at least one sensor selected from the group consisting of a pulse oximeter, an electrocardiogram sensor, a heart rate sensor, a blood pressure sensor, a temperature sensor, a force sensor, and a continuous glucose monitor sensor.

14. The computer-implemented method of claim 8, wherein the one or more machine learning models are trained to implement a photoplethysmography algorithm or an electrocardiogram algorithm.

15. One or more tangible, non-transitory computer-readable media storing instructions that, when executed, cause one or more processing devices to:
  receive, from one or more sensors while a user performs a treatment plan on an electromechanical machine, one or more measurements associated with the user,
  determine, using one or more machine learning models, a probability that the one or more measurements indicate that the user satisfies a threshold for a condition associated with an abnormal heart rhythm, and
  perform one or more preventative actions responsive to determining that the one or more measurements indicate the user satisfies the threshold for the condition associated with the abnormal heart rhythm, wherein the one or more preventative actions are determined using the one or more machine learning models, and wherein the one or more preventative actions comprise at least one preventative action selected from the group consisting of initiating a telecommunications transmission, stopping operation of the electromechanical machine, and modifying one or more parameters associated with the operation of the electromechanical machine.

16. The one or more computer-readable media of claim 15, wherein, to perform the one or more preventative actions, the instructions further cause the one or more processing devices to initiate a call to an emergency service provider or a telemedicine session with a computing device associated with a healthcare professional.

17. The one or more computer-readable media of claim 15, wherein, to perform the one or more preventative actions, the instructions further cause the one or more processing devices to present, on a display, one or more instructions to modify usage of the electromechanical machine.

18. The one or more computer-readable media of claim 15, wherein the condition associated with the abnormal heart rhythm comprises at least one condition selected from the group consisting of atrial fibrillation, atrial flutter, supraventricular tachycardia, ventricular fibrillation, and ventricular tachycardia.

19. The one or more computer-readable media of claim 15, wherein the one or more sensors comprise at least one sensor selected from the group consisting of a pulse oximeter, an electrocardiogram sensor, a heart rate sensor, a blood pressure sensor, a temperature sensor, a force sensor, and a continuous glucose monitor sensor.

20. The one or more computer-readable media of claim 15, wherein the one or more machine learning models are trained to implement a photoplethysmography algorithm or an electrocardiogram algorithm.

\* \* \* \* \*